US010577664B2

(12) United States Patent
Huletsky et al.

(10) Patent No.: US 10,577,664 B2
(45) Date of Patent: *Mar. 3, 2020

(54) METHOD FOR THE DETECTION AND IDENTIFICATION OF METHICILLIN-RESISTANT *STAPHYLOCOCCUS AUREUS*

(71) Applicant: GENEOHM SCIENCES CANADA, INC., Quebec (CA)

(72) Inventors: Ann Huletsky, Sillery (CA); Valery Rossbach, Gatineau (CA)

(73) Assignee: GeneOhm Sciences Canada, Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,421

(22) Filed: Sep. 18, 2017

(65) Prior Publication Data

US 2018/0208972 A1 Jul. 26, 2018

Related U.S. Application Data

(63) Continuation of application No. 11/416,500, filed on May 2, 2006, now Pat. No. 9,777,335, which is a continuation of application No. 10/479,674, filed as application No. PCT/CA02/00824 on Jun. 4, 2002, now Pat. No. 7,449,289.

(30) Foreign Application Priority Data

Jun. 4, 2001 (CA) ..................................... 2348042

(51) Int. Cl.
*C12Q 1/689* (2018.01)

(52) U.S. Cl.
CPC ....... *C12Q 1/689* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 4,683,195 | A | 7/1987 | Mullis et al. |
| 4,683,202 | A | 7/1987 | Mullis |
| 5,272,236 | A | 12/1993 | Lai et al. |

(Continued)

FOREIGN PATENT DOCUMENTS

| | | |
|---|---|---|
| AU | 731850 | 4/2001 |
| AU | 775763 | 8/2004 |

(Continued)

OTHER PUBLICATIONS

Al-Soud, et al. "Capacity of nine thermostable DNA Polymerases to mediate DNA amplification in the presence of PCR-Inhibiting samples." Appl. Environ. Microbiol. 64(10): 3748-3753 (1998).

(Continued)

*Primary Examiner* — Diana B Johannsen
(74) *Attorney, Agent, or Firm* — Knobbe, Martens, Olson & Bear, LLP

(57) ABSTRACT

The present invention describes novel SCCmec right extremity junction sequences for the detection of methicillin-resistant *Staphyloccocus aureus* (MRSA). It relates to the use of these DNA sequences for diagnostic purposes.

27 Claims, 10 Drawing Sheets

Specification includes a Sequence Listing.

(56) References Cited

U.S. PATENT DOCUMENTS

| | | | |
|---|---|---|---|
| 5,437,978 | A | 8/1995 | Ubukata et al. |
| 5,475,610 | A | 12/1995 | Atwood et al. |
| 5,496,706 | A | 3/1996 | Kuusela et al. |
| 5,538,871 | A | 7/1996 | Nuovo et al. |
| 5,602,756 | A | 2/1997 | Atwood et al. |
| 5,612,473 | A | 3/1997 | Wu et al. |
| 5,702,895 | A | 12/1997 | Matsunaga et al. |
| 5,776,712 | A | 7/1998 | Kuusela et al. |
| 5,780,610 | A | 7/1998 | Collins et al. |
| 5,783,638 | A | 7/1998 | Lai et al. |
| 5,866,366 | A | 2/1999 | Kallender |
| 5,994,066 | A | 11/1999 | Bergeron et al. |
| 6,001,564 | A | 12/1999 | Bergeron et al. |
| 6,083,587 | A | 7/2000 | Smith et al. |
| 6,090,592 | A | 7/2000 | Adams et al. |
| 6,117,635 | A | 9/2000 | Nazarenko et al. |
| 6,117,986 | A | 9/2000 | Nardone et al. |
| 6,156,507 | A | 12/2000 | Hiramatsu et al. |
| 6,271,351 | B1 | 8/2001 | Gawryl et al. |
| 6,380,370 | B1 | 4/2002 | Doucette-Stamm et al. |
| 7,108,974 | B2 | 9/2006 | Ecker et al. |
| 7,205,111 | B2 | 4/2007 | Christensen et al. |
| 7,226,739 | B2 | 6/2007 | Ecker et al. |
| 7,255,992 | B2 | 8/2007 | Ecker et al. |
| 7,399,590 | B2 | 7/2008 | Piepenburg et al. |
| 7,435,561 | B2 | 10/2008 | Piepenburg et al. |
| 7,449,289 | B2 | 11/2008 | Huletsky et al. |
| 7,466,908 | B1 | 12/2008 | Lem et al. |
| 7,666,588 | B2 | 2/2010 | Ecker et al. |
| 7,666,592 | B2 | 2/2010 | Ecker et al. |
| 7,718,354 | B2 | 5/2010 | Ecker et al. |
| 7,741,036 | B2 | 6/2010 | Ecker et al. |
| 7,781,162 | B2 | 8/2010 | Ecker et al. |
| 7,838,221 | B2 | 11/2010 | Huletsky et al. |
| 7,955,796 | B2 | 6/2011 | Schrenzel et al. |
| 7,956,175 | B2 | 6/2011 | Sampath et al. |
| 8,013,142 | B2 | 9/2011 | Sampath et al. |
| 8,017,322 | B2 | 9/2011 | Ecker et al. |
| 8,017,337 | B2 | 9/2011 | Paitan |
| 8,017,358 | B2 | 9/2011 | Ecker et al. |
| 8,017,743 | B2 | 9/2011 | Ecker et al. |
| 8,034,588 | B2 | 10/2011 | Bergeron et al. |
| 8,062,850 | B2 | 11/2011 | Piepenburg et al. |
| 8,067,207 | B2 | 11/2011 | Bergeron et al. |
| 8,071,309 | B2 | 12/2011 | Ecker et al. |
| 8,084,207 | B2 | 12/2011 | Sampath et al. |
| 8,097,416 | B2 | 1/2012 | Hall et al. |
| 8,114,601 | B2 | 2/2012 | Bergeron et al. |
| 8,163,895 | B2 | 4/2012 | Sampath et al. |
| 8,182,992 | B2 | 5/2012 | Sampath |
| 8,182,996 | B2 | 5/2012 | Bergeron et al. |
| 8,187,812 | B2 | 5/2012 | Zhang et al. |
| 8,187,814 | B2 | 5/2012 | Ecker et al. |
| 8,214,154 | B2 | 7/2012 | Ecker et al. |
| 8,242,254 | B2 | 8/2012 | Sampath et al. |
| 8,265,848 | B2 | 9/2012 | Ecker et al. |
| 8,268,565 | B2 | 9/2012 | Ecker et al. |
| 8,288,523 | B2 | 10/2012 | Sampath et al. |
| 8,323,898 | B2 | 12/2012 | Niimi et al. |
| 8,362,228 | B2 | 1/2013 | Paitan |
| 8,367,337 | B2 | 2/2013 | Jay et al. |
| 8,394,945 | B2 | 3/2013 | Sampath et al. |
| 8,426,137 | B2 | 4/2013 | Bergeron et al. |
| 8,518,646 | B2 | 8/2013 | Jean et al. |
| 9,777,335 | B2 * | 10/2017 | Huletsky ................ C12Q 1/689 |
| 2002/0055101 | A1 | 5/2002 | Bergeron et al. |
| 2002/0103338 | A1 | 8/2002 | Choi |
| 2002/0106646 | A1 | 8/2002 | Remacle et al. |
| 2003/0027135 | A1 | 2/2003 | Ecker et al. |
| 2003/0049636 | A1 | 3/2003 | Bergeron et al. |
| 2003/0054436 | A1 | 3/2003 | Kunsch et al. |
| 2003/0124556 | A1 | 7/2003 | Ecker et al. |
| 2003/0175695 | A1 | 9/2003 | Ecker et al. |
| 2003/0175696 | A1 | 9/2003 | Ecker et al. |
| 2003/0175697 | A1 | 9/2003 | Ecker et al. |
| 2003/0180733 | A1 | 9/2003 | Bergeron et al. |
| 2003/0190605 | A1 | 10/2003 | Ecker et al. |
| 2003/0198943 | A1 | 10/2003 | Remacle et al. |
| 2004/0082002 | A1 | 4/2004 | Choi |
| 2004/0110138 | A1 | 6/2004 | Lem et al. |
| 2004/0110169 | A1 | 6/2004 | Ecker et al. |
| 2004/0121309 | A1 | 6/2004 | Ecker et al. |
| 2004/0121310 | A1 | 6/2004 | Ecker et al. |
| 2004/0121311 | A1 | 6/2004 | Ecker et al. |
| 2004/0121313 | A1 | 6/2004 | Ecker et al. |
| 2004/0121314 | A1 | 6/2004 | Ecker et al. |
| 2004/0121335 | A1 | 6/2004 | Ecker et al. |
| 2004/0161770 | A1 | 8/2004 | Ecker et al. |
| 2004/0180328 | A1 | 9/2004 | Ecker et al. |
| 2004/0185437 | A1 | 9/2004 | Hermet et al. |
| 2004/0185438 | A1 | 9/2004 | Ecker |
| 2004/0185478 | A1 | 9/2004 | Bergeron et al. |
| 2004/0202997 | A1 | 10/2004 | Ecker et al. |
| 2004/0219517 | A1 | 11/2004 | Ecker et al. |
| 2004/0241824 | A1 | 12/2004 | Schrenzel et al. |
| 2004/0253583 | A1 | 12/2004 | Ecker et al. |
| 2004/0253619 | A1 | 12/2004 | Ecker et al. |
| 2005/0019893 | A1 | 1/2005 | Huletsky et al. |
| 2005/0037408 | A1 | 2/2005 | Christensen et al. |
| 2005/0059064 | A1 | 3/2005 | Obst et al. |
| 2005/0112631 | A1 | 5/2005 | Piepenburg et al. |
| 2005/0115903 | A1 | 6/2005 | Hallier-Soulier et al. |
| 2006/0057613 | A1 | 3/2006 | Ramakrishnan et al. |
| 2006/0105354 | A1 | 5/2006 | Remacle et al. |
| 2006/0121520 | A1 | 6/2006 | Ecker et al. |
| 2006/0205040 | A1 | 9/2006 | Sampath |
| 2006/0240412 | A1 | 10/2006 | Hall et al. |
| 2006/0252069 | A1 | 11/2006 | Zhang et al. |
| 2006/0252078 | A1 | 11/2006 | Huletsky et al. |
| 2006/0263810 | A1 | 11/2006 | Bergeron et al. |
| 2006/0275749 | A1 | 12/2006 | Sampath et al. |
| 2006/0275788 | A1 | 12/2006 | Ecker et al. |
| 2006/0281112 | A1 | 12/2006 | Remacle et al. |
| 2007/0009947 | A1 | 1/2007 | Bergeron et al. |
| 2007/0037187 | A1 | 2/2007 | Alexandre et al. |
| 2007/0048735 | A1 | 3/2007 | Ecker et al. |
| 2007/0054296 | A1 | 3/2007 | Piepenburg et al. |
| 2007/0082340 | A1 | 4/2007 | Huletsky et al. |
| 2007/0099204 | A1 | 5/2007 | Alexandre et al. |
| 2007/0105129 | A1 | 5/2007 | Bergeron et al. |
| 2007/0218489 | A1 | 9/2007 | Sampath et al. |
| 2007/0224614 | A1 | 9/2007 | Sampath et al. |
| 2007/0238116 | A1 | 10/2007 | Sampath et al. |
| 2007/0243544 | A1 | 10/2007 | Sampath et al. |
| 2007/0248969 | A1 | 10/2007 | Sampath et al. |
| 2007/0298423 | A1 | 12/2007 | Remacle et al. |
| 2008/0038737 | A1 | 2/2008 | Smith et al. |
| 2008/0057544 | A1 | 3/2008 | Lem et al. |
| 2008/0085515 | A1 | 4/2008 | Remacle et al. |
| 2008/0138808 | A1 | 6/2008 | Hall et al. |
| 2008/0145847 | A1 | 6/2008 | Hall et al. |
| 2008/0146455 | A1 | 6/2008 | Hall et al. |
| 2008/0160512 | A1 | 7/2008 | Ecker et al. |
| 2008/0220428 | A1 | 9/2008 | Aichinger et al. |
| 2008/0227087 | A1 | 9/2008 | Huletski et al. |
| 2008/0233570 | A1 | 9/2008 | Hall et al. |
| 2008/0311558 | A1 | 12/2008 | Ecker et al. |
| 2009/0004643 | A1 | 1/2009 | Ecker et al. |
| 2009/0035780 | A1 | 2/2009 | McCarthy et al. |
| 2009/0047665 | A1 | 2/2009 | Hall et al. |
| 2009/0047669 | A1 | 2/2009 | Zhang et al. |
| 2009/0047671 | A1 | 2/2009 | Bergeron et al. |
| 2009/0053702 | A1 | 2/2009 | Bergeron et al. |
| 2009/0053703 | A1 | 2/2009 | Bergeron et al. |
| 2009/0061446 | A1 | 3/2009 | Niimi et al. |
| 2009/0068641 | A1 | 3/2009 | Bergeron et al. |
| 2009/0111134 | A1 | 4/2009 | Zhang et al. |
| 2009/0148829 | A1 | 6/2009 | Ecker et al. |
| 2009/0148836 | A1 | 6/2009 | Ecker et al. |
| 2009/0148837 | A1 | 6/2009 | Ecker et al. |
| 2009/0181395 | A1 | 7/2009 | Becker et al. |
| 2009/0182511 | A1 | 7/2009 | Ecker et al. |
| 2009/0203013 | A1 | 8/2009 | Jay et al. |
| 2009/0220937 | A1 | 9/2009 | Sampath |

(56) References Cited

U.S. PATENT DOCUMENTS

| | | | |
|---|---|---|---|
| 2009/0239224 | A1 | 9/2009 | Ecker et al. |
| 2009/0280471 | A1 | 11/2009 | Ecker et al. |
| 2010/0035232 | A1 | 2/2010 | Ecker et al. |
| 2010/0035239 | A1 | 2/2010 | Sampath et al. |
| 2010/0099860 | A1 | 4/2010 | Remacle et al. |
| 2010/0129811 | A1 | 5/2010 | Sampath et al. |
| 2010/0136515 | A1 | 6/2010 | Sampath et al. |
| 2010/0145626 | A1 | 6/2010 | Ecker et al. |
| 2010/0152432 | A1 | 6/2010 | Wu et al. |
| 2010/0204266 | A1 | 8/2010 | Ecker et al. |
| 2010/0267012 | A1 | 10/2010 | Bergeron et al. |
| 2010/0304366 | A1 | 12/2010 | Wu et al. |
| 2011/0091886 | A1 | 4/2011 | Hirama et al. |
| 2011/0151452 | A1 | 6/2011 | Jean et al. |
| 2012/0015349 | A1 | 1/2012 | Sampath et al. |
| 2012/0015367 | A1 | 1/2012 | Piepenburg et al. |
| 2012/0035071 | A1 | 2/2012 | Bergeron et al. |
| 2012/0058487 | A1 | 3/2012 | Bergeron et al. |
| 2012/0077684 | A1 | 3/2012 | O'Hara |
| 2012/0107795 | A1 | 5/2012 | Ecker et al. |
| 2012/0122086 | A1 | 5/2012 | Ecker et al. |
| 2012/0122096 | A1 | 5/2012 | Sampath et al. |
| 2012/0122097 | A1 | 5/2012 | Sampath et al. |
| 2012/0122098 | A1 | 5/2012 | Sampath et al. |
| 2012/0122099 | A1 | 5/2012 | Sampath et al. |
| 2012/0122100 | A1 | 5/2012 | Sampath et al. |
| 2012/0122101 | A1 | 5/2012 | Sampath et al. |
| 2012/0122102 | A1 | 5/2012 | Sampath et al. |
| 2012/0122103 | A1 | 5/2012 | Sampath et al. |
| 2012/0142085 | A1 | 6/2012 | Ecker et al. |
| 2012/0164625 | A1 | 6/2012 | Ecker et al. |
| 2012/0171679 | A1 | 7/2012 | Ecker et al. |
| 2012/0171692 | A1 | 7/2012 | Sampath et al. |
| 2012/0208179 | A1 | 8/2012 | Sampath et al. |
| 2013/0065774 | A1 | 3/2013 | Zhang et al. |
| 2013/0338036 | A1 | 12/2013 | Jean et al. |
| 2013/0338037 | A1 | 12/2013 | Jean et al. |
| 2015/0232919 | A1 | 8/2015 | Menard et al. |

FOREIGN PATENT DOCUMENTS

| | | | |
|---|---|---|---|
| AU | 2008255266 | | 1/2009 |
| AU | 2010202418 | | 7/2010 |
| AU | 2012247038 | | 11/2012 |
| CA | 2283458 | | 3/2001 |
| CA | 2348042 | A1 | 12/2002 |
| CN | 1505685 | | 6/2004 |
| DE | 10051174 | | 5/2002 |
| EP | 0 497 272 | | 8/1992 |
| EP | 0 526 876 | A1 | 2/1993 |
| EP | 0 527 628 | | 2/1993 |
| EP | 0 543 942 | | 6/1993 |
| EP | 0 887 424 | | 12/1998 |
| EP | 1 136 566 | A | 9/2001 |
| EP | 1 522 595 | | 4/2005 |
| EP | 1 529 847 | A | 5/2005 |
| EP | 1 541 696 | A | 6/2005 |
| EP | 1 659 183 | A | 5/2006 |
| EP | 1 788 095 | A1 | 5/2007 |
| EP | 1 903 116 | A1 | 3/2008 |
| EP | 1 997 886 | A1 | 12/2008 |
| EP | 0 943 009 | B1 | 6/2009 |
| EP | 1 397 510 | B1 | 11/2009 |
| EP | 2 128 268 | A1 | 12/2009 |
| EP | 2 150 625 | A2 | 2/2010 |
| EP | 2 236 621 | A1 | 10/2010 |
| EP | 2 253 712 | A1 | 11/2010 |
| EP | 1 934 613 | B1 | 1/2011 |
| EP | 2 302 074 | | 3/2011 |
| EP | 2 311 992 | | 4/2011 |
| EP | 2 322 649 | | 5/2011 |
| EP | 2 322 655 | A1 | 5/2011 |
| EP | 2 322 661 | A1 | 5/2011 |
| EP | 2 322 663 | A1 | 5/2011 |
| EP | 2 322 664 | A1 | 5/2011 |
| EP | 2 322 666 | A2 | 5/2011 |
| EP | 2 322 667 | A2 | 5/2011 |
| EP | 2 322 668 | A2 | 5/2011 |
| EP | 2 322 930 | A2 | 5/2011 |
| EP | 2 325 643 | A2 | 5/2011 |
| EP | 2 325 644 | A2 | 5/2011 |
| EP | 2 325 645 | A2 | 5/2011 |
| EP | 2 325 646 | A2 | 5/2011 |
| EP | 2 325 647 | A2 | 5/2011 |
| EP | 2 333 118 | | 6/2011 |
| EP | 2 336 364 | A1 | 6/2011 |
| EP | 2 336 365 | A1 | 6/2011 |
| EP | 2 336 366 | A2 | 6/2011 |
| EP | 2 339 033 | A1 | 6/2011 |
| EP | 2 339 034 | A1 | 6/2011 |
| EP | 2 345 746 | A1 | 7/2011 |
| EP | 2 385 140 | A1 | 11/2011 |
| EP | 2 064 332 | B1 | 7/2012 |
| EP | 2 016 186 | B1 | 1/2013 |
| EP | 1 929 049 | B1 | 4/2013 |
| JP | H11056371 | | 3/1999 |
| JP | 2006271370 | | 10/2006 |
| JP | 2010057495 | | 3/2010 |
| KR | 20030003576 | | 1/2003 |
| MX | PA03007927 | | 10/2004 |
| MY | 141881 | A | 7/2010 |
| WO | WO 1992/02638 | | 2/1992 |
| WO | WO 1992/05281 | | 4/1992 |
| WO | WO 1995/13395 | A1 | 5/1995 |
| WO | WO 1996/008582 | | 3/1996 |
| WO | WO 1997/31125 | | 8/1997 |
| WO | WO 1998/20157 | | 5/1998 |
| WO | WO 1999/47706 | | 9/1999 |
| WO | WO 2001/016292 | | 3/2001 |
| WO | WO 2001/023604 | A2 | 4/2001 |
| WO | WO 2001/077372 | | 10/2001 |
| WO | WO 2002/070664 | | 9/2002 |
| WO | WO 2002/082086 | | 10/2002 |
| WO | WO 2002/099034 | | 12/2002 |
| WO | WO 2004/052175 | | 6/2004 |
| WO | WO 2004/053076 | | 6/2004 |
| WO | WO 2004/053141 | | 6/2004 |
| WO | WO 2004/053164 | | 6/2004 |
| WO | WO 2004/055205 | | 7/2004 |
| WO | WO 2004/060278 | | 7/2004 |
| WO | WO 2005/014857 | | 2/2005 |
| WO | WO 2005/024046 | | 3/2005 |
| WO | WO 2005/094421 | | 10/2005 |
| WO | WO 2005/098047 | | 10/2005 |
| WO | WO 2005/100538 | | 10/2005 |
| WO | WO 2006/028601 | | 3/2006 |
| WO | WO 2006/053769 | | 5/2006 |
| WO | WO 2006/053770 | | 5/2006 |
| WO | WO 2006/071241 | | 7/2006 |
| WO | WO 2006/094238 | | 9/2006 |
| WO | WO 2006/111028 | | 10/2006 |
| WO | WO 2006/116127 | | 11/2006 |
| WO | WO 2006/135400 | | 12/2006 |
| WO | WO 2007/023461 | | 3/2007 |
| WO | WO 2007/044873 | | 4/2007 |
| WO | WO 2007/086904 | | 8/2007 |
| WO | WO 2007/096702 | | 8/2007 |
| WO | WO 2007/100397 | | 9/2007 |
| WO | WO 2007/130951 | A2 | 11/2007 |
| WO | WO 2007/131995 | | 11/2007 |
| WO | WO 2007/131999 | | 11/2007 |
| WO | WO 2007/132001 | | 11/2007 |
| WO | WO 2007/132002 | | 11/2007 |
| WO | WO 2007/133732 | | 11/2007 |
| WO | WO 2008/061376 | | 5/2008 |
| WO | WO 2008/080620 | | 7/2008 |
| WO | WO 2008/140612 | | 11/2008 |
| WO | WO 2008/143627 | | 11/2008 |
| WO | WO 2009/049007 | | 4/2009 |
| WO | WO 2009/090310 | | 7/2009 |

(56) References Cited

FOREIGN PATENT DOCUMENTS

| | | |
|---|---|---|
| WO | WO 2009/123667 | 10/2009 |
| WO | WO 2011/038197 | 3/2011 |

OTHER PUBLICATIONS

Al-Soud, et. al. "Effects of amplification facilitators on diagnostic PCR in the presence of blood, feces, and meat." J. Clin. Microbiol. 38(12): 4463-4470 (2002).

Arakere, et al. "A novel type-III *Staphylococcal cassette chromosome mec* (SCCmec) variant among Indian isolates of methicillin-resistant *Staphylococcus aureus*." FEMS Microbiol. Lett. 292(1): 141-148 (Mar. 2009).

Archer, et al. "Origin and evolution of DNA associated with resistance to methicillin in *Staphylococci*." Trends in Microbiology. 2(10):343-347 (1994).

Archer, et al. "Dissemination among *Staphylococci* of DNA sequences associated with methicillin resistance." Antimicrobial Agents and Chemotherapy. 38(3):447-54 (1994).

Arnheim, et al "Polymerase Chain Reaction." C&EN. 36-47 (1990).

Ausubel et al., Current Protocols in Molecular Biology, 3rd Ed. Wiley Interscience Publishers (1995) [Table of Contents Only].

Baba, et al. "Genome and virulence determinants of high virulence community-acquired MRSA." Lancet. 359(9320): 1819-1827 (2002).

Baba et al. "*Staphylococcus aureus* subsp. Aureus MW2 DNA, complete genome", retrieved from EBI Database accession No. AP004822 (May 27, 2002), replaced by Accession No. BA000033.

Barany et al., "Genetic disease detection and DNA amplification using cloned thermostable ligase," Proc Natl Acad Sci. USA (Jan. 1991) 88: 189-193.

Barberis-Maino. IS431, a *Staphylococcal* insertion sequence-like element related to IS26 from *Proteus vulgaris*. Gene. 59:107-13 (1983).

Barringer, et al. "Blunt-end and single strand ligations by *Escherichia coli* ligase: Influence on an in vitro amplification scheme." Gene. 89:117-122 (1990).

Barski et al., "Rapid assay for detection of methicillin-resistant *Staphylococcus aureus* using multiplex PCR," Mol Cell Probes (1996) 10(6):471-475.

Bartels et al., "An unexpected location of the Arginine Catabolic Mobile Element (ACME) in a USA300-related MRSA." PLoS ONE 6(1): e16193 (Jan. 2011).

Bastos et al., "Molecular characterization and transfer among *Staphylococcus* strains of a plasmid conferring high-level resistance to mupirocin", Eur. J. Clin. Microbiol. Infect. Dis. (1999) 18(6):393-8.

Beaucage et al. "Deoxynucleoside Phosphoramidites—A New Class of Key Intermediates for Deoxypolynucleotide Syntesis," Tetra Lttrs. (1981) 22(20): 1859-1862.

Becker et al., "Thermonuclease gene as a target for specific identification of *Staphylococcus intermedius* isolates: use of a PCR-DNA enzyme immunoassay", Diagn. Microbiol. Infect. Dis. (Apr. 2005) 51(4):237-44.

Becker et al., "Does Nasal Cocolonization by Methicillin-Resistant Coagulase-Negative *Staphylococci* and Methicillin-Susceptible *Staphylococcus aureus* Strains Occur Frequently Enough to Represent a Risk of False Positive Methicillin-Resistant *S. aureus* Determinations by Molecular Methods?", J Clin Microbiol. (Jan. 2006) 44(1): 229-231.

Benson et al., "Direct detection of mecA and nuc genes for rapid species and resistance determination of *Staphylococci* from blood cultures," Abstracts of the Interscience Conference on Antimicrobial Agents and Chemotherapy, (1999) vol. 39, Abstract #877; pp. 208. cd-rom; 39th Interscience Conference on Antimicrobial Agents and Chemotherapy. San Francisco, California, USA. Sep. 26-29, 1999. American Society for Microbiology.

Berger-Bächi, et al. "Insertional inactivation of *Staphylococcal methicillin* resistance by Tn551." J. Bacter. 154(1):479-87 (1983).

Bishop et al., "Concurrent Analysis of Nose and Groin Swab Specimens by the IDI-MRSA PCR Assay is Comparable to Analysis by Individual-Specimen PCR and Routine Culture Assays for Detection of Colonization by Methicillin-Resistant *Staphylococcus aureus*", J Clin Microbiol. (Aug. 2006) 44(8): 2904-2908.

Boye et al., "A new multiplex PCR for easy screening of methicillin-resistant *Staphylococcus aureus* SCCmec types I-V. ", Clin Microbiol Infect. (Jul. 2007) 13(7): 725-727.

Brakstad et al., "Detection of *Staphylococcus aureus* by polymerase chain reaction amplification of the nuc gene", *J. Clin. Microbiol.* (1992) 30(7):1654-60.

Brakstad et al., "Multiplex polymerase chain reaction for detection of genes for *Staphylococcus aureus* thermonuclease and methicillin resistance and correlation with oxacillin resistance," APMIS (1993) 101(:681-688.

Brakstad et al., "Simultaneous detection of the *Staphylococcal* MecA and Nuc genes by a multiplex PCR," Zentralblatt für Bakteriologie (Inter'l J Med Microbiol.), (1994) Supplement 26, 246-248.

Brakstad et al., "Comparison of tests designed to identify *Staphylococcus aureus* thermostable nuclease", *APMIS* (1995) 103(3):219-24.

Brown et al., "Chemical Synthesis and Cloning of a Tyrosine tRNA Gene," Meth Enzymol. (1979) 68: 109-151.

Brown et al., "Real-time PCR detection of *S-aureus* and MRSA from wound, fluid and respiratory samples," Abstracts of the General Meeting of the American Society for Microbiology, (2006) vol. 106, Abs. C-074, pp. 110-111; 106th General Meeting of the American Society for Microbiology. Orlando, FL, USA. May 21-25, 2006.

Buck, et al. "Design strategies and performance of custom DNA sequencing primers." BioTechniques, 27(3): 528-536, (Sep 1999).

Bustin S.A., "Absolute quantification of mRNA using real-time reverse transcription polymerase chain reaction assays", J Mol Endocrinol. (2000) 25: 169-193.

Carroll, K.C. "Rapid diagnostics for methicillin-resistant *Staphylococcus aureus*", Mol Diagn Therapy, (Jan. 2008) 12(1): 15-24.

Chakrabarti, et al. "Novel sulfoxides facilitate GC-rich template amplification." Biotechniques. 32: 866-874 (2002).

Chesneau et al., "Thermonuclease gene as a target nucleotide sequence for specific recognition of *Staphylococcus aureus*", Mol. Cell. Probes. (1993) 7(4):301-10.

Cheng et al., "Effective amplification of long targets from cloned inserts and human genomic DNA," Proc Natl Acad Sci. USA, (Jun. 1994) 91: 5695-5699.

Ciardo et al., "GeneXpert Captures Unstable Methicillin-Resistant *Staphylococcus aureus* Prone to Rapidly Losing the mecAGene," J. Clin. Microbio. (Aug. 2010) 48(8):3030-3031.

Cho et al., "Detection of methicillin resistance in *Staphylococcus aureus* isolates using two-step triplex PCR and conventional methods", J Microbiol Biotechnol. (Apr. 2007) 17(4): 673-676.

Chongtrakool et al., "*Staphylococcal* cassette chromosome mec (SCCmec) typing of methicillin-resistant *Staphylococcus aureus* strains isolated in 11 Asian countries: a proposal for a new nomenclature for SCCmec elements", Antimicrob. Agents Chemother. (2006) 50(3):1001-12.

Costa et al., "Rapid detection of mecA and nuc genes in *Staphylococci* by real-time multiplex polymerase chain reaction", Diagn. Microbiol. Infect. Dis. (Jan. 2005) 51(1):13-17.

Crisóstomo et al., "The evolution of methicillin resistance in *Staphylococcus aureus*: Similarity of genetic backgrounds in historically early methicillin-susceptible and—resistant isolates and contemporary epidemic clones", Proc Natl Acad Sci USA, (Aug. 2001) 98(17): 9865-9870.

Cuny et al., "PCR for the identification of methicillin-resistant *Staphylococcus aureus* (MRSA) strains using a single primer pair specific for SCCmec elements and the neighbouring chromosome-borne orfX."—Research Note, Clin Microbio Infect., 11(10): 834-837 (Oct. 2005).

Database Geneseq [Online]. "Polymorphic right extremity junction (MREJ) DNA #1." EBI accession No. GSN:ACD02065; Database accession No. ACD02065 (2003).

Database Geneseq [Online]. Sequence provided in Fig. 4 of JP11056371. Retrieved from EBI accession No. GSN:AAX32450 (Oct. 25, 2010).

(56) References Cited

OTHER PUBLICATIONS

Database Geneseq [Online]. "Identification method" JP1999056371, Retrieved from EBI accession No. EM-PRO:E60314 (Oct. 26, 2010).
Database Geneseq [Online]. "Sequence of Primer KC1". Retrieved from EBI accession No. GSN:AAX32446 (Jun. 22, 1999).
Database Geneseq [Online]. "*Staphylococcus aureus* downstream junction sequence Psj10-3J3rc.", Retrieved from EBI accession No. GSN:AAT84818 (Mar. 23, 1998).
Database EMBL [Online]. "*Staphylococcus aureus* DNA, 3' flanking region of MecDNA, strain 64/4176", Retrieved from EBI accession No. AB014434 (Jan. 7, 2000).
Database EMBL [Online]. "*Staphylococcus aureus* M type 1 capsular polysaccharide biosynthesis gene cluster, complete sequence and unknown genes", Retrieved from EBI accession No. SA10927 (Nov. 8, 1994).
Database EMBL [Online]. "*Staphylococcus aureus* DNA, type-IV.1 (Iva) *Staphylococcal* cassette chromosome mec: strain CA05 (JCSC1968)", retrieved from EBI accession No. AB063172 (Nov. 21, 2001).
De Lencastre, et al. Methicillin-resistant *Staphylococcus aureus* disease in a Portuguese Hospital: Characterization of clonal types by a combination of DNA typing methods. Eur. J. Clin. Microbiol. Infect. Dis. 13(1): 64-73 (1994).
Denis et al., "Rapid screening of methicillin resistant *Staphylococcus aureus* carriers by direct PCR on enrichment broth culture of superficial swab samples," Abstracts of the Interscience Conference on Antimicrobial Agents and Chemotherapy, (2002) vol. 42, Abs. K-101, pp. 304; 42nd Interscience Conference on Antimicrobial Agents and Chemotherapy. San Diego, CA, USA. Sep. 27-30, 2002. American Society for Microbiology.
Deplano, et al. "In Vivo deletion of the methicillin resistance mec region from the chromosome of *Staphylococcus aureus* strains." J. Antimicrob. Chemother., 46-617-619 (2000).
Derbise, et al. "Mapping the regions carrying the three contiguous antibiotic resistance genes aadE, sat4, and aphA-3 in the genomes of *Staphylococci*." Antimicro. Agen. Chemother. 41(5): 1024-32 (1997).
De San et al., Controlled Evaluation of the IDI-MRSA Assay for Detection of Colonization by Methicillin-Resistant *Staphylococcus aureus* in Diverse Mucocutaneous Specimens, J Clin Microbiol. (2007) 45(4): 1098-1101.
Desbouchages et al., "Direct screening of MRSA from swab specimens using duplex real-time PCR assay: implication for antibiotic prophylaxis," International Journal of Antimicrobial Agents, (2004) vol. 24 (212/47O, pp. S104-S105; 6th European Congress of Chemotherapy and Infection/24th Interdisciplinary Meeting on Anti-Infectious Chemotherapy. Paris, France. Dec. 1-3, 2004.
Desjardins et al., "Evaluation of the IDI-MRSA Assay for Detection of Methicillin-Resistant *Staphylococcus aureus* from Nasal and Rectal Specimens Pooled in a Selective Broth", J Clin Microbiol. (Apr. 2006) 44(4): 1219-1223.
Dieffenbach et al. "PCR Primer: A Laboratory Manual", 1995, Cold Spring Harbor Laboratory Press (Cover & Contents pages only).
Dieffenbach et al. "General Concepts for PCR Primer Design." Genome Res. 3: S30-S37 (1993).
Domann et al. "Schneller and zuverlaessiger Nachweis multiresistenter multiplex-PCR." Deutsche Medizinische Wochenschrift. 125(20): 613-618 (2000). w/EN Abstract.
Donnio et al., "Partial Excision of the Chromosomal Cassette Containing the Methicillin Resistance Determinant Results in Methicillin-Susceptible *Staphylococcus aureus*", J Clin Microbiol. (Aug. 2005) 43(8): 4191-4193.
Dubin, et al. "Physical mapping of the mec region of an American methicillin-resistant *Staphylococcus aureus* strain." Antimicrob. Agents Chemother. 35(8):1661-65 (1991).
Edwards et al., "Multiplex PCR: advantages, development, and applications", Genome Res. (1994) 3: S65-75.
Egholm,et al. "PNA hybridizes to complementary oligonucleotides obeying the Watson-Crick hydrogen-bonding rules." Nature. 365: 566-568 (1993).
Elghanian et al. "Selective Colorimetric Detection of Polynucleotides Based on the Distance-Dependent Optical Properties of Gold Nanoparticles." (1997) Science 277:1078-1081.
Elsayed et al., "Development and Validation of a Molecular Beacon Probe-Based Real-Time Polymerase Chain Reaction Assay for Rapid Detection of Methicillin Resistance in *Staphylococcus aureus*", Arch Pathol Lab Med. (Jul. 2003) 127(7): 845-849.
Fan et al., "Rapid detection of methicillin-resistant *Staphylococci* by DNA probe," Linchuang Jianyan Zazhi 24(5) 351-352 (2006).
Fang et al. "Rapid Screening and Identification of Methicillin-Resistant *Staphylococcus aureus* from Clinical Samples by Selective-Broth and Real-Time PCR Assay." (Jul. 2003) 41(7): 2894-2899 and 1 page Erratum.
Flores, et. al. "A rapid, inexpensive method for eluting DNA from Agarose or Acrylamide gel slices without using toxic or chaotropic materials." Biotechniques. 13(2): 205-206 (1992).
Francois et al., "Evaluation of Three Molecular Assays for Rapid Identification of Methicillin-Resistant *Staphylococcus aureus*", J Clin Microbiol. (2007) 45(6): 2011-2013.
García-Álvarez et al. "Meticillin-resistant *Staphylococcus aureus* with a novel mecA homologue in human and bovine populations in the UK and Denmark: a descriptive study," Lancet Infect Dis. (Aug. 2011) 11(8): 595-603.
GenBank accession No. D86934.1, "*Staphylococcus aureus* genes, mec region, partial and complete cds.", Jul. 3, 1999; pp. 25.
GenBank accession No. X53818.1, "*Staphylococcus aureus* IS431mec gene associated with methilicillin resistance", Oct. 23, 2008.
Gerberding, et al. Comparison of conventional susceptibility tests with direct detection of penicillin-binding protein 2a in borderline oxacillin-resistant strains of *Staphylococcus aureus*. Antimicrob. Agents Chemother. 35(12):2574-79 (1991).
Goldmeyer et al., "Identification of *Staphylococcus aureus* and Determination of Methicillin Resistance Directly from Positive Blood Cultures by Isothermal Amplification and a Disposable Detection Device," J. Clin. Microbiol. (2008) vol. 46 No. 4, 1534-1536.
Grisold et al., "Detection of Methicillin-Resistant *Staphylococcus aureus* and Simultaneous Confirmation by Automated Nucleic Acid Extraction and Real-Time PCR," J Clin. Microbiol. (2002) 40(7):2392-2397.
Grisold et al., "Use of hybridization probes in a real-time PCR assay on the LightCycler® for the detection of methicillin-resistant *Staphylococcus aureus*", Methods Mol. Biol. (2006) 345:79-89.
Gröbner et al., "Development of a real-time *Staphylococcus aureus* and MRSA (SAM-) PCR for routine blood culture," European Journal of Clinical Microbiology & Infectious Diseases (2007) (26)10:751-754.
Guatelli, et al. "Isotherma, in vitro amplification of nucleic acids by a multienzyme reaction modeled after retroviral replication." Proc. Natl. Acad. Sci. USA, 87:1874-1878 (1990).
Guintu et al., "Detection of MRSA Directly from Positive Blood Culture Bottles using MRSA Evigene (Advandx)," Abstracts of the Interscience Conference on Antimicrobial Agents and Chemotherapy, 45th Interscience Conference on Antimicrobial Agents and Chemotherapy. Washington, DC, USA.; Abs. D-1716; (2005) vol. 45, pp. 151.
Hanaki et al., Loop-mediated isothermal amplification assays for identification of antiseptic- and methicillin-resistant *Staphylococcus aureus*, J Microbiol Meth. (2011) 84(2): 251-254; Epub Dec. 16, 2010.
Hagen, et al. "Development of a real-time PCR assay for rapid identification of methicillin-resistant *Staphylococcus aureus* from clinical samples." International Journal of Medical Microbiology, Urban and Fischer, DE. 295(2):77-86 (2005).
Hanssen et al., "Local Variants of *Staphylococcal* Cassette Chromosome mec in Sporadic Methicillin-Resistant *Staphylococcus aureus* and Methicillin-Resistant Coagulase-Negative *Staphylococci*: Evidence of Horizontal Gene Transfer?" Antimicrob Agents Chemothera., 48(1): 285-296 (Jan. 2004).

(56) References Cited

OTHER PUBLICATIONS

Hanssen et al., Mini Review "SCCmecin staphylococci: genes on the move." FEMS Immunol Med Microbiol., 46: 8-20 (Sep. 2005).
He et al., "Identification of *Staphylococcus aureus* and detection of its multiple-resistant genes by multiplex PCR," Linchuang Jianyan Zazhi (2004) 22(4): 249-251.
Hiramatsu, et al. "Molecular cloning and nucleotide sequence determination of the regulator region of mecA gene in methicillin-resistant *Staphylococcus aureus*." FEBS. 298(2.3):133-36 (1992).
Hiramatsu et al. "Analysis of borderline-resistant strains of methicillin-resistant *Staphylococcus aureus* using polymerase chain reaction," Microbiol Immunol. (1992) 36(5): 445-453.
Hiramatsu, et al. "Genetic basis for molecular epidemiology of MRSA." J Infect Chemother. 2:117-129 (1996).
Hiramatsu, et al. "The emergence and evolution of methicillin-resistant *Staphylococcus aureu*." Trends in Microbiology. 9(10): 486-493 (2001).
Hiramatsu et al. "*Staphylococcus aureus* DNA, type-IV.1 (IV a) *Staphylococcal* cassette chromosome mec: strain CA05 (JCSC1968)." GenBank accession No. AB063172, version AB063172.2, Jun. 12, 2001.
Holden et al. "*Staphylococcus aureus* subsp. Aureus strain MRSA252, complete genome." GenBank accession No. BX571856, version BX571856.1, Jun. 23, 2004.
Holden, et al. "Complete genomes of two clinical *Staphylococcus aureus* strains: Evidence for the rapid evolution of virulence and drug resistance." PNAS. 101(26):9786-9791 (2004).
Hope et al., "A PCR method for the identification of methicillin-resistant *Staphylococcus aureus* (MRSA) from screening swabs," Pathology (2004) 36(3):265-268.
Hougardy et al., "Direct and fast detection of methicillin resistant *Staphylococcus aureus* carriage by automated nucleic acid extraction and real time PCR" [English Abstract Only], Pathologie-Biologie, (Oct.-Nov. 2006) vol. 54, No. 8-9, pp. 477-481. Electronic Publication Date: Oct. 5, 2006.
Huletsky, et al. "New real-time PCR assay for rapid detection of methicillin-resistant *Staphylococcus aureus* directly from specimens containing a mixture of *Staphylococci*." J. Clin. Microbio. 42(5): 1875-84 (May 2004) XP003003502.
Huletsky, et al. "Identification of Methicillin-Resistant *Staphylococcus aureus* Carriage in Less than 1 Hour during a Hospital Surveillance Program." Clin. Infect. Dis. (Apr. 2005) 40: 976-981.
Huletsky, A.—Declaration in Reexamination of U.S. Pat. No. 7,449,289 dated Jul. 30, 2011; pp. 3.
Inglis, et al. "Induced deletions within a cluster of resistance genes in the mec region of the chromosome of *Staphylococcus aureus*." Gen. Microbiol. 136(11):2231-2239 (1990).
Inglis, et al. "Methicillin-sensitive and -resistant homologues of *Staphylococcus aureus* occur together among clinical isolates." J. Infect. Dis. 167(2):323-328 (1993).
Innis et al Eds. PCR Protocols, A Guide to Methods and Applications, Academic Press (1990) Table of Contents.
Ito, et al. "Acquisition of methicillin resistance and progression of multiantibiotic resistance in methicillin-resistant *Staphylococcus aureus*." Yonsei Med. J. 39(6):526-33 (1998).
Ito et al. "*Staphylococcus aureus* genes for orf1, orfX, orf2, orf3, partial and complete cds." GenBank accession No. AB014440, version AB014440.1, Jun. 6, 1999, 2 pages.
Ito et al. "Cloning and nucleotide sequence determination of the entire mec DNA of pre-methicillin-resistant *Staphylococcus aureus* N315." Antimicrob. Agents Chemother. 43(6):1449-1458 (1999).
Ito et al. "*Staphylococcus aureus* DNA, 3' flanking region of mecDNA, strain 61/6219." GenBank accession No. AB014433, Jan. 7, 2000—Abstract only.
Ito et al. "*Staphylococcus aureus* DNA, 3' flanking region of mecDNA, strain 64/4176." GenBank accession No. AB014434, Jan. 7, 2000—Abstract only.
Ito et al. "Structural comparison of three types of *Staphylococcal* cassette chromosome mec integrated in the chromsome in methicillin-resistant *Staphylococcus aureus*." Antimicrob. Agents Chemother. 45(5):1323-1336 (2001).
Ito et al. "*Staphylococcus aureus* DNA, type III *Staphylococcal* cassette chromosome mec, strain 85/2082." GenBank accession No. AB037671, version AB037671.1, May 14, 2001.
GenBank accession No. AB037671, "*Staphylococcus aureus* DNA, type-III *Staphylococcal* cassette chromosome mec and SCCmercury: strain 85/2082", May 12, 2000, pp. 30.
Blast Sequence-Alignment 1 between AB037671 (strain 85/2082) and SEQ ID No. 42, printed on Apr. 1, 2011, pp. 2.
Sequence Alignment 3 printed on Mar. 31, 2011 aligning the Nucleotide Sequence of *Staphylococcal aureas* strains 85/2082, HDG2, and N315(D86934) downstream of mecA, pp. 23.
Ito et al. GenBank accession No. AB121219, version AB121219.1, Sep. 26, 2003.
Ito et al. "Novel type V *Staphylococcal* cassette chromosome mec driven by a novel cassette chromosome recombinase, ccrC." Antimicrob. Agents Chemother. 48(7):2637-2651 (2004).
Jayaratne et al., "DNA-based detection of methicillin-resistant *Staphylococcus aureus* (MRSA) from nosocomial screening: Comparison with culture and cost-benefit analysis," Abstracts of the Interscience Conference on Antimicrobial Agents and Chemotherapy, 38th Interscience Conference on Antimicrobial Agents and Chemotherapy. San Diego, California, USA. Sep. 24-27, 1998. American Society for Microbiology (1998) vol. 38, Abs. D-56; pp. 144-145.
Jiang et al., "Review on Progress of *Staphylococcus aureus* by PCR", Shipin Kexue (Beijing, China) (2006), 27(5): 265-269. [English Abstract].
Jonas et al., "Evaluation of the mecA femB duplex polymerase chain reaction for detection of methicillin-resistant *Staphylococcus aureus*," Eur J Clin Microbiol Infect Dis. (1999) 18(9):643-647.
Jonas et al., "Rapid PCR-based identification of methicillin-resistant *Staphylococcus aureus* from screening swabs," J Clin. Microbiol. (2002) 40(5):1821-1823.
Jovanic et al., "Rapid detection of methicillin-resistant *Staphylococcus aureus* by real-time PCR from clinical specimens", International Journal of Antimicrobial Agents, Abs P907; (Mar. 2007) 29(Suppl. 2): S235-S236.
Kang et al., "The enhancement of PCR amplification of a random sequence DNA library by DMSO and betaine: application to in vitro combinatorial selection of aptamers", J Biochem Biophys Methods. (Aug. 2005) 64(2):147-51.
Katayama, et al. "A new class of genetic element, *Staphylococcus* cassette chromosome mec, encodes methicillin resistance in *Staphylococcus aureus*." Antimicrob. Agents Chemother. 44(6):1549-1555 (2000).
Kearns et al., "Rapid detection of methicillin-resistant *Staphylococci* by multiplex PCR." Journal of Hospital Infection. 43(1):33-37 (1999).
Kellogg, et al. "TaqStart Antibody™: "Hot Start" PCR facilitated by a neutralizing monoclonal antibody directed against Taq DNA Polymerase." Biotechniques. 16:1134-1137 (1994).
Kimmel, et al. "Preparations of cDNA and the generation of cDNA libraries: Overview." Meth Enzymol. 152:307-316 (1987).
Kimmerly et al. "*Staphylococcus epidermidis* strains SR1 clone step. 1043h05 genomic sequence." GenBank accession No. AF270046, version AF270046.1, Aug. 1, 2000.
Kitagawa, et al. "Rapid diagnosis of methicillin-resistant *Staphylococcus aureus* bacteremia by nested polymerase chain reaction." Annals of Surgery. 224(5):665-71 (1996).
Kloos et al., "Updated on clinical significance of coagulase-negative *Staphylococci*", Clin. Microbiol. Rev. (1994) 7(1):117-40.
Klotz et al., "Detection of *Staphylococcus aureus* Enterotoxins A to D by Real-Time Fluorescence PCR Assay," J Clin Microbiol. (2003) 41(10): 4683-4687.
Kluytmans, et al. "Food-initiated outbreak of methicillin-resistant *Staphylococcus aureus* analyzed by Pheno- and Genotyping." J. Clin. Microbio. 33(5):1121-28 (1995).

(56) References Cited

OTHER PUBLICATIONS

Kobayashi et al., "Genomic diversity of mec regulator genes in methicillin-resistant *Staphylococcus aureus* and *Staphylococcus epidermidis*", Epidemiol Infect. (1996) 117(2): 289-295.
Kobayashi et al., "Analysis on distribution of insertion sequence IS431 *in clinical isolates of staphylococci*", Diag. Micro. Infect. Dis. (2001) 39: 61-64.
Kobayashi et al., "Detection of mecA, femA, and femB genes in clinical strains of *Staphylococci* using polymerase chain reaction," Epidemiol Infect. (1994) 113(2):259-266.
Koshkin, et al. "LNA (locked nucleic acids): Synthesis of the adenine, cytosine, guanine, 5-methylcytosine, thymine and uracil bicyclonucleoside monomers, oligomerisation, and unprecedented nucleic acid recognition." Tetrahedron. 54:3607-3630 (1998).
Kovacevic et al., "Secretion of *Staphylococcal* nuclease by Bacillus subtilis", J. Bacteriol. (1985), 162(2):521-8.
Kowalski et al., "Evaluation of the SmartCycler II System for Real-Time Detection of Viruses and *Chlamydia*from Ocular Specimens", Arch Ophthalmol. (Aug. 2006) 124: 1135-1139.
Kuroda, et al. "Whole genome sequencing of meticillin-resistant *Staphylococcus aureus*." The Lancet. 357(9264): 1225-1240 (2001).
Kwoh, et al. "Transcription-based amplification system and detection of amplified human immunodeficiency virus type 1 with a bead-based sandwich hybridization format." Proc. Natl. Acad. Sci. USA 86: 1173-1177 (1989).
Landegren, et al. "A ligase-mediated gene detection technique." Science 241:1077-1080 (1988).
Lawrence et al. "Consecutive isolation of homologous strains of methicillin-resistant and methicillin-susceptible *Staphylococcus aureus* from a hospitalized child." J. Hosp. Infect. 33:49-53 (1996).
Lawrence, et al. "Use of the coagulase gene typing method for detection of carriers of methicillin-resistant *Staphylococcus aureus*." J. Antimicro. Chemo. 37:687-96 (1996).
Leach et al. "Theoretical investigations of novel nucleic acid bases." J. Am. Chem. Soc. 114:3675-3683 (1992).
Lee et al., "Detection of MecA gene in clinical isolates of *Staphylococcus aureus* by multiplex-PCR, and antimicrobial susceptibility of MRSA," Journal of Microbiology and Biotechnology 13(3) 354-359 (2003).
Lee et al., "Nucleic Acid Amplification Technologies: Application to Disease Diagnosis", 1997, Eaton Publishing (Cover pages Only).
Lem et al., "Direct detection of mecA, nuc and 16S rRNA genes in BacT/Alert blood culture bottles," Diagn Microbiol Infect Dis. 41(3):165-168 (2001).
Levenson, Deborah, "The Path to Better MRSA Control", Clin Lab News. (Aug. 2007) 33(8): 6 pages.
Levi et al., "Evaluation of an Isothermal Signal Amplification Method for Rapid Detection of Methicillin-Resistant *Staphylococcus aureus* from Patient-Screening Swabs", J Clin Microbiol. (Jul. 2003) 41(7): 3187-3191.
Levi et al., "Detection of methicillin-resistant *Staphylococcus aureus* (MRSA) in blood with the EVIGENE MRSA detection kit", J. Clin. Microbiol. (2003) 41(8):3890-2.
Lewin, "Genes IV", 1990, John Wiley & Sons, Chapter 3, Genes are Mutable Units, pp. 41-56.
Li et al., "Typing SCCmec Gene of Methicillin-Resistant *Staphylococcus aureus* by Novel Multiplex PCR Method," Journal of Modern Laboratory Medicine (2008) 23(1): 32-35. [English Abstract].
Liao et al., "Blinded comparison of repetitive-sequence PCR and multilocus sequence typing for genotyping methicillin-resistant *Staphylococcus aureus* isolates from a children's hospital in St. Louis, Missouri", J Clin Microbiol. (Jun. 2006) 44(6): 2254-2257.
Lin, et al. "Sequence analysis and molecular characterization of genes required for the biosynthesis of type 1 capsular polysaccharide in *Staphylococcus aureus*." J. Bacter. 176(22):7005-16 (1994).
Lin et al. "*Staphylococcus aureus* M type 1 capsular polysaccharide biosynthesis gene cluster, complete sequence and unknown genes." GenBank accession No. U10927, version U10927.2, Nov. 1, 2001.
Lizardi et al., "Exponential Amplification of Recombinant-RNA Hybridization Probes," BioTech. (Oct. 1988) 6: 1197-1202.
Lomell et al. "Quantitative assays based on the use of replicatable hybridization probes." Clin. Chem. 35(9):1826-1831 (1989).
Louahabi et al., "Screening of methicillin-resistant *Staphylococcus aureus* directly from clinical specimens by real-time PCR," International Journal of Antimicrobial Agents, (Dec. 2004) vol. 24S, Abstract 365/79P, pp. S130. Meeting Info.: 6th European Congress of Chemotherapy and Infection/24th Interdisciplinary Meeting on Anti-Infectious Chemotherapy. Paris, France. Dec. 1-3, 2004.
Louie et al., "Rapid Detection of Methicillin-Resistant *Staphylococci* from Blood Culture Bottles by Using a Multiplex PCR Assay," J Clin Microbiol. 40(8):2786-2790 (2002).
Lu et al., "One tube multiplex PCR for simple screening of SCCmec I-V types of methicillin-resistant *Staphylococcus aureus*", J Chemother. (Dec. 2008) 20(6): 690-696.
Luchansky et al. "Isolation of transposon Tn551 insertions near chromosomal markers of interest in *Staphylococcus aureus*." J. Bacter. 159(3):894-99 (1984).
Luijendijk, et al. "Comparison of five tests for identification of *Staphylococcus aureus* clinical samples." J. Clin. Microbio. 34(9):2267-69 (1996).
Luong, et al. "Type I capsule genes of *Staphylococcus aureus* are carried in a *Staphyloccal* cassette chromosome genetic element." J Bacter. 184(13):3623-3629 (2002).
Ma et al. "*Staphylococcus aureus* DNA, type-IV.2 (Ivb) *Staphylococcal* cassette chromosome mec: strain JCSC1978 (8/6-3P)", EBI GenBank accession No. AB063173, Nov. 21, 2001.
Ma et al. "Novel type of *Staphylococcal* cassette chromosome mec identified in community-acquired methicillin-resistant *Staphylococcus aureus* strains." Antimicrob. Agents Chemother. 46(4):1147-1152 (2002).
Maes et al., "Evaluation of a triplex PCR assay to discriminate *Staphylococcus aureus* from coagulase-negative *Staphylococci* and determine methicillin resistance from blood cultures", J. Clin. Microbiol. (2002) 40(4):1514-7.
Mantsch et al. "Structural and enzymatic properties of adenine 1-oxide nucleotides." Biochem. 14(26):5593-5601 (1975).
Marin et al., "Molecular Diagnosis of Infective Endocarditis by Real-Time Broad-Range Polymerase Chain Reaction (PCR) and Sequencing Directly From Heart Valve Tissue," Medicine (2007) 86(4) 195-202.
Martineau et al., "Species-Specific and Ubiquitous-DNA-Based Assays for Rapid Identification of *Staphylococcus aureus*," J Clin Microb. (Mar. 1998) 36(3): 618-623.
Martineau, et. al. "Correlation between the resistance genotype determined by multiplex PCR assays and the antibiotic susceptibility patterns of *Staphylococcus aureus* and *Staphylococcus epidermidis*." Antimicrob. Chemotherapy. 44(2): 231-238 (2000).
Mason et al., "Multiplex PCR Protocol for the Daignosis of *Staphylococcal* Infection," J Clin Microbiol. 39(9): 3332-3338 (2001).
McBride et al., "Quantitative PCR Technology" in *Gene Quantification*, The Immune Response Corporation, Francois Ferre (Ed.), Birkhaeuser Boston (1998) pp. 97-110.
McDonald et al., "Development of a triplex real-time PCR assay for detection of Panton-Valentine leukocidin toxin genes in clinical isolates of methicillin-resistant *Staphylococcus aureus*", J. Clin. Microbiol. (Dec. 2005) 43(12):6147-9.
Menon et al., "Comparison of rapid method of DNA extraction using microwave irradiation with conventional phenol chloroform technique for use in multiplex PCR for mec A and fem B genes to identify genotypes of MRSA from cultures," Medical Journal Armed Forces India, (2001) 57(3): 194-196.
Merlino et al., "Detection and expression of methicillin/oxacillin resistance in multidrug-resistant and non-multidrug-resistant *Staphylococcus aureus* in Central Sydney, Australia," J Antimicrob Chemother. (2002) 49: 793-801.
Mongkolrattanothai et al. "TPA exp: *Staphylococcus epidermidis* ATCC 12228 composite island SCCpbp4 region." GenBank accession No. BK001539, version BK001539.1, Aug. 15, 2003.
Mongkolrattanothai et al. "Novel Non-mecA-Containing *Staphylococcal* Chromosomal Cassette Composite Island Containing pbp4 and tagF Genes in a Commensal *Staphylococcal* Species: A Possible Reservoir for Antibiotic Resistance Islands in *Staphylococcus aureus*." Antimicrob. Agents Chemother. (May 2004) 48(5): 1823-1836.

(56) References Cited

OTHER PUBLICATIONS

Mulligan, et al. "Methicillin-resistant *Staphylococcus aureus*: A consensus review of the microbiology, pathogenesis, and epidemiology with implications for prevention and management." Am J Med. 94(3):313-28 (1993). (Abstract Only).
Murakami, et al. "Identification of methicillin-resistant strains of *Staphylococci* by polymerase chain reaction." J. Clin Microbiol. 29(10):2240-2244 (1991).
Muraki, et al. Detection of methicillin-resistant *Staphylococcus aureus* using PCR and non-radioactive DNA probes (II). Rinsho Byori. 41(10): 1159-66 (1993).
Murray et al., Manual of Clinical Microbiology, 8th Ed., ASM Press (2003) [Content pages only].
Narang et al. "Improved Phosphotriester Method for the Synthesis of Gene Fragments," Meth Enzymol. (1979) 68: 90-98.
NCBI BLAST Sequence Alignment 1 between AB037671 (strain 85/2082) and SEQ ID No. 42, printed on Apr. 1, 2011.
NCBI BLAST 2 Sequence—AF411934.1—*Staphylococcus aureus* strain HDG2 genomic sequence downstream of mecA, printed on Mar. 16, 2012, pp. 2.
NCBI BLAST 2 Sequences downloaded Aug. 13, 2013 from http://blast.ncbi.nlm.nih.gov/Blast.cgi, 4 pages.
NCBI BLAST AX720590: Sequence 167 from Patent WO02099034; [D16—Exhibit in European Opposition Proceeding: EP 2 322 655] downloaded on Aug. 21, 2015; 57 pages.
Newton et al. "Instrumentation, Reagents and Consumables." PCR, 2nd Ed., Springer-Verlag (New York: 1997), Chapter 2, p. 8-28.
Nichols, et al. "A universal nucleoside for use at ambiguous sites in DNA primers." Nature. 369:492-493 (1994).
Niemeyer et al., "Rapid DNA extraction for direct PCR identification of methicillin resistant *Staphylococci* in clinical samples," Abstracts of the General Meeting of the American Society for Microbiology, (1998) vol. 98, Abs. C-419, pp. 201; 98th General Meeting of the American Society for Microbiology. Atlanta, Georgia, USA. May 17-21, 1998. American Society for Microbiology.
Ohno, Akira, Japan Medical Journal (2001) 4051: 19-24.
Okuma et al., "Dissemination of new methicillin-resistant *Staphylococcus aureus* clones in the community." J Clin Microbio., 40(11): 4289-4294 (Nov. 2002).
Oliveira et al. "Genetic organization of the downstream region of the mecA element in methicillin-resistant *Staphylococcus aureus* isolates carrying different polymorphisms of this region." Antimicrob. Agents Chemother. 44(7):1906-1910 (2000).
Oliveira et al. "The evolution of pandemic clones of methicillin-resistant *Staphylococcus aureus*: Identification of two ancestral genetic backgrounds and the associated mec elements." Microb. Drug Resist. 7(4):349-361 (2001).
Oliveira, et al. "Multiplex PCR strategy for rapid identification of structural types and variants of the mec element in methicillin-resistant *Staphylococcus aureu*." Antimicrob. Agents Chemother. 46:2155-2161 (2002).
Oliveira et al. "Secrets of success of a human pathogen: molecular evolution of pandemic clones of meticillin-resistant *Staphylococcus aureus*." Lancet Infect Dis. 2:180-9 (2002).
Oliveira et al. "*Staphylococcus aureus* staphylococcal cassette chromosome mec type III sequence; and putative transposase gene, partial cds." GenBank Accession Version No. AF422691, Apr. 29, 2002, pp. 2. (Abstract Only).
Oliveira et al. "*Staphylococcus aureus* strain HDG2 genomic sequence downstream of mecA." GenBank Accession Version No. AF411934, Mar. 5, 2002, pp. 2. (Abstract Only).
Alignment of SEQ ID Nos. 42-46 and 51 with HDG2 sequence; GenBank Accession Version No. AF411934; Exhibit D9a in European Opposition of Patent No. 1397510, issued Mar. 17, 2004; pp. 10.
Oliveira et al. "*Staphylococcus aureus* strain HDE288 type-VI SCCmec element, complete sequence" GenBank Accession Version No. AF411935, Mar. 5, 2002, pp. 8.
Oliveira et al. "*Staphylococcus aureus* strain PL72 genomic sequence upstream of mecA" GenBank Accession Version No. AF411936, Mar. 5, 2002, pp. 3.
Oliveira et al., "Redefining a structural variant of *Staphylococcal* cassette chromosome mec, SCCmec type VI", Antimicrob. Agents Chemother. (Oct. 2006) 50(10):3457-9.
Oliveira, D.—Email re Sequence Question with Hema Pande, Beckman Coulter, Inc. (Jul. 2010).
Oliveira, D—Declaration in Opposition to EP Patent 1397510 dated Nov. 29, 2012; pp. 2.
Pattee, et al. "Genetic and physical mapping of the chromosome of *Staphylococcus aureus*." Molecular Biology of the *Staphylococci*. VCH Publishers.pp. 41-58 (1990).
Perez-Roth et al., "Multiplex PCR for Simultaneous Identification of *Staphylococcus aureus* and Detection of Methicillin and Mupirocin Resistance," J Clin Microbiol. 39(11):4037-4041 (2001).
Persing et al., Diagnostic Molecular Microbiology: Principles and Applications, American Society for Microbiology, Washington, D.C. (1993), Contents pages only.
Piccirilli et al. "Enzymatic incorporation of a new base pair into DNA and RNA extends the genetic alphabet." Nature. 343:33-37 (1990).
Podzorski et al., Evaluation of the MVPlex Assay for Direct and Rapid Detection of Methicillin-Resistant *Staphylcoccus aureus* from Nares and Other Swab Speciments, (Abstract C-237), American Society for Microbiology 107$^{th}$ Meeting, Toronto, Canada May 21-25, 2007, p. 186.
Podzorski et al., MVPlex Assay for Direct Detection of Methicillin-Resistant *Staphylococcus aureus* in Naris and Other Swab Specimens, J Clin Microbiol. (Sep. 2008) 46(9): 3107-3109.
Poulsen et al., "Detection of methicillin resistance in coagulase-negative *Staphylococci* and in *Staphylococci* directly from simulated blood cultures using the EVIGENE MRSA Detection Kit", J. Antimicrob. Chemother. (2003) 51(2):419-21.
Ralser et al., "An efficient and economic enhancer mix for PCR", Biochem. Biophys. Res. Communi. (Sep. 2006) 347(3):747-51.
Ramos-Trujillo et al., Multiplex PCR for simultaneous detection of enterococcal genes vanA and vanB and *Staphylococcal* genes mecA, ileS-2 and femB, Int Microbiol. (2003) 6(2):113-115.
Random House Unabridged Dictionary, (1993) Definition of "extremity", p. 686.
Reischl et al., "Rapid identification of methicillin-resistant *Staphylococcus aureus* and simultaneous species confirmation using real-time fluorescence PCR," J Clin. Microbiol. (2000) 38:2429-2433.
Ruiz-Pérez de Pipaón et al., "Detection of methicillin resistance and identification of *Staphylococcus* spp. from positive blood culture bottles using the mecA and nucA genes with the LightCycler System", Enfermedades infecciosas y microbiologia clinica (2005) vol. 23, No. 4, pp. 208-212.
Rupp et al., "Be Aware of the Possibility of False-Positive Results in Single-Locus PCR Assays for Methicillin-Resistant *Staphylococcus aureus*", (Jun. 2006) 44(6): 2317-8.
Rushdy et al., "Detection of methicillin/oxacillin resistant *Staphylococcus aureus* isolated from some clinical hospitals in Cairo using Meca/Nuc genes and antibiotic susceptibility profile," Internaitonal Journal of Agriculture and Biology (2007) 9(6):800-806.
Sabat et al., "Comparison of PCR-based methods for typing *Stapholococcus aureus* isolates," J Clin Micrbiol. 44(10) 3804-3807 (2006).
Sabet et al., "Simultaneous species identification and detection of methicillin resistance in *Staphylococci* using triplex real-time PCR assay", Diagn Microbiol Infect Dis. Sep. 2006;56(1):13-8. Epub May 2, 2006.
Saiful et al., "Detection of methicillin-resistant *Staphylococcus aureus* using mecA/nuc genes and antibiotic susceptibility profile of Malaysian clnical isolates," World J Microbiol Biotechnol. (2006) 22: 1289-1294 [online: Apr. 20, 2006].
Saiki et al., "Enzymatic amplification of beta-globin genomic sequences and restriction site analysis for diagnosis of sickle cell anemia," Science (Dec. 1985) 230(4732): 1350-1354.

(56) References Cited

OTHER PUBLICATIONS

Saito, et. al. "Immunological detection of penicillin-binding protein 2' of methicillin-resistant *Staphylococci* by using monoclonal antibodies prepared from synthetic peptides." J. Clin. Microbiol. 33(9): 2498-2500 (1995).
Sambrook et al., "Molecular Cloning: A Laboratory Manual", 1989 Cold Spring Harbor Laboratory Press (Cover & Contents pages only) & pp. 14.15-14.16.
Sanches et al., "Tracing the Origin of an Outbreak of Methicillin-Resistant *Staphylococcus aureus* Infections in a Portuguese Hospital by Molecular Fingerprinting Methods." Microbial Drug Resist. 2(3): 319-329 (1996).
Schuenck et al., "Improved and rapid detection of methicillin-resistant *Staphylococcus aureus* nasal carriage using selective broth and multiplex PCR", Res. Microbiol. (Sep. 2006) 157(10):971-5.
Seki et al., Amplification of long targets of approximately 50 kb from cloned cosmid inserts of *Arabidopsis thaliana*, DNA Research (Jul. 1996) 3: 107-108.
Sekiguchi et al., "Rapid and simple method for detecting qacA, mecA and femB in antiseptics- and methicillin-resistant *Staphylococcus aureus* by loop-mediated isothermal amplification," Abstracts of the General Meeting of the American Society for Microbiology, (2006) vol. 106, pp. 108; 106th General Meeting of the American Society for Microbiology. Orlando, FL, USA. May 21-25, 2006. Amer Soc Microbiol.
Shittu et al., "Molecular identification and characterization of mannitol-negative methicillin-resistant *Staphylococcus aureus*", Diagn. Microbiol. Infect Dis. (2007) 57(1):93-5.
Shore et al. "Characterization of a Novel Arginine Catabolic Mobile Element (ACME) and *Staphylococcal* Chromosomal Cassette mec Composite Island with Significant Homology to *Staphylococcus epidermidis* ACME Type II in Methicillin-Resistant *Staphylococcus aureus* Genotype ST22-MRSA-IV." Antimicrob Agents Chemother. (May 2011) 55(5): 1896-1905.
Simor, et al. "Characterization and proposed nomenclature of epidemic strains of methicillin-resistant *Staphylococcus aureus* in Canada." CCDR 25(12):105-112 (Jun. 1999).
Simor, et al. "Characterization and proposed nomenclature of epidemic strains of methicillin-resistant *Staphylococcus aureus* in Canada." Can J Infect Dis. Sep.-Oct. 1999; 10(5): 333-336.
Singh et al. "PCR Primer Design." Mol Biol Today 2(2): 27-32 (2001).
Singleton P., DNA Methods in Clinical Microbiology, (2000) Dordrecht, Boston: Kluwer Academic. TOC only.
Sinsimer et al., "Use of a Multiplex Molecular Beacon Platform for Rapid Detection of Methicillin and Vancomycin Resistance in *Staphylococcus aureus* ", J Clin Microbiol. (2005) 45(9): 4585-4591.
Sooknanan et al. NASBA. A detection and amplification system uniquely suited for RNA. (1995) Biotechnology 13:563-564.
Spiess et al. "Trehalose Is a Potent PCR Enhancer: Lowering of DNA Melting Temperature and Thermal Stabilization of Taq Polymerase by the Disaccharide Trehalose," Clin Chem., Jul. 2004, 50(7):1256-1259.
Stewart, et al. "IS257 and small plasmid insertions in the mec region of the chromosome of *Staphylococcus aureus*." Plasmid. 31:12-20 (1994).
Stratidis et al., Use of real-time polymerase chain reaction for identification of methicillin-resistant *Staphylococcus aureus* directly from positive blood culture bottles, Diagn Microbiol Infect Dis. (2007) 58(2): 199-202.
Suzuki, et al. "Survey of methicillin-resistant clinical strains of coagulase-negative *Staphylococci* for mecA gene distribution." Antimicrob. Agents Chemother. 36(2): 429-434 (1992).
Suzuki, et al. "Distribution of mec regulator genes in methicillin-resistant *Staphylococcus* clinical strains." Antimicro. Agents Chemother.. 37(6):1219-26 (1993).
Switzer et al. "Enzymatic Recognition of the Base Pair between Isocytidine and Isoguanosine." Biochemistry 32:10489-10496 (1993).
Tan et al., "Rapid identification of methicillin-resistant *Staphylococcus aureus* from positive blood cultures by real-time fluorescence PCR," Journal of Clinical Microbiology (2001) 39(12):4529-4531.
Tang et al., StaphPlex System for Rapid and Simultaneous Identification of Antibiotic Resistance Determinants and Panton-Valentine Leukocidin Detection of *Staphylococci* from Positive Blood Cultures, J Clin Microbiol. (Jun. 2007) 45(6): 1867-1873.
Taylor et al. GenBank accession No. AF270046, version AF270046.1, May 22, 2000.
Thelwell et al. "Mode of action and application of Scorpion primers to mutation detection." Nucl. Acids Res. 28(19):3752-3761 (2000).
Thomas et al., "Development of a real-time *Staphylococcus aureus* and MRSA (SAM-) PCR for routine blood culture," J Microbiol Methods (2007) 38(2):296-302 [Online: Oct. 12, 2006].
Tijssen, Laboratory Techniques in Biochemistry and Molecular Biology—Hybridization with Nucleic Acid Probes, (1993) Part I, Chapter 2, pp. 19-78 (Elsevier, New York).
Tokue, et al. "Comparison of a polymerase chain reaction assay and a conventional microbiologic method for detection of methicillin-resistant *Staphylococcus aureus*." Antimicro. Agents Chemother. 36(1):6-9 (1992).
Tor et al. "Site-specific enzymatic incorporation of an unnatural base, $N^6$-(6-Aminohexyl)isoguanosine, into RNA." J. Am. Chem. Soc. 115:4461-4467 (1993).
Towner et al., "Development and evaluation of a PCR-based immunoassay for the rapid detection of methicillin-resistant *Staphylococcus aureus*," J Med Microbiol (1998) 47(7):607-613.
Turbeville et al., "Amplification of the complete mitochondrial genome of two protostome worms: a useful technique for comparative studies of metazoan mitochondrial DNA", Mol Marine Bio Biotech., 6(2): 141-143 (1997).
Tyagi et al. "Molecular beacons: Probes that fluoresce upon hybridization." Nat. Biotech. 14:303-308 (1996).
Tyagi et al., "Molecular Beacons: Hybridization Probes for Detection of Nucleic Acids in Homogeneous Solutions," in *Nonradioactive Analysis of Biomolecules* (Part D); Springer Lab Manuals pp. 606-616; [Exh. D29]; 2000; 8 pages.
Ubukata, et al. "Restriction maps of the regions coding for methicillin and tobramycin resistances on chromosomal DNA in methicillin-resistant *Staphylococci*." Antimicrob. Agents Chemother. 33(9):1624-26 (1989).
Ubukata, et. al. "Homology of mecA gene in methicillin-resistant *Staphylococcus haemolyticus* and *Staphylococcus simulans* to that of *Staphylococcus aureus*." Antimicrob. Agents Chemother. 34(1):170-172 (1990).
Ubukata, et. al. "Rapid detection of the mecA gene in methicillin-resistant *Staphylococci* by enzymatic detection of polymerase chain reaction products. J. Clin. Microbiol." 30(7):1728-1733 (1992).
Ünal, et al. "Detection of methicillin-resistant *Staphylococci* by using the polymerase chain reaction." J Clin. Microbiol. 30(7):1685-91 (1992).
Ünal, et al. "Comparison of tests for detection of methicillin-resistant *Staphylococci aureus* in a clinical microbiology laboratory." Antimicrob. Agents Chemother. 38(2):345-47 (1994).
Van Belkum, et al. "Comparison of phage typing and DNA fingerprinting by polymerase chain reaction of discrimination of methicillin-resistant *Staphylococcus aureus* strains." J. Clin. Microbiol. 31(4):798-803 (1993).
Van Brunt, J. "Amplifying genes: PCR and its alternatives." Biotechnology, 8:291-294 (1990).
Van Hal et al., "Methicillin-Resistant *Staphylococcus aureus* (MRSA) Detection: Comparison of Two Molecular Methods (IDI-MRSA PCR Assay and GenoType MRSA Direct PCR Assay) with Three Selective MRSA Agars (MRSA ID, MRSASelect, and CHROMagar MRSA) for Use with Infection-Control Swabs", J Clin MIcrobiol. (Aug. 2007) 45(8): 2486-2490.
Van Leeuwen et al., "Genetic diversification of methicillin-resistant *Staphylococcus aureus* as a function of prolonged geographic dissemination and as measured by binary typing and other genotyping methods," Res Microbiol, 149: 497-507 (1998).

(56) References Cited

OTHER PUBLICATIONS

Vanguilder et al., "Twenty-five years of quantitative PCR for gene expression analysis", Biotechniques 25th Anniversary (2008) 44(5): 619-626.
Vannuffel, et al. "Specific detection of methicillin-resistant *Staphylococcus* species by multiplex PCR." J. Clin. Microbiol. 33(11):2864-67 (1995).
Wada, et al. "Southern hybridization analysis of the mecA deletion from methicillin-resistant *Staphylococcus aureus*." Biochem. Biophys. Res. Comm., 176(3):1319-1326 (1991).
Walker, et al., "Isothermal in vitro Amplification of DNA by a Restriction Enzyme/DNA Polymerase System," Proc Natl Acad Sci. USA, 89: 392-396 (Jan. 1992).
Walker et al., "Strand displacement amplification—an isothermal, in vitro DNA amplification technique," Nucl Acids Res. (1992) 20(7): 1691-1696.
Wallet, et al. "Choice of a routine method for detecting methicillin-resistance in *Staphylococci*." J. Antimicrob. Chemother. 37:901-909 (1996).
Wang at al., "Rapid detection of methicillin-resistant *Staphylococcus aureus* with duplex real-time PCR assay," Zhongguo Kangshengsu Zazhi (2007) 32(4) 225-228.
Warren et al., "Detection of Methicillin-Resistant *Staphylococcus aureus* Directly from Nasal Swab Specimens by a Real-Time PCR Assay", J Clin Microbiol. (Dec. 2004) 42(12): 5578-5581.
Watson et al., "Molecular Biology of the Gene", 1987, The Benjamin/Cummings Publishing Company (Cover pages only).
Wei et al., "Detection of *Staphylococcus* isolates and their multidrug resistance genes by multiple PCR," Zhongguo Renshou Gonghuanbing Zazhi (Sep. 2004) 20(9), 814.
Westin, et al. "Anchored multiplex amplification on a microelectronic chip array." Nat. Biotechnol. 18:199-204 (2000).
White, "Molecular Cloning to Genetic Engineering", in Methods in Molecular Biology Humana Press (1997) vol. 67, Contents pages only.
Wichelhaus et al., "Rapid molecular typing of methicillin-resistant *Staphylococcus aureus* by PCR-RFLP", Infect Cont Hosp Epidem. (May 2001) 22(5): 294-298.
Wilson et al., "Detection of enterotoxigenic *Staphylococcus aureus* in dried skimmed milk: use of the polymerase chain reaction for amplification and detection of *Staphylococcal* enterotoxin genes entB and entC1 and the thermonuclease gene nuc", Appl. Environ. Microbiol. (1991) 57:1793-8.
Wilson, et al. "Inhibition and facilitation of nucleic acid amplification." Appl. Environ. Microbiol. 63(10): 3741-3751 (1997).
Wisplinghoff et al., "Related clonges containing SCCmec type IV predominate among clinically significant *Staphylococcus epidermidis* Isolates." Antimicrob Agents Chemothera. 47(11): 3574-3579 (2003).
Wittwer et al., "Fluorescence Monitoring of Rapid Cycle PCR for Quantification" in Gene Quantification, The Immune Response Corporation, Francois Ferre (Ed.), Birkhaeuser Boston (1998) pp. 97-110.
Woron et al., "Multiplex rt-PCR detection of MRSA from bacterial isolates," Abstracts of the General Meeting of the American Society for Microbiology, (2004) vol. 104, ABS C-116, pp. 143; 104th General Meeting of the American Society for Microbiology. New Orleans, LA, USA.
Wren et al., "Rapid molecular detection of methillin-resistant *Staphylococcus aureus*," Journal of Clinical Microbiology (2006) 44(4):1604-1605.
Wu, et a. "The ligation amplification reaction (LAR)—Amplification of specific DNA sequences using sequential sounds of template-dependent ligation." Genomics 4:560-569 (1989).
Wu, et al. "Genetic organization of the mecA region in methicillin-susceptible and methicillin-resistant strains of *Staphylococcus sciuri*." J. Bacter. 180(2):236-42 (1998).
Wu et al., "Rapid detection of *Staphylococcus aureus* and methicillin resistance from blood cultures using a real-time PCR SmartCycler assay," Abstracts of the General Meeting of the American Society for Microbiology, 105th General Meeting of the American-Society-for-Microbiology. Atlanta, GA, USA; Abs. C-085; (2005) vol. 105, pp. 119.
Xue, et al. "*Staphylococcus aureus* DNA, type-V *Staphylococcal* cassette chromosome mec: strain JCSC3624." GenBank accession No. AB121219, Jan. 7, 2000—Abstract only.
Zhang, et al. "Genome-based analysis of virulence genes in a non-biofilm-forming *Staphylococcus epidermidis* strain (ATCC 12228)." Molecular Microbiology. 49(6): 1577-1593 (2003).
Zhang et al., "New quadriplex PCR assay for detection of methicillin and mupirocin resistance and simultaneous discrimination of *Staphylococcus aureus* from coagulase-negative *Staphylococci*", J. Clin. Microbiol. (2004) 42(11):4947-55.
Zhang et al., "Novel multiplex PCR assay for characterization and concomitant subtyping of *Staphylococcal* cassette chromosome mec types I to V in methicillin-resistant *Staphylococcus aureus*.", J. Clin. Microbiol. (Oct. 2005) 43(10): 5026-33.
Zhang et al., "Novel multiplex PCR assay for simultaneous identification of community-associated methicillin-resistant *Staphylococcus aureus* strains USA300 and USA400 and detection of mecA and Panton-Valentine leukocidin genes, with discrimination of *Staphylococcus aureus* from coagulase-negative *Staphylococci*", J Clin Microbiol. (Mar. 2008) 46(3): 1118-1122; Epub Dec. 26, 2007.
Electronic File History of Inter Partes Reexamination Control No. 95/001599, filed Apr. 8, 2011 containing Office Actions dated Apr. 19, 2011, Jun. 1, 2011, Dec. 29, 2011, and Jul. 18, 2012, Requestor submissions Apr. 8, 2011, Aug. 31, 2011, Apr. 5, 2012, Aug. 17, 2012, Oct. 17, 2012 and Dec. 21, 2012 and Applicant Responses filed Aug. 5, 2011, Feb. 29, 2012, Aug. 16, 2012, Oct. 17, 2012 and Nov. 21, 2012 as of Aug. 28, 2014.
Electronic File History [Part 2] Inter Partes Reexam Control No. 95/001599, filed Apr. 8, 2011 including Examiner's Answer Aug. 2, 2013, Rebuttal Brief of Sep. 3, 2013, and Third Party Request for Oral Hearing Oct. 1, 2013.
U.S. PTAB Record of Oral Hearing dated Jul. 16, 2014 in Inter Partes Reexam Control No. 95/001599 [Appeal No. 2014-002900]; 65 pages.
U.S. PTAB Decision on Appeal dated Aug. 28, 2014 in Inter Partes Reexam Control No. 95/001599 [Appeal No. 2014-002900]; 43 pages.
Requests for Rehearing and PTAB Decision for Requests dated Sep. 26, Sep. 29, 2014 and May 26, 2015 in Inter Partes Reexam Control No. 95/001599 [Appeal No. 2014-002900]; 45 pages.
U.S. PTAB Appeal's Decision dated Aug. 18, 2015 in Inter Partes Reexam Control No. 95/001599 [Appeal No. 2014-002900]; 12 pages.
D36—Exhibit in European Opposition Proceeding: Alignment of SEQ ID No. 18 from U.S. Appl. No. 11/248,438 and WO 2007/044873 With OrfX sequence from Ito et al., AB014440; 3 pages.
D37—Exhibit in European Opposition Proceeding: Alignment of SEQ ID No. 19 from U.S. Appl. No. 11/248,438 and WO 2007/044873 with orfX sequence from Ito et al., AB014440; 1 page.
D38—Exhibit in European Opposition Proceeding: Alignment of MREJ type xi (SEQ ID No. 17) and mrfj Type iii (SEQ ID No. 184 from WO 2002/099034 showing asserted binding sites of primers pair (SEQ ID Nos. 64/98) from WO 2002/099034; 3 pages.
D39—Exhibit in European Opposition Proceeding: Alignment of MREJ type xi (SEQ ID No. 17) and MREJ type iii (SEQ ID No. 184 From wo 2002/099034 showing asserted binding sites of primers (SEQ ID Nos. 1-5) from EP 1 529 847; 1 page.
Comparison of the nucleotide sequence of MRSA strain V14 (deposited under Accession No. AB425427) with the nucleotide sequence of SEQ ID No. 165 from the Patent. Primer binding sites for some of the primers claimed in claim 4 of the EP2236621 [D12] cited on May 8, 2013; pp. 1-7.
Nucleotide Sequence of MRSA strain M08/1026 ACME/SCCmecCI of ST22-MRSA-Ivh deposited in Genbank Accession No. FR753166 with orfX and SCCmec portions of Seq ID No. 165 highlighted thereon. Also shown are primers binding sites for the primers of SEQ ID Nos. 64 and 112 from claim 5 of the EP2236621 [D14] cited on May 8, 2013; pp. 1-16.
ClustalW2 Multiple nucleotide sequence alignment (generated using ClustalW2). The sequence of each of MREJ types I to xx (excluding

(56) References Cited

OTHER PUBLICATIONS type x) is aligned around the integratioin site. The sequence of the rjmec primer from D7 is also included; [D9] cited on May 8, 2013; p. 1.
Nucleotide Sequence alignment of SEQ ID No. 165 of EP2236621 [D17] with *Staphylococcus epidermidis* strain ATCC 12228 (Accession No. AE015929.1) cited on May 8, 2013; p. 1.
Blast Sequence-Alignment between the orfX sequence from *Staphyloccocus aureus* and the equivalent *Staphylococcus epidermidis* sequence taken from a nukber of strains; [D19] cited on May 8, 2013; pp. 1-6.
SEQ ID No. 6—Figure 19 of D1 and D2. Primer biding sites for SEQ ID Nos. 64 and 98 from EP2236621 as underlined; [D22] cited on May 8, 2013; p. 1.
European Decision T 1496/11 of the Technical Boards of Appeal in re EP Patent No. 930979 [D28] of Sep. 12, 2012; pp. 1-28.
Annotated version of figure 4A of EP 2236621 cited on May 8, 2013; p. 1.
Sequence Alignment of SEQ ID No. 64 and SEQ ID No. 98 on SEQ ID No. 165 and SEQ ID No. 166 of EP2236621 [D31] cited on May 8, 2013; pp. 1-3.
Partial International Search Report dated May 12, 2003 for International Application No. PCT/CA 02/00824, filed Jun. 4, 2002.
International Search Report dated Sep. 24, 2003 for International Patent Application No. PCT/CA02/000824, filed Jun. 4, 2002.
International Search Report and Written Opinion dated Nov. 23, 2007 for International Patent Application No. PCT/US06/39996, filed Oct. 10, 2006.
International Preliminary Report on Patentability (Rule 44bis) dated Apr. 16, 2008 for International Patent Application No. PCT/US06/39996, filed Oct. 10, 2006.
Australian Office Action dated Jun. 6, 2011 for Australian Application No. 2006302044, filed Oct. 10, 2006.
Supplementary European Search Report dated Apr. 7, 2009 for European Application No. 06825875.5, filed Oct. 10, 2006.
Partial European Search Report dated Mar. 31, 2011 for European Patent Application No. 10016072.0, filed Oct. 10, 2006.
Extended European Search Report dated Aug. 10, 2011 for European Patent Application No. 10016072.0, filed Oct. 10, 2006.
Office Action dated Sep. 11, 2012 for European Patent Application No. 10016072.0, filed Oct. 10, 2006.
Partial European Search Report dated Mar. 31, 2011 for European Patent Application No. 10016073.8, filed Oct. 10, 2006.
Extended European Search Report dated Aug. 10, 2011 for European Patent Application No. 10016073.8, filed Oct. 10, 2006.
Office Action dated Sep. 11, 2012 for European Patent Application No. 10016073.8, filed Oct. 10, 2006.
Partial European Search Report dated Mar. 10, 2011 for European Patent Application No. 10016074.6, filed Oct. 10, 2006.
Extended European Search Report dated Jul. 20, 2011 for European Patent Application No. 10016074.6, filed Oct. 10, 2006.
Office Action dated Sep. 11, 2012 for European Patent Application No. 10016074.6, filed Oct. 10, 2006.
Partial European Search Report dated Mar. 31, 2011 for European Patent Application No. 10016031.6, filed Oct. 10, 2006.
Extended European Search Report dated Aug. 10, 2011 for European Patent Application No. 10016031.6, filed Oct. 10, 2006.
Office Action dated Sep. 11, 2012 for European Patent Application No. 10016031.6, filed Oct. 10, 2006.
Partial European Search Report dated Mar. 30, 2011 for European Patent Application No. 10016019.1, filed Oct. 10, 2006.
Extended European Search Report dated Aug. 10, 2011 for European Patent Application No. 10016019.1, filed Oct. 10, 2006.
Office Action dated Sep. 11, 2012 for European Patent Application No. 10016019.1, filed Oct. 10, 2006.
Partial European Search Report dated Mar. 30, 2011 for European Patent Application No. 10016020.9, filed Oct. 10, 2006.
Extended European Search Report dated Aug. 10, 2011 for European Patent Application No. 10016020.9, filed Oct. 10, 2006.
Office Action dated Sep. 12, 2012 for European Patent Application No. 10016020.9, filed Oct. 10, 2006.
Japanese Office Action dated Mar. 13, 2012 for JP Patent Application No. 2008-535692, filed Oct. 10, 2006.
Japanese Office Action dated Aug. 8, 2012 for JP Patent Application No. 2008-535692, filed Oct. 10, 2006.
Partial International Search Report dated Dec. 19, 2008 for International Application No. PCT/US07/088004, filed Dec. 18, 2007.
International Preliminary Report on Patentability and Written Opinion dated Jul. 2, 2009 for International Application No. PCT/US07/088004, filed Dec. 18, 2007.
European Search Report dated Dec. 3, 2009 for European Application No. 07874372.1, filed Dec. 18, 2007.
European Office Action dated Sep. 28, 2011 for European Application No. 07874372.1, filed Dec. 18, 2007.
European Office Action dated Apr. 16, 2012 for European Application No. 07874372.1, filed Dec. 18, 2007.
Australian Office Action dated Sep. 5, 2012 for Australian Application No. 2007353522, filed Dec. 19, 2006.
Japanese Office Action dated Nov. 27, 2012 in Japanese Patent Application No. 2009-543155, filed Dec. 18, 2007.
Japanese Office Action dated Dec. 24, 2013 in Japanese Patent Application No. 2009-543155, filed Dec. 18, 2007.
European Extended Search Report dated Apr. 18, 2011 in European Patent Application No. 10181533.0, filed Jun. 4, 2002.
European Extended Search Report dated Apr. 18, 2011 in European Patent Application No. 10181534.8, filed Jun. 4, 2002.
European Extended Search Report dated Apr. 18, 2011 in European Patent Application No. 10181535.8, filed Jun. 4, 2002.
European Extended Search Report dated Apr. 15, 2011 in European Patent Application No. 10181536.3, filed Jun. 4, 2002.
European Extended Search Report dated Aug. 10, 2010 in European Patent Application No. 09174581.0, filed Jun. 4, 2002. [D33].
Response to Extended Search Report filed Mar. 3, 2011 in European Patent Application No. 09174581.0, filed Jun. 4, 2002. [D34].
Supplementary Response to Extended Search Report filed Nov. 16, 2011 in European Patent Application No. 09174581.0, filed Jun. 4, 2002. [D35].
European Office Action dated Apr. 26, 2011 in European Patent Application No. 09174581.0, filed Jun. 4, 2002.
International Search Report and Written Opinion dated Aug. 13, 2013 for International Patent Application No. PCT/IB2013/000900, filed Mar. 14, 2013.
Third Party Observations dated Jan. 17, 2008 in European Patent Application No. 02740158.7, filed Jun. 4, 2002.
Notice of Opposition dated Aug. 4, 2010 in European Opposition to Patent No. 1397510.
Notice of Opposition dated Aug. 3, 2010 in in European Opposition to Patent No. 1397510.
EPO Communication dated Sep. 10, 2010 in in European Opposition to Patent No. 1397510.
Patentee Response to Opposition dated Mar. 17, 2011 in European Opposition to Patent No. 1397510.
EPO Communication dated May 10, 2012 re Oral Proceeding Schedule in European Opposition to Patent No. 1397510.
Patentee Response dated Nov. 19, 2012 to EP Summons to Oral Proceeding in European Opposition to Patent No. 1397510.
Opposer Hain Lifescience GmbH Response dated Nov. 26, 2012 to EP Summons to Oral Proceeding in European Opposition to Patent No. 1397510. (English Translation Only).
Opposer Beckman Coulter, Inc. further Response dated Nov. 30, 2012 to EP Summons to Oral Proceeding in European Opposition to Patent No. 1397510.
Minutes of the Oral Proceedings on Jan. 30, 2013 in European Opposition to Patent No. No 1397510 [D37] mailed Apr. 5, 2013.
EPO Decision of the Opposition Division of Apr. 5, 2013 in European Opposition to Patent No. No 1397510 [ D36].
Notice of Opposition filed May 8, 2013 against European Patent No. 2236621, granted Aug. 8, 2012.
EPO Opposition Notice dated May 17, 2013 by Beckman Coulter, Inc. against European Patent No. 2236621, granted Aug. 8, 2012.
Notice of Opposition & Discussion filed Oct. 19, 2011 against European Patent No. 1934613 (Koenig et al.).
Notice of Opposition and Statement filed Oct. 18, 2011 against European Patent No. 1934613 (BC).

(56) References Cited

OTHER PUBLICATIONS

EPO Communication dated Nov. 25, 2011 in European Opposition to Patent No. 1934613.
Patentee Reply filed May 30, 2012 in European Opposition to Patent No. 1934613.
EPO Summons to Oral Proceedings dated Nov. 23, 2012 in European Opposition to Patent No. 1934613.
EPO Board Decision and Minutes of Oral Proceedings dated Aug. 2, 2013 in European Opposition to Patent No. 1934613.
Australian Office Action dated May 1, 2015 for Australian Application No. 2013200217, filed Jan. 16, 2013.
Australian Office Action dated May 1, 2015 for Australian Application No. 2013200218, filed Jan. 16, 2013.
Australian Office Action dated May 1, 2015 for Australian Application No. 2013200220, filed Jan. 16, 2013.
Canadian Office Action dated Feb. 13, 2014 for Canadian Application No. 2,673,357, filed Dec. 18, 2007.
Canadian Office Action dated May 1, 2015 for Canadian Application No. 2,673,357, filed Dec. 18, 2007.
Canadian Office Action dated Jul. 23, 2014 for Canadian Application No. 2,625,072, filed Oct. 10, 2006.
European Extended Search Report dated Oct. 9, 2015 in European Patent Application No. 13772940.6, filed Oct. 24, 2014.
European Extended Search Report dated Aug. 25, 2014 in European Patent Application No. 14168417.5, filed May 15, 2014.
Notice of Observations by 3rd Party dated Nov. 18, 2015 in European Patent Application No. 14168417.5, filed May 15, 2014.
European Office Action dated Dec. 9, 2014 in European Patent Application No. 14168417.5, filed May 15, 2014.
European Extended Search Report dated Aug. 25, 2014 in European Patent Application No. 14168420.9, filed May 15, 2014.
European Office Action dated Dec. 17, 2014 in European Patent Application No. 14168420.9, filed May 15, 2014.
EPO Interlocutory Decision of Apr. 10, 2015 in EP Opposition proceedings against Patent No. EP 2236621.
Patentee Appeal dated Jun. 3, 2013 and Grounds for Appeal dated Aug. 12, 2013 against EPO Decision of Apr. 5, 2013 to Revoke Patent No. 1397510 [T 1294/13-3.3.08].
Opponent Beckman Coulters Response dated Dec. 16, 2013 to Patentee's EPO Appeal and Grounds for Appeal in T 1294/13-3.3.08 against EPO Decision in Re EP Patent No. 1397510.
Opponent Hain Lifescience's Response dated Dec. 20, 2013 to Patentee's EPO Appeal and Grounds for Appeal in T 1294/13-3.3.08 against EPO Decision in Re EP Patent No. 1397510.
EPO Notice of Opposition and supporting documents filed by Beckman Coulter on Dec. 17, 2015 against European Patent No. 2322663, granted Mar. 18, 2015 (50 pages).
EPO Notice of Opposition and supporting documents filed by R-Biopharm AG on Dec. 18, 2015 against European Patent No. 2322663, granted Mar. 18, 2015 (84 pages).
EPO Notice of Opposition and supporting documents filed by Beckman Coulter on Aug. 25, 2015 against European Patent No. 2322664, granted Oct. 30, 2014.
EPO Notice of Opposition and supporting documents filed by R-Biopharm AG on Aug. 26, 2015 against European Patent No. 2322664, granted Oct. 30, 2014.
EPO Notice of Opposition and supporting documents filed by Beckman Coulter on Aug. 26, 2015 against European Patent No. 2322655, granted Nov. 26, 2014.
EPO Notice of Opposition and supporting documents filed by R-Biopharm AG on Aug. 26, 2015 against European Patent No. 2322655, granted Nov. 26, 2014.
EPO Notice of Opposition and supporting documents filed by Beckman Coulter on Aug. 26, 2015 against European Patent No. 2322661, granted Nov. 26, 2014.
EPO Notice of Opposition and supporting documents filed by R-Biopharm AG on Aug. 26, 2015 against European Patent No. 2322661, granted Nov. 26, 2014.
Patent Proprietors Reply to both Oppositions and supporting documents filed Apr. 11, 2016 in EP 2322661 granted Nov. 26, 2014 (446 pages).
Patentee Reply filed Dec. 23, 2013 in EP Opposition proceedings against Patent No. 2236621.
Appeal by Patentee/Appellant against EPO Interlocutory Decision filed May 28, 2015 including Grounds for Appeal filed Aug. 5, 2015 in EP Opposition proceedings against Patent No. 2236621; 119 pages.
Opponent Beckman Coulters Reply to Patentee's Grounds for Appeal filed Dec. 29, 2015 & Opponent's Reply to same filed Jan. 4, 2016 in EP Opposition proceedings against Patent No. 2236621; 19 pages.
Stegger et al. "Rapid detection, differentiation and typing of methicillin-resistant *Staphylococcus aureus* harbouring either mecA or the new mecA homologue mecALGA251", Clin Microbiol Infect (Online: Nov. 7, 2011); (2012) 18:395-400.
D71—Exhibit in European Opposition Proceeding/Appeal: EP 2 322 661; Declaration of Marie-Hélène Tremblay (with 1 Annex (CV) in 7 Pages, Jan. 10, 2018.
D75—Exhibit in European Opposition Proceeding/Appeal: EP 2 322 661; Maloy S.R., (1990) *Experimental Techniques in bacterial genetics*. Jones & Bartlett Learning; Genetic Nomenclature in 5 Pages.
D77—Exhibit in European Opposition Proceeding/Appeal: EP 2 322 661; Rosenbach *Staphylococcus aureus* subsp. *Aureus*—ATTC BAA-40, Strain Designations CPS22 in 2 Pages, Jan. 13, 2018.
D78—Exhibit in European Opposition Proceeding/Appeal: EP 2 322 661; Third Declaration of Prof Mark C. Enright dated Mar. 9, 2018 in 2 pages.
D79—Exhibit in European Opposition Proceeding/Appeal: EP 2 322 661; Declaration of Dr Duarte C. Oliveira dated Mar. 13, 2018 including Appendices in 16 pages.
European Office Action dated Aug. 2, 2018 in EP Application No. 15195621.6, filed Nov. 20, 2015.
EPO Interlocutory Decision in Opposition Proceedings and supporting documents dated Apr. 19, 2018 against EP 2322664; (263 pages).
EPO Notice re Beckman Coulter Response to Summons to Oral Proceedings dated Dec. 6, 2017 against European Patent No. 2322655, granted Nov. 26, 2014 (154 pages).
EPO Notice re Beckman Coulter Response to Summons to Oral Proceedings dated Dec. 6, 2017 against European Patent No. 2322661, granted Nov. 26, 2014 (153 pages).
EPO Interlocutory Decision of Apr. 19, 2018 in EP Opposition proceedings against Patent No. 2322661, granted Nov. 26, 2014 (38 pages).
EPO Notice re Appeal (No. T1521/18-3.3.08) filed Aug. 29, 2018 by Beckman Coulter in EP Opposition proceedings against Patent No. 2322661, granted Nov. 26, 2014 (70 pages).
Patentee Geneohm's Statement re Grounds of Appeal ((No. T1521/18-3.3.08) filed Aug. 28, 2018 EP Opposition proceedings against Patent No. 2322661, granted Nov. 26, 2014 (19 pages).
Opponent Beckman Coulter's Submission in Opposition Appeal No. T1146/15-3.3.08 (EP 2236621) dated Nov. 30, 2017 in 221 pages.
EPO Decision to Revoke EP 2781603 & Minutes of Oral Proceedings in Opposition Proceedings dated Jun. 25, 2018 ; 37 pages.
EPO Interlocutory Decision of Jul. 5, 2018 and Minutes of Oral Proceeding in EP Opposition against Patent No. 2781604; 40 pages.
Diekema et al., "Survey of infections due to *Staphylococcus* species: frequency of occurrence and antimicrobial susceptibility of isolates collected in the United States, Canada, Latin America, Europe, and the Western Pacific region for the SENTRY Antimicrobial Surveillance Program, 1997-1999", Clin Infect Dis. (2001) 32(Suppl. 2):S114-132.
International Working Group on the Classification of SCC Elements [IWG-SCC]. "Classification of *Staphylococcal* cassette chromosome mec (SCCmec): guidelines for reporting novel SCCmec elements", Antimicrob Agents Chemother. (2009) 53(12):4961-4967.
BLAST® Microbes RID-V9G669R4015, URL: <https://blast.ncbi.nlm.nik.gov/Blast.cgi, downloaded Oct. 3, 2018, pp. 7.

(56) References Cited

OTHER PUBLICATIONS

BLAST® Microbes RID-V9C1J132014, SEQ ID No. 45; URL: <https://blast.ncbi.nlm.nik.gov/Blast.cgi, downloaded Oct. 3, 2018 in pp. 9.
Jones, R.N., "Use of Surveillance Programs as a Platform for Testing New Antimicrobials Against Multidrug Resistant Bacteria, Recent Experiences", Tufts University School of Medicine, Presentation of JMI Laboratories (61 pages).
Wu et al., Caenorhabditis elegans as a host model for community-associated methicillin-resistant *Staphylococcus aureus*. (2010) 16(3):245-254.
D57—Exhibit in Appeal Procedure—2nd Declaration by Prof. Mark C. Enright on Jan. 19, 2018 re 1st declaration of Sep. 29, 2017 in 2 pages.
EPO Notice re Beckman Coulter's Response to Summons to Oral Proceedings dated Nov. 30, 2017 in Opposition of European Patent No. 2322663, granted Nov. 26, 2014 (306 pages).
EPO Interlocutory Decision in Opposition Proceedings and supporting documents dated Apr. 11, 2018 against EP 2322663; (52 pages).
Patentee/Appellant Submission re Appeal filed Jun. 18, 2018 and Grounds for Appeal dated Aug. 21, 2018 against EPO Decision in European Patent No. 2322663 [T 1522/18-3.3.08]; (111 Pages).
Reply by Beckman Coulter to Opposition Appeal on Jan. 7, 2019 in EP 2322663, granted Mar. 18, 2015 (157 pages).
Patentee/Appellant Submission re Appeal dated Aug. 18, 2018 and Grounds for Appeal dated Aug. 16, 2018 against EPO Decision of Apr. 19, 2018 to Revoke Patent No. 2322664 [T 1582/18-3.3.08]; 236 pages.
Reply by Opposer Beckman Coulter to Opposition Appeal on Jan. 10, 2019 in EP 2322664, granted Mar. 18, 2015 (158 pages).
EPO Interlocutory Decision in Opposition Proceedings dated Mar. 27, 2018 against EP 2322655; (29 pages).
Patentee/Appellant Submission re Appeal dated Aug. 6, 2018 and Grounds for Appeal against EPO Decision of Mar. 27, 2018 in re Patent No. 2322655 [T1421/18-3.3.08] (82 pages).
Reply by Opposer Beckman Coulter to Opposition Appeal on Dec. 19, 2018 in EP 2322655 (258 pages).
Patentee/Appellant Submission re Opposition Appeal dated Jan. 14, 2019 in re Patent No. 2322661 [T1521/18-3.3.08] (118 pages).
Patentee's/Appellant's Written Submission on Grounds of Appeal filed Sep. 26, 2018 and additional Appendices/Exhibits in Opposition Appeal No. T1146/15-3.3.08 (EP 2236621); in 227 pages.
Patentee/Appellant Submission re Appeal dated Sep. 5, 2018 against EPO Interlocutory Decision including Grounds for Appeal filed Nov. 5, 2018 in EP Opposition proceedings against Revocation of Patent No. 2781603; [T2261/18-3.3.08]; (27 pages).
Patentee's/Appellant's Written Submission on Grounds of Appeal filed Nov. 15, 2018 and additional Appendices/Exhibits in Opposition Appeal No. T2255/18-3.3.08 (EP 2781604); in 188 pages.
EPO Minutes of Oral Proceedings dated May 24, 2017 in Appeal No. T2002/13-3.3.08 against revocation of EP Patent No. 1934613; 6 pages.
EPO Board Decision dated Nov. 9, 2017 in Appeal No. T2002/13-3.3.08 against revocation of EP Patent No. 1934613; 32 pages.
Electronic File History of Inter Partes Reexamination Control No. 95/002,216, filed Sep. 13, 2012 for U.S. Appl. No. 11/248,438, filed Oct. 11, 2005 (U.S. Pat. No. 7,838,221) as of Feb. 26, 2013.
PTO Action closing prosecution dated Sep. 20, 2013 of Inter Partes Reexamination Control No. 95/002,216, filed Sep. 13, 2012 for U.S. Appl. No. 11/248,438, filed Oct. 11, 2005 (U.S. Pat. No. 7,838,221). Part 2.
PTO 2nd Action closing prosecution dated Apr. 8, 2014, Patentee Response and 3rd Party Comments in Inter Partes Reexamination Control No. 95/002,216, filed Sep. 13, 2012 for U.S. Appl. No. 11/248,438, filed Oct. 11, 2005 (U.S. Pat. No. 7,838,221) Part 3.
Third Party [Applicant Requestor] Appeal Brief dated Nov. 26, 2014 in Inter Partes Reexamination Control No. 95/002,216, filed Sep. 13, 2012 for U.S. Appl. No. 11/248,438, filed Oct. 11, 2005 (U.S. Pat. No. 7,838,221).
Respondent's Brief dated Dec. 29, 2014 in Inter Partes Reexamination Control No. 95/002,216, filed Sep. 13, 2012 for U.S. Appl. No. 11/248,438, filed Oct. 11, 2005 (U.S. Pat. No. 7,838,221).
Examiner's Answer dated Apr. 21, 2015, Rebuttal Brief dated May 21, 2015 & Patent Board Decision on Appeal dated Feb. 25, 2016 in Inter Partes Reexamination Control No. 95/002,216, filed Sep. 13, 2012 for U.S. Appl. No. 11/248,438, filed Oct. 11, 2005 (U.S. Pat. No. 7,838,221).
D3—Exhibit in European Opposition Proceeding: Applicant Response dated Dec. 2, 2009 in EP Application No. 06825875.5, filed Oct. 10, 2006; 5 pages.
D6—Exhibit in European Opposition Proceeding:: BLAST alignment of SEQ ID 46 from EP 1 397 510 and SEQ ID 19 from EP 1 934 613; 1 page.
D7—Exhibit in European Opposition Proceeding:: EP 1 93 4613 Claimed sequences with EP 1 397 510 primer binding sites shown; 3 pages.
D13—Exhibit in European Opposition Proceeding: CLUSTALW2 Multiple sequence alignment of rjmec primer from Cuny et al. and various MREJ type sequences; 1 page.
D14—Exhibit in European Opposition Proceeding: Primer binding sites of Cuny et al. In EP 1 934 613; 2 pages.
D17—Exhibit in European Opposition Proceeding: Primer binding site for SEQ ID No. 35 in SEQ ID No. 20 of EP 1 934 613; 1 page.
D18—Exhibit in European Opposition Proceeding: Overlap between ORFX2r primer binding sites of Cuny et al. and primer binding site of SEQ ID No. 45 from EP 1 934 613 in type xi MREJ sequences claimed in the EP patent; 6 pages.
D19—Exhibit in European Opposition Proceeding: Primer binding sites for primers of Cuny et al. in MREJ Types I-XX (sequences taken from EP 1934 613 and EP 1 397 510; 10 pages.
D32—Exhibit in European Opposition Proceeding: Lawrence et al. "Poisonous EPC Divisionals—Implications for Risk Management and Opportunistic Advantage." epi Information Feb. 2011; 54-61 (D32—Exhibit in European Opposition Proceeding).
EPO Opposition Notice dated Dec. 2, 2016 with supporting documentation by Beckman Coulter Inc. against European Patent No. 2781603, granted Mar. 2, 2016; 234 pages.
Reply of the Patent Proprietor to Notice of Opposition dated May 19, 2017 in European Patent No. EP 2781603; 49 pages.
EPO Opposition Notice dated Dec. 2, 2016 with supporting documentation by Beckman Coulter Inc. against European Patent No. 2781604, granted Mar. 2, 2016; 186 pages.
Reply of the Patent Proprietor to Notice of Opposition dated May 19, 2017 in European Patent No. EP 2781604; pages.
Patentee Appeal dated Sep. 12, 2013 and Grounds for Appeal dated Dec. 11, 2013 against EPO Decision of Aug. 2, 2013 to Revoke Patent No. 1934613 [T 2002/13-3.3.08].
Opponent Koenig et al. Response dated Apr. 30, 2014 to Patentee's EPO Appeal and Grounds for Appeal in T 2002/13-3.3.08 against EPO Decision in Re EP Patent No. 1934613.
D7—Exhibit in EP 2 322 661, EP 2 322 664 and EP 2 322 655; MREJ type viii sequence (SEQ ID No. 167) with orfX and SCCmec portions highlighted; 1 page.
D8—Exhibit in European Opposition Proceeding: EP 2 322 661, EP 2 322 664 and EP 2 322 655; MREJ type i, ii and iii sequences with orfX and SCCmec portions highlighted—WO2002099034 Sequence 1; 14 pages.
D9—Exhibit in European Opposition Proceeding: EP 2 322 661, EP 2 322 664 and EP 2 322 655; Alignment of type ii (SEQ ID No. 2) and type viii (SEQ ID No. 167) MREJ sequences confirming lack of MREJ specificity of primers in patent; 2 pages.
D10—Exhibit in European Opposition Proceeding: EP 2 322 661, EP 2 322 664 and EP 2 322 655; Alignment of type ii (SEQ ID No. 2) and type ix (SEQ ID No. 168) MREJ sequences confirming lack of MREJ specificity of primers in the Patent; AX720425; 2 pages.
D11—Exhibit in European Opposition Proceeding: EP 2 322 661, EP 2 322 664 & 2 322 655 Alignment of type iii (SEQ ID No. 104) and type vii (SEQ ID No. 165) MREJ sequences confirming lack of MREJ specificity of primers in the patent; 1 page.
D12'Exhibit in European Opposition Proceeding: EP 2 322 664 and EP 2 322 655; Alignment of type vi (SEQ ID No. 171) and *S.*

(56) References Cited

OTHER PUBLICATIONS

*haemolyticus* MREJ sequences confirming lack of MRSA specificity of primers in the patent; 2 pages.
D12a—Exhibit in European Opposition Proceeding: EP 2 322 661; Example of overlap between type ix (SEQ ID No. 168) and other category of MRSA sequences confirming lack of MREJ specificity of primers claimed in the Patent; AB774374; 3 pages.
D12b—Exhibit in European Opposition Proceeding: EP 2 322 661; Example of overlap between type ix (SEQ ID No. 168) and other category of MRSA sequences confirming lack of MREJ specificity of primers claimed in the Patent; HF569115; 2 pages.
D16—Exhibit in European Opposition Proceeding: EP 2 322 664; Results of BLAST search using MREJ type vi sequence as query (SEQ ID No. 171)—AB665981; 19 pages.
D22—Exhibit in European Opposition Proceeding: EP 2 322 664 and EP 2 322 655; Alignment of MREJ type iii sequence from D1 and MREJ type vi sequence of SEQ ID No. 171—AX720594; 1 page.
D22—Exhibit in European Opposition Proceeding: EP 2 322 661; Alignment of MREJ type ii sequence from D1 and MREJ type ix sequence of SEQ ID No. 168; Mec lower junction around DNA of MRSA; E13725; p. 1.
D25—Exhibit in European Opposition Proceeding: EP 2 322 664 and EP 2 322 655; MREJ type iv sequence of HDG2 strain showing orfX and SCCmec sequence; 1 page.
European Extended Search Report dated Aug. 10, 2016 in European Patent Application No. 15195621.6, filed Nov. 20, 2015.
EPO Notice of Opposition and supporting documents filed by Beckman Coulter on Dec. 17, 2015 against European Patent No. 2322663, granted Mar. 18, 2015.
EPO Notice of Opposition and supporting documents filed by R-Biopharm AG on Dec. 18, 2015 against European Patent No. 2322663, granted Mar. 18, 2015.
Patent Proprietor's Reply to both Oppositions and supporting documents filed Aug. 3, 2016 in EP 2322663, granted Mar. 18, 2015 (231 pages).
Patent Proprietor's Reply to both Oppositions and supporting documents filed Apr. 11, 2016 in EP 2322664, granted Oct. 30, 2014 (201 pages).
Patent Proprietor's Reply to both Oppositions and supporting documents filed Apr. 10, 2016 in EP 2322655, granted Nov. 26, 2014 (251 pages).
EPO Interlocutory Decision of Apr. 10, 2015 in EP Opposition proceedings against Patent No. 2236621.
Appeal by Patentee/Appellant against EPO Interlocutory Decision filed May 28, 2015 including Grounds for Appeal filed Aug. 5, 2015 in EP Opposition proceedings against Patent No. 2236621.
Opponent Beckman Coulter's Reply to Patentee's Grounds for Appeal filed Dec. 29, 2015 & Opponent's Reply to same filed Jan. 4, 2016 in EP Opposition proceedings against Patent No. 2236621.
Reply of the Patent Proprietor to Notice of Opposition dated May 19, 2017 in European Patent No. EP 2781604; 35 pages.

* cited by examiner

MREP type i
MREP type ii
MREP type iii
SCCmec integration site
orfX
S. aureus chromosome
52
53
54
55
56
57
58
59
62
61
60
63
or Prime
S. aureus Chromosome
orfX
MREP type i
MREP type ii
MREP type iii

SEQUENCE LISTING

<160> NUMBER OF SEQ ID NOS: 269

<210> SEQ ID NO 1
<211> LENGTH: 3050
<212> TYPE: DNA
<213> ORGANISM: Staphylococcus aureus

<400> SEQUENCE: 1

```
tcgtgccatt gatgcagagg gacatacatt agatatttgg ttgcgtaagc aacgagataa      60

tcattcagca tatgcgttta tcaaacgtct cattaaacaa tttggtaaac ctcaaaaggt     120

aattacagat caggcacctt caacgaaggt agcaatggct aaagtaatta aagcttttaa     180

acttaaacct gactgtcatt gtacatcgaa atatctgaat aacctcattg agcaagatca     240
```

-continued

```
ccgtcatatt aaagtaagaa agacaaggta tcaaagtatc aatacagcaa agaatacttt    300
aaaaggtatt gaatgtattt acgctctata taaaaagaac cgcaggtctc ttcagatcta    360
cggattttcg ccatgccacg aaattagcat catgctagca agttaagcga acactgacat    420
gataaattag tggttagcta tattttttta ctttgcaaca gaaccgaaaa taatctcttc    480
aatttatttt tatatgaatc ctgtgactca atgattgtaa tatctaaaga tttcagttca    540
tcatagacaa tgttcttttc aacatttttt atagcaaatt gattaaataa attctctaat    600
ttctcccgtt tgatttcact accatagatt atattatcat tgatatagtc aatgaataat    660
gacaaattat cactcataac agtcccaacc cctttatttt gatagactaa ttatcttcat    720
cattgtaaaa caaattacac cctttaaatt taactcaact taaatatcga caaattaaaa    780
aacaataaaa ttacttgaat attattcata atatattaac aactttatta tactgctctt    840
tatatataaa atcattaata attaaacaag ccttaaaata tttaactttt ttgtgattat    900
tacacattat cttatctgct ctttatcacc ataaaaatag aaaaaacaag attcctaaag    960
aatataggaa tcttgtttca gactgtggac aaactgattt tttatcagtt agcttattta   1020
gaaagtttta tttaaattac agtttctatt tttattagat cacaatttta ttttagctct   1080
tgttcaagta atcattttc gccaaaaact ttatactgaa tagcttctac attaaatact   1140
ttgtcaatga gatcatctac atctttaaat tcagaataat ttgcatatgg atctataaaa   1200
taaaattgtg gttctttacc ggaaacatta aatattctta atattaaata tttctgctta   1260
tattctttca tagcaaacat ttcatttagc gacataaaaa atggttcctc aatactagaa   1320
gatgtagatg ttttaatttc aataaatttt tctacagctt tatctgtatt tgttggatca   1380
aaagctacta aatcatagcc atgaccgtgt tgagagcctg gattatcatt taaaatattc   1440
ctaaactgtt ctttcttatc ttcgtctatt ttattatcaa ttagctcatt aaagtaattt   1500
agcgctaatt tttctccaac tttaccggtt aatttattct ctttatttga tttttcaatt   1560
tctgaatcat ttttagtagt ctttgataca cctttttttat attttggaat tattccttta   1620
ggtgcttcca cttccttgag tgtcttatct ttttgtgctg ttctaatttc ttcaatttcg   1680
ctgtcttcct gtatttcgtc tatgctattg accaagctat cataggatgt ttttgtaact   1740
tttgaagcta attcattaaa tagttctaaa aatttcttta aatcctctag catatcttct   1800
tctgtgaatc cttcattcaa atcataatat ttgaatctta ttgatccatg agaatatcct   1860
gatggataat catttttttaa atcataagat gaatctttat tttctgcgta ataaaatctt   1920
ccagtattaa attcatttga tgtaatatat ttattgagtt cggaagataa agttaatgct   1980
ctttgttttg cagcattttt atcccgcgga aacatatcac ttatctttga ccatccttga   2040
ttcaaagata agtatatgcc ttctccttcc ggatgaaaaa gatataccaa ataatatcca   2100
tcctttgttt cttttgttat attctcatca tatattgaaa tccaaggaac tttactatag   2160
ttcccagtag caaccttccc tacaactgaa tatttatctt cttttatatg cacttttaac   2220
tgcttgggta acttatcatg gactaaagtt ttatatagat cacctttatc ccaatcagat   2280
tttttaacta cattattggt acgtttctct ttaattaatt taaggacctg cataaagttg   2340
tctatcattt gaaattccct cctattataa aatatattat gtctcatttt cttcaatatg   2400
tacttattta tattttaccg taatttacta tatttagttg cagaaagaat tttctcaaag   2460
ctagaacttt gcttcactat aagtattcag tataaagaat atttcgctat tatttacttg   2520
aaatgaaaga ctgcggaggc taactatgtc aaaaatcatg aacctcatta cttatgataa   2580
gcttctcctc gcataatctt aaatgctctg tacacttgtt caattaacac aacccgcatc   2640
```

```
atttgatgtg ggaatgtcat tttgctgaat gatagtgcgt agttactgcg ttgtaagacg   2700

tccttgtgca ggccgtttga tccgccaatg acgaaaacaa agtcgctttg cccttgggtc   2760

atgcgttggt tcaattcttg ggccaatcct tcggaagata gcatctttcc ttgtatttct   2820

aatgtaatga ctgtggattg tggtttgatt ttggctagta ttcgttggcc ttctttttct   2880

tttacttgct caatttcttt gtcactcata ttttctggtg ctttttcgtc tggaacttct   2940

atgatgtcta tcttggtgta tgggcctaaa cgtttttcat attctgctat ggcttgcttc   3000

caatatttct cttttagttt ccctacagct aaaatggtga ttttcatgtc             3050
```

<210> SEQ ID NO 2
<211> LENGTH: 3050
<212> TYPE: DNA
<213> ORGANISM: Staphylococcus aureus

<400> SEQUENCE: 2

```
acctcattga gcaagatcac cgtcatatta aagtaagaaa gacaaggtat caaagtatca     60

atacagcaaa gaatacttta aaaggtattg aatgtattta cgctctatat aaaaagaacc    120

gcaggtctct tcagatctac ggattttcgc catgccacga aattagcatc atgctagcaa    180

gttaagcgaa cactgacatg ataaattagt ggttagctat attttttac tttgcaacag    240

aaccgaaaat aatctcttca atttattttt atatgaatcc tgtgactcaa tgattgtaat    300

atctaaagat ttcagttcat catagacaat gttcttttca acatttttta tagcaaattg    360

attaaataaa ttctctaatt tctcccgttt gatttcacta ccatagatta tattatcatt    420

gatatagtca atgaataatg acaaattatc actcataaca gtcccaaccc ctttcttttg    480

atagactaat tatcttcatc attgtaaaac aaattacacc ctttaaattt aactcaactt    540

aaatatcgac aaattaaaaa acaataaaat tacttgaata ttattcataa tatattaaca    600

actttattat actgctcttt atatataaaa tcattaataa ttaaacaagc cttaaaatat    660

ttaacttttt tgtgattatt acacattatc ttatctgctc tttatcacca taaaaataga    720

aaaaacaaga ttcctaaaga atataggaat cttgtttcag actgtggaca aactgatttt    780

ttatcagtta gcttatttag aaagttttat ttaaattaca gtttctattt ttattagatc    840

acaattttat tttagctctt gttcaagtaa tcatttttcg ccaaaaactt tatactgaat    900

agcttctaca ttaaatactt tgtcaatgag atcatctaca tctttaaatt cagaataatt    960

tgcatatgga tctataaaat aaaattgtgg ttctttaccg gaaacattaa atattcttaa   1020

tattaaatat ttctgcttat attctttcat agcaaacatt tcatttagcg acataaaaaa   1080

tggttcctca atactagaag atgtagatgt tttaatttca ataaattttt ctacagcttt   1140

atctgtattt gttggatcaa aagctactaa atcatagcca tgaccgtgtt gagagcctgg   1200

attatcattt aaaatattcc taaactgttc tttcttatct tcgtctattt tattatcaat   1260

tagctcatta aagtaattta gcgctaattt ttctccaact ttaccggtta atttattctc   1320

tttatttgat ttttcaattt ctgaatcatt tttagtagtc tttgatacac ctttttttata   1380

ttttggaatt attcctttag gtgcttccac ttccttgagt gtcttatctt tttgtgctgt   1440

tctaatttct tcaatttcgc tgtcttcctg tatttcgtct atgctattga ccaagctatc   1500

ataggatgtt tttgtaactt ttgaagctaa ttcattaaat agttctaaaa atttctttaa   1560

atcctctagc atatcttctt ctgtgaatcc ttcattcaaa tcataatatt tgaatcttat   1620

tgatccatga gaatatcctg atggataatc attttttaaa tcataagatg aatctttatt   1680
```

ttctgcgtaa taaaatcttc cagtattaaa ttcatttgat gtaatatatt tattgagttc 1740
ggaagataaa gttaatgctc tttgttttgc agcattttta tcccgcggaa acatatcact 1800
tatctttgac catccttgat tcaaagataa gtatatgcct tctccttccg gatgaaaaag 1860
atataccaaa taatatccat cctttgtttc ttttgttata ttctcatcat atattgaaat 1920
ccaaggaact ttactatagt tcccagtagc aaccttccct acaactgaat atttatcttc 1980
ttttatatgc acttttaact gcttgggtaa cttatcatgg actaaagttt tatatagatc 2040
acctttatcc caatcagatt ttttaactac attattggta cgtttctctt taattaattt 2100
aaggacctgc ataaagttgt ctatcatttg aaattccctc ctattataaa atatattatg 2160
tctcattttc ttcaatatgt acttatttat attttaccgt aatttactat atttagttgc 2220
agaaagaatt ttctcaaagc tagaactttg cttcactata agtattcagt ataaagaata 2280
tttcgctatt atttacttga aatgaaagac tgcggaggct aactatgtca aaaatcatga 2340
acctcattac ttatgataag cttcttaaaa acataacagc aattcacata aacctcatat 2400
gttctgatac attcaaaatc cctttatgaa gcggctgaaa aaaccgcatc atttatgata 2460
tgcttctcca cgcataatct taaatgctct atacacttgc tcaattaaca caacccgcat 2520
catttgatgt gggaatgtca ttttgctgaa tgatagtgcg tagttactgc gttgtaagac 2580
gtccttgtgc aggccgtttg atccgccaat gacgaataca aagtcgcttt gcccttgggt 2640
catgcgttgg ttcaattctt gggccaatcc ttcggaagat agcatctttc cttgtatttc 2700
taatgtaatg actgtggatt gtggtttaat tttggctagt attcgttggc cttctttttc 2760
ttttacttgc tcaatttctt tgtcgctcat attttctggt gctttttcgt ctggaacttc 2820
tatgatgtct atcttggtgt atgggcctaa acgtttttca tattctgcta tggcttgctt 2880
ccaatatttc tcttttagtt tccctacagc taaaatggtg attttcatgt cgtttggtcc 2940
tccaaattgt tatcaacttt ccagttatcc acaagttatt aacttgttca cactgttccc 3000
tcttattata ccaatatttt ttgcagtttt tgatattttc ctgacattta 3050

<210> SEQ ID NO 3
<211> LENGTH: 3183
<212> TYPE: DNA
<213> ORGANISM: Staphylococcus aureus

<400> SEQUENCE: 3
ctgcagaggt aattattcca aacaatacca ttgatttcaa aggagaaaga gatgacgtta 60
gaacgcgtga aacaaattta ggaaacgcga ttgcagatgc tatggaagcg tatggcgtta 120
agaatttctc taaaaagact gactttgccg tgacaaatgg tggaggtatt cgtgcctcta 180
tcgcaaaagg taaggtgaca cgctatgatt taatctcagt attaccattt ggaaatacga 240
ttgcgcaaat tgatgtaaaa ggttcagacg tctggacggc tttcgaacat agtttaggcg 300
caccaacaac acaaaaggac ggtaagacag tgttaacagc gaatggcggt ttactacata 360
tctctgattc aatccgtgtt tactatgata taaataaacc gtctggcaaa cgaattaatg 420
ctattcaaat tttaaataaa gagacaggta agtttgaaaa tattgattta aaacgtgtat 480
atcacgtaac gatgaatgac ttcacagcat caggtggcga cggatatagt atgttcggtg 540
gtcctagaga agaaggtatt tcattagatc aagtactagc aagttattta aaaacagcta 600
acttagctaa gtatgatacg acagaaccac aacgtatgtt attaggtaaa ccagcagtaa 660
gtgaacaacc agctaaagga caacaaggta gcaaaggtag taagtctggt aaagatacac 720
aaccaattgg tgacgacaaa gtgatggatc cagcgaaaaa accagctcca ggtaaagttg 780

```
ttttgttgct agcgcataga ggaactgtta gtagcggtac agaaggttct ggtcgcacaa    840
tagaaggagc tactgtatca agcaagagtg ggaaacaatt ggctagaatg tcagtgccta    900
aaggtagcgc gcatgagaaa cagttaccaa aaactggaac taatcaaagt tcaagcccag    960
aagcgatgtt tgtattatta gcaggtatag gtttaatcgc gactgtacga cgtagaaaag   1020
ctagctaaaa tatattgaaa ataatactac tgtatttctt aaataagagg tacggtagtg   1080
ttttttttatg aaaaaaagcg ataaccgttg ataaatatgg gatataaaaa cgaggataag   1140
taataagaca tcaaggtgtt tatccacaga aatggggata gttatccaga attgtgtaca   1200
atttaaagag aaataccccac aatgcccaca gagttatcca caaatacaca ggttatacac   1260
taaaaatcgg gcataaatgt caggaaaata tcaaaaactg caaaaaaatat tggtataata   1320
agagggaaca gtgtgaacaa gttaataact tgtggataac tggaaagttg ataacaattt   1380
ggaggaccaa acgacatgaa aatcaccatt ttagctgtag ggaaactaaa agagaaatat   1440
tggaagcaag ccatagcaga atatgaaaaa cgtttaggcc catacaccaa gatagacatc   1500
atagaagttc cagacgaaaa agcaccagaa aatatgagtg acaaagaaat tgagcaagta   1560
aaagaaaaag aaggccaacg aatactagcc aaaatcaaac cacaatccac agtcattaca   1620
ttagaaatac aaggaaagat gctatcttcc gaaggattgg cccaagaatt gaaccaacgc   1680
atgacccaag ggcaaagcga ctttgttttc gtcattggcg gatcaaacgg cctgcacaag   1740
gacgtcttac aacgcagtaa ctacgcacta tcattcagca aaatgacatt cccacatcaa   1800
atgatgcggg ttgtgttaat tgaacaagtg tacagagcat ttaagattat gcgaggagag   1860
gcgtatcata agtaaaacta aaaaattctg tatgaggaga taataatttg gagggtgtta   1920
aatggtggac attaaatcca cgttcattca atatataaga tatatcacga taattgcgca   1980
tataacttaa gtagtagcta acagttgaaa ttaggcccta tcaaattggt ttatatctaa   2040
aatgattaat atagaatgct tctttttgtc cttattaaat tataaaagta actttgcaat   2100
agaaacagtt atttcataat caacagtcat tgacgtagct aagtaatgat aaataatcat   2160
aaataaaatt acagatattg acaaaaaata gtaaatattc caatgaagtt tcaaaagaac   2220
aattccaaga aattgagaat gtaaataata aggtcaaaga attttattaa gatttgaaag   2280
agtatcaatc aagaaagatg tagttttttta ataaactatt tggaaaataa ttatcataat   2340
ttaaaaactg acaatttgcg agactcataa aatgtaataa tggaaataga tgtaaaatat   2400
aattaagggg tgtaatatga agattaatat ttataaatct atttataatt ttcaggaaac   2460
aaatacaaat tttttagaga atctagaatc tttaaatgat gacaattatg aactgcttaa   2520
tgataaagaa cttgttagtg attcaaatga attaaaatta attagtaaag tttatatacg   2580
taaaaaagac aaaaaactat tagattggca attattaata aagaatgtat acctagatac   2640
tgaagaagat gacaatttat tttcagaatc cggtcatcat tttgatgcaa tattatttct   2700
caaagaagat actacattac aaaataatgt atatattata ccttttggac aagcatatca   2760
tgatataaat aatttgattg attatgactt cggaattgat tttgcagaaa gagcaatcaa   2820
aaatgaagac atagttaata aaaatgttaa ttttttttcaa caaaacaggc ttaaagagat   2880
tgttaattat agaaggaata gtgtagatta cgttagacct tcagaatctt atatatcagt   2940
ccaaggacat ccacagaatc ctcaaatttt tggaaaaaca atgacttgtg gtacaagtat   3000
ttcattgcgt gtaccgaata gaaagcagca attcatagat aaaaattagtg tgataatcaa   3060
agaaataaac gctattatta atcttcctca aaaaattagt gaatttccta gaatagtaac   3120
```

-continued

```
tttaaaagac ttgaataaaa tagaagtatt agatacttta ttgctaaaaa aactatcgaa   3180

ttc                                                                 3183


<210> SEQ ID NO 4
<211> LENGTH: 479
<212> TYPE: DNA
<213> ORGANISM: Staphylococcus aureus

<400> SEQUENCE: 4

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaaca     479


<210> SEQ ID NO 5
<211> LENGTH: 480
<212> TYPE: DNA
<213> ORGANISM: Staphylococcus aureus

<400> SEQUENCE: 5

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataac atgcctacga ttaataaaag gaagtttatt agattttgtg ttagaaacag    480


<210> SEQ ID NO 6
<211> LENGTH: 480
<212> TYPE: DNA
<213> ORGANISM: Staphylococcus aureus

<400> SEQUENCE: 6

ttcgtcattg gcggatcaaa cggcctgcac aaggacgtct tacaacgcag taactacgca     60

ctatcattca gcaaaatgac atccccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agatttgtgt tagaaacagt    480


<210> SEQ ID NO 7
<211> LENGTH: 480
```

<212> TYPE: DNA
<213> ORGANISM: Staphylococcus aureus

<400> SEQUENCE: 7
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaacag 480

<210> SEQ ID NO 8
<211> LENGTH: 309
<212> TYPE: DNA
<213> ORGANISM: Staphylococcus aureus
<220> FEATURE:
<221> NAME/KEY: misc_feature
<222> LOCATION: 237
<223> OTHER INFORMATION: n = A,T,C or G

<400> SEQUENCE: 8
ggcggatcaa acggcctgca caaggacgtc ttacaacgca gtaactacgc actatcattc 60
agcaaaatga cattcccaca tcaaatgatg cgggttgtgt taattgaaca agtgtacaga 120
gcatttaaga ttatgcgtgg agaagcgtat cataaataaa actaaaaatt aggttgtgta 180
taatttaaaa atctaatgag atgtggagga attacatata tgaaatattg gattatncct 240
tgcaatatca tacgatgttt atagagtgtt taataaacca tttttcaact attgatgatc 300
tacaatata 309

<210> SEQ ID NO 9
<211> LENGTH: 471
<212> TYPE: DNA
<213> ORGANISM: Staphylococcus aureus

<400> SEQUENCE: 9
ttggcggatc aaacggcctg cacaaggacg tcttacaacg cagtaactac gcactatcat 60
tcagcaaaat gacattccca catcaaatga tgcgggttgt gttaattgaa caagtgtaca 120
gagcatttaa gattatgcgt ggagaagcgt atcataaata aaactaaaaa ttaggttgtg 180
tataatttaa aaatttaatg agatgtggag gaattacata tatgaaatat tggattatac 240
cttgcaatat catacgatgt ttatagagtg tttaataaac catttttcaa ctattgatga 300
tctagaatat ataataactg tacaaattat attgattatg gaactacaat taaattaaga 360
aattgatgat gaaattttaa atttaaacta atggaatcaa gaaagaatga aaggaaatat 420
acaatgccta cgattaataa aaggaagttt attagatttt gtgttagaaa c 471

<210> SEQ ID NO 10
<211> LENGTH: 480
<212> TYPE: DNA
<213> ORGANISM: Staphylococcus aureus

<400> SEQUENCE: 10
ttcgtcattg gcggatcaaa cggcctgcac aaggacgtct tacaacgcag taactacgca 60

-continued

```
ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaacag    480


<210> SEQ ID NO 11
<211> LENGTH: 480
<212> TYPE: DNA
<213> ORGANISM: Staphylococcus aureus

<400> SEQUENCE: 11

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaacag    480


<210> SEQ ID NO 12
<211> LENGTH: 480
<212> TYPE: DNA
<213> ORGANISM: Staphylococcus aureus

<400> SEQUENCE: 12

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaacag    480


<210> SEQ ID NO 13
<211> LENGTH: 478
<212> TYPE: DNA
<213> ORGANISM: Staphylococcus aureus

<400> SEQUENCE: 13

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300
```

```
ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaac      478


<210> SEQ ID NO 14
<211> LENGTH: 479
<212> TYPE: DNA
<213> ORGANISM: Staphylococcus aureus

<400> SEQUENCE: 14

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaaca     479


<210> SEQ ID NO 15
<211> LENGTH: 480
<212> TYPE: DNA
<213> ORGANISM: Staphylococcus aureus
<220> FEATURE:
<221> NAME/KEY: misc_feature
<222> LOCATION: 406
<223> OTHER INFORMATION: n = A,T,C or G

<400> SEQUENCE: 15

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcncgaa agaatgaaag    420

gaaatataca atgcctacga ttaataaaag gaagtttatt agattttgtg ttagaaacag    480


<210> SEQ ID NO 16
<211> LENGTH: 480
<212> TYPE: DNA
<213> ORGANISM: Staphylococcus aureus

<400> SEQUENCE: 16

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360
```

-continued attaagaaat tgatgatgaa attttaaatt taaactaatg gaatcaagaa agaatgaaag 420
gaaatataca atgcctacga ttaataaaag gaagtttatt agattttgtg ttagaaacag 480

<210> SEQ ID NO 17
<211> LENGTH: 480
<212> TYPE: DNA
<213> ORGANISM: Staphylococcus aureus

<400> SEQUENCE: 17
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcatatc ataaatgatg cggttttttc 180
agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagacata atatatttta taataggagg 480

<210> SEQ ID NO 18
<211> LENGTH: 480
<212> TYPE: DNA
<213> ORGANISM: Staphylococcus aureus

<400> SEQUENCE: 18
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcatatc ataaatgatg cggttttttc 180
agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagacata atatatttta taataggagg 480

<210> SEQ ID NO 19
<211> LENGTH: 458
<212> TYPE: DNA
<213> ORGANISM: Staphylococcus aureus

<400> SEQUENCE: 19
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcatatc ataaatgatg cggttttttc 180
agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagaca 458

<210> SEQ ID NO 20
<211> LENGTH: 385

-continued

<212> TYPE: DNA
<213> ORGANISM: Staphylococcus aureus

<400> SEQUENCE: 20
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 21
<211> LENGTH: 385
<212> TYPE: DNA
<213> ORGANISM: Staphylococcus aureus

<400> SEQUENCE: 21
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 22
<211> LENGTH: 385
<212> TYPE: DNA
<213> ORGANISM: Staphylococcus aureus

<400> SEQUENCE: 22
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 23
<211> LENGTH: 385
<212> TYPE: DNA
<213> ORGANISM: Staphylococcus aureus

<400> SEQUENCE: 23
ttcgtcattg gcggatcaaa cggcctgcac aaggacgtct tacaacgcag taactacgcg 60
ctatcattca gcaaaatgac attcccacat caaatgatgc gggttgtgtt aattgaacaa 120
gtgtacaaag catttaagat tatgcgagga gaagcttatc ataagtaatg aggttcatga 180
tttttgacat agttagcctc cgcagtcttt catttcaagt aaataatagc gaaatattct 240

```
ttatactgaa tacttatagt gaagcaaagt tctagctttg agaaaattct ttctgcaact    300

aaatatagta aattacggta aaatataaat aagtacatat tgaagaaaat gagacataat    360

atattttata ataggaggga atttc                                          385
```

<210> SEQ ID NO 24
<211> LENGTH: 340
<212> TYPE: DNA
<213> ORGANISM: Staphylococcus aureus

<400> SEQUENCE: 24

```
cgcagtaact acgcgctatc attcagcaaa atgacattcc cacatcaaat gatgcgggtt     60

gtgttagttg agcaagtgta catagcattt aagattatgc gaggagaagc ttatcataag    120

taatgaggtt catgattttt gacatagtta gcctccgcag tctttcattt caagtaaata    180

atagcgaaat attctttata ctgaatactt atagtgaagc aaagttctag ctttgagaaa    240

attctttctg caactaaata tagtaaatta cggtaaaata taaataagta catattgaag    300

aaaatgagac ataatatatt ttataatagg agggaatttc                          340
```

<210> SEQ ID NO 25
<211> LENGTH: 369
<212> TYPE: DNA
<213> ORGANISM: Staphylococcus aureus

<400> SEQUENCE: 25

```
caaacggcct gcacaaggac gtcttacaac gcagtaacta cgcactatca ttcagcaaaa     60

tgacattccc acatcaaatg atgcgggttg tgttaattga acaagtgtac agagcattta    120

agattatgcg aggagaagct tatcataagt aatgaggttc atgatttttg acatagttag    180

cctccgcagt ctttcatttc aagtaaataa tagcgaaata ttctttatac tgaatactta    240

tagtgaagca aagttctagc tttgagaaaa ttctttctgc aactaaatat agtaaattac    300

ggtaaaatat aaataagtac atattgaaga aaatgagaca taatatattt tataatagga    360

gggaatttc                                                            369
```

<210> SEQ ID NO 26
<211> LENGTH: 3050
<212> TYPE: DNA
<213> ORGANISM: Staphylococcus aureus

<400> SEQUENCE: 26

```
aatttggtaa acctcaaaag gtaattacag atcaggcacc ttcaacgaag gtagcaatgg     60

ctaaagtaat taaagctttt aaacttaaac ctgactgtca ttgtacatcg aaatatctga    120

ataacctcat tgagcaagat caccgtcata ttaaagtaag aaagacaagg tatcaaagta    180

tcaatacagc aaagaatact ttaaaaggta ttgaatgtat tcacgctcta tataaaaaga    240

accgcaggtc tcttcagatc tacggatttt cgccatgcca cgaaattagc atcatgctag    300

caagttaagc gaacactgac atgataaatt agtggttagc tatatttttt tactttgcaa    360

cagaaccgaa aataatctct tcaatttatt tttatatgaa tcctgtgact caatgattgt    420

aatatctaaa gatttcagtt catcatagac aatgttcttt tcaacatttt ttatagcaaa    480

ttgattaaat aaattctcta atttctcccg tttgatttca ctaccataga ttatattatc    540

attgatatag tcaatgaata atgacaaatt atcactcata acagtcccaa cccctttatt    600

ttgatagact aattatcttc atcattgtaa aacaaattac accctttaaa tttaactcaa    660

cttaaatatc gacaaattaa aaaacaataa aattacttga atattattca taatatatta    720
```

acaactttat tatactgctc tttatatata aaatcattaa taattaaaca agccttaaaa 780
tatttaactt ttttgtgatt attacacatt atcttatctg ctctttatca ccataaaaat 840
agaaaaaaca agattcctaa agaatatagg aatcttgttt cagactgtgg acaaactgat 900
tttttatcag ttagcttatt tagaaagttt tatttaaatt acagtttcta tttttattag 960
atcacaattt tattttagct cttgttcaag taatcatttt tcgccaaaaa ctttatactg 1020
aatagcttct acattaaata cttgtcaatg agatcatcta catctttaaa ttcagaataa 1080
ttcgcatatg gatctataaa ataaaattgt ggttctttac cggaaacatt aaatattctt 1140
aatattaaat atttctgctt atattctttc atagcaaaca tttcatttag cgacataaaa 1200
aatggttcct caatactaga agatgtagat gttttaattt caataaattt ttctacagct 1260
ttatctgtat ttgttggatc aaaagctact aaatcatagc catgaccgtg ttgagagcct 1320
ggattatcat ttaaaatatt cctaaactgt tctttcttat cttcgtctat tttattatca 1380
attagctcat taaagtaatt tagcgctaat ttttctccaa ctttaccggt taatttattc 1440
tctttatttg atttttcaat ttctgaatca tttttagtag tctttgatac accttttta 1500
tattttggaa ttattccttt aggtgcttcc acttccttga gtgtcttatc tttttgtgct 1560
gttctaattt cttcaatttc gctgtcttcc tgtatttcgt ctatgctatt gaccaagcta 1620
tcataggatg tttttgtaac ttttgaagct aattcattaa atagttctaa aaatttcttt 1680
aaatcctcta gcatatcttc ttctgtgaat ccttcattca aatcataata tttgaatctt 1740
attgatccat gagaatatcc tgatggataa tcatttttta aatcataaga tgaatcttta 1800
ttttctgcgt aataaaatct tccagtatta aattcatttg atgtaatata tttattgagt 1860
tcggaagata aagttaatgc tctttgtttt gcagcatttt tatcccgcgg aaacatatca 1920
cttatctttg accatccttg attcaaagat aagtatatgc cttctccttc cggatgaaaa 1980
agatatacca aataatgtcc atcctttgtt tcttttgtta tattctcatc atatattgaa 2040
atccaaggaa ctttactata gttcccagta gcaaccttcc ctacaactga atatttatct 2100
tcttttatat gcacttttaa ctgcttgggt aacttatcat ggactaaagt tttatataga 2160
tcacctttat cccaatcaga ttttttaact acattattgg tacgtttctc tttaattaat 2220
ttaaggacct gcataaagtt gtctatcatt tgaaattccc tcctattata aaatatatta 2280
tgtctcattt tcttcaatat gtacttattt atattttacc gtaatttact atatttagtt 2340
gcagaaagaa ttttctcaaa gctagaactt tgcttcacta taagtattca gtataaagaa 2400
tatttcgcta ttatttactt gaaatgaaag actgcggagg ctaactatgt caaaaatcat 2460
gaacctcatt acttatgata agcttcttaa aaacataaca gcaattcaca taaacctcat 2520
atgttctgat acattcaaaa tccctttatg aagcggctga aaaaaccgca tcatttatga 2580
tatgcttctc ctcgcataat cttaaatgct ctgtacactt gttcaattaa cacaacccgc 2640
atcatttgat gtgggaatgt cattttgctg aatgatagtg cgtagttact gcgttgtaag 2700
acgtccttgt gcaggccgtt tgatccgcca atgacgaaaa caaagtcgct ttgcccttgg 2760
gtcatgcgtt ggttcaattc ttgggccaat ccttcggaag atagcatctt tccttgtatt 2820
tctaatgtaa tgactgtgga ttgtggtttg attttggcta gtattcgttg gccttctttt 2880
tcttttactt gctcaatttc tttgtcactc atattttctg gtgctttttc gtctggaact 2940
tctatgatgt ctatcttggt gtatgggcct aaacgttttt catattctgc tatggcttgc 3000
ttccaatatt tctcttttag tttccctaca gctaaaatgg tgattttcat 3050

<210> SEQ ID NO 27
<211> LENGTH: 657
<212> TYPE: DNA
<213> ORGANISM: Staphylococcus aureus

<400> SEQUENCE: 27
ccaccttcat atgacgtcta tccatttatg tatggcatga gtaacgaaga atataataaa 60
ttaaccgaag ataaaaaaga acctctgctc aacaagttcc agattacaac ttcaccaggt 120
tcaactcaaa aaatattaac agcaatgatt gggttaaata acaaaacatt agacgataaa 180
acaagttata aaatcgatgg taaaggttgg caaaaagata aatcttgggg tggttacaac 240
gttacaagat atgaagtggt aaatggtaat atcgacttaa aacaagcaat agaatcatca 300
gataacattt tctttgctag agtagcactc gaattaggca gtaagaaatt tgaaaaaggc 360
atgaaaaaac taggtgttgg tgaagatata ccaagtgatt atccatttta taatgctcaa 420
atttcaaaca aaaatttaga taatgaaata ttattagctg attcaggtta cggacaaggt 480
gaaatactga ttaacccagt acagatcctt tcaatctata gcgcattaga aaataatggc 540
aatattaacg cacctcactt attaaaagac acgaaaaaca aagtttggaa gaaaaatatt 600
atttccaaag aaaatatcaa tctattaact gatggtatgc aacaagtcgt aaataaa 657

<210> SEQ ID NO 28
<211> LENGTH: 782
<212> TYPE: DNA
<213> ORGANISM: Staphylococcus aureus

<400> SEQUENCE: 28
caccttcata tgacgtctat ccatttatgt atggcatgag taacgaagaa tataataaat 60
taaccgaaga taaaaaagaa cctctgctca acaagttcca gattacaact tcaccaggtt 120
caactcaaaa aatattaaca gcaatgattg ggttaaataa caaaacatta gacgataaaa 180
caagttataa aatcgatggt aaaggttggc aaaaagataa atcttggggt ggttacaacg 240
ttacaagata tgaagtggta aatggtaata tcgacttaaa acaagcaata gaatcatcag 300
ataacatttt ctttgctaga gtagcactcg aattaggcag taagaaattt gaaaaaggca 360
tgaaaaaact aggtgttggt gaagatatac caagtgatta tccattttat aatgctcaaa 420
tttcaaacaa aaatttagat aatgaaatat tattagctga ttcaggttac ggacaaggtg 480
aaatactgat taacccagta cagatccttt caatctatag cgcattagaa aataatggca 540
atattaacgc acctcactta ttaaaagaca cgaaaaacaa agtttggaag aaaaatatta 600
tttccaaaga aaatatcaat ctattaactg atggtatgca acaagtcgta aataaaacac 660
ataaagaaga tatttataga tcttatgcaa acttaattgg caaatccggt actgcagaac 720
tcaaaatgaa acaaggagaa actggcagac aaattgggtg gtttatatca tatgataaag 780
at 782

<210> SEQ ID NO 29
<211> LENGTH: 744
<212> TYPE: DNA
<213> ORGANISM: Staphylococcus aureus

<400> SEQUENCE: 29
tatgacgtct atccatttat gtatggcatg agtaacgaag aatataataa attaaccgaa 60
gataaaaaag aacctctgct caacaagttc cagattacaa cttcaccagg ttcaactcaa 120
aaaatattaa cagcaatgat tgggttaaat aacaaaacat tagacgataa aacaagttat 180

```
aaaatcgatg gtaaaggttg gcaaaaagat aaatcttggg gtggttacaa cgttacaaga    240

tatgaagtgg taaatggtaa tatcgactta aaacaagcaa tagaatcatc agataacatt    300

ttctttgcta gagtagcact cgaattaggc agtaagaaat ttgaaaaagg catgaaaaaa    360

ctaggtgttg gtgaagatat accaagtgat tatccatttt ataatgctca aatttcaaac    420

aaaaatttag ataatgaaat attattagct gattcaggtt acggacaagg tgaaatactg    480

attaacccag tacagatcct ttcaatctat agcgcattag aaaataatgg caatattaac    540

gcacctcact tattaaaaga cacgaaaaac aaagtttgga agaaaaatat tatttccaaa    600

gaaaatatca atctattaac tgatggtatg caacaagtcg taaataaaac acataaagaa    660

gatatttata gatcttatgc aaacttaatt ggcaaatccg gtactgcaga actcaaaatg    720

aaacaaggag aaactggcag acaa                                           744
```

<210> SEQ ID NO 30
<211> LENGTH: 652
<212> TYPE: DNA
<213> ORGANISM: Staphylococcus aureus

<400> SEQUENCE: 30

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaaacatt agacgataaa   180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aa            652
```

<210> SEQ ID NO 31
<211> LENGTH: 2436
<212> TYPE: DNA
<213> ORGANISM: Staphylococcus aureus

<400> SEQUENCE: 31

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaaacatt agacgataaa   180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600
```

```
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga aacaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct ttttctttat ctatatgcat atattgagga tcaaaagttg ttgcaaattg   1320
gataatttct tcttctgtaa tatgaaggct ttttgttttg aatgtttctc ctactataaa   1380
atcatcgtat ttcatatatg tctctctttc ttattcaaat taattttttta gtatgtaaca   1440
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
acttttagaa agtgctagtc cattcggtcc agtaatacct tttaattcta catttaaatt   1920
catattatat tcatttgcta tttttactac atcatcgaaa gttggcaaat gttcatcttt   1980
gaatttttca ccaaaccaag atcctgcaga agcatcttta atttcatcat aattcaattc   2040
agttatttcc ccggacatat ttgtagtccg ttctaaataa tcatcatgaa tgataatcag   2100
ttgttcatct tttgtaattg caacatctaa ctccaaccag tttatacctt ctacttctga   2160
agcagcttta aatgatgcaa ttgtattttc cggagcttta ctaggtaatc ctctatgtcc   2220
atatacagtt agcatattac ctctccttgc atttttattt ttttaattaa cgtaactgta   2280
ttatcacatt aatcgcactt ttatttccat taaaaagaga tgaatatcat aaataaagaa   2340
gtcgatagat tcgtattgat tatggagtta atctacgtct catctcattt ttaaaaaatc   2400
atttatgtcc caagctccat tttgtaatca agtcta                             2436

<210> SEQ ID NO 32
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 32

cgcttgccac atcaaatgat gcgggttgtg caagcg                               36


<210> SEQ ID NO 33
<211> LENGTH: 336
<212> TYPE: DNA
<213> ORGANISM: Staphylococcus epidermis
```

<400> SEQUENCE: 33
ctcattactt atgataagct tcttaaaaac ataacagcaa ttcacataaa cctcatatgt 60
tctgatacat tcaaaatccc tttatgaagc ggctgaaaaa accgcatcat ttatgatatg 120
cttcgcctct catgatctta aatgcgcgat aaatttgttc gatcaatatg acgcgcatat 180
ttggtgtggg aaggtcatat tgctaaaaga taaagcatag ttgctgcgtt gtaagacgtc 240
ttggtgtaaa ccattggagc cacctatgac aaatgtaaag tcgctttgac cttgtgtcat 300
gcgtgtttgt agttctttag cgagtccttc tgaaga 336

<210> SEQ ID NO 34
<211> LENGTH: 260
<212> TYPE: DNA
<213> ORGANISM: Staphylococcus haemolyticus

<400> SEQUENCE: 34
ctcattactt atgataagct tcttaaaaac ataacagcaa tccacataaa cctcatatgt 60
tctgatacat tcaaaatccc tttatgaagc ggctgaaaaa accgcatcat ttatgatatg 120
cttccctcgc atgattttaa atgctctgta tacttgctcg attaagacaa cgcgcatcat 180
ttgatgtggg aatgtcattt tactgaatga aagtgcgtag ttgctgcgtt gtaagacgtc 240
ctcatgcaat ccatttgatc 260

<210> SEQ ID NO 35
<211> LENGTH: 225
<212> TYPE: DNA
<213> ORGANISM: Staphylococcus aureus

<400> SEQUENCE: 35
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaggcgtatc acaaataaaa ctaaaaatgg 180
agtaactatt aatatagtat aaattcaata tggtgataaa aacag 225

<210> SEQ ID NO 36
<211> LENGTH: 225
<212> TYPE: DNA
<213> ORGANISM: Staphylococcus aureus

<400> SEQUENCE: 36
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaggcgtatc acaaataaaa ctaaaaatgg 180
agtaactatt aatatagtat aaattcaata tggtgataaa aacag 225

<210> SEQ ID NO 37
<211> LENGTH: 225
<212> TYPE: DNA
<213> ORGANISM: Staphylococcus aureus

<400> SEQUENCE: 37
ttcgtcattg gcggatcaaa cggcctgcac aaggacgtct tacaacgtag taactacgca 60
ctatcattca gcaaaatgac atttccacat caaatgatgc gggttgtgtt aattgaacaa 120
gtgtacagag catttaagat tatgcgtgga gaggcgtatc ataagtaatg aggttcatga 180

-continued tttttgacat agttagcctc cgcagtcttt caagtaaata atatc 225

<210> SEQ ID NO 38
<211> LENGTH: 225
<212> TYPE: DNA
<213> ORGANISM: Staphylococcus aureus

<400> SEQUENCE: 38
ttcgtcattg gcggatcaaa cggcctgcac aaggacgtct tacaacgcag taactacgca 60
ctatcattta gcaaaatgac attcccacat caaatgatgc gggttgtgtt aattgaacaa 120
gtgtatagag catttaagat tatgcgtgga gaggcgtatc ataagtgatg cttgttagaa 180
tgatttttaa caatatgaaa tagctgtgga agctcaaaca tttgt 225

<210> SEQ ID NO 39
<211> LENGTH: 1500
<212> TYPE: DNA
<213> ORGANISM: Staphylococcus aureus

<400> SEQUENCE: 39
tgagtctggt aaagatacac aaccaattgg taaagagaaa gtgatgaatc cagcgaaaca 60
accagcgaca ggtaaagttg tgttgttacc agcgcataga ggaactgtta gtagcggtac 120
agaaggttct gatcgcgcat tagaaggaac tgctgtatca agtaagagtg ggaaacaatt 180
ggctaacatg tcagcgccta aaggtagcgc acatgagaaa cagttaccaa aaactggaac 240
tgatcaaagt tcaagcccag cagcgatgtt tgtattagta acaggtatag gtttaatcgc 300
gactgtacga cgtagaaaag ctagctaaaa tatattgaaa acaatactac tgtatttctt 360
aaataagagg tacggtagtg ttttttttatg gaaaaaagct ataaccgttg ataaatatgg 420
gatataaaaa cggggataag taataagaca tcaaggtatt tatccacaga aatggggata 480
gttatccaga attgtgtaca atttaaagag aaatacccac aatgcccaca gagttatcca 540
caaatacaca agttatacac tgaaaattgg gcatgaatgt cagaaaaata tcaaaaactg 600
caaaaaaact tggtataata agagggaaaa gtgtgaacaa gttaataact tgtggataac 660
tggaaagttg ataacaattt ggaggaccaa acgacatgaa aatcaccatt ttagctgtag 720
ggaaactaaa agagaaatat tggaagcaag ccatagcaga atatgaaaaa cgtttaggcc 780
catacaccaa gatagacatc atagaagtta cagacgaaaa agcaccagaa aatatgagcg 840
acaaagaaat cgagcaagta aaagaaaaag aaggccaacg aatactagcc aaaatcaaac 900
cacaatccac agtcattaca ttagaaatac aaggaaagat gctatcttcc gaaggattgg 960
cccaagaatt gaaccaacgc atgacccaag ggcaaagcga ctttgtattc gtcattggcg 1020
gatcaaacgg cctgcacaag gacgtcttac aacgtagtaa ctacgcacta tcattcagca 1080
aaatgacatt tccacatcaa atgatgcggg ttgtgttaat tgaacaagtg tacagagcat 1140
ttaagattat gcgtggagaa gcttatcata aatgatgcgg ttttttcttg aaaaatttaa 1200
ttagatatta gaatccttta atttatttga aaatcagaag tgagtaacaa tggtaagtga 1260
aatagttagt gcaataattg gaattatagg gatttattga gatgtatgga gatgcggggc 1320
atttatcgag tagattacaa ttagagcatg taggtgattt gctttttcat gcaagtaaag 1380
ataaactttt aaaaatccta taagaattta gaaactttag aataactaaa tattaaaaaa 1440
atatcgtatg aaagtgaaat taggatgaga gaccatagct aaattaaaaa ttttagcaaa 1500

<210> SEQ ID NO 40
<211> LENGTH: 1501

<212> TYPE: DNA
<213> ORGANISM: Staphylococcus aureus

<400> SEQUENCE: 40

```
ttgcacaacc aattggtaaa gacaaagtga tggatccagc gaaacaacca gcgccaagta     60
aagttgtatt gttgccagcg catagaggaa ctgttagtag tggtagagaa ggttctgatc    120
gcgcattgga aggaactgct gtatcaagta agagcgggaa acaattggct agcatgtcag    180
cgcctaaagg tagcacacat gagaagcagt taccaaaaac tggaactgat caaagttcaa    240
gcccagcagc gatgtttgta ttagtagcag gtataggttt aattgcgact gtacgacgta    300
gaaaagctag ctaaaatata ttgaaaacaa tactactgta tttcttaaac aagaggtacg    360
gtagtgtttt tttatgaaaa aaagctataa ccgttgataa atatgggata taaaaacggg    420
gataagtaat aagacatcaa ggtatttatc cacagaaatg gggatagtta tccagaattg    480
tgtacaattt aaagagaaat acccacaatg cccacagagt tatccacaaa tacacaggtt    540
atacactaaa aattgggcat gaatgtcaga aaaatatcaa aaactgcaaa gaatattggt    600
ataataagag ggaacagtgt gaacaagtta ataacttgtg gataactgga aagttgataa    660
caatttggag gaccaaacga catgaaaatc accattttag ctgtagggaa actaaaagag    720
aaatattgga agcaagccat agcagaatat gaaaaacgtt taggcccata caccaagata    780
gacatcatag aagttccaga cgaaaaagca ccagaaaata tgagcgacaa agaaattgag    840
caagtaaaag aaaaagaagg ccaacgaata ctagccaaaa tcaaaccaca atcaacagtc    900
attacattag aaatacaagg aaagatgcta tcttccgaag gattggccca agaattgaac    960
caacgcatga cccaagggca aagcgacttt gtattcgtca ttggcggatc aaacggcctg   1020
cacaaggacg tcttacaacg cagtaactac gcactatcat tcagcaaaat gacattccca   1080
catcaaatga tgcgggttgt gttaattgaa caagtgtaca gagcatttaa gattatgcgt   1140
ggagaagcat atcataaatg atgcggtttt ttcagccgct tcataaaggg attttgaatg   1200
tatcagaaca tatgaggttt atgtgaattg ctgttatgtt tttaagaagc ttatcataag   1260
taatgaggtt catgattttt gacatagtta gcctccgcag tctttcattt caagtaaata   1320
atagcgaaat attctttata ctgaatactt atagtgaagc aaagttctag ctttgagaaa   1380
attctttctg caactaaata tagtaaatta cggtaaaata taaataagta catattgaag   1440
aaaatgagac ataatatatt ttataatagg agggaatttc aaatgataga caactttatg   1500
c                                                                   1501
```

<210> SEQ ID NO 41
<211> LENGTH: 2480
<212> TYPE: DNA
<213> ORGANISM: Staphylococcus aureus

<400> SEQUENCE: 41

```
aaaccgtctg gcaaacgaat taatgctatt caaattttaa ataaagagac aggtaagttt     60
gaaaatattg atttaaaacg tgtatatcac gtaacgatga atgacttcac agcatcaggt    120
ggcgacggat atagtatgtt cggtggtcct agagaagaag gtatttcatt agatcaagta    180
ctagcaagtt atttaaaaac agctaactta gctaagtatg atacgacaga accacaacgt    240
atgttattag gtaaaccagc agtaagtgaa caaccagcta aaggacaaca aggtagcaaa    300
ggtagtaagt ctggtaaaga tacacaacca attggtgacg acaaagtgat ggatccagcg    360
aaaaaaccag ctccaggtaa agttgtattg ttgctagcgc atagaggaac tgttagtagc    420
```

-continued

```
ggtacagaag gttctggtcg cacaatagaa ggagctactg tatcaagcaa gagtgggaaa    480
caattggcta gaatgtcagt gcctaaaggt agcgcgcatg agaaacagtt accaaaaact    540
ggaactaatc aaagttcaag cccagaagcg atgtttgtat tattagcagg tataggttta    600
atcgcgactg tacgacgtag aaaagctagc taaaatatat tgaaaataat actactgtat    660
ttcttaaata agaggtacgg tagtgttttt ttatgaaaaa aagcgataac cgttgataaa    720
tatgggatat aaaaacgagg ataagtaata agacatcaag gtgtttatcc acagaaatgg    780
ggatagttat ccagaattgt gtacaattta aagagaaata cccacaatgc ccacagagtt    840
acccacaaat acacaggtta tacactaaaa atcgggcata aatgtcagga aaatatcaaa    900
aactgcaaaa aatattggta taataagagg gaacagtgtg aacaagttaa taacttgtgg    960
ataactggaa agttgataac aatttggagg accaaacgac atgaaaatca ccattttagc   1020
tgtagggaaa ctaaaagaga aatattggaa gcaagccata gcagaatatg aaaaacgttt   1080
aggcccatac accaagatag acatcataga agttccagac gaaaaagcac cagaaaatat   1140
gagtgacaaa gaaattgagc aagtaaaaga aaaagaaggc caacgaatac tagccaaaat   1200
caaaccacaa tccacagtca ttacattaga aatacaagga aagatgctat cttccgaagg   1260
attggcccaa gaattgaacc aacgcatgac ccaagggcaa agcgactttg ttttcgtcat   1320
tggcggatca aacggcctgc acaaggacgt cttacaacgc agtaactacg cactatcatt   1380
cagcaaaatg acattcccac atcaaatgat gcgggttgtg ttaattgaac aagtgtacag   1440
agcatttaag attatgcgag gagaagctta tcataagtaa tgaggttcat gatttttgac   1500
atagttagcc tccgcagtct ttcatttcaa gtaaataata gcgaaatatt ctttatactg   1560
aatacttata gtgaagcaaa gttctagctt tgagaaaatt ctttctgcaa ctaaatatag   1620
taaattacgg taaaatataa ataagtacat attgaagaaa atgagacata atatatttta   1680
taataggagg gaatttcaaa tgatagacaa ctttatgcag gtccttaaat taattaaaga   1740
gaaacgtacc aataatgtag ttaaaaaatc tgattgggat aaaggtgatc tatataaaac   1800
tttagtccat gataagttac ccaagcagtt aaaagtgcat ataaaagaag ataaatattc   1860
agttgtaggg aaggttgcta ctgggaacta tagtaaagtt ccttggattt caatatatga   1920
tgagaatata acaaaagaaa caaaggatgg atattatttg gtatatcttt ttcatccgga   1980
aggagaaggc atatacttat ctttgaatca aggatggtca aagataagtg atatgtttcc   2040
gcgggataaa aatgctgcaa aacaaagagc attaacttta tcttccgaac tcaataaata   2100
tattacatca aatgaattta atactggaag attttattac gcagaaaata aagattcatc   2160
ttatgattta aaaaatgatt atccatcagg atattctcat ggatcaataa gattcaaata   2220
ttatgatttg aatgaaggat tcacagaaga agatatgcta gaggatttaa agaaattttt   2280
agaactattt aatgaattag cttcaaaagt tacaaaaaca tcctatgata gcttggtcaa   2340
tagcatagac gaaatacagg aagacagcga aattgaagaa attagaacag cacaaaaaga   2400
taagacactc aaggaagtgg aagcacctaa aggaataatt ccaaaatata aaaaaggtgt   2460
atcaaagact actaaaaatg                                               2480
```

<210> SEQ ID NO 42
<211> LENGTH: 1045
<212> TYPE: DNA
<213> ORGANISM: Staphylococcus aureus

<400> SEQUENCE: 42

```
ccagtttttt gtttaatgaa caaggtaaat tacgagataa tatttgaaga aaacaataaa     60
```

gtagagatgg atttccatat cctctttagt agcggttttt atctgtaagg tttattaata 120
attaaataaa taggcgggat agttatatat agcttattaa tgaaagaata tgattattaa 180
tttagtatta tattttaata ttaaaaagaa gatatgaaat aattattcat accttccacc 240
ttacaataat tagttttcaa tcgaatatta agattattag tagtcttaaa agttaagact 300
tccttatatt aatgacctaa tttattattt gcctcatgaa ttatcttttt atttctttga 360
tatgtcccaa accacatcgt gatatacact acaataaata ttatgatgaa actaataata 420
ttctcaaagt tcagatggaa ccaacctgct agaatagcga gtgggaagaa taggattatc 480
atcaatataa agtgaactac agtctgtttt gttatactcc aatcggtatc tgtaaatatc 540
aaattaccat aagtaaacaa aattccaatc aatgcccata gtgctacaca tattagcata 600
ataaccgctt cattaaagtt ttcataataa attttaccca taaaagaatc tggatatagt 660
ggtacatatt tatcccttga aaaaaataag tgaagtaatg acagaaatca taagaccagt 720
gaacgcacct tttgaacag cgtggaataa tttttcata gtgagatgga ccattccatt 780
tgtttctaac ttcaagtgat caatgtaatt tagattgata atttctgatt ttgaaatacg 840
cacgaatatt gaaccgacaa gctcttcaat ttggtaaagt cgctgataaa gttttaaagc 900
tttattattc attgttatcg catacctgtt tatcttctac tatgaactgt gcaatttgtt 960
ctagatcaat tgggtaaaca tgatggttct gttgcaaagt aaaaaaatat agctaaccac 1020
taatttatca tgtcagtgtt cgctt 1045

<210> SEQ ID NO 43
<211> LENGTH: 1118
<212> TYPE: DNA
<213> ORGANISM: Staphylococcus aureus

<400> SEQUENCE: 43
cagagcattt aagattatgc gtggagaagc gtaccacaaa tgatgcggtt ttttatccag 60 tttttgttt aatgaacaag gtaaattacg agataatatt tgaagaaaac aataaagtag 120
agatggattt ccatatcctc tttagtagcg gtttttatct gtaaggttta ttaataatta 180
aataaatagg cgggatagtt atatatagct tattaatgaa agaatatgat tattaattta 240
gtattatatt ttaatattaa aaagaagata tgaaataatt attcatacct tccaccttac 300
aataattagt tttcaatcga atattaagat tattagtagt cttaaaagtt aagacttcct 360
tatattaatg acctaattta ttatttgcct catgaattat ctttttattt ctttgatatg 420
tcccaaacca catcgtgata tacactacaa taaatattat gatgaaacta ataatattct 480
caaagttcag atggaaccaa cctgctagaa tagcgagtgg gaagaatagg attatcatca 540
atataaagtg aactacagtc tgttttgtta tactccaatc ggtatctgta aatatcaaat 600
taccataagt aaacaaaatt ccaatcaatg cccatagtgc tacacatatt agcataataa 660
ccgcttcatt aaagttttca taataaattt tacccataaa agaatctgga tatagtagta 720
catatttatc ccttgaaaaa aataagtgaa gtaatgacag aaatcataag accagtgaac 780
gcaccttttt gaacagcgtg gaataatttt ttcatagtga gatggaccat tccatttgtt 840
tctaacttca agtgatcaat gtaatttaga ttgataattt ctgattttga aatacgcacg 900
aatattgaac cgacaagctc ttcaatttgg taaagtcgct gataaagttt taaagcttta 960
ttattcattg ttatcgcata cctgtttatc ttctactatg aactgtgcaa tttgttctag 1020
atcaattggg taaacatgat ggttctgttg caaagtaaaa aaatatagct aaccactaat 1080
ttatcatgtc agtgttcgct taacttgcta gcatgatg 1118

<210> SEQ ID NO 44
<211> LENGTH: 1118
<212> TYPE: DNA
<213> ORGANISM: Staphylococcus aureus

<400> SEQUENCE: 44
cagagcattt aagattatgc gtggagaagc gtaccacaaa tgatgcggtt ttttatccag 60
ttttttgttt aatgaacaag gtaaattacg agataatatt tgaagaaaac aataaagtag 120
agatggattt ccatatcctc tttagtagcg gtttttatct gtaaggttta ttaataatta 180
aataaatagg cgggatagtt atatatagct tattaatgaa agaatatgat tattaattta 240
gtattatatt ttaatattaa aaagaagata tgaaataatt attcatacct tccaccttac 300
aataattagt tttcaatcga atattaagat tattagtagt cttaaaagtt aagacttcct 360
tatattaatg acctaattta ttatttgcct catgaattat ctttttattt ctttgatatg 420
tcccaaacca catcgtgata tacactacaa taaatattat gatgaaacta ataatattct 480
caaagttcag atggaaccaa cctgctagaa tagcgagtgg gaagaatagg attatcatca 540
atataaagtg aactacagtc tgttttgtta tactccaatc ggtatctgta aatatcaaat 600
taccataagt aaacaaaatt ccaatcaatg cccatagtgc tacacatatt agcataataa 660
ccgcttcatt aaagttttca taataaattt tacccataaa agaatctgga tatagtagta 720
catatttatc ccttgaaaaa aataagtgaa gtaatgacag aaatcataag accagtgaac 780
gcaccttttt gaacagcgtg gaataatttt ttcatagtga gatggaccat tccatttgtt 840
tctaacttca agtgatcaat gtaatttaga ttgataattt ctgattttga aatacgcacg 900
aatattgaac cgacaagctc ttcaatttgg taaagtcgct gataaagttt taaagcttta 960
ttattcattg ttatcgcata cctgtttatc ttctactatg aactgtgcaa tttgttctag 1020
atcaattggg taaacatgat ggttctgttg caaagtaaaa aaatatagct aaccactaat 1080
ttatcatgtc agtgttcgct taacttgcta gcatgatg 1118

<210> SEQ ID NO 45
<211> LENGTH: 1113
<212> TYPE: DNA
<213> ORGANISM: Staphylococcus aureus

<400> SEQUENCE: 45
agcatttaag attatgcgtg gagaagcgta ccacaaatga tgcggttttt tatccagttt 60
tttgtttaat gaacaaggta aattacgaga taatatttga agaaaacaat aaagtagaga 120
tggatttcca tatcctcttt agtagcggtt tttatctgta aggtttatta ataattaaat 180
aaataggcgg gatagttata tatagcttat taatgaaaga atatgattat taatttagta 240
ttatatttta atattaaaaa gaagatatga aataattatt catacttcc accttacaat 300 aattagtttt caatcgaata ttaagattat tagtagtctt aaaagttaag acttccttat 360
attaatgacc taatttatta tttgcctcat gaattatctt tttatttctt tgatatgtcc 420
caaaccacat cgtgatatac actacaataa atattatgat gaaactaata atattctcaa 480
agttcagatg gaaccaacct gctagaatag cgagtgggaa gaataggatt atcatcaata 540
taaagtgaac tacagtctgt tttgttatac tccaatcggt atctgtaaat atcaaattac 600
cataagtaaa caaaattcca atcaatgccc atagtgctac acatattagc ataataaccg 660
cttcattaaa gttttcataa taaattttac ccataaaaga atctggatat agtggtacat 720
atttatccct tgaaaaaaat aagtgaagta atgacagaaa tcataagacc agtgaacgca 780
cctttttgaa cagcgtggaa taatttttc atagtgagat ggaccattcc atttgtttct 840
aacttcaagt gatcaatgta atttagattg ataatttctg attttgaaat acgcacgaat 900
attgaaccga caagctcttc aatttggtaa agtcgctgat aaagttttaa agctttatta 960
ttcattgtta tcgcatacct gtttatcttc tactatgaac tgtgcaattt gttctagatc 1020
aattgggtaa acatgatggt tctgttgcaa agtaaaaaaa tatagctaac cactaattta 1080
tcatgtcagt gttcgcttaa cttgctagca tga 1113

<210> SEQ ID NO 46
<211> LENGTH: 2153
<212> TYPE: DNA
<213> ORGANISM: Staphylococcus aureus

<400> SEQUENCE: 46
ctgtagggaa actaaaagag aaatactgga agcaagccat agcagaatat gaaaaacgtt 60
taggcccata caccaagata gacatcatag aagttccaga cgaaaaagca ccagaaaata 120
tgagcgacaa agaaatcgag caagtaaaag aaaaagaagg ccaacgaata ctagccaaaa 180
tcaaaccaca atccacagtc attacattag aaatacaagg aaagatgcta tcttccgaag 240
gattggccca agaattgaac caacgcatga cccaagggca aagcgacttt gtattcgtca 300
ttggcggatc aaacggcctg cacaaggacg tcttacaacg cagtaactac gcactatcat 360
tcagcaaaat gacattccca catcaaatga tgcgggttgt gttaattgaa caagtgtaca 420
gagcatttaa gattatgcgt ggagaagcgt accacaaatg atgcggtttt ttatccagtt 480
ttttgtttaa tgaacaaggt aaattacgag ataatatttg aagaaaacaa taaagtagag 540
atggatttcc atatcctctt tagtagcggt ttttatctgt aaggtttatt aataattaaa 600
taaataggcg ggatagttat atatagctta ttaatgaaag aatatgatta ttaatttagt 660
attatatttt aatattaaaa agaagatatg aaataattat tcataccttc caccttacaa 720
taattagttt tcaatcgaat attaagatta ttagtagtct taaaagttaa gacttcctta 780
tattaatgac ctaatttatt atttgcctca tgaattatct ttttatttct ttgatatgtc 840
ccaaaccaca tcgtgatata cactacaata aatattatga tgaaactaat aatattctca 900
aagttcagat ggaaccaacc tgctagaata gcgagtggga agaataggat tatcatcaat 960
ataaagtgaa ctacagtctg ttttgttata ctccaatcgg tatctgtaaa tatcaaatta 1020
ccataagtaa acaaaattcc aatcaatgcc catagtgcta cacatattag cataataacc 1080
gcttcattaa agttttcata ataaatttta cccataaaag aatctggata tagtggtaca 1140
tatttatccc ttgaaaaaaa taagtgaagt aatgacagaa atcataagac cagtgaacgc 1200
acctttttga acagcgtgga ataatttttt catagtgaga tggaccattc catttgtttc 1260
taacttcaag tgatcaatgt aatttagatt gataatttct gattttgaaa tacgcacgaa 1320
tattgaaccg acaagctctt caatttggta aagtcgctga taaagtttta aagctttatt 1380
attcattgtt atcgcatacc tgtttatctt ctactatgaa ctgtgcaatt tgttctagat 1440
caattgggta aacatgatgg ttctgttgca aagtaaaaaa atatagctaa ccactaattt 1500
atcatgtcag tgttcgctta acttgctagc atgatgctaa tttcgtggca tggcgaaaat 1560
ccgtagatct gatgagacct gcggttcttt ttatatagag cgtaaataca ttcaatacct 1620
tttaaagtat tctttgctgt attgatactt tgataccttg tctttcttac tttaatatga 1680

```
cggtgatctt gctcaatgag gttattcaaa tatttcgatg tacaatgaca gtcaggttta   1740

agtttaaaag ctttaattac tttagccatt gctaccttcg ttgaaggtgc ctgatctgta   1800

attacctttt gaggtttacc aaattgttta atgagacgtt taataaacgc atatgctgaa   1860

tgattatctc gttgcttacg caaccaaata tctaatgtat gtccctctgc atcaatggca   1920

cgatataaat agctccattt tccttttatt ttgatgtacg tctcatcaat acgccatttg   1980

taataagctt ttttatgctt tttcttccaa atttgatata aaattggggc atattcttga   2040

acccaacggt agaccgttga atgatgaacg tttacaccac gtccccttaa tatttcagat   2100

atatcacgat aactcaatgc atatcttaga tagtagccaa cggctacagt gat          2153
```

```
<210> SEQ ID NO 47
<211> LENGTH: 737
<212> TYPE: DNA
<213> ORGANISM: Staphylococcus aureus

<400> SEQUENCE: 47

tttaagatta tgcgtggaga agcatatcat aaatgatgcg gttatttcag ccgtaatttt     60

ataatataaa gcagagttta ttaaatttta atgattactt tttattaaga attaattcta    120

gttgatatat tataatgtga aacacaaaat aataatttgt aattgttagt ttataggcat    180

ctgtatttgg aatttttttgt agactattta aaaaatagtg tatataagta ttgagttcat    240

gtattaactg tcttttttca tcgttcatca agtataagga tgtagagatt tgttggataa    300

tttcttcgga tgtttttaaa attatcatta aattagatgg tatctgatct tgagttttgt    360

ttttagtgta tgtatatttt aaaaaatttt tgattgttgt tatttgactc tcttttaatt    420

tgacaccctc atcaataaat gtgttaaata tatcttcatt tgtacttaaa tcatcaaaat    480

ttgccaacaa atatttgaac gtctctaaat cattatgttt gagttccgtt ttgctattcc    540

ataattccaa accatttggt agaaagccca agctgtgatt ttgatctccc catatagctg    600

aatttaaatc agtgagttga ttaatttttt caacacagaa atgtaatttt ggaatgagga    660

atcgaagttg ttcttctact tgctgtactt ttcttttgtt ttcaataaaa tttctacacc    720

atactgttat caaaccg                                                   737
```

```
<210> SEQ ID NO 48
<211> LENGTH: 1592
<212> TYPE: DNA
<213> ORGANISM: Staphylococcus aureus

<400> SEQUENCE: 48

aactaaaaga gaaatattgg aagcaagcca tagcagaata tgaaaaacgt ttaggcccat     60

acaccaagat agacatcata gaagttccag acgaaaaagc accagaaaat atgagtgaca    120

aagaaattga gcaagtaaaa gaaaaagaag gccaacgaat actagccaaa atcaaaccac    180

aatccacagt cattacatta gaaatacaag gaaagatgct atcttccgaa ggattggccc    240

aagaattgaa ccaacgcatg acccaagggc aaagcgactt tgttttcgtc attggcggat    300

caaacggcct gcacaaggac gtcttacaac gcagtaacta cgcactatca ttcagcaaaa    360

tgacattccc acatcaaatg atgcgggttg tgttaattga acaagtgtac agagcattta    420

agattatgcg aggagaagca tatcataaat gatgcggtta tttcagccgt aattttataa    480

tataaagcag agtttattaa attttaatga ttactttta ttaagaatta attctagttg     540

atatattata atgtgaaaca caaaataata atttgtaatt gttagtttat aggcatctgt    600

atttggaatt ttttgtagac tatttaaaaa atagtgtata taagtattga gttcatgtat    660
```

taactgtctt ttttcatcgt tcatcaagta taaggatgta gagatttgtt ggataatttc 720
ttcggatgtt tttaaaatta tcattaaatt agatggtatc tgatcttgag ttttgttttt 780
agtgtatgta tattttaaaa aatttttgat tgttgttatt tgactctctt ttaatttgac 840
accctcatca ataaatgtgt taaatatatc ttcatttgta cttaaatcat caaaatttgc 900
caacaaatat ttgaacgtct ctaaatcatt atgtttgagt tccgttttgc tattccataa 960
ttccaaacca tttggtagaa agcccaagct gtgattttga tctccccata tagctgaatt 1020
taaatcagtg agttgattaa tttttcaac acagaaatgt aattttggaa tgaggaatcg 1080
aagttgttct tctacttgct gtacttttct tttgttttca ataaaatttc tacaccatac 1140
tgttatcaaa ccgccaatta ttgtgcacaa tcctccaatg attgtagata aaattgacaa 1200
tatattacac acctttctta gaggtttatt aacatctatt tttgaattta aaattattac 1260
tttggtagcg ttataaccta tttaacagat tagagaaaaa ttgaatgatc gattgaagaa 1320
tttccaaaat accgtcccat atgcgttgaa ggagatttct attttcttct gtattcaaat 1380
ctttggcttt atcctttgct ttattcaata aatcatctga gttttttca atatttttta 1440 atacatcttt ggcattttgt ttaaatactt taggatcgga agttagggca ttagagtttg 1500
ccacattaat catattatta ttaatcattt gaatttgatt atctgataat atctctgata 1560
acctacgctc atcgaggact ttattaacag tg 1592

<210> SEQ ID NO 49
<211> LENGTH: 730
<212> TYPE: DNA
<213> ORGANISM: Staphylococcus aureus

<400> SEQUENCE: 49
agcatttaag attatgcgtg gagaagcata tcataaatga tgcggttatt tcagccgtaa 60
ttttataata taaagcagag tttattaaat tttaatgatt actttttatt aagaattaat 120
tctagttgat atattataat gtgaaacaca aaataataat ttgtaattgt tagtttatag 180
gcatctgtat ttggaatttt ttgtagacta tttaaaaaat agtgtatata agtattgagt 240
tcatgtatta actgtctttt ttcatcgttc atcaagtata aggatgtaga gatttgttgg 300
ataatttctt cggatgtttt taaaattatc attaaattag atggtatctg atcttgagtt 360
ttgtttttag tgtatgtata ttttaaaaaa tttttgattg ttgttatttg actctctttt 420
aatttgacac cctcatcaat aaatgtgtta aatatatctt catttgtact taaatcatca 480
aaatttgcca acaaatattt gaacgtctct aaatcattat gtttgagttc cgttttgcta 540
ttccataatt ccaaaccatt tggtagaaag cccaagctgt gattttgatc tccccatata 600
gctgaattta aatcagtgag ttgattaatt ttttcaacac agaaatgtaa ttttggaatg 660
aggaatcgaa gttgttcttc tacttgctgt acttttcttt tgttttcaat aaaatttcta 720
caccatactg 730

<210> SEQ ID NO 50
<211> LENGTH: 1696
<212> TYPE: DNA
<213> ORGANISM: Staphylococcus aureus

<400> SEQUENCE: 50
aaagagaaat attggaagca agccatagca gaatatgaaa aacgtttagg cccatacacc 60
aagatagaca tcatagaagt tccagacgaa aaagcaccag aaaatatgag tgacaaagaa 120
attgagcaag taaaagaaaa agaaggccaa cgaatactag ccaaaatcaa accacaatcc 180
acagtcatta cattagaaat acaaggaaag atgctatctt ccgaaggatt ggcccaagaa 240
ttgaaccaac gcatgaccca agggcaaagc gactttgttt tcgtcattgg cggatcaaac 300
ggcctgcaca aggacgtctt acaacgcagt aactacgcac tatcattcag caaaatgaca 360
ttcccacatc aaatgatgcg ggttgtgtta attgaacaag tgtacagagc atttaagatt 420
atgcgaggag aagcatatca taaatgatgc ggttatttca gccgtaattt tataatataa 480
agcagagttt attaaatttt aatgattact ttttattaag aattaattct agttgatata 540
ttataatgtg aaacacaaaa taataatttg taattgttag tttataggca tctgtatttg 600 gaatttttg tagactattt aaaaaatagt gtatataagt attgagttca tgtattaact 660
gtcttttttc atcgttcatc aagtataagg atgtagagat ttgttggata atttcttcgg 720
atgtttttaa aattatcatt aaattagatg gtatctgatc ttgagttttg tttttagtgt 780
atgtatattt taaaaaattt ttgattgttg ttatttgact ctcttttaat ttgacaccct 840
catcaataaa tgtgttaaat atatcttcat ttgtacttaa atcatcaaaa tttgccaaca 900
aatatttgaa cgtctctaaa tcattatgtt tgagttccgt tttgctattc cataattcca 960
aaccatttgg tagaaagccc aagctgtgat tttgatctcc ccatatagct gaatttaaat 1020
cagtgagttg attaattttt tcaacacaga aatgtaattt tggaatgagg aatcgaagtt 1080
gttcttctac ttgctgtact tttcttttgt tttcaataaa atttctacac catactgtta 1140
tcaaaccgcc aattattgtg cacaatcctc caatgattgt agataaaatt gacaatatat 1200
tacacacctt tcttagaggt ttattaacat ctatttttga atttaaaatt attactttgg 1260
tagcgttata acctatttaa cagattagag aaaaattgaa tgatcgattg aagaatttcc 1320
aaaataccgt cccatatgcg ttgaaggaga tttctatttt cttctgtatt caaatctttg 1380
gctttatcct ttgctttatt caataaatca tctgagtttt tttcaatatt ttttaataca 1440
tctttggcat tttgtttaaa tactttagga tcggaagtta gggcattaga gtttgccaca 1500
ttaatcatat tattattaat catttgaatt tgattatctg ataatatctc tgataaccta 1560
cgctcatcga ggactttatt aacagtgtct tcaacttgtt gttgtgtgat ttgtttatct 1620
tgattttgtt taatatctgc aagttgttct ttaatatctg ctatagaagc atttaaagct 1680
tcatctgaat acccat 1696

<210> SEQ ID NO 51
<211> LENGTH: 2122
<212> TYPE: DNA
<213> ORGANISM: Staphylococcus aureus

<400> SEQUENCE: 51
ggaaactaaa agagaaatat tggaagcaag ccatagcaga atatgaaaaa cgtttaggcc 60
catacaccaa gatagacatc atagaagttc cagacgaaaa agcaccagaa aatatgagcg 120
acaaagaaat tgagcaagta aaagaaaaag aaggccaacg aatactagcc aaaatcaaac 180
cacaatcaac agtcattaca ttagaaatac aaggaaagat gctatcttcc gaaggattgg 240
cccaagaatt gaaccaacgc atgacccaag ggcaaagcga ctttgtattc gtcattggcg 300
gatcaaacgg cctgcacaag gacgtcttac aacgcagtaa ctacgcacta tcattcagca 360
aaatgacatt cccacatcaa atgatgcggg ttgtgttaat tgaacaagtg tacagagcat 420
ttaagattat gcgtggagaa gcgtaccaca aatgatgcgg ttttttatcc agttttttgt 480
ttaatgaaca aggtaaatta cgagataata tttgaagaaa acaataaagt agagatggat 540

-continued

```
ttccatatcc tctttagtag cggtttttat ctgtaaggtt tattaataat taaataaata    600

ggcgggatag ttatatatag cttattaatg aaagaatatg attattaatt tagtattata    660

ttttaatatt aaaaagaaga tatgaaataa ttattcatac cttccacctt acaataatta    720

gttttcaatc gaatattaag attattagta gtcttaaaag ttaagacttc cttatattaa    780

tgacctaatt tattatttgc ctcatgaatt atctttttat ttctttgata tgtcccaaac    840

cacatcgtga tatacactac aataaatatt atgatgaaac taataatatt ctcaaagttc    900

agatggaacc aacctgctag aatagcgagt gggaagaata ggattatcat caatataaag    960

tgaactacag tctgttttgt tatactccaa tcggtatctg taaatatcaa attaccataa   1020

gtaaacaaaa ttccaatcaa tgcccatagt gctacacata ttagcataat aaccgcttca   1080

ttaaagtttt cataataaat tttacccata aaagaatctg gatatagtgg tacatattta   1140

tcccttgaaa aaaataagtg aagtaatgac agaaatcata agaccagtga acgcaccttt   1200

ttgaacagcg tggaataatt ttttcatagt gagatggacc attccatttg tttctaactt   1260

caagtgatca atgtaattta gattgataat ttctgatttt gaaatacgca cgaatattga   1320

accgacaagc tcttcaattt ggtaaagtcg ctgataaagt tttaaagctt tattattcat   1380

tgttatcgca tacctgttta tcttctacta tgaactgtgc aatttgttct agatcaattg   1440

ggtaaacatg atggttctgt tgcaaagtaa aaaaatatag ctaaccacta atttatcatg   1500

tcagtgttcg cttaacttgc tagcatgatg ctaatttcgt ggcatggcga aaatccgtag   1560

atctgatgag acctgcggtt ctttttatat agagcgtaaa tacattcaat accttttaaa   1620

gtattctttg ctgtattgat actttgatac cttgtctttc ttactttaat atgacggtga   1680

tcttgctcaa tgaggttatt cagatatttc gatgtacaat gacagtcagg tttaagttta   1740

aaagctttaa ttactttagc cattgctacc ttcgttgaag gtgcctgatc tgtaattacc   1800

ttttgaggtt taccaaattg tttaatgaga cgtttgataa acgcatatgc tgaatgatta   1860

tctcgttgct tacgcaacca aatatctaat gtatgtccct ctgcatcaat ggcacgatat   1920

aaatagctcc attttccttt tattttgatg tacgtctcat caatacgcca tttgtaataa   1980

gctttttat gctttttctt ccaaatttga tacaaaattg gggcatattc ttgaacccaa   2040

cggtagaccg ttgaatgatg aacgtttaca ccacgttccc ttaatatttc agatatatca   2100

cgataactca atgtatatct ta                                            2122
```

<210> SEQ ID NO 52
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 52

```
gatagactaa ttatcttcat c                                               21
```

<210> SEQ ID NO 53
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 53

```
cagactgtgg acaaactgat t                                               21
```

<210> SEQ ID NO 54
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 54
tgagatcatc tacatcttta 20

<210> SEQ ID NO 55
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 55
ggatcaaaag ctactaaatc 20

<210> SEQ ID NO 56
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 56
atgctctttg ttttgcagca 20

<210> SEQ ID NO 57
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 57
atgaaagact gcggaggcta act 23

<210> SEQ ID NO 58
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 58
atattctaga tcatcaatag ttg 23

<210> SEQ ID NO 59
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 59
aagaattgaa ccaacgcatg a 21

<210> SEQ ID NO 60
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 60
gttcaagccc agaagcgatg t 21

<210> SEQ ID NO 61
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 61
tcgggcataa atgtcaggaa aat 23

<210> SEQ ID NO 62
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 62
aaacgacatg aaaatcacca t 21

<210> SEQ ID NO 63
<211> LENGTH: 33
<212> TYPE: DNA
<213> ORGANISM: Artificial Sequence
<220> FEATURE:
<223> OTHER INFORMATION: Synthetic nucleic acid sequence

<400> SEQUENCE: 63
ttattaggta aaccagcagt aagtgaacaa cca 33

<210> SEQ ID NO 64
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 64
ggatcaaacg gcctgcaca 19

<210> SEQ ID NO 65
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 65
cacagaaatg taattttgga atgagg 26

<210> SEQ ID NO 66
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 66
gtcaaaaatc atgaacctca ttacttatg 29

<210> SEQ ID NO 67

<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 67
atttcatata tgtaattcct ccacatctc 29

<210> SEQ ID NO 68
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 68
tctacggatt ttcgccatgc 20

<210> SEQ ID NO 69
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 69
aacaggtgaa ttattagcac ttgtaag 27

<210> SEQ ID NO 70
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 70
atcaaatgat gcgggttgtg t 21

<210> SEQ ID NO 71
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 71
tcattggcgg atcaaacgg 19

<210> SEQ ID NO 72
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 72
acaacgcagt aactacgcac ta 22

<210> SEQ ID NO 73
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 73
taactacgca ctatcattca gc 22

<210> SEQ ID NO 74
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 74
acatcaaatg atgcgggttg tg 22

<210> SEQ ID NO 75
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 75
tcaaatgatg cgggttgtgt ta 22

<210> SEQ ID NO 76
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 76
caaatgatgc gggttgtgtt aatt 24

<210> SEQ ID NO 77
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 77
ctactatgaa ctgtgcaatt tgttct 26

<210> SEQ ID NO 78
<211> LENGTH: 2007
<212> TYPE: DNA
<213> ORGANISM: Staphylococcus aureus

<400> SEQUENCE: 78
atgaaaaaga taaaaattgt tccacttatt ttaatagttg tagttgtcgg gtttggtata 60
tatttttatg cttcaaaaga taaagaaatt aataatacta ttgatgcaat tgaagataaa 120
aatttcaaac aagtttataa agatagcagt tatatttcta aaagcgataa tggtgaagta 180
gaaatgactg aacgtccgat aaaaatatat aatagtttag gcgttaaaga tataaacatt 240
caggatcgta aaataaaaaa agtatctaaa aataaaaaac gagtagatgc tcaatataaa 300
attaaaacaa actacggtaa cattgatcgc aacgttcaat ttaattttgt taaagaagat 360
ggtatgtgga agttagattg ggatcatagc gtcattattc caggaatgca gaaagaccaa 420
agcatacata ttgaaaattt aaaatcagaa cgtggtaaaa ttttagaccg aaacaatgtg 480
gaattggcca atacaggaac acatatgaga ttaggcatcg ttccaaagaa tgtatctaaa 540
aaagattata aagcaatcgc taaagaacta agtatttctg aagactatat caacaacaaa 600
tggatcaaaa ttgggtacaa gatgatacct tcgttccact ttaaaaccgt taaaaaaatg 660
gatgaatatt taagtgattt cgcaaaaaaa tttcatctta caactaatga aacagaaagt 720
cgtaactatc ctctagaaaa agcgacttca catctattag gttatgttgg tcccattaac 780
tctgaagaat taaaacaaaa agaatataaa ggctataaag atgatgcagt tattggtaaa 840
aagggactcg aaaaacttta cgataaaaag ctccaacatg aagatggcta tcgtgtcaca 900
atcgttgacg ataatagcaa tacaatcgca catacattaa tagagaaaaa gaaaaaagat 960
ggcaaagata ttcaactaac tattgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc attttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaaacaaagt ttggaagaaa 1680
aatattattt ccaaagaaaa tatcaatcta ttaaatgatg gtatgcaaca agtcgtaaat 1740
aaaacacata aagaagatat ttatagatct tatgcaaact taattggcaa atccggtact 1800
gcagaactca aaatgaaaca aggagaaagt ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa 2007

<210> SEQ ID NO 79
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 79
caaatattat ctcgtaattt accttgttc 29

<210> SEQ ID NO 80
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 80
ctctgcttta tattataaaa ttacggctg 29

<210> SEQ ID NO 81
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 81
attgctgtta atatttttg agttgaa 27

<210> SEQ ID NO 82
<211> LENGTH: 2007
<212> TYPE: DNA
<213> ORGANISM: Staphylococcus aureus

<400> SEQUENCE: 82
atgaaaaaga taaaaattgt tccacttatt ttaatagttg tagttgtcgg gtttggtata 60
tatttttatg cttcaaaaga taaagaaatt aataatacta ttgatgcaat tgaagataaa 120
aatttcaaac aagtttataa agatagcagt tatatttcta aaagcgataa tggtgaagta 180
gaaatgactg aacgtccgat aaaaatatat aatagtttag gcgttaaaga tataaacatt 240
caggatcgta aaataaaaaa agtatctaaa aataaaaaac gagtagatgc tcaatataaa 300
attaaaacaa actacggtaa cattgatcgc aacgttcaat ttaattttgt taaagaagat 360
ggtatgtgga agttagattg ggatcatagc gtcattattc caggaatgca gaaagaccaa 420
agcatacata ttgaaaattt aaaatcagaa cgtggtaaaa ttttagaccg aaacaatgtg 480
gaattggcca atacaggaac agcatatgag ataggcatcg ttccaaagaa tgtatctaaa 540
aaagattata aagcaatcgc taaagaacta agtatttctg aagactatat caaacaacaa 600
atggatcaaa attgggtaca agatgatacc ttcgttccac ttaaaaccgt taaaaaaatg 660
gatgaatatt taagtgattt cgcaaaaaaa tttcatctta caactaatga aacagaaagt 720
cgtaactatc ctctagaaaa agcgacttca catctattag gttatgttgg tcccattaac 780
tctgaagaat taaaacaaaa agaatataaa ggctataaag atgatgcagt tattggtaaa 840
aagggactcg aaaaacttta cgataaaaag ctccaacatg aagatggcta tcgtgtcaca 900
atcgttgacg ataatagcaa tacaatcgca catacattaa tagagaaaaa gaaaaaagat 960
ggcaaagata ttcaactaac tattgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc attttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaacaaaagt ttggaagaaa 1680
aatattattt ccaaagaaaa tatcaatcta ttaactgatg gtatgcaaca agtcgtaaat 1740
aaaacacata aagaagatat ttatagatct tatgcaaact taattggcaa atccggtact 1800
gcagaactca aaatgaaaca aggagaaact ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa 2007

<210> SEQ ID NO 83
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 83
cccaccccac atcaaatgat gcgggttgtg ggtggg 36

<210> SEQ ID NO 84
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 84
cccgcgcgta gttactgcgt tgtaagacgt ccgcggg 37

<210> SEQ ID NO 85
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 85
gtttttatca ccatattgaa tttatac 27

<210> SEQ ID NO 86
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 86
atttacttga aagactgcgg aggag 25

<210> SEQ ID NO 87
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 87
tgtttgagct tccacagcta tttc 24

<210> SEQ ID NO 88
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 88
ccctataatt ccaattattg cactaac 27

<210> SEQ ID NO 89
<211> LENGTH: 25
<212> TYPE: DNA
<213> ORGANISM: Artificial Sequence

```
<220> FEATURE:
<223> OTHER INFORMATION: Synthetic nucleic acid sequence

<400> SEQUENCE: 89

atgaggagat aataatttgg agggt                                          25


<210> SEQ ID NO 90
<211> LENGTH: 2007
<212> TYPE: DNA
<213> ORGANISM: Staphylococcus aureus

<400> SEQUENCE: 90

atgaaaaaga taaaaattgt tccacttatt ttaatagttg tagttgtcgg gtttggtata     60

tatttttatg cttccaaaga taaagaaatt aataatacta ttgatgcaat tgaagataaa    120

aatttcaaac aagtttataa agatagcagt tatatttcta aaagcgataa tggtgaagta    180

gaaatgactg aacgtccgat aaaaatatat aatagtttag gcgttaaaga tataaacatt    240

caggatcgta aaataaaaaa agtatctaaa aataaaaaac gagtagatgc tcaatataaa    300

attaaaacaa actacggtaa cattgatcgc aacgttcaat ttaattttgt taaagaagat    360

ggtatgtgga agttagattg ggatcatagc gtcattattc caggaatgca gaaagaccaa    420

agcatacata ttgaaaattt aaaatcagaa cgtggtaaaa ttttagaccg aaacaatgtg    480

gaattggcca atacaggaac agcatatgag ataggcatcg ttccaaagaa tgtatctaaa    540

aaagattata aagcaatcgc taaagaacta agtatttctg aagactatat caaacaacaa    600

atggatcaaa attgggtaca agatgatacc ttcgttccac ttaaaaccgt taaaaaaatg    660

gatgaatatt taagtgattt cgcaaaaaaa tttcatctta caactaatga aacagaaagt    720

cgtaactatc ctctaggaaa agcgacttca catctattag gttatgttgg tcccattaac    780

tctgaagaat taaaacaaaa agaatataaa ggctataaag atgatgcagt tattggtaaa    840

aagggactcg aaaaacttta cgataaaaag ctccaacatg aagatggcta tcgtgtcaca    900

atcgttgacg ataatagcaa tacaatcgca catacattaa tagagaaaaa gaaaaaagat    960

ggcaaagata ttcaactaac tattgatgct aaagttcaaa agagtattta taacaacatg   1020

aaaaatgatt atggctcagg tactgctatc caccctcaaa caggtgaatt attagcactt   1080

gtaagcacac cttcatatga cgtctatcca tttatgtatg gcatgagtaa cgaagaatat   1140

aataaattaa ccgaagataa aaaagaacct ctgctcaaca agttccagat tacaacttca   1200

ccaggttcaa ctcaaaaaat attaacagca atgattgggt taaataacaa aacattagac   1260

gataaaacaa gttataaaat cgatggtaaa ggttggcaaa aagataaatc ttggggtggt   1320

tacaacgtta caagatatga agtggtaaat ggtaatatcg acttaaaaca agcaatagaa   1380

tcatcagata acattttctt tgctagagta gcactcgaat taggcagtaa gaaatttgaa   1440

aaaggcatga aaaaactagg tgttggtgaa gatataccaa gtgattatcc attttataat   1500

gctcaaattt caaacaaaaa tttagataat gaaatattat tagctgattc aggttacgga   1560

caaggtgaaa tactgattaa cccagtacag atcctttcaa tctatagcgc attagaaaat   1620

aatggcaata ttaacgcacc tcacttatta aaagacacga aaaacaaagt ttggaagaaa   1680

aatattattt ccaaagaaaa tatcaatcta ttaactgatg gtatgcaaca agtcgtaaat   1740

aaaacacata aagaagatat ttatagatct tatgcaaact taattggcaa atccggtact   1800

gcagaactca aaatgaaaca aggagaaact ggcagacaaa ttgggtggtt tatatcatat   1860

gataaagata atccaaacat gatgatggct attaatgtta aagatgtaca agataaagga   1920
```

atggctagct acaatgccaa aatctcaggt aaagtgtatg atgagctata tgagaacggt 1980
aataaaaaat acgatataga tgaataa 2007

<210> SEQ ID NO 91
<211> LENGTH: 2007
<212> TYPE: DNA
<213> ORGANISM: Staphylococcus aureus

<400> SEQUENCE: 91
atgaaaaaga taaaaattgt tccacttatt ttaatagttg tagttgtcgg gtttggtata 60
tatttttatg cttcaaaaga taaagaaatt aataatacta ttgatgcaat tgaagataaa 120
aatttcaaac aagtttataa agatagcagt tatatttcta aaagcgataa tggtgaagta 180
gaaatgactg aacgtccgat aaaaatatat aatagtttag gcgttaaaga tataaacatt 240
caggatcgta aaataaaaaa agtatctaaa aataaaaaac gagtagatgc tcaatataaa 300
attaaaacaa actacggtaa cattgatcgc aacgttcaat ttaattttgt taaagaagat 360
ggtatgtgga agttagattg ggatcatagc gtcattattc caggaatgca gaaagaccaa 420
agcatacata ttgaaaattt aaaatcagaa cgtggtaaaa ttttagaccg aaacaatgtg 480
gaattggcca atacaggaac agcatatgag ataggcatcg ttccaaagaa tgtatctaaa 540
aaagattata aagcaatcgc taaagaacta agtatttctg aagactatat caaacaacaa 600
atggatcaaa agtgggtaca agatgatacc ttcgttccac ttaaaaccgt taaaaaaatg 660
gatgaatatt taagtgattt cgcaaaaaaa tttcatctta caactaatga aacagaaagt 720
cgtaactatc ctctagaaaa agcgacttca catctattag gttatgttgg tcccattaac 780
tctgaagaat taaaacaaaa agaatataaa ggctataaag atgatgcagt tattggtaaa 840
aagggactcg aaaaacttta cgataaaaag ctccaacatg aagatggcta tcgtgtcaca 900
atcgttgacg ataatagcaa tacaatcgca catacattaa tagagaaaaa gaaaaaaagat 960 ggcaaagata ttcaactaac tattgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc attttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaaacaaagt ttggaagaaa 1680
aatattattt ccaaagaaaa tatcaatcta ttaactgatg gtatgcaaca agtcgtaaat 1740
aaaacacata aagaagatat ttatagatct tatgcaaact taattggcaa atccggtact 1800
gcagaactca aaatgaaaca aggagaaact ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa 2007

<210> SEQ ID NO 92
<211> LENGTH: 675
<212> TYPE: DNA
<213> ORGANISM: Staphylococcus aureus

<400> SEQUENCE: 92
atgaactatt tcagatataa acaatttaac aaggatgtta tcactgtagc cgttggctac 60
tatctaagat atacattgag ttatcgtgat atatctgaaa tattaaggga acgtggtgta 120
aacgttcatc attcaacggt ctaccgttgg gttcaagaat atgccccaat tttgtatcaa 180
atttggaaga aaaagcataa aaaagcttat tacaaatggc gtattgatga gacgtacatc 240
aaaataaaag gaaaatggag ctatttatat cgtgccattg atgcagaggg acatacatta 300
gatatttggt tgcgtaagca acgagataat cattcagcat atgcgtttat caaacgtctc 360
attaaacaat ttggtaaacc tcaaaaggta attacagatc aggcaccttc aacgaaggta 420
gcaatggcta aagtaattaa agcttttaaa cttaaacctg actgtcattg tacatcgaaa 480
tatctgaata acctcattga gcaagatcac cgtcatatta aagtaagaaa gacaaggtat 540
caaagtatca atacagcaaa gaatacttta aaaggtattg aatgtattta cgctctatat 600
aaaaagaacc gcaggtctct tcagatctac ggattttcgc catgccacga aattagcatc 660
atgctagcaa gttaa 675

<210> SEQ ID NO 93
<211> LENGTH: 675
<212> TYPE: DNA
<213> ORGANISM: Staphylococcus aureus

<400> SEQUENCE: 93
atgaactatt tcagatataa acaatttaac aaggatgtta tcactgtagc cgttggctac 60
tatctaagat atacattgag ttatcgtgat atatctgaaa tattaaggga acgtggtgta 120
aacgttcatc attcaacggt ctaccgttgg gttcaagaat atgccccaat tttgtatcaa 180
atttggaaga aaaagcataa aaaagcttat tacaaatggc gtattgatga gacgtacatc 240
aaaataaaag gaaaatggag ctatttatat cgtgccattg atgcagaggg acatacatta 300
gatatttggt tgcgtaagca acgagataat cattcagcat atgcgtttat caaacgtctc 360
attaaacaat ttggtaaacc tcaaaaggta attacagatc aggcaccttc aacgaaggta 420
gcaatggcta aagtaattaa agcttttaaa cttaaacctg actgtcattg tacatcgaaa 480
tatctgaata acctcattga gcaagatcac cgtcatatta aagtaagaaa gacaaggtat 540
caaagtatca atacagcaaa gaatacttta aaaggtattg aatgtattta cgctctatat 600
aaaaagaacc gcaggtctct tcagatctac ggattttcgc catgccacga aattagcatc 660
atgctagcaa gttaa 675

<210> SEQ ID NO 94
<211> LENGTH: 675
<212> TYPE: DNA
<213> ORGANISM: Staphylococcus aureus

<400> SEQUENCE: 94
atgaactatt tcagatataa acaatttaac aaggatgtta tcactgtagc cgttggctac 60
tatctaagat atacattgag ttatcgtgat atatctgaaa tattaaggga acgtggtgta 120
aacgttcatc attcaacggt ctaccgttgg gttcaagaat atgccccaat tttgtatcaa 180
atttggaaga aaaagcataa aaaagcttat tacaaatggc gtattgatga gacgtacatc 240
aaaataaaag gaaaatggag ctatttatat cgtgccattg atgcagaggg acatacatta 300
gatatttggt tgcgtaagca acgagttaat cattcagcat atgcgtttat caaacgtctc 360
attaaacaat ttggtaaacc tcaaaaggta attacagatc aggcaccttc aacgaaggta 420
gcaatggcta aagtaattaa agcttttaaa cttaaacctg actgtcattg tacatcgaaa 480
tatctgaata acctcattga gcaagatcac cgtcatatta aagtaagaaa gacaaggtat 540
caaagtatca atacagcaaa gaatacttta aaaggtattg aatgtattca cgctctatat 600
aaaaagaacc gcaggtctct tcagatctac ggattttcgc catgccacga aattagcatc 660
atgctagcaa gttaa 675

<210> SEQ ID NO 95
<211> LENGTH: 675
<212> TYPE: DNA
<213> ORGANISM: Staphylococcus aureus

<400> SEQUENCE: 95
atgaactatt tcagatataa acaatttaac aaggatgtta tcactgtagc cgttggctac 60
tatctaagat atacattgag ttatcgtgat atatctgaaa tattaaggga acgtggtgta 120
aacgttcatc attcaacggt ctaccgttgg gttcaagaat atgccccaat tttgtatcaa 180
atttggaaga aaaagcataa aaaagcttat tacaaatggc gtattgatga gacgtacatc 240
aaaataaaag gaaaatggag ctatttatat cgtgccattg atgcagaggg acatacatta 300
gatatttggt tgcgtaagca acgagataat cattcagcat atgcgtttat caaacgtctc 360
attaaacaat ttggtaaacc tcaaaaggta attacagatc aggcaccttc aacgaaggta 420
gcaatggcta aagtaattaa agcttttaaa cttaaacctg actgtcattg tacatcgaaa 480
tatctgaata acctcattga gcaagatcac cgtcatatta aagtaagaaa gacaaggtat 540
caaagtatca atacagcaaa gaatacttta aaaggtattg aatgtattta cgctctatat 600
aaaaagaacc gcaggtctct tcagatctac ggattttcgc catgccacga aattagcatc 660
atgctagcaa gttaa 675

<210> SEQ ID NO 96
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 96
gtaaagtgta tgatgagcta tatgagaa 28

<210> SEQ ID NO 97
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 97
gctgaaaaaa ccgcatcatt trtgrta 27

<210> SEQ ID NO 98
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 98
tttagtttta tttatgatac gcttctcca 29

<210> SEQ ID NO 99
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 99
gctgaaaaaa ccgcatcatt tatgata 27

<210> SEQ ID NO 100
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 100
ctatgtcaaa aatcatgaac ctcattac 28

<210> SEQ ID NO 101
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 101
ggaggctaac tatgtcaaaa atc 23

<210> SEQ ID NO 102
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 102
ctctataaac atcgtatgat attgc 25

<210> SEQ ID NO 103
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 103
accaaacgac atgaaaatca 20

<210> SEQ ID NO 104
<211> LENGTH: 1256
<212> TYPE: DNA
<213> ORGANISM: Staphylococcus aureus

<400> SEQUENCE: 104
ttcagaaaaa tgattaatgt gtttcaataa aatctctcct tctttgtgaa catattcatt 60
tttatactaa ttaatataat ttccaaaaaa gtttctgttt aaaagtgaaa aatattattt 120

```
accgtttgac ttaaatcttc aatatatagg tgtttatatg tatcattttg cgccaatttg    180

aataaacggg aatcaagtct gtttctgagt ttatttcaac tttcttatag taaacattgt    240

cttaatatga tgaacttcaa taaaactttc cctatgcccc ataaaatttt ctcaaaatca    300

aaaataacat accttacaac ttttaccgtc gatatcaatt gctcttttct taatttagga    360

ttgctttcaa attttgtact ataacgtgaa actacttttc cttctttata attaaaattt    420

actaattcac aatcattttt acttccattt acaaaaacat ccactgtttc taacacaaaa    480

tctaataaac ttccttttat taatcgtagg cattgtatat ttcctttcat tctttcttga    540

ttccattagt ttaaatttaa aatttcatcc atcaatttct taatttaatt gtagttccat    600

aatcaatata atttgtacag ttattatata ttctagatca tcaatagttg aaaaatggtt    660

tattaaacac tctataaaca tcgtatgata ttgcaaggta taatccaata tttcatatat    720

gtaattcctc cacatctcat taaattttta aattatacac aacctaattt ttagttttat    780

ttatgatacg cttctccacg cataatctta aatgctctgt acacttgttc aattaacaca    840

acccgcatca tttgatgtgg gaatgtcatt ttgctgaatg atagtgcgta gttactgcgt    900

tgtaagacgt ccttgtgcag gccgtttgat ccgccaatga cgaatacaaa gtcgctttgc    960

ccttgggtca tgcgttggtt caattcttgg gccaatcctt cggaagatag catctttcct   1020

tgtatttcta atgtaatgac tgttgattgt ggtttgattt tggctagtat tcgttggcct   1080

tctttttctt ttacttgctc aatttctttg tcgctcatat tttctggtgc tttttcgtct   1140

ggaacttcta tgatgtctat cttggtgtat gggcctaaac gtttttcata ttctgctatg   1200

gcttgcttcc aatatttctc ttttagtttc cctacagcta aaatggtgat tttcat       1256
```

<210> SEQ ID NO 105
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 105

```
tcatgaacct cattacttat gataagnt                                         28
```

<210> SEQ ID NO 106
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 106

```
gaaaaaaccg catcatttat gatatgnt                                         28
```

<210> SEQ ID NO 107
<211> LENGTH: 30
<212> TYPE: DNA
<213> ORGANISM: Artificial Sequence
<220> FEATURE:
<221> NAME/KEY: misc_feature
<222> LOCATION: 29
<223> OTHER INFORMATION: n = inosine
<220> FEATURE:
<223> OTHER INFORMATION: Synthetic nucleic acid sequence

<400> SEQUENCE: 107 cctaatttt agttttattt atgatacgnt 30

<210> SEQ ID NO 108
<211> LENGTH: 35
<212> TYPE: DNA
<213> ORGANISM: Artificial Sequence
<220> FEATURE:
<221> NAME/KEY: misc_feature
<222> LOCATION: 34
<223> OTHER INFORMATION: n = inosine
<220> FEATURE:
<223> OTHER INFORMATION: Synthetic nucleic acid sequence

<400> SEQUENCE: 108
cacaacctaa tttttagttt tatttatgat acgnt 35

<210> SEQ ID NO 109
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 109
tgataagcca ttcattcacc ctaa 24

<210> SEQ ID NO 110
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 110
aaggactcct aatttatgtc taattcc 27

<210> SEQ ID NO 111
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 111
atgggagtcc ttcgctattc tgtg 24

<210> SEQ ID NO 112
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 112
cactttttat tcttcaaaga tttgagc 27

<210> SEQ ID NO 113
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 113
atggaaattc ttaatcttta cttgtacc 28

<210> SEQ ID NO 114
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 114
agcatcttct ttacatcgct tact 24

<210> SEQ ID NO 115
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 115
cagcaattcw cataaacctc ata 23

<210> SEQ ID NO 116
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 116
acaaactttg aggggatttt tagtaaa 27

<210> SEQ ID NO 117
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 117
tatattgtgg catgatttct tc 22

<210> SEQ ID NO 118
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 118
cgaatggact agcactttct aaa 23

<210> SEQ ID NO 119
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 119
ttgaggatca aaagttgttg c 21

<210> SEQ ID NO 120
<211> LENGTH: 21

<212> TYPE: DNA
<213> ORGANISM: Artificial Sequence
<220> FEATURE:
<223> OTHER INFORMATION: Synthetic nucleic acid sequence

<400> SEQUENCE: 120
cgatgatttt atagtaggag a 21

<210> SEQ ID NO 121
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 121
ttcaatctct aaatctaaat cagttttg 28

<210> SEQ ID NO 122
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 122
aggcgagaaa atggaacata tcaa 24

<210> SEQ ID NO 123
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 123
ggtacaagta aagattaaga atttcc 26

<210> SEQ ID NO 124
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 124
agacaacttt atgcaggtcc tt 22

<210> SEQ ID NO 125
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 125
taactgcttg ggtaacctta tc 22

<210> SEQ ID NO 126
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 126
tattgcaggt ttcgatgttg a 21

<210> SEQ ID NO 127
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 127
tgacccatat cgcctaaaat ac 22

<210> SEQ ID NO 128
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 128
aaaggacaac aaggtagcaa ag 22

<210> SEQ ID NO 129
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 129
tctgtggata aacaccttga tg 22

<210> SEQ ID NO 130
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 130
gtttgatccg ccaatgac 18

<210> SEQ ID NO 131
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 131
ggcataaatg tcaggaaaat atc 23

<210> SEQ ID NO 132
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 132
gaggaccaaa cgacatgaaa atc 23

<210> SEQ ID NO 133
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 133
ttcgaggttg atgggaagca 20

<210> SEQ ID NO 134
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 134
cgctcgactc agggtgtt 18

<210> SEQ ID NO 135
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 135
cgttgaagat gcctttga 18

<210> SEQ ID NO 136
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 136
ttttgcaaca gccattcg 18

<210> SEQ ID NO 137
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 137
gcacacatgt tgtaagtttg c 21

<210> SEQ ID NO 138
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 138
acgcaaactt acaacatgtg tg 22

<210> SEQ ID NO 139
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 139
cgtttgtctg atttggagga ag 22

<210> SEQ ID NO 140
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 140
tttcttcatc atcggtcata aaat 24

<210> SEQ ID NO 141
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 141
ctacgtgaat caaaaacaat gga 23

<210> SEQ ID NO 142
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 142
tactgcaaag tctcgttcat cc 22

<210> SEQ ID NO 143
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 143
cataccattt tgaacgatga cctc 24

<210> SEQ ID NO 144
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 144
atgtctggtc aactttccga ctc 23

<210> SEQ ID NO 145
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 145
caatcggtat ctgtaaatat caaat 25

<210> SEQ ID NO 146
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 146
tcgcatacct gtttatcttc tact 24

<210> SEQ ID NO 147
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 147
ttggttccat ctgaactttg ag 22

<210> SEQ ID NO 148
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 148
aatggcttat caaagtgaat atgc 24

<210> SEQ ID NO 149
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 149
taatttcctt tttttccatt cctc 24

<210> SEQ ID NO 150
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 150
actagaatct ccaaatgaat ccagt 25

<210> SEQ ID NO 151
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 151
tggagttaat ctacgtctca tctc 24

<210> SEQ ID NO 152
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 152
gttcatacag aagactcctt tttg 24

<210> SEQ ID NO 153

<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 153
agttttgatt atccgaataa atgct 25

<210> SEQ ID NO 154
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 154
tttaaattca gctatatggg gaga 24

<210> SEQ ID NO 155
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 155
ttccgttttg ctattccata at 22

<210> SEQ ID NO 156
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 156
cctctgataa aaaacttgtg aaat 24

<210> SEQ ID NO 157
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 157
actactcctg gaattacaaa ctgg 24

<210> SEQ ID NO 158
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 158
gccaaaatta aaccacaatc cac 23

<210> SEQ ID NO 159
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 159
cattttgctg aatgatagtg cgta 24

<210> SEQ ID NO 160
<211> LENGTH: 48
<212> TYPE: DNA
<213> ORGANISM: Artificial Sequence
<220> FEATURE:
<223> OTHER INFORMATION: Synthetic nucleic acid sequence

<400> SEQUENCE: 160
cgaccggatt cccacatcaa atgatgcggg ttgtgttaat tccggtcg 48

<210> SEQ ID NO 161
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 161
cccgcgcrta gttactrcgt tgtaagacgt ccgcggg 37

<210> SEQ ID NO 162
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 162
ccccgtagtt actgcgttgt aagacgggg 29

<210> SEQ ID NO 163
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 163
cccgcgcata gttactgcgt tgtaagacgt ccgcggg 37

<210> SEQ ID NO 164
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 164
cccgcgcgta gttactacgt tgtaagacgt ccgcggg 37

<210> SEQ ID NO 165
<211> LENGTH: 1282
<212> TYPE: DNA
<213> ORGANISM: Staphylococcus aureus

<400> SEQUENCE: 165
accattttag ctgtagggaa actaaaagag aaatattgga agcaagccat agcagaatat 60
gaaaaacgtt taggcccata caccaagata gacatcatag aagttccaga cgaaaaagca 120
ccagaaaata tgagcgacaa agaaattgag caagtaaaag aaaaagaagg ccaacgaata 180
ctagccaaaa tcaaaccaca atccacagtc attacattag aaatacaagg aaagatgcta 240

-continued

```
tcttccgaag gattggccca agaattgaac caacgcatga cccaagggca aagcgacttt    300

gtattcgtca ttggcggatc aaacggcctg cacaaggacg tcttacaacg cagtaactat    360

gcactatcat ttagcaaaat gacattccca catcaaatga tgcgggttgt gttaattgaa    420

caagtgtata gagcatttaa gattatgcgt ggagaagcgt accacaaata aaactaaaaa    480

atatgagaaa attattaaat tagctcaaat ctttgaagaa taaaaagtga atattaagtt    540

tgataattta ggtacaagta aagattaaga atttccatta tttaatacat ggtgtgtaaa    600

tcgacttctt tttgtattag atgtttgcag taagcgatgt aaagaagatg ctaataaata    660

tgtgaggaat gattacgata ctagataagc ggctaatgaa atttttttaaa gtacatatat    720

agacatattt ttcatttagt aaaattttga atttcacttt gctaagacta gtgtctagaa    780

atttataatg atttattaac acctatttga aacttaagta taataaatga ttcggatttt    840

atttttaata aagacaaact tgaacgtagc aaagtagttt ttatgataaa taataagttt    900

taataatgtg acgcttttat ataagcacat tattatgaac aatgtgaatt gagcatctac    960

aattacatta ataaatatat aaatgatgat ttaaattcac atatatttat aatacacata   1020

ctatatgaaa gttttgatta tccgaataaa tgctaaaatt aataaaataa ttaaaggaat   1080

catacttatt atacgtatac gtttagctac tgaactactg gattcatttg gagattctag   1140

tagttctttt tcaatctcta aatctaaatc agttttgtaa taaccattaa ttcctaatct   1200

ttcatctagc tctgtacttt tttcatcatt tttatctttg ttgatatgtt ccattttctc   1260

gcctcttttt aatcaagtag aa                                            1282


<210> SEQ ID NO 166
<211> LENGTH: 1108
<212> TYPE: DNA
<213> ORGANISM: Staphylococcus aureus

<400> SEQUENCE: 166

accattttag ctgtagggaa actaaaagag aaatattgga agcaagccat agcagaatat     60

gaaaaacgtt taggcccata caccaagata gacatcatag aagttccaga cgaaaaagca    120

ccagaaaata tgagcgacaa agaaattgag caagtaaaag aaaaagaagg ccaacgaata    180

ctagccaaaa tcaaaccaca atccacagtc attacattag aaatacaagg aaagatgcta    240

tcttccgaag gattggccca agaattgaac caacgcatga cccaagggca aagcgacttt    300

gtattcgtca ttggcggatc aaacggcctg cacaaggacg tcttacaacg cagtaactat    360

gcactatcat ttagcaaaat gacattccca catcaaatga tgcgggttgt gttaattgaa    420

caagtgtata gagcatttaa gattatgcgt ggagaagcgt accacaaata aaactaaaaa    480

atatgagaaa attattaaat tagctcaaat ctttgaagaa taaaaagtga atattaagtt    540

tgataattta ggtacaagta aagattaaga atttccatta tttaatacat ggtgtgtaaa    600

tcgacttctt tttgtattag atgtttgcag taagcgatgt aaagaagatg ctaataaata    660

tgtgaggaat gattacgata ctagataagc ggctaatgaa atttttttaaa gtacatatat    720

agacatattt ttcatttagt aaaattttga atttcacttt gctaagacta gtgtctagaa    780

atttataatg atttattaac acctatttga aacttaagta taataaatga ttcggatttt    840

atttttaata aagacaaact tgaacgtagc aaagtagttt ttatgataaa taataagttt    900

taataatgtg acgcttttat ataagcacat tattatgaac aatgtgaatt gagcatctac    960

aattacatta ataaatatat aaatgatgat ttaaattcac atatatttat aatacacata   1020

ctatatgaaa gttttgatta tccgaataaa tgctaaaatt aataaaataa ttaaaggaat   1080
```

-continued

```
catacttatt atacgtatac gtttagct                                        1108

<210> SEQ ID NO 167
<211> LENGTH: 1530
<212> TYPE: DNA
<213> ORGANISM: Staphylococcus aureus

<400> SEQUENCE: 167

ttagctgtag ggaaactaaa agagaaatat tggaagcaag ccatagcaga atatgaaaaa      60

cgtttaggcc catacaccaa gatagacatc atagaagttc cagacgaaaa agcaccagaa     120

aatatgagcg acaaagaaat tgagcaagta aaagaaaaag aaggccaacg aatactagcc     180

aaaatcaaac cacaatccac agtcattaca ttagaaatac aaggaaagat gctatcttcc     240

gaaggattgg cccaagaatt gaaccaacgc atgacccaag ggcaaagcga ctttgtattc     300

gtcattggcg gatcaaacgg cctgcacaag gacgtcttac aacgcagtaa ctatgcacta     360

tcatttagca aaatgacatt cccacatcaa atgatgcggg ttgtgttaat tgaacaagtg     420

tatagagcat ttaagattat gcgtggagaa gcatatcata aatgatgcgg tttttttcagc     480

cgcttcataa agggggtga tcatatcgga acgtatgagg tttatgagaa ttgctgctat     540

gtttttatga agcgtatcat aaatgatgca gtttttgata atttttctt tatcagagat     600

tttactaaaa atcccctcaa agtttgtttt tttcaacttc aactttgaag ggaataaata     660

aggaacttat ttatatttat cctttatctc attaatatct attttttat taataatatt      720

ataaatatta aattctttag aaaagtcact atcactctta ttcttcatac taaacgttat     780

taatctaata atatcagcta ctatttcttt aaattctatt gcatcttctt ttttataagt     840

agcgcctgta tgaacaattt tatttctcat accatagtaa tctttcatat atttttttac     900

acaattttta atttcattag aattatccaa atctagatta tcaattgtct ttaataaatg     960

atcattaaca acattagcat acccacatcc aagcttcttt tttatctctt catcacttaa    1020

attttcatct aatttataat atctttctaa aaaatttgtg ataaaaactt ctaatgcagt    1080

ctgaatttgt acaattgcta aattatagtc agatttataa aaagaacgtt caccttttct    1140

catagccaaa acataaatat tgctaggatg attattgaaa atattataat tttttttaat    1200

atttaataaa tcactttttt tgatagatga atactgatct tcttctatct ttccaggcat    1260

gtcaatcatg aaaatactca tctcttttat atttccatct atagtatata ttatataata    1320

tggaatactt aatatatccc ctaatgatag ctggtatata ttatgatact gatatttaac    1380

gctaataatt ttaataagat tatttagaca attaaattgc ttattaaaaa ttttcgttag    1440

actattactt ttctttgatt ccctagaagt agaatttgat ttcaattttt taaactgatt    1500

gtgcttgatt attgaagtta tttcaacata                                      1530

<210> SEQ ID NO 168
<211> LENGTH: 1256
<212> TYPE: DNA
<213> ORGANISM: Staphylococcus aureus

<400> SEQUENCE: 168

gctgtaggga aactaaaaga gaaatattgg aagcaagcca tagcagaata tgaaaaacgt      60

ttaggcccat acaccaagat agacatcata gaagttccag acgaaaaagc accagaaaat     120

atgagcgaca aagaaattga gcaagtaaaa gaaaaagaag gccaacgaat actagccaaa     180

attaaaccac aatccacagt cattacatta gaaatacaag gaaagatgct atcttccgaa     240
```

```
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gattttgaat gtatcagaac atatgaggtt tatgtgaatt gctgttatgt    540
ttttaagaag catatcataa gtgatgcggt ttttattaat tagttgctaa aaaatgaagt    600
atgcaatatt aattattatt aaattttgat atatttaaag aaagattaag tttagggtga    660
atgaatggct tatcaaagtg aatatgcatt agaaaatgaa gtacttcaac aacttgagga    720
attgaactat gaaagagtaa atatacataa tattaaatta gaaattaatg aatatctcaa    780
agaactagga gtgttgaaaa atgaataagc agacaaatac tccagaacta agatttccag    840
agtttgatga ggaatggaaa aaaaggaaat taggtgaagt agtaaattat aaaaatggtg    900
gttcatttga aagtttagtg aaaaaccatg gtgtatataa actcataact cttaaatctg    960
ttaatacaga aggaaagttg tgtaattctg gaaaatatat cgatgataaa tgtgttgaaa   1020
cattgtgtaa tgatacttta gtaatgatac tgagcgagca agcaccagga ctagttggaa   1080
tgactgcaat tatacctaat aataatgagt atgtactaaa tcaacgagta gcagcactag   1140
tgcctaaaca atttatagat agtcaatttc tatctaagtt aattaataga aaccagaaat   1200
atttcagtgt gagatctgct ggaacaaaag tgaaaaatat ttctaaagga catgta       1256
```

<210> SEQ ID NO 169
<211> LENGTH: 846
<212> TYPE: DNA
<213> ORGANISM: Staphylococcus aureus

<400> SEQUENCE: 169

```
ttacattaga aatacaagga aagatgctat cttccgaagg attggcccaa gaattgaacc     60
aacgcatgac ccaagggcaa agcgactttg ttttcgtcat tggcggatca aacggcctgc    120
acaaggacgt cttacaacgc agtaactacg cactatcatt cagcaaaatg acattcccac    180
atcaaatgat gcgggttgtg ttaattgaac aagtgtacag agcatttaag attatgcgag    240
gagaagctta tcataagtaa tgaggttcat gatttttgac atagttagcc tccgcagtct    300
ttcatttcaa gtaaataata gcgaaatatt ctttatactg aatacttata gtgaagcaaa    360
gttctagctt tgagaaaatt ctttctgcaa ctaaatatag taaattacgg taaaatataa    420
ataagtacat attgaagaaa atgagacata atatatttta taataggagg gaatttcaaa    480
tgatagacaa ctttatgcag gtccttaaat taattaaaga gaaacgtacc aataatgtag    540
ttaaaaaatc tgattgggat aaaggtgatc tatataaaac tttagtccat gataagttac    600
ccaagcagtt aaaagtgcat ataaaagaag ataaatattc agttgtaggg aaggttgcta    660
ctgggaacta tagtaaagtt ccttggattt caatatatga tgagaatata acaaaagaaa    720
caaaggatgg atattatttg gtatatcttt ttcatccgga aggagaaggc atatacttat    780
ctttgaatca aggatggtca aagataagtg atatgtttcc gcgggataaa aatgctgcaa    840
aacaaa                                                               846
```

<210> SEQ ID NO 170
<211> LENGTH: 1270
<212> TYPE: DNA
<213> ORGANISM: Staphylococcus aureus

<400> SEQUENCE: 170

```
cattagaaat acaaggaaag atgctatctt ccgaaggatt ggcccaagaa ttgaaccaac     60
gcatgaccca agggcaaagc gactttgtat tcgtcattgg cggatcaaac ggcctgcaca    120
aggacgtctt acaacgcagt aactatgcac tatcatttag caaaatgaca ttcccacatc    180
aaatgatgcg ggttgtgtta attgaacaag tgtatagagc atttaagatt atgcgtggag    240
aagcatatca taaatgatgc ggttttttca gccgcttcat aaagggattt tgaatgtatc    300
agaacatatg aggtttatgt gaattgctgt tatgttttta agaagcttat cataagtaat    360
gaggttcatg atttttgaca tagttagcct ccgcagtctt tcatttcaag taaataatag    420
cgaaatattc tttatactga atacttatag tgaagcaaag ttctagcttt gagaaaattc    480
tttctgcaac taaatatagt aaattacggt aaaatataaa taagtacata ttgaagaaaa    540
tgagacataa tatattttat aataggaggg aatttcaaat gatagacaac tttatgcagg    600
tccttaaatt aattaaagag aaacgtacca ataatgtagt taaaaaatct gattgggata    660
aaggtgatct atataaaact ttagtccatg ataagttacc caagcagtta aaagtgcata    720
taaaagaaga taaatattca gttgtaggga aggttgctac tgggaactat agtaaagttc    780
cttggatttc aatatatgat gagaatataa caaaagaaac aaaggatgga tattatttgg    840
tatatctttt tcatccggaa ggagaaggca tatacttatc tttgaatcaa ggatggtcaa    900
agataagtga tatgtttccg cgggataaaa atgctgcaaa acaaagagca ttaactttat    960
cttccgaact caataaatat attacatcaa atgaatttaa tactggaaga ttttattacg   1020
cagaaaataa agattcatct tatgatttaa aaaatgatta tccatcagga tattctcatg   1080
gatcaataag attcaaatat tatgatttga atgaaggatt cacagaagaa gatatgctag   1140
aggatttaaa gaaattttta gaactattta atgaattagc ttcaaaagtt acaaaaacat   1200
cctatgatag cttggtcaat agcatagacg aaatacagga agacagcgaa attgaagaaa   1260
ttagaacagc                                                           1270
```

<210> SEQ ID NO 171
<211> LENGTH: 991
<212> TYPE: DNA
<213> ORGANISM: Staphylococcus aureus

<400> SEQUENCE: 171

```
accattttag ctgtagggaa actaaaagag aaatactgga agcaagccat agcagaatat     60
gaaaaacgtt taggcccata caccaagata gacatcatag aagttccaga cgaaaaagca    120
ccagaaaata tgaactacaa agaaattgag caagtaaaag aaaaagaagg ccaacgaata    180
ctagccaaaa tcaaaccaca atcaacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgaa    420
caagtgtaca gagcatttaa gattatgcga ggagaagcgt atcataagtg atggtaaaaa    480
atatgagtaa gtagatgaag agtgaaaatc agattaatta ataataatgt atcaaattta    540
aataaagggg tttttaagta tgaatttaag aggtcatgaa aatagactta aatttcatgc    600
gaaatatgat gtgacaccta tatcacattt aaaattatta gaaggtcaaa agaaagacgg    660
tgaaggcggc atactgacag atagctatta ctgtttttca tacagcttaa aaggtaattc    720
taaaaaagtt ttaggtacgt ttaattgtgg ttatcatatt gctgaagatt tactaaaatt    780
```

atcaaatcaa gataaattac ctttatttaa cccgtttaaa gtaattaatg aaggtaatca 840
attgcagggc gtaacgaata aaggtaattt aaatattaat aggcaaagaa aacagtataa 900
tgaagtggct ttacagcttt caaatgctat taatttaatc ataatttgtt atgaggataa 960
tattaaagaa ccactttcaa cgataaaata c 991

<210> SEQ ID NO 172
<211> LENGTH: 748
<212> TYPE: DNA
<213> ORGANISM: Staphylococcus aureus

<400> SEQUENCE: 172
atcgtttaac gtgtcacatg atgcgataga tccgcaattt tatattttcc ataataacta 60
taagaagttt acgattttaa cagatacggg ttacgtgtct gatcgtatga aaggtatgat 120
acgtggcagc gatgcattta tttttgagag taatcatgac gtcgatatgt tgagaatgtg 180
tcgttatcca tggaagacga aacaacgcat tttaggcgat atgggtcatg tatctaatga 240
ggatgcgggt catgcgatga cagacgtgat tacaggtaac acgaaacgta tttacttatc 300
gcatttatca caagataata atatgaaaga tttggcgcgt atgagtgttg gccaagtatt 360
gaacgaacac gatattgata cggaaaaaga agtattgcta tgtgatacgg ataaagctat 420
tccaacacca atatatacaa tataaatgag agtcatccga taaagttccg cactgctgtg 480
aaacgacttt atcgggtgct tttttatgtt gttggtggga aatggctgtt gttgagttga 540
atcggattga ttgaaatgtg taaaataatt cgatattaaa tgtaatttat aaataattta 600
cataaaatca aacattttaa tataaggatt atgataatat attggtgtat gacagttaat 660
ggagggaacg aaatgaaagc tttattactt aaaacaagtg tatggctcgt tttgcttttt 720
agtgtgatgg gattatggca tgtctcga 748

<210> SEQ ID NO 173
<211> LENGTH: 917
<212> TYPE: DNA
<213> ORGANISM: Staphylococcus aureus

<400> SEQUENCE: 173
aaatacaagg aaagatgcta tcttccgaag gattggccca agaattgaac caacgcatga 60
cccaagggca aagcgacttt gtattcgtca ttggcggatc aaacggcctg cacaaggacg 120
tcttacaacg tagtaactac gcactatcat tcagcaaaat gacattccca catcaaatga 180
tgcgggttgt gttaattgag caagtgtata gagcatttaa gattatgcgt ggagaagcat 240
atcataaatg atgcggtttt ttcagccgct tcataaaggg attttgaatg tatcagaaca 300
tatgaggttt atgtgaattg ctgttatgtt tttaagaagc ttatcataag taatgaggtt 360
catgattttt gacatagtta gcctccgcag tctttcattt caagtaaata atagcgaaat 420
attctttata ctgaatactt atagtgaagc aaagttctag ctttgagaaa attctttctg 480
caactaaata tagtaaatta cggtaaaata taaataagta catattgaag aaaatgagac 540
ataatatatt ttataatagg agggaatttc aaatgataga caactttatg caggtcctta 600
aattaattaa agagaaacgt accaataatg tagttaaaaa atctgattgg gataaaggtg 660
atctatataa aactttagtc catgataagt tacccaagca gttaaaagtg catataaaag 720
aagataaata ttcagttgta gggaaggttg ctactgggaa ctatagtaaa gttccttgga 780
tttcaatata tgatgagaat ataacaaaag aaacaaagga tggatattat ttggtatatc 840
tttttcatcc ggaaggagaa ggcatatact tatctttgaa tcaaggatgg tcaaagataa 900
gtgatatgtt tccgcgg 917

<210> SEQ ID NO 174
<211> LENGTH: 1132
<212> TYPE: DNA
<213> ORGANISM: Staphylococcus aureus

<400> SEQUENCE: 174
gctgtaggga aactaaaaga gaaatattgg aagcaagcca tagcagaata tgaaaaacgt 60
ttaggcccat acaccaagat agacatcata gaagttccag acgaaaaagc accagaaaat 120
atgagcgaca aagaaattga gcaagtaaaa gaaaaagaag gccaacgaat actagccaaa 180
atcaaaccac aatcaacagt cattacatta gaaatacaag gaaagatgct atcttccgaa 240
ggattggccc aagaattgaa ccaacgcatg acccaagggc aaagcgactt tgtattcgtc 300
attggcggat caaacggcct gcacaaggac gtcttacaac gtagtaacta cgcactatca 360
ttcagcaaaa tgacattccc acatcaaatg atgcgggttg tgttaattga gcaagtgtat 420
agagcattta agattatgcg tggagaagca tatcataaat gatgcggttt tttcagccgc 480
ttcataaagg gattttgaat gtatcagaac atatgaggtt tatgtgaatt gctgttatgt 540
ttttaagaag cttatcataa gtaatgaggt tcatgatttt tgacatagtt agcctccgca 600
gtctttcatt tcaagtaaat aatagcgaaa tattctttat actgaatact tatagtgaag 660
caaagttcta gctttgagaa aattctttct gcaactaaat atagtaaatt acggtaaaat 720
ataaataagt acatattgaa gaaaatgaga cataatatat tttataatag gagggaattt 780
caaatgatag acaactttat gcaggtcctt aaattaatta aagagaaacg taccaataat 840
gtagttaaaa aatctgattg ggataaaggt gatctatata aaactttagt ccatgataag 900
ttacccaagc agttaaaagt gcatataaaa gaagataaat attcagttgt agggaaggtt 960
gctactggga actatagtaa agttccttgg atttcaatat atgatgagaa tataacaaaa 1020
gaaacaaagg atggatatta tttggtatat ctttttcatc cggaaggaga aggcatatac 1080
ttatctttga atcaaggatg gtcaaagata agtgatatgt ttccgcggga ta 1132

<210> SEQ ID NO 175
<211> LENGTH: 1133
<212> TYPE: DNA
<213> ORGANISM: Staphylococcus aureus

<400> SEQUENCE: 175
agctgtaggg aaactaaaag agaaatattg gaagcaagcc atagcagaat atgaaaaacg 60
tttaggccca tacaccaaga tagacatcat agaagttcca gacgaaaaag caccagaaaa 120
tatgagcgac aaagaaattg agcaagtaaa agaaaaagaa ggccaacgaa tactagccaa 180
aatcaaacca caatcaacag tcattacatt agaaatacaa ggaaagatgc tatcttccga 240
aggattggcc caagaattga accaacgcat gacccaaggg caaagcgact ttgtattcgt 300
cattggcgga tcaaacggcc tgcacaagga cgtcttacaa cgtagtaact acgcactatc 360
attcagcaaa atgacattcc cacatcaaat gatgcgggtt gtgttaattg agcaagtgta 420
tagagcattt aagattatgc gtggagaagc atatcataaa tgatgcggtt ttttcagccg 480
cttcataaag ggattttgaa tgtatcagaa catatgaggt ttatgtgaat tgctgttatg 540
tttttaagaa gcttatcata agtaatgagg ttcatgattt ttgacatagt tagcctccgc 600
agtctttcat ttcaagtaaa taatagcgaa atattcttta tactgaatac ttatagtgaa 660

```
gcaaagttct agctttgaga aaattctttc tgcaactaaa tatagtaaat tacggtaaaa    720

tataaataag tacatattga agaaaatgag acataatata ttttataata ggagggaatt    780

tcaaatgata gacaacttta tgcaggtcct taaattaatt aaagagaaac gtaccaataa    840

tgtagttaaa aaatctgatt gggataaagg tgatctatat aaaactttag tccatgataa    900

gttacccaag cagttaaaag tgcatataaa agaagataaa tattcagttg tagggaaggt    960

tgctactggg aactatagta aagttccttg gatttcaata tatgatgaga atataacaaa   1020

agaaacaaag gatggatatt atttggtata tctttttcat ccggaaggag aaggcatata   1080

cttatctttg aatcaaggat ggtcaaagat aagtgatatg tttccgcggg ata          1133
```

<210> SEQ ID NO 176
<211> LENGTH: 1087
<212> TYPE: DNA
<213> ORGANISM: Staphylococcus aureus

<400> SEQUENCE: 176

```
actaaaagag aaatattgga agcaagccat agcagaatat gaaaaacgtt taggcccata     60

caccaagata gacatcatag aagttccaga cgaaaaagca ccagaaaata tgagcgacaa    120

agaaattgag caagtaaaag aaaaagaagg ccaacgaata ctagccaaaa tcaaaccaca    180

atcaacagtc attacattag aaatacaagg aaagatgcta tcttccgaag gattggcaca    240

agaattgaac caacgcatga cccaagggca aagcgacttt gtattcgtca ttggcggatc    300

aaacggcctg cacaaggacg tcttacaacg tagtaactac gcactatcat tcagcaaaat    360

gacattccca catcaaatga tgcgggttgt gttaattgag caagtgtata gagcgtttaa    420

gattatgcgt ggagaagcat atcataaatg atgcggtttt ttcagccgct tcataaaggg    480

attttgaatg tatcagaaca tatgaggttt atgtgaattg ctgttatgtt tttaagaagc    540

ttatcataag taatgaggtt catgattttt gacatagtta gcctccgcag tctttcattt    600

caagtaaata atagcgaaat attctttata ctgaatactt atagtgaagc aaagttctag    660

ctttgagaaa attctttctg caactaaata tagtaaatta cggtaaaata taaataagta    720

catattgaag aaaatgagac ataatatatt ttataatagg agggaatttc aaatgataga    780

caactttatg caggtcctta aattaattaa agagaaacgt accaataatg tagttaaaaa    840

atctgattgg gataaaggtg atctatataa aactttagtc catgataagt tacccaagca    900

gttaaaagtg catataaaag aagataaata ttcagttgta gggaaggttg ctactgggaa    960

ctatagtaaa gttccttgga tttcaatata tgatgagaat ataacaaaag aaacaaagga   1020

tggatattat ttggtatatc tttttcatcc ggaaggagaa ggcatatact tatctttgaa   1080

tcaagga                                                             1087
```

<210> SEQ ID NO 177
<211> LENGTH: 903
<212> TYPE: DNA
<213> ORGANISM: Staphylococcus aureus

<400> SEQUENCE: 177

```
caaggaaaga tgctatcttc cgaaggattg gcccaagaat tgaaccaacg catgacccaa     60

gggcaaagcg actttgtatt cgtcattggc ggatcaaacg gcctgcacaa ggacgtctta    120

caacgtagta actacgcact atcattcagc aaaatgacat tcccacatca aatgatgcgg    180

gttgtgttaa ttgagcaagt gtatagagca tttaagatta tgcgtggaga agcatatcat    240

aaatgatgcg gtttttcag ccgcttcata aagggatttt gaatgtatca gaacatatga    300
```

ggtttatgtg aattgctgtt atgtttttaa gaagcttatc ataagtaatg aggttcatga 360
tttttgacat agttagcctc cgcagtcttt catttcaagt aaataatagc gaaatattct 420
ttatactgaa tacttatagt gaagcaaagt tctagctttg agaaaattct ttctgcaact 480
aaatatagta aattacggta aaatataaat aagtacatat tgaagaaaat gagacataat 540
atattttata ataggaggga atttcaaatg atagacaact ttatgcaggt ccttaaatta 600
attaaagaga aacgtaccaa taatgtagtt aaaaaatctg attgggataa aggtgatcta 660
tataaaactt tagtccatga taagttaccc aagcagttaa aagtgcatat aaaagaagat 720
aaatattcag ttgtagggaa ggttgctact gggaactata gtaaagttcc ttggatttca 780
atatatgatg agaatataac aaaagaaaca aaggatggat attatttggt atatcttttt 840
catccggaag gagaaggcat atacttatct ttgaatcaag gatggtcaaa gataagtgat 900
atg 903

<210> SEQ ID NO 178
<211> LENGTH: 1114
<212> TYPE: DNA
<213> ORGANISM: Staphylococcus aureus

<400> SEQUENCE: 178
ggaaactaaa agagaaatat tggaagcaag ccatagcaga atatgaaaaa cgtttaggcc 60
catacaccaa gatagacatc atagaagttc cagacgaaaa agcaccagaa aatatgagcg 120
acaaagaaat tgagcaagta aaagaaaaag aaggccaacg aatactagcc aaaatcaaac 180
cacaatcaac agtcattaca ttagaaatac aaggaaagat gctatcttcc gaaggattgg 240
cccaagaatt gaaccaacgc atgacccaag ggcaaagcga ctttgtattc gtcattggcg 300
gatcaaacgg cctgcacaag gacgtcttac aacgtagtaa ctacgcacta tcattcagca 360
aaatgacatt cccacatcaa atgatgcggg ttgtgttaat tgagcaagtg tatagagcat 420
ttaagattat gcgtggagaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtt 1114

<210> SEQ ID NO 179
<211> LENGTH: 1121
<212> TYPE: DNA
<213> ORGANISM: Staphylococcus aureus

<400> SEQUENCE: 179
ggaaactaaa agagaaatat tggaagcaag ccatagcaga atatgaaaaa cgtttaggcc 60

```
catacaccaa gatagacatc atagaagttc cagacgaaaa agcaccagaa aatatgagcg    120
acaaagaaat tgagcaagta aaagaaaaag aaggccaacg aatactagcc aaaatcaaac    180
cacaatccac agtcattaca ttagaaatac aaggaaagat gctatcttcc gaaggattgg    240
cccaagaatt gaaccaacgc atgacccaag ggcaaagcga ctttgtattc gtcattggcg    300
gatcaaacgg cctgcacaag gacgtcttac aacgcagtaa ctatgcacta tcatttagca    360
aaatgacatt cccacatcaa atgatgcggg ttgtgttaat tgaacaagtg tatagagcat    420
ttaagattat gcgtggagaa gcatatcata aatgatgcgg ttttttcagc cgcttcataa    480
agggattttg aatgtatcag aacatatgag gtttatgtga attgctgtta tgtttttaag    540
aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aaagaagata aatattcagt tgtagggaag gttgctactg    960
ggaactatag taaagttcct tggatttcaa tatatgatga gaatataaca aaagaaacaa   1020
aggatggata ttatttggta tatctttttc atccggaagg agaaggcata tacttatctt   1080
tgaatcaagg atggtcaaag ataagtgata tgtttccgcg g                       1121
```

<210> SEQ ID NO 180
<211> LENGTH: 1121
<212> TYPE: DNA
<213> ORGANISM: Staphylococcus aureus

<400> SEQUENCE: 180

```
tagctgtagg gaaactaaaa gagaaatatt ggaagcaagc catagcagaa tatgaaaaac     60
gtttaggccc atacaccaag atagacatca tagaagttcc agacgaaaaa gcaccagaaa    120
atatgagcga caaagaaatt gagcaagtaa aagaaaaaga aggccaacga atactagcca    180
aaatcaaacc acaatccaca gtcattacat tagaaataca aggaaagatg ctatcttccg    240
aaggattggc ccaagaattg aaccaacgca tgacccaagg gcaaagcgac tttgtattcg    300
tcattggcgg atcaaacggc ctgcacaagg acgtcttaca acgcagtaac tatgcactat    360
catttagcaa aatgacattc ccacatcaaa tgatgcgggt tgtgttaatt gaacaagtgt    420
atagagcatt taagattatg cgtggagaag catatcataa atgatgcggt tttttcagcc    480
gcttcataaa gggattttga atgtatcaga acatatgagg tttatgtgaa ttgctgttat    540
gtttttaaga agcttatcat aagtaatgag gttcatgatt tttgacatag ttagcctccg    600
cagtctttca tttcaagtaa ataatagcga aatattcttt atactgaata cttatagtga    660
agcaaagttc tagctttgag aaaattcttt ctgcaactaa atatagtaaa ttacggtaaa    720
atataaataa gtacatattg aagaaaatga gacataatat attttataat aggagggaat    780
ttcaaatgat agacaacttt atgcaggtcc ttaaattaat taaagagaaa cgtaccaata    840
atgtagttaa aaaatctgat tgggataaag gtgatctata taaaacttta gtccatgata    900
agttacccaa gcagttaaaa gtgcatataa aagaagataa atattcagtt gtagggaagg    960
ttgctactgg gaactatagt aaagttcctt ggatttcaat atatgatgag aatataacaa   1020
aagaaacaaa ggatggatat tatttggtat atctttttca tccggaagga gaaggcatat   1080
```

acttatcttt gaatcaagga tggtcaaaga taagtgatat g 1121

<210> SEQ ID NO 181
<211> LENGTH: 1131
<212> TYPE: DNA
<213> ORGANISM: Staphylococcus aureus

<400> SEQUENCE: 181
ctgtagggaa actaaaagag aaatattgga agcaagccat agcagaatat gaaaaacgtt 60
taggcccata caccaagata gacatcatag aagttccaga cgaaaaagca ccagaaaata 120
tgagcgacaa agaaattgag caagtaaaag aaaaagaagg ccaacgaata ctagccaaaa 180
tcaaaccaca atccacagtc attacattag aaatacaagg aaagatgcta tcttccgaag 240
gattggccca agaattgaac caacgcatga cccaagggca aagcgacttt gtattcgtca 300
ttggcggatc aaacggcctg cacaaggacg tcttacaacg cagtaactat gcactatcat 360
ttagcaaaat gacattccca catcaaatga tgcgggttgt gttaattgaa caagtgtata 420
gagcatttaa gattatgcgt ggagaagcat atcataaatg atgcggtttt ttcagccgct 480
tcataaaggg attttgaatg tatcagaaca tatgaggttt atgtgaattg ctgttatgtt 540
tttaagaagc ttatcataag taatgaggtt catgattttt gacatagtta gcctccgcag 600
tctttcattt caagtaaata atagcgaaat attctttata ctgaatactt atagtgaagc 660
aaagttctag ctttgagaaa attctttctg caactaaata tagtaaatta cggtaaaata 720
taaataagta catattgaag aaaatgagac ataatatatt ttataatagg agggaatttc 780
aaatgataga caactttatg caggtcctta aattaattaa agagaaacgt accaataatg 840
tagttaaaaa atctgattgg gataaaggtg atctatataa aactttagtc catgataagt 900
tacccaagca gttaaaagtg catataaaag aagataaata ttcagttgta gggaaggttg 960
ctactgggaa ctatagtaaa gttccttgga tttcaatata tgatgagaat ataacaaaag 1020
aaacaaagga tggatattat ttggtatatc tttttcatcc ggaaggagaa ggcatatact 1080
tatctttgaa tcaaggatgg tcaaagataa gtgatatgtt tccgcgggat a 1131

<210> SEQ ID NO 182
<211> LENGTH: 896
<212> TYPE: DNA
<213> ORGANISM: Staphylococcus aureus

<400> SEQUENCE: 182
cattagaaat acaaggaaag atgctatctt ccgaaggatt ggcccaagaa ttgaaccaac 60
gcatgaccca agggcaaagc gactttgtat tcgtcattgg cggatcaaac ggcctgcaca 120
aggacgtctt acaacgcagt aactatgcac tatcatttag caaaatgaca ttcccacatc 180
aaatgatgcg ggttgtgtta attgaacaag tgtatagagc atttaagatt atgcgtggag 240
aagcatatca taaatgatgc ggttttttca gccgcttcat aaagggattt tgaatgtatc 300
agaacatatg aggtttatgt gaattgctgt tatgttttta agaagcttat cataagtaat 360
gaggttcatg atttttgaca tagttagcct ccgcagtctt tcatttcaag taaataatag 420
cgaaatattc tttatactga atacttatag tgaagcaaag ttctagcttt gagaaaattc 480
tttctgcaac taaatatagt aaattacggt aaaatataaa taagtacata ttgaagaaaa 540
tgagacataa tatattttat aataggaggg aatttcaaat gatagacaac tttatgcagg 600
tccttaaatt aattaaagag aaacgtacca ataatgtagt taaaaaatct gattgggata 660
aaggtgatct atataaaact ttagtccatg ataagttacc caagcagtta aaagtgcata 720
taaaagaaga taaatattca gttgtaggga aggttgctac tgggaactat agtaaagttc 780
cttggatttc aatatatgat gagaatataa caaaagaaac aaaggatgga tattatttgg 840
tatatctttt tcatccggaa ggagaaggca tatacttatc tttgaatcaa ggatgg 896

<210> SEQ ID NO 183
<211> LENGTH: 1125
<212> TYPE: DNA
<213> ORGANISM: Staphylococcus aureus

<400> SEQUENCE: 183
ggaaactaaa agagaaatat tggaagcaag ccatatcaga atatgaaaaa cgtttaggcc 60
catacaccaa gatagacatc atagaagttc cagacgaaaa agcaccagaa aatatgagcg 120
acaaagaaat cgagcaagta aaagaaaaag aaggccaacg aatactagcc aaaatcaaac 180
cacaatcaac agtcattaca ttagaaatac aaggaaagat gctatcttcc gaaggattgg 240
ctcaagaatt gaaccaacgc atgacccaag ggcaaagcga ctttgtattc gttattggcg 300
gatcaaacgg cctgcacaag gacgtcttac aacgcagtaa ctatgcacta tcattcagca 360
aaatgacatt tccacatcag atgatgcggg ttgtgttaat tgagcaagtg tatagagcat 420
ttaagattat gcgtggggaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtttccgcg ggata 1125

<210> SEQ ID NO 184
<211> LENGTH: 679
<212> TYPE: DNA
<213> ORGANISM: Staphylococcus aureus

<400> SEQUENCE: 184
ataagaggga acagtgtgaa caagttaata acttgtggat aactggaaag ttgataacaa 60
tttggaggac caaacgacat gaaaatcacc attttagctg tagggaaact aaaagagaaa 120
tattggaagc aagccatagc agaatatgaa aaacgtttag gcccatacac caagatagac 180
atcatagaag ttccagacga aaaagcacca gaaaatatga gcgacaaaga aattgagcaa 240
gtaaaagaaa aagaaggcca acgaatacta gccaaaatca aaccacaatc cacagtcatt 300
acattagaaa tacaaggaaa gatgctatct tccgaaggat tggcccaaga attgaaccaa 360
cgcatgaccc aagggcaaag cgactttgta ttcgtcattg gcggatcaaa cggcctgcac 420
aaggacgtct tacaacgcag taactatgca ctatcattta gcaaaatgac attcccacat 480
caaatgatgc gggttgtgtt aattgaacaa gtgtatagag catttaagat tatgcgtgga 540
gaggcttatc ataaataaaa ctaaaaatta gattgtgtat aatttaaaaa tttaatgaga 600
tgtggaggaa ttacatatat gaaatattgg agtatacctt gcaatatcat acgatgttta 660
tagagtgttt aataaacca 679

<210> SEQ ID NO 185
<211> LENGTH: 1125
<212> TYPE: DNA
<213> ORGANISM: Staphylococcus aureus

<400> SEQUENCE: 185
ggaaactaaa agagaaatat tggaagcaag ccatagcaga atatgaaaaa cgtttaggcc 60
catacaccaa gatagacatc atagaagttc cagacgaaaa agcaccagaa aatatgagcg 120
acaaagaaat tgagcaagta aaagaaaaag aaggccaacg aatactagcc aaaatcaaac 180
cacaatcaac agtcattaca ttagaaatac aaggaaagat gctatcttcc gaaggattgg 240
cacaagaatt gaaccaacgc atgacccaag ggcaaagcga ctttgtattc gtcattggcg 300
gatcaaacgg cctgcacaag gacgtcttac aacgtagtaa ctacgcacta tcattcagca 360
aaatgacatt cccacatcaa atgatgcggg ttgtgttaat tgagcaagtg tatagagcgt 420
ttaagattat gcgtggagaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtttccgcg ggata 1125

<210> SEQ ID NO 186
<211> LENGTH: 926
<212> TYPE: DNA
<213> ORGANISM: Staphylococcus aureus

<400> SEQUENCE: 186
tacattagaa atacaaggaa agatgctatc ttccgaagga ttggcccaag aattgaacca 60
acgcatgacc caagggcaaa gcgactttgt attcgtcatt ggcggatcaa acggcctgca 120
caaggacgtc ttacaacgca gtaactatgc actatcattt agcaaaatga cattcccaca 180
tcaaatgatg cgggttgtgt taattgaaca agtgtataga gcatttaaga ttatgcgtgg 240
agaagcatat cataaatgat gcggtttttt cagccgcttc ataaagggat tttgaatgta 300
tcagaacata tgaggtttat gtgaattgct gttatgtttt taagaagctt atcataagta 360
atgaggttca tgatttttga catagttagc ctccgcagtc tttcatttca agtaaataat 420
agcgaaatat tctttatact gaatacttat agtgaagcaa agttctagct ttgagaaaat 480
tctttctgca actaaatata gtaaattacg gtaaaatata aataagtaca tattgaagaa 540
aatgagacat aatatatttt ataataggag ggaatttcaa atgatagaca actttatgca 600
ggtccttaaa ttaattaaag agaaacgtac caataatgta gttaaaaaat ctgattggga 660
taaaggtgat ctatataaaa ctttagtcca tgataagtta cccaagcagt taaaagtgca 720
tataaaagaa gataaatatt cagttgtagg gaaggttgct actgggaact atagtaaagt 780
tccttggatt tcaatatatg atgagaatat aacaaaagaa acaaaggatg gatattattt 840
ggtatatctt tttcatccgg aaggagaagg catatactta tctttgaatc aaggatggtc 900
aaagataagt gatatgtttc cgcggg 926

<210> SEQ ID NO 187
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 187
ggatgtgggt atgctaatgt tgtt 24

<210> SEQ ID NO 188
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 188
tgaacaattt tatttctcat accatag 27

<210> SEQ ID NO 189
<211> LENGTH: 2154
<212> TYPE: DNA
<213> ORGANISM: Staphylococcus aureus

<400> SEQUENCE: 189
cggtaataaa aaatacgata tagatgaata acaaaacagt gaagcaatcc gtaacgatgg 60
ttgcttcact gttttattat gaattattaa taagtgctgt tacttctccc ttaaatacaa 120
tttcttcatt ttcattgtat gttgaaagtg acactgtaac gagtccattt tcttttttta 180
tggatttctt atttgtaatt tcagcgataa cgtacaatgt attacctggg tatacaggtt 240
taataaattt aacgttattc atttgtgttc ctgctacaac ttcttctccg tatttacctt 300
cttctaccca taatttaaat gatattgaaa gtgtatgcat gccagatgca atgatacctt 360
taaatctact ttgttctgct ttttctttat ctatatgcat atattgagga tcaaaagttg 420
ttgcaaattg gataatttct tcttctgtaa tatgaaggct ttttgttttg aatgtttctc 480
ctactataaa atcatcgtat ttcatatatg tctctctttc ttattcaaat taattttta 540 gtatgtaaca tgttaaaggt aagtctaccg tcactgaaac gtaagactca cctctaactt 600
tctattgaga caaatgcacc attttatctg cattgtctgt aaagatacca tcaactcccc 660
aattagcaag ttggtttgca cgtgctggtt tgtttacagt ccatacgttc aattcataac 720
ccgcttcttt taccattttt acttttgctt tagtaagttt ggcatcttca gtgtttacta 780
ttttagcatt acagtaatct aaaagtgttc tccagtcttc acgaaacgaa gttgtatgga 840
atataactgc tctgttatat tgtggcatga tttcttctgc aagtttaaca agcacaacat 900
taaagcttga aatgagcact tcttgattct gatttaagtt tgttaattgt tcttccactt 960
gcttaaccat acttttagaa agtgctagtc cattcggtcc agtaatacct tttaattcta 1020

```
catttaaatt catattatat tcatttgcta tttttactac atcatcgaaa gttggcaaat   1080

gttcatcttt gaatttttca ccaaaccaag atcctgcaga agcatcttta atttcatcat   1140

aattcaattc agttatttcc ccggacatat ttgtagtccg ttctaaataa tcatcatgaa   1200

tgataatcag ttgttcatct tttgtaattg caacatctaa ctccaaccag tttatacctt   1260

ctacttctga agcagcttta aatgatgcaa ttgtattttc cggagcttta ctaggtaatc   1320

ctctatgtcc atatacagtt agcatattac ctctccttgc atttttattt ttttaattaa   1380

cgtaactgta ttatcacatt aatcgcactt ttatttccat taaaaagaga tgaatatcat   1440

aaataaagaa gtcgatagat tcgtattgat tatggagtta atctacgtct catctcattt   1500

ttaaaaaatc atttatgtcc caagctccat tttgtaatca agtctagttt ttcggttctg   1560

ttgcaaagtt gaatttatag tataatttta acaaaaagga gtcttctgta tgaactattt   1620

cagatataaa caatttaaca aggatgttat cactgtagcc gttggctact atctaagata   1680

tacattgagt tatcgtgata tatctgaaat attaagggaa cgtggtgtaa acgttcatca   1740

ttcaacggtc taccgttggg ttcaagaata tgccccaatt ttgtatcaaa tttggaagaa   1800

aaagcataaa aaagcttatt acaaatggcg tattgatgag acgtacatca aaataaaagg   1860

aaaatggagc tatttatatc gtgccattga tgcagaggga catacattag atatttggtt   1920

gcgtaagcaa cgagataatc attcagcata tgcgtttatc aaacgtctca ttaaacaatt   1980

tggtaaacct caaaaggtaa ttacagatca ggcaccttca acgaaggtag caatggctaa   2040

agtaattaaa gcttttaaac ttaaacctga ctgtcattgt acatcgaaat atctgaataa   2100

cctcattgag caagatcacc gtcatattaa agtaagaaag acaaggtatc aaag         2154
```

```
<210> SEQ ID NO 190
<211> LENGTH: 2410
<212> TYPE: DNA
<213> ORGANISM: Staphylococcus aureus

<400> SEQUENCE: 190

ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaacatt agacgataaa    180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aaataaaaca    660

cataaagaag atatttatag atcttatgca aacttaattg gcaaatccgg tactgcagaa    720

ctcaaaatga aacaaggaga aactggcaga caaattgggt ggtttatatc atatgataaa    780

gataatccaa acatgatgat ggctattaat gttaaagatg tacaagataa aggaatggct    840

agctacaatg ccaaaatctc aggtaaagtg tatgatgagc tatatgagaa cggtaataaa    900

aaatacgata tagatgaata acaaaacagt gaagcaatcc gtaacgatgg ttgcttcact    960
```

-continued gttttattat gaattattaa taagtgctgt tacttctccc ttaaatacaa tttcttcatt 1020
ttcattgtat gttgaaagtg acactgtaac gagtccattt tctttttta tggatttctt 1080 atttgtaatt tcagcgataa cgtacaatgt attacctggg tatacaggtt taataaattt 1140
aacgttattc atttgtgttc ctgctacaac ttcttctccg tatttacctt cttctaccca 1200
taatttaaat gatattgaaa gtgtatgcat gccagatgca atgatacctt taaatctact 1260
ttgttctgct ttttctttat ctatatgcat atattgagga tcaaaagttg ttgcaaattg 1320
gataatttct tcttctgtaa tatgaaggct ttttgttttg aatgtttctc ctactataaa 1380
atcatcgtat ttcatatatg tctctctttc ttattcaaat taattttta gtatgtaaca 1440 tgttaaaggt aagtctaccg tcactgaaac gtaagactca cctctaactt tctattgaga 1500
caaatgcacc attttatctg cattgtctgt aaagatacca tcaactcccc aattagcaag 1560
ttggtttgca cgtgctggtt tgtttacagt ccatacgttc aattcataac ccgcttcttt 1620
taccattttt actttgctt tagtaagttt ggcatcttca gtgtttacta ttttagcatt 1680
acagtaatct aaaagtgttc tccagtcttc acgaaacgaa gttgtatgga atataactgc 1740
tctgttatat tgtggcatga tttcttctgc aagtttaaca agcacaacat taaagcttga 1800
aatgagcact tcttgattct gatttaagtt tgttaattgt tcttccactt gcttaaccat 1860
acttttagaa agtgctagtc cattcggtcc agtaatacct tttaattcta catttaaatt 1920
catattatat tcatttgcta tttttactac atcatcgaaa gttggcaaat gttcatcttt 1980
gaatttttca ccaaaccaag atcctgcaga agcatcttta atttcatcat aattcaattc 2040
agttatttcc ccggacatat ttgtagtccg ttctaaataa tcatcatgaa tgataatcag 2100
ttgttcatct tttgtaattg caacatctaa ctccaaccag tttatacctt ctacttctga 2160
agcagcttta aatgatgcaa ttgtattttc cggagcttta ctaggtaatc ctctatgtcc 2220
atatacagtt agcatattac ctctccttgc atttttattt ttttaattaa cgtaactgta 2280
ttatcacatt aatcgcactt ttatttccat taaaaagaga tgaatatcat aaataaagaa 2340
gtcgatagat tcgtattgat tatggagtta atctacgtct catctcattt ttaaaaaatc 2400
atttatgtcc 2410

<210> SEQ ID NO 191
<211> LENGTH: 1858
<212> TYPE: DNA
<213> ORGANISM: Staphylococcus aureus

<400> SEQUENCE: 191
caccttcata tgacgtctat ccatttatgt atggcatgag taacgaagaa tataataaat 60
taaccgaaga taaaaaagaa cctctgctca acaagttcca gattacaact tcaccaggtt 120
caactcaaaa aatattaaca gcaatgattg ggttaaataa caaaacatta gacgataaaa 180
caagttataa aatcgatggt aaaggttggc aaaaagataa atcttggggt ggttacaacg 240
ttacaagata tgaagtggta aatggtaata tcgacttaaa acaagcaata gaatcatcag 300
ataacatttt ctttgctaga gtagcactcg aattaggcag taagaaattt gaaaaaggca 360
tgaaaaaact aggtgttggt gaagatatac caagtgatta tccattttat aatgctcaaa 420
tttcaaacaa aaatttagat aatgaaatat tattagctga ttcaggttac ggacaaggtg 480
aaatactgat taacccagta cagatccttt caatctatag cgcattagaa aataatggca 540
atattaacgc acctcactta ttaaaagaca cgaaaaacaa agtttggaag aaaaatatta 600
tttccaaaga aaatatcaat ctattaactg atggtatgca acaagtcgta aataaaacac 660

```
ataaagaaga tatttataga tcttatgcaa acttaattgg caaatccggt actgcagaac    720

tcaaaatgaa acaaggagaa actggcagac aaattgggtg gtttatatca tatgataaag    780

ataatccaaa catgatgatg gctattaatg ttaaagatgt acaagataaa ggaatggcta    840

gctacaatgc caaaatctca ggtaaagtgt atgatgagct atatgagaac ggtaataaaa    900

aatacgatat agatgaataa caaaacagtg aagcaatccg taacgatggt tgcttcactg    960

ttttattatg aattattaat aagtgctgtt acttctccct taaatacaat ttcttcattt   1020

tcattgtatg ttgaaagtga cactgtaacg agtccatttt cttttttat ggatttctta   1080

tttgtaattt cagcgataac gtacaatgta ttacctgggt atacaggttt aataaattta   1140

acgttattca tttgtgttcc tgctacaact tcttctccgt atttaccttc ttctacccat   1200

aatttaaatg atattgaaag tgtatgcatg ccagatgcaa tgataccttt aaatctactt   1260

tgttctgctt tttctttatc tatatgcata tattgaggat caaaagttgt tgcaaattgg   1320

ataatttctt cttctgtaat atgaaggctt tttgttttga atgtttctcc tactataaaa   1380

tcatcgtatt tcatatatgt ctctctttct tattcaaatt aattttttag tatgtaacat   1440

gttaaaggta agtctaccgt cactgaaacg taagactcac ctctaacttt ctattgagac   1500

aaatgcacca ttttatctgc attgtctgta aagataccat caactcccca attagcaagt   1560

tggtttgcac gtgctggttt gtttacagtc catacgttca attcataacc cgcttctttt   1620

accattttta cttttgcttt agtaagtttg gcatcttcag tgtttactat tttagcatta   1680

cagtaatcta aaagtgttct ccagtcttca cgaaacgaag ttgtatggaa tataactgct   1740

ctgttatatt gtggcatgat ttcttctgca agtttaacaa gcacaacatt aaagcttgaa   1800

atgagcactt cttgattctg atttaagttt gttaattgtt cttccacttg cttaacca     1858
```

<210> SEQ ID NO 192
<211> LENGTH: 1861
<212> TYPE: DNA
<213> ORGANISM: Staphylococcus aureus

<400> SEQUENCE: 192

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaacatt agacgataaa    180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aaataaaaca    660

cataaagaag atatttatag atcttatgca aacttaattg gcaaatccgg tactgcagaa    720

ctcaaaatga aacaaggaga aactggcaga caaattgggt ggtttatatc atatgataaa    780

gataatccaa acatgatgat ggctattaat gttaaagatg tacaagataa aggaatggct    840

agctacaatg ccaaaatctc aggtaaagtg tatgatgagc tatatgagaa cggtaataaa    900
```

```
aaatacgata tagatgaata acaaaacagt gaagcaatcc gtaacgatgg ttgcttcact    960

gttttattat gaattattaa taagtgctgt tacttctccc ttaaatacaa tttcttcatt   1020

ttcattgtat gttgaaagtg acactgtaac gagtccattt tcttttttta tggatttctt   1080

atttgtaatt tcagcgataa cgtacaatgt attacctggg tatacaggtt taataaattt   1140

aacgttattc atttgtgttc ctgctacaac ttcttctccg tatttacctt cttctaccca   1200

taatttaaat gatattgaaa gtgtatgcat gccagatgca atgatacctt taaatctact   1260

ttgttctgct ttttctttat ctatatgcat atattgagga tcaaaagttg ttgcaaattg   1320

gataatttct tcttctgtaa tatgaaggct ttttgttttg aatgtttctc ctactataaa   1380

atcatcgtat ttcatatatg tctctctttc ttattcaaat taattttta gtatgtaaca    1440

tgttaaaggt aagtctaccg tcactgaaac gtaagactca cctctaactt tctattgaga   1500

caaatgcacc attttatctg cattgtctgt aaagatacca tcaactcccc aattagcaag   1560

ttggtttgca cgtgctggtt tgtttacagt ccatacgttc aattcataac ccgcttcttt   1620

taccattttt actttttgctt tagtaagttt ggcatcttca gtgtttacta ttttagcatt  1680

acagtaatct aaaagtgttc tccagtcttc acgaaacgaa gttgtatgga atataactgc   1740

tctgttatat tgtggcatga tttcttctgc aagtttaaca agcacaacat taaagcttga   1800

aatgagcact tcttgattct gatttaagtt tgttaattgt tcttccactt gcttaaccat   1860

a                                                                   1861
```

<210> SEQ ID NO 193
<211> LENGTH: 1861
<212> TYPE: DNA
<213> ORGANISM: Staphylococcus aureus

<400> SEQUENCE: 193

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaacatt agacgataaa    180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccattttta taatgctcaa  420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aaataaaaca    660

cataaagaag atatttatag atcttatgca aacttaattg gcaaatccgg tactgcagaa    720

ctcaaaatga aacaaggaga aactggcaga caaattgggt ggtttatatc atatgataaa    780

gataatccaa acatgatgat ggctattaat gttaaagatg tacaagataa aggaatggct    840

agctacaatg ccaaaatctc aggtaaagtg tatgatgagc tatatgagaa cggtaataaa    900

aaatacgata tagatgaata acaaaacagt gaagcaatcc gtaacgatgg ttgcttcact    960

gttttattat gaattattaa taagtgctgt tacttctccc ttaaatacaa tttcttcatt   1020

ttcattgtat gttgaaagtg acactgtaac gagtccattt tcttttttta tggatttctt   1080

atttgtaatt tcagcgataa cgtacaatgt attacctggg tatacaggtt taataaattt   1140
```

aacgttattc atttgtgttc ctgctacaac ttcttctccg tatttacctt cttctaccca 1200
taatttaaat gatattgaaa gtgtatgcat gccagatgca atgatacctt taaatctact 1260
ttgttctgct ttttctttat ctatatgcat atattgagga tcaaaagttg ttgcaaattg 1320
gataatttct tcttctgtaa tatgaaggct ttttgttttg aatgtttctc ctactataaa 1380
atcatcgtat ttcatatatg tctctctttc ttattcaaat taatttttta gtatgtaaca 1440
tgttaaaggt aagtctaccg tcactgaaac gtaagactca cctctaactt tctattgaga 1500
caaatgcacc attttatctg cattgtctgt aaagatacca tcaactcccc aattagcaag 1560
ttggtttgca cgtgctggtt tgtttacagt ccatacgttc aattcataac ccgcttcttt 1620
taccattttt acttttgctt tagtaagttt ggcatcttca gtgtttacta ttttagcatt 1680
acagtaatct aaaagtgttc tccagtcttc acgaaacgaa gttgtatgga atataactgc 1740
tctgttatat tgtggcatga tttcttctgc aagtttaaca agcacaacat taaagcttga 1800
aatgagcact tcttgattct gatttaagtt tgttaattgt tcttccactt gcttaaccat 1860
a 1861

<210> SEQ ID NO 194
<211> LENGTH: 1052
<212> TYPE: DNA
<213> ORGANISM: Staphylococcus aureus

<400> SEQUENCE: 194
cggtaataaa aaatacgata tagatgaata acaaaacagt gaagcaatcc gtaacgatgg 60
ttgcttcact gttttattat gaattattaa taagtgctgt tacttctccc ttaaatacaa 120
tttcttcatt ttcattgtat gttgaaagtg acactgtaac gagtccattt tcttttttta 180
tggatttctt atttgtaatt tcagcgataa cgtacaatgt attacctggg tatacaggtt 240
taataaattt aacgttattc atttgtgttc ctgctacaac ttcttctccg tatttacctt 300
cttctaccca taatttaaat gatattgaaa gtgtatgcat gccagatgca atgatacctt 360
taaatctact ttgttctgct ttttctttat ctatatgcat atattgagga tcaaaagttg 420
ttgcaaattg gataatttct tcttctgtaa tatgaaggct ttttgttttg aatgtttctc 480
ctactataaa atcatcgtat ttcatatatg tctctctttc ttattcaaat taatttttta 540
gtatgtaaca tgttaaaggt aagtctaccg tcactgaaac gtaagactca cctctaactt 600
tctattgaga caaatgcacc attttatctg cattgtctgt aaagatacca tcaactcccc 660
aattagcaag ttggtttgca cgtgctggtt tgtttacagt ccatacgttc aattcataac 720
ccgcttcttt taccattttt acttttgctt tagtaagttt ggcatcttca gtgtttacta 780
ttttagcatt acagtaatct aaaagtgttc tccagtcttc acgaaacgaa gttgtatgga 840
atataactgc tctgttatat tgtggcatga tttcttctgc aagtttaaca agcacaacat 900
taaagcttga aatgagcact tcttgattct gatttaagtt tgttaattgt tcttccactt 960
gcttaaccat acttttagaa agtgctagtc cattcggtcc agtaatacct tttaattcta 1020
catttaaatt catattatat tcatttgcta tt 1052

<210> SEQ ID NO 195
<211> LENGTH: 3101
<212> TYPE: DNA
<213> ORGANISM: Staphylococcus aureus

<400> SEQUENCE: 195

-continued

```
cttcatatga cgtctatcca tttatgtatg gcatgagtaa cgaagaatat aataaattaa     60
ccgaagataa aaaagaacct ctgctcaaca agttccagat tacaacttca ccaggttcaa    120
ctcaaaaaat attaacagca atgattgggt taaataacaa aacattagac gataaaacaa    180
gttataaaat cgatggtaaa ggttggcaaa aagataaatc ttggggtggt tacaacgtta    240
caagatatga agtggtaaat ggtaatatcg acttaaaaca agcaatagaa tcatcagata    300
acattttctt tgctagagta gcactcgaat taggcagtaa gaaatttgaa aaaggcatga    360
aaaaactagg tgttggtgaa gatataccaa gtgattatcc attttataat gctcaaattt    420
caaacaaaaa tttagataat gaaatattat tagctgattc aggttacgga caaggtgaaa    480
tactgattaa cccagtacag atcctttcaa tctatagcgc attagaaaat aatggcaata    540
ttaacgcacc tcacttatta aaagacacga aaaacaaagt ttggaagaaa aatattattt    600
ccaaagaaaa tatcaatcta ttaactgatg gtatgcaaca agtcgtaaat aaaacacata    660
aagaagatat ttatagatct tatgcaaact taattggcaa atccggtact gcagaactca    720
aaatgaaaca aggagaaact ggcagacaaa ttgggtggtt tatatcatat gataaagata    780
atccaaacat gatgatggct attaatgtta aagatgtaca agataaagga atggctagct    840
acaatgccaa aatctcaggt aaagtgtatg atgagctata tgagaacggt aataaaaaat    900
acgatataga tgaataacaa aacagtgaag caatccgtaa cgatggttgc ttcactgttt    960
tattatgaat tattaataag tgctgttact tctcccttaa atacaatttc ttcattttca   1020
ttgtatgttg aaagtgacac tgtaacgagt ccattttctt tttttatgga tttcttattt   1080
gtaatttcag cgataacgta caatgtatta cctgggtata caggtttaat aaatttaacg   1140
ttattcattt gtgttcctgc tacaacttct tctccgtatt taccttcttc tacccataat   1200
ttaaatgata ttgaaagtgt atgcatgcca gatgcaatga tacctttaaa tctactttgt   1260
tctgcttttt ctttatctat atgcatatat tgaggatcaa aagttgttgc aaattggata   1320
atttcttctt ctgtaatatg aaggcttttt gttttgaatg tttctcctac tataaaatca   1380
tcgtatttca tatatgtctc tctttcttat tcaaattaat tttttagtat gtaacatgtt   1440
aaaggtaagt ctaccgtcac tgaaacgtaa gactcacctc taactttcta ttgagacaaa   1500
tgcaccattt tatctgcatt gtctgtaaag ataccatcaa ctccccaatt agcaagttgg   1560
tttgcacgtg ctggtttgtt tacagtccat acgttcaatt cataacccgc ttcttttacc   1620
atttttactt ttgctttagt aagtttggca tcttcagtgt ttactatttt agcattacag   1680
taatctaaaa gtgttctcca gtcttcacga aacgaagttg tatggaatat aactgctctg   1740
ttatattgtg gcatgatttc ttctgcaagt ttaacaagca caacattaaa gcttgaaatg   1800
agcacttctt gattctgatt taagtttgtt aattgttctt ccacttgctt aaccatactt   1860
ttagaaagtg ctagtccatt cggtccagta ataccttta attctacatt taaattcata   1920
ttatattcat ttgctatttt tactacatca tcgaaagttg gcaaatgttc atctttgaat   1980
ttttcaccaa accaagatcc tgcagaagca tctttaattt catcataatt caattcagtt   2040
atttccccgg acatatttgt agtccgttct aaataatcat catgaatgat aatcagttgt   2100
tcatcttttg taattgcaac atctaactcc aaccagttta taccttctac ttctgaagca   2160
gctttaaatg atgcaattgt attttccgga gctttactag gtaatcctct atgtccatat   2220
acagttagca tattacctct ccttgcattt ttattttttt aattaacgta actgtattat   2280
cacattaatc gcacttttat ttccattaaa aagagatgaa tatcataaat aaagaagtcg   2340
atagattcgt attgattatg gagttaatct acgtctcatc tcatttttaa aaaatcattt   2400
```

atgtcccaag ctccattttg taatcaagtc tagtttttcg gttctgttgc aaagttgaat 2460
ttatagtata attttaacaa aaaggagtct tctgtatgaa ctatttcaga tataaacaat 2520
ttaacaagga tgttatcact gtagccgttg gctactatct aagatataca ttgagttatc 2580
gtgatatatc tgaaatatta agggaacgtg gtgtaaacgt tcatcattca acggtctacc 2640
gttgggttca agaatatgcc ccaattttgt atcaaatttg gaagaaaaag cataaaaaag 2700
cttattacaa atggcgtatt gatgagacgt acatcaaaat aaaaggaaaa tggagctatt 2760
tatatcgtgc cattgatgca gagggacata cattagatat ttggttgcgt aagcaacgag 2820
ataatcattc agcatatgcg tttatcaaac gtctcattaa acaatttggt aaacctcaaa 2880
aggtaattac agatcaggca ccttcaacga aggtagcaat ggctaaagta attaaagctt 2940
ttaaacttaa acctgactgt cattgtacat cgaaatatct gaataacctc attgagcaag 3000
atcaccgtca tattaaagta agaaagacaa ggtatcaaag tatcaataca gcaaagaata 3060
ctttaaaagg tattgaatgt atttacgctc tatataaaaa g 3101

<210> SEQ ID NO 196
<211> LENGTH: 3506
<212> TYPE: DNA
<213> ORGANISM: Staphylococcus aureus

<400> SEQUENCE: 196
ccaccttcat atgacgtcta tccatttatg tatggcatga gtaacgaaga atataataaa 60
ttaaccgaag ataaaaaaga acctctgctc aacaagttcc agattacaac ttcaccaggt 120
tcaactcaaa aaatattaac agcaatgatt gggttaaata acaaaacatt agacgataaa 180
acaagttata aaatcgatgg taaaggttgg caaaaagata aatcttgggg tggttacaac 240
gttacaagat atgaagtggt aaatggtaat atcgacttaa aacaagcaat agaatcatca 300
gataacattt tctttgctag agtagcactc gaattaggca gtaagaaatt tgaaaaaggc 360
atgaaaaaac taggtgttgg tgaagatata ccaagtgatt atccatttta taatgctcaa 420
atttcaaaca aaaatttaga taatgaaata ttattagctg attcaggtta cggacaaggt 480
gaaatactga ttaacccagt acagatcctt tcaatctata gcgcattaga aaataatggc 540
aatattaacg cacctcactt attaaaagac acgaaaaaca aagtttggaa gaaaaatatt 600
atttccaaag aaaatatcaa tctattaact gatggtatgc aacaagtcgt aaataaaaca 660
cataaagaag atatttatag atcttatgca aacttaattg gcaaatccgg tactgcagaa 720
ctcaaaatga aacaaggaga aactggcaga caaattgggt ggtttatatc atatgataaa 780
gataatccaa acatgatgat ggctattaat gttaaagatg tacaagataa aggaatggct 840
agctacaatg ccaaaatctc aggtaaagtg tatgatgagc tatatgagaa cggtaataaa 900
aaatacgata tagatgaata acaaaacagt gaagcaatcc gtaacgatgg ttgcttcact 960
gttttattat gaattattaa taagtgctgt tacttctccc ttaaatacaa tttcttcatt 1020
ttcattgtat gttgaaagtg acactgtaac gagtccattt tcttttttta tggatttctt 1080
atttgtaatt tcagcgataa cgtacaatgt attacctggg tatacaggtt taataaattt 1140
aacgttattc atttgtgttc ctgctacaac ttcttctccg tatttacctt cttctaccca 1200
taatttaaat gatattgaaa gtgtatgcat gccagatgca atgatacctt taaatctact 1260
ttgttctgct ttttctttat ctatatgcat atattgagga tcaaaagttg ttgcaaattg 1320
gataatttct tcttctgtaa tatgaaggct ttttgttttg aatgtttctc ctactataaa 1380

-continued

```
atcatcgtat ttcatatatg tctctctttc ttattcaaat taatttttta gtatgtaaca   1440
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
acttttagaa agtgctagtc cattcggtcc agtaatacct tttaattcta catttaaatt   1920
catattatat tcatttgcta tttttactac atcatcgaaa gttggcaaat gttcatcttt   1980
gaatttttca ccaaaccaag atcctgcaga agcatcttta atttcatcat aattcaattc   2040
agttatttcc ccggacatat ttgtagtccg ttctaaataa tcatcatgaa tgataatcag   2100
ttgttcatct tttgtaattg caacatctaa ctccaaccag tttatacctt ctacttctga   2160
agcagcttta aatgatgcaa ttgtattttc cggagcttta ctaggtaatc ctctatgtcc   2220
atatacagtt agcatattac ctctccttgc atttttattt ttttaattaa cgtaactgta   2280
ttatcacatt aatcgcactt ttatttccat taaaaagaga tgaatatcat aaataaagaa   2340
gtcgatagat tcgtattgat tatggagtta atctacgtct catctcattt ttaaaaaatc   2400
atttatgtcc caagctccat tttgtaatca agtctagttt ttctgtaccc cttatctgca   2460
attttactta ggattgcttt taacttaccc cttatcagca attttactga gaactgcttt   2520
taacgcacct cttatctgca attttgccta gaactgcttt taacgtacct cttatctgca   2580
attttactga gaactgcttt taacttaccc cttatcagca attttgcatg gaattgcttt   2640
taacgtacct cttatctgca attttactta gaactgcttt taacaaacct cttatctgca   2700
attttactta gaactgcttt taacgtacct cttatctgta attttactga gaactgcttt   2760
taacaaacct cttatctgca attttactta gaactgcttt taacaaacct cttatctgca   2820
attttactta gaattgcttt tactattcct cttattagta taatctcagt aagaatgcgt   2880
ataaaaatga aaattacaac cgattttgta agtgctgacg cctgagggaa tagtatgtgc   2940
gagagactaa tggctcgagc cataccccta ggcaagcatg cacgtacaaa atcgtaagat   3000
aaaaaaataa gcatatcact gtaaacttta aaaaatcagt ttagtgatat gcttatttat   3060
ttcgagttag gatttatgtc ccaagctcat caagcacaat cggccactag tttatttctc   3120
tatcttatat gttctgatat ggtcttctat actgtataag tatacttttg aatatggatc   3180
ttgtgtcaat tcacgttcga aatcaaattc ttgattatca aatctgttaa agaatgtttc   3240
gtattcttcg actgataatt gctctctaga ttctagcata tttaagtgtt tctctttatc   3300
taatgctttg tcatatcctt taacgattga accactaaag atttctccta ctgctcctga   3360
accataacta aatagacata ctttctcttc tggttggaat gtgtggttct gtaataacga   3420
aattaaactt aagtataatg atcctgtata aatgttacca acatctctat tccataatac   3480
ggttctgttg caaagttgaa tttata                                        3506
```

<210> SEQ ID NO 197
<211> LENGTH: 928
<212> TYPE: DNA
<213> ORGANISM: Staphylococcus aureus

<400> SEQUENCE: 197

```
tacattagaa atacaaggaa agatgctatc ttccgaagga ttggcccaag aattgaacca     60
acgcatgacc caagggcaaa gcgactttgt attcgtcatt ggcggatcaa acggcctgca    120
caaggacgtc ttacaacgca gtaactacgc actatcattc agcaaaatga cattcccaca    180
tcaaatgatg cgggttgtgt taattgaaca agtgtacaga gcatttaaga ttatgcgtgg    240
agaagcatat cataaatgat gcggtttttt cagccgcttc ataaagggat tttgaatgta    300
tcagaacata tgaggtttat gtgaattgct gttatgtttt taagaagctt atcataagta    360
atgaggttca tgatttttga catagttagc ctccgcagtc tttcatttca agtaaataat    420
agcgaaatat tctttatact gaatacttat agtgaagcaa agttctagct ttgagaaaat    480
tctttctgca actaaatata gtaaattacg gtaaaatata aataagtaca tattgaagaa    540
aatgagacat aatatatttt ataataggag ggaatttcaa atgatagaca actttatgca    600
ggtccttaaa ttaattaaag agaaacgtac caataatgta gttaaaaaat ctgattggga    660
taaaggtgat ctatataaaa ctttagtcca tgataagtta cccaagcagt taaaagtgca    720
tataaaagaa gataaatatt cagttgtagg gaaggttgct actgggaact atagtaaagt    780
tccttggatt tcaatatatg atgagaatat aacaaaagaa acaaaggatg gatattattt    840
ggtatatctt tttcatccgg aaggagaagg catatactta tctttgaatc aaggatggtc    900
aaagataagt gatatgtttc cgcgggat                                        928
```

<210> SEQ ID NO 198
<211> LENGTH: 782
<212> TYPE: DNA
<213> ORGANISM: Staphylococcus aureus

<400> SEQUENCE: 198

```
caatgcccac agagttatcc acaaatacac aggttataca ctaaaaattg ggcatgaatg     60
tcagaaaaat atcaaaaact gcaaagaata ttggtataat aagagggaac agtgtgaaca    120
agttaataac ttgtggataa ctggaaagtt gataacaatt tggaggacca aacgacatga    180
aaatcaccat tttagctgta gggaaactaa aagagaaata ttggaagcaa gccatagcag    240
aatatgaaaa acgtttaggc ccatacacca agatagacat catagaagtt ccagacgaaa    300
aagcaccaga aaatatgagc gacaaagaaa ttgagcaagt aaaagaaaaa gaaggccaac    360
gaatactagc caaaatcaaa ccacaatcaa cagtcattac attagaaata caaggaaaga    420
tgctatcttc cgaaggattg gcccaagaat tgaaccaacg catgacccaa gggcaaagcg    480
actttgtatt cgtcattggc ggatcaaacg gcctgcacaa ggacgtctta caacgcagta    540
actacgcact atcattcagc aaaatgacat tcccacatca aatgatgcgg gttgtgttaa    600
ttgaacaagt gtacagagca tttaagatta tgcgtggaga agcgtatcat aaataaaact    660
aaaaattagg ttgtgtataa tttaaaaatt taatgagatg tggaggaatt acatatatga    720
aatattggat tataccttgc aatatcatac gatgtttata gagtgtttaa taaaccattt    780
tt                                                                    782
```

<210> SEQ ID NO 199
<211> LENGTH: 709
<212> TYPE: DNA
<213> ORGANISM: Staphylococcus aureus

<400> SEQUENCE: 199

```
tacattagaa atacaaggaa agatgctatc ttccgaagga ttggcccaag aattgaacca     60
```

-continued

```
acgcatgacc caagggcaaa gcgactttgt tttcgtcatt ggcggatcaa acggcctgca    120

caaggacgtc ttacaacgca gtaactacgc actatcattc agcaaaatga cattcccaca    180

tcaaatgatg cgggttgtgt taattgaaca agtgtacaga gcatttaaga ttatgcgagg    240

agaagcttat cataagtaat gaggttcatg atttttgaca tagttagcct ccgcagtctt    300

tcatttcaag taaataatag cgaaatattc tttatactga atacttatag tgaagcaaag    360

ttctagcttt gagaaaattc tttctgcaac taaatatagt aaattacggt aaaatataaa    420

taagtacata ttgaagaaaa tgagacataa tatattttat aataggaggg aatttcaaat    480

gatagacaac tttatgcagg tccttaaatt aattaaagag aaacgtacca ataatgtagt    540

taaaaaatct gattgggata aaggtgatct atataaaact ttagtccatg ataagttacc    600

caagcagtta aaagtgcata taaaagaaga taaatattca gttgtaggga aggttgctac    660

tgggaactat agtaaagttc cttggatttc aatatatgat gagaatata                709
```

<210> SEQ ID NO 200
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 200
gtgggaaatg gctgttgttg ag 22

<210> SEQ ID NO 201
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 201
ttcgttccct ccattaactg tc 22

<210> SEQ ID NO 202
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 202
aaaagaaaga cggtgaaggc 20

<210> SEQ ID NO 203
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 203
cacttcatta tactgttttc tttgc 25

<210> SEQ ID NO 204
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 204
tcaccgtctt tcttttgacc tt 22

<210> SEQ ID NO 205
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 205
tgagatctgc tggaacaaaa gtgaa 25

<210> SEQ ID NO 206
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 206
cggtcgagtt tgctgaagaa 20

<210> SEQ ID NO 207
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 207
tcccctaatg atagctggta tatatt 26

<210> SEQ ID NO 208
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 208
tctagggaat caaagaaaag taatagt 27

<210> SEQ ID NO 209
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 209
caacaargrc aatgtgayrt attatgytgt ta 32

<210> SEQ ID NO 210
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 210
gataayatwg gmgaacaagt caraaatgg 29

<210> SEQ ID NO 211
<211> LENGTH: 35
<212> TYPE: DNA

<213> ORGANISM: Artificial Sequence
<220> FEATURE:
<223> OTHER INFORMATION: Synthetic nucleic acid sequence

<400> SEQUENCE: 211
ccrtattgat tgwtracacg rccacartaa ttwgg 35

<210> SEQ ID NO 212
<211> LENGTH: 32
<212> TYPE: DNA
<213> ORGANISM: Artificial Sequence
<220> FEATURE:
<221> NAME/KEY: misc_feature
<222> LOCATION: 30
<223> OTHER INFORMATION: n = inosine
<220> FEATURE:
<223> OTHER INFORMATION: Synthetic nucleic acid sequence

<400> SEQUENCE: 212
atrttsartg gttcattttt gaaatagatn cc 32

<210> SEQ ID NO 213
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 213
acgtgtcggt atctatgtwc gtgtatcaac rg 32

<210> SEQ ID NO 214
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 214
tgttatgrtc tacaaaacaa accgaytagc 30

<210> SEQ ID NO 215
<211> LENGTH: 34
<212> TYPE: DNA
<213> ORGANISM: Artificial Sequence
<220> FEATURE:
<223> OTHER INFORMATION: Synthetic nucleic acid sequence

<400> SEQUENCE: 215
gawtaataat rggggaatgc ttaccttcag ctat 34

<210> SEQ ID NO 216
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 216
ggtttttgac tgacttgttt tttacg 26

<210> SEQ ID NO 217
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 217
tagaaytgtt ttttatgatt accrtcttt 29

<210> SEQ ID NO 218
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 218
ggcaaaaaya aagacgaagt gctgag 26

<210> SEQ ID NO 219
<211> LENGTH: 721
<212> TYPE: DNA
<213> ORGANISM: Staphylococcus aureus

<400> SEQUENCE: 219
tgtagcttta ggtgaagggt taggtccttc aatagggggga ataatagcac attatattca 60
ttggtcttac ctacttatac ttcctatgat tacaatagta actatacctt ttcttattaa 120
agtaatggta cctggtaaat caacaaaaaa tacattagat atcgtaggta ttgttttaat 180
gtctataagt attatatgtt ttatgttatt tacgacaaat tataattgga cttttttaat 240
actcttcaca atcttttttg tgatttttat taaacatatt tcaagagttt ctaacccttt 300
tattaatcct aaactaggga aaaacattcc gtttatgctt ggtttgtttt ctggtgggct 360
aatattttct atagtagctg gttttatatc aatggtgcct tatatgatga aaactattta 420
tcatgtaaat gtagcgacaa taggtaatag tgttattttt cctggaacca tgagtgttat 480
tgtttttggt tattttggtg gttttttagt ggatagaaaa ggatcattat ttgtttttat 540
tttaggatca ttgtctatct ctataagttt tttaactatt gcattttttg ttgagtttag 600
tatgtggttg actactttta tgtttatatt tgttatgggc ggattatctt ttactaaaac 660
agttatatca aaaatagtat caagtagtct ttctgaagaa gaagttgctt ctggaagagt 720
t 721

<210> SEQ ID NO 220
<211> LENGTH: 1791
<212> TYPE: DNA
<213> ORGANISM: Staphylococcus aureus

<400> SEQUENCE: 220
atccggtact gcagaactca aaatgaaaca aggagaaact ggcagacaaa ttgggtggtt 60
tatatcatat gataaagata atccaaacat gatgatggct attaatgtta aagatgtaca 120
agataaagga atggctagct acaatgccaa aatctcaggt aaagtgtatg atgagctata 180
tgagaacggt aataaaaaat acgatataga tgaataacaa aacagtgaag caatccgtaa 240
cgatggttgc ttcactgttt tattatgaat tattaataag tgctgttact tctcccttaa 300
atacaatttc ttcattttca ttgtatgttg aaagtgacac tgtaacgagt ccattttctt 360
tttttatgga tttcttattt gtaatttcag cgataacgta caatgtatta cctgggtata 420
caggtttaat aaatttaacg ttattcattt gtgttcctgc tacaacttct tctccgtatt 480
taccttcttc tacccataat ttaaatgata ttgaaagtgt atgcatgcca gatgcaatga 540
tacctttaaa tctactttgt tctgcttttt ctttatctat atgcatatat tgaggatcaa 600

```
aagttgttgc aaattggata atttcttctt ctgtaatatg aaggcttttt gttttgaatg    660
tttctcctac tataaaatca tcgtatttca tatatgtctc tctttcttat tcaaattaat    720
tttttagtat gtaacatgtt aaaggtaagt ctaccgtcac tgaaacgtaa gactcacctc    780
taactttcta ttgagacaaa tgcaccattt tatctgcatt gtctgtaaag ataccatcaa    840
ctccccaatt agcaagttgg tttgcacgtg ctggtttgtt tacagtccat acgttcaatt    900
cataacccgc ttcttttacc atttttactt ttgctttagt aagtttggca tcttcagtgt    960
ttactatttt agcattacag taatctaaaa gtgttctcca gtcttcacga aacgaagttg   1020
tatggaatat aactgctctg ttatattgtg gcatgatttc ttctgcaagt ttaacaagca   1080
caacattaaa gcttgaaatg agcacttctt gattctgatt taagtttgtt aattgttctt   1140
ccacttgctt aaccatactt ttagaaagtg ctagtccatt cggtccagta atacctttta   1200
attctacatt taaattcata ttatattcat ttgctatttt tactacatca tcgaaagttg   1260
gcaaatgttc atctttgaat ttttcaccaa accaagatcc tgcagaagca tctttaattt   1320
catcataatt caattcagtt atttccccgg acatatttgt agtccgttct aaataatcat   1380
catgaatgat aatcagttgt tcatcttttg taattgcaac atctaactcc aaccagttta   1440
taccttctac ttctgaagca gctttaaatg atgcaattgt attttccgga gctttactag   1500
gtaatcctct atgtccatat acagttagca tattacctct ccttgcattt ttattttttt   1560
aattaacgta actgtattat cacattaatc gcacttttat ttccattaaa aagagatgaa   1620
tatcataaat aaagaagtcg atagattcgt attgattatg gagttaatct acgtctcatc   1680
tcatttttaa aaaatcattt atgtcccaag ctccattttg taatcaagtc tagtttttct   1740
gtaccccta tctgcaattt tacttaggat tgcttttaac ttacccctta t             1791
```

<210> SEQ ID NO 221
<211> LENGTH: 600
<212> TYPE: DNA
<213> ORGANISM: Staphylococcus aureus

<400> SEQUENCE: 221

```
aagtgctgac gcctgaggga atagtatgtg cgagagacta atggctcgag ccataccccct    60
aggcaagcat gcacgtacaa aatcgtaaga taaaaaaata agcatatcac tgtaaacttt   120
aaaaaatcag tttagtgata tgcttattta tttcgagtta ggatttatgt cccaagctca   180
tcaagcacaa tcggccacta gtttatttct ctatcttata tgttctgata tggtcttcta   240
tactgtataa gtatactttt gaatatggat cttgtgtcaa ttcacgttcg aaatcaaatt   300
cttgattatc aaatctgtta aagaatgttt cgtattcttc gactgataat tgctctctag   360
attctagcat atttaagtgt ttctctttat ctaatgcttt gtcatatcct ttaacgattg   420
aaccactaaa gatttctcct actgctcctg aaccataact aaatagacat actttctctt   480
ctggttggaa tgtgtggttc tgtaataacg aaattaaact taagtataat gatcctgtat   540
aaatgttacc aacatctcta ttccataata cggttctgtt gcaaagttga atttatagta   600
```

<210> SEQ ID NO 222
<211> LENGTH: 1640
<212> TYPE: DNA
<213> ORGANISM: Staphylococcus aureus

<400> SEQUENCE: 222

```
gggtggttta tatcatatga taaagataat ccaaacatga tgatggctat taatgttaaa    60
gatgtacaag ataaaggaat ggctagctac aatgccaaaa tctcaggtaa agtgtatgat   120
```

```
gagctatatg agaacggtaa taaaaaatac gatatagatg aataacaaaa cagtgaagca    180
atccgtaacg atggttgctt cactgtttta ttatgaatta ttaataagtg ctgttacttc    240
tcccttaaat acaatttctt cattttcatt gtatgttgaa agtgacactg taacgagtcc    300
attttctttt tttatggatt tcttatttgt aatttcagcg ataacgtaca atgtattacc    360
tgggtataca ggtttaataa atttaacgtt attcatttgt gttcctgcta caacttcttc    420
tccgtattta ccttcttcta cccataattt aaatgatatt gaaagtgtat gcatgccaga    480
tgcaatgata cctttaaatc tactttgttc tgctttttct ttatctatat gcatatattg    540
aggatcaaaa gttgttgcaa attggataat ttcttcttct gtaatatgaa ggctttttgt    600
tttgaatgtt tctcctacta taaaatcatc gtatttcata tatgtctctc tttcttattc    660
aaattaattt tttagtatgt aacatgttaa aggtaagtct accgtcactg aaacgtaaga    720
ctcacctcta actttctatt gagacaaatg caccatttta tctgcattgt ctgtaaagat    780
accatcaact ccccaattag caagttggtt tgcacgtgct ggtttgttta cagtccatac    840
gttcaattca taacccgctt cttttaccat ttttactttt gctttagtaa gtttggcatc    900
ttcagtgttt actattttag cattacagta atctaaaagt gttctccagt cttcacgaaa    960
cgaagttgta tggaatataa ctgctctgtt atattgtggc atgatttctt ctgcaagttt   1020
aacaagcaca acattaaagc ttgaaatgag cacttcttga ttctgattta agtttgttaa   1080
ttgttcttcc acttgcttaa ccatactttt agaaagtgct agtccattcg gtccagtaat   1140
accttttaat tctacattta aattcatatt atattcattt gctattttta ctacatcatc   1200
gaaagttggc aaatgttcat ctttgaattt ttcaccaaac caagatcctg cagaagcatc   1260
tttaatttca tcataattca attcagttat ttccccggac atatttgtag tccgttctaa   1320
ataatcatca tgaatgataa tcagttgttc atcttttgta attgcaacat ctaactccaa   1380
ccagtttata ccttctactt ctgaagcagc tttaaatgat gcaattgtat tttccggagc   1440
tttactaggt aatcctctat gtccatatac agttagcata ttacctctcc ttgcattttt   1500
attttttaa ttaacgtaac tgtattatca cattaatcgc acttttattt ccattaaaaa   1560
gagatgaata tcataaataa agaagtcgat agattcgtat tgattatgga gttaatctac   1620
gtctcatctc atttttaaaa                                                1640
```

<210> SEQ ID NO 223
<211> LENGTH: 592
<212> TYPE: DNA
<213> ORGANISM: Staphylococcus aureus

<400> SEQUENCE: 223

```
aattcaactt tgcaacagaa ccgtattatg gaatagagat gttggtaaca tttatacagg     60
atcattatac ttaagtttaa tttcgttatt acagaaccac acattccaac cagaagagaa    120
agtatgtcta tttagttatg gttcaggagc agtaggagaa atctttagtg gttcaatcgt    180
taaaggatat gacaaagcat tagataaaga gaaacactta aatatgctag aatctagaga    240
gcaattatca gtcgaagaat acgaaacatt ctttaacaga tttgataatc aagaatttga    300
tttcgaacgt gaattgacac aagatccata ttcaaaagta tacttataca gtatagaaga    360
ccatatcaga acatataaga tagagaaata aactagtggc cgattgtgct tgatgagctt    420
gggacataaa tcctaactcg aaataaataa gcatatcact aaactgattt tttaaagttt    480
acagtgatat gcttattttt ttatcttacg attttgtacg tgcatgcttg cctaggggta    540
```

tggctcgagc cattagtctc tcgcacatac tattccctca ggcgtcagca ct 592

<210> SEQ ID NO 224
<211> LENGTH: 2386
<212> TYPE: DNA
<213> ORGANISM: Staphylococcus aureus

<400> SEQUENCE: 224
caccttcata tgacgtctat ccatttatgt atggcatgag taacgaagaa tataataaat 60
taaccgaaga taaaaaagaa cctctgctca acaagttcca gattacaact tcaccaggtt 120
caactcaaaa aatattaaca gcaatgattg ggttaaataa caaaacatta gacgataaaa 180
caagttataa aatcgatggt aaaggttggc aaaaagataa atcttggggt ggttacaacg 240
ttacaagata tgaagtggta aatggtaata tcgacttaaa acaagcaata gaatcatcag 300
ataacatttt ctttgctaga gtagcactcg aattaggcag taagaaattt gaaaaaggca 360
tgaaaaaact aggtgttggt gaagatatac caagtgatta tccattttat aatgctcaaa 420
tttcaaacaa aaatttagat aatgaaatat tattagctga ttcaggttac ggacaaggtg 480
aaatactgat taacccagta cagatccttt caatctatag cgcattagaa aataatggca 540
atattaacgc acctcactta ttaaaagaca cgaaaaacaa agtttggaag aaaaatatta 600
tttccaaaga aaatatcaat ctattaactg atggtatgca acaagtcgta aataaaacac 660
ataaagaaga tatttataga tcttatgcaa acttaattgg caaatccggt actgcagaac 720
tcaaaatgaa acaaggagaa actggcagac aaattgggtg gtttatatca tatgataaag 780
ataatccaaa catgatgatg gctattaatg ttaaagatgt acaagataaa ggaatggcta 840
gctacaatgc caaaatctca ggtaaagtgt atgatgagct atatgagaac ggtaataaaa 900
aatacgatat agatgaataa caaaacagtg aagcaatccg taacgatggt tgcttcactg 960
ttttattatg aattattaat aagtgctgtt acttctccct taaatacaat ttcttcattt 1020
tcattgtatg ttgaaagtga cactgtaacg agtccatttt cttttttat ggatttctta 1080 tttgtaattt cagcgataac gtacaatgta ttacctgggt atacaggttt aataaattta 1140
acgttattca tttgtgttcc tgctacaact tcttctccgt atttaccttc ttctacccat 1200
aatttaaatg atattgaaag tgtatgcatg ccagatgcaa tgataccttt aaatctactt 1260
tgttctgctt tttctttatc tatatgcata tattgaggat caaaagttgt tgcaaattgg 1320
ataatttctt cttctgtaat atgaaggctt tttgttttga atgtttctcc tactataaaa 1380
tcatcgtatt tcatatatgt ctctctttct tattcaaatt aatttttag tatgtaacat 1440 gttaaaggta agtctaccgt cactgaaacg taagactcac ctctaacttt ctattgagac 1500
aaatgcacca ttttatctgc attgtctgta aagataccat caactcccca attagcaagt 1560
tggtttgcac gtgctggttt gtttacagtc catacgttca attcataacc cgcttctttt 1620
accattttta cttttgcttt agtaagtttg gcatcttcag tgtttactat tttagcatta 1680
cagtaatcta aaagtgttct ccagtcttca cgaaacgaag ttgtatggaa tataactgct 1740
ctgttatatt gtggcatgat ttcttctgca agtttaacaa gcacaacatt aaagcttgaa 1800
atgagcactt cttgattctg atttaagttt gttaattgtt cttccacttg cttaaccata 1860
cttttagaaa gtgctagtcc attcggtcca gtaatacctt ttaattctac atttaaattc 1920
atattatatt catttgctat ttttactaca tcatcgaaag ttggcaaatg ttcatctttg 1980
aatttttcac caaaccaaga tcctgcagaa gcatctttaa tttcatcata attcaattca 2040
gttatttccc cggacatatt tgtagtccgt tctaaataat catcatgaat gataatcagt 2100

```
tgttcatctt ttgtaattgc aacatctaac tccaaccagt ttataccttc tacttctgaa   2160

gcagctttaa atgatgcaat tgtattttcc ggagctttac taggtaatcc tctatgtcca   2220

tatacagtta gcatattacc tctccttgca tttttatttt tttaattaac gtaactgtat   2280

tatcacatta atcgcacttt tatttccatt aaaaagagat gaatatcata aataaagaag   2340

tcgatagatt cgtattgatt atggagttaa tctacgtctc atctca                  2386
```

<210> SEQ ID NO 225
<211> LENGTH: 623
<212> TYPE: DNA
<213> ORGANISM: Staphylococcus aureus

<400> SEQUENCE: 225

```
tgaaaattac aaccgatttt gtaagtgctg acgcctgagg gaatagtatg tgcgagagac     60

taatggctcg agccataccc ctaggcaagc atgcacgtac aaaatcgtaa gataaaaaaa    120

taagcatatc actgtaaact ttaaaaaatc agtttagtga tatgcttatt tatttcgagt    180

taggatttat gtcccaagct catcaagcac aatcggccac tagtttattt ctctatctta    240

tatgttctga tatggtcttc tatactgtat aagtatactt ttgaatatgg atcttgtgtc    300

aattcacgtt cgaaatcaaa ttcttgatta tcaaatctgt taaagaatgt ttcgtattct    360

tcgactgata attgctctct agattctagc atatttaagt gtttctcttt atctaatgct    420

ttgtcatatc ctttaacgat tgaaccacta aagatttctc ctactgctcc tgaaccataa    480

ctaaatagac atactttctc ttctggttgg aatgtgtggt tctgtaataa cgaaattaaa    540

cttaagtata atgatcctgt ataaatgtta ccaacatctc tattccataa tacggttctg    600

ttgcaaagtt gaatttatag tat                                            623
```

<210> SEQ ID NO 226
<211> LENGTH: 651
<212> TYPE: DNA
<213> ORGANISM: Staphylococcus aureus

<400> SEQUENCE: 226

```
atgaaaaata tttcagaatt ctcagcccaa cttgatcaaa cttttgatca aggggaagcc     60

gtctctatgg agtggttatt ccgtccgttg ctaaaaatgc tggcggaggg cgatccagtc    120

cccgttgagg acatcgcggc ggagaccggg aagcccgtcg aggaagttaa gcaagtccta    180

cagactctac ctagtgtgga acttgatgag cagggccgtg tcgtcggtta tggcctcaca    240

ctgttcccta ccccccatcg cttcgaggtt gatgggaagc aactatatgc atggtgcgcc    300

cttgacacac ttatgttccc agcactcatc ggccggacgg tccacatcgc ttcgccttgt    360

cacggcaccg gtaagtccgt ccggttgacg gtggaaccgg accgcgttgt aagcgtcgag    420

ccttcaacag ccgttgtctc gattgttaca ccagatgaaa tggcctcggt tcggtcggcc    480

ttctgtaacg acgttcactt tttcagttca ccgagtgcag cccaagactg gcttaaccaa    540

caccctgagt cgagcgtttt gcccgttgaa gatgcctttg aactgggtcg ccatttggga    600

gcgcgttatg aggagtcagg acctactaat gggtcctgtt gtaacattta a            651
```

<210> SEQ ID NO 227
<211> LENGTH: 563
<212> TYPE: DNA
<213> ORGANISM: Staphylococcus aureus

<400> SEQUENCE: 227

-continued

```
atgaatcttg aaaaagggaa tatagaaagg aaaaaacatg gtgtccatgt taatgagtat     60

ttgcaaagtg taagtaaccc gaatgtctat gcagctggag atgctgcagc aacggatggc    120

ttgcccctca cacctgtagc cagtgcagat tctcatgtcg tagcatctaa tttattgaaa    180

gggaacagca aaaaaattga atatcccgtg attccatctg ctgtatttac cgtacctaaa    240

atggcatcgg taggtatgag cgaggaggaa gccaaaaact ctggccggaa tattaaagta    300

aagcagaaaa acatctccga ctggtttacg tataaacgga caaatgagga ctttgctgcg    360

tttaaagtgc tgattgacga agatcatgat caaattgttg gtgctcattt gattagtaat    420

gaagccgatg aactgattaa tcattttgca acagccattc gttttgggat ttcaaccaaa    480

gaattgaaac aaatgatatt tgcctatcca acggcagctt cggacattgc acacatgttg    540

taagtttgcg ttttgtgaga tgt                                            563
```

<210> SEQ ID NO 228
<211> LENGTH: 1380
<212> TYPE: DNA
<213> ORGANISM: Staphylococcus aureus

<400> SEQUENCE: 228

```
ttgtttagtt tatataaaaa atttaaaggt ttgttttata gcgttttatt ttggctttgt     60

attctttcat tttttagtgt attaaatgaa atggttttaa atgtttcttt acctgatatt    120

gcaaatcatt ttaatactac tcctggaatt acaaactggg taaacactgc atatatgtta    180

actttttcga taggaacagc agtatatgga aaattatctg attatataaa tataaaaaaa    240

ttgttaatta ttggtattag tttgagctgt cttggttcat tgattgcttt tattggtcac    300

aatcactttt ttattttgat ttttggtagg ttagtacaag gagtaggatc tgctgcattc    360

ccttcactga ttatggtggt tgtagctaga aatattacaa gaaaaaaaca aggcaaagcc    420

tttggtttta taggatcaat tgtagcttta ggtgaagggt taggtccttc aatagggggga    480

ataatagcac attatattca ttggtcttac ctacttatac ttcctatgat tacaatagta    540

actatacctt ttcttattaa agtaatggta cctggtaaat caacaaaaaa tacattagat    600

atcgtaggta ttgttttaat gtctataagt attatatgtt ttatgttatt tacgacaaat    660

tataattgga ctttttttaat actcttcaca atcttttttg tgatttttat taaacatatt    720

tcaagagttt ctaacccttt tattaatcct aaactaggga aaaacattcc gtttatgctt    780

ggtttgtttt ctggtgggct aatattttct atagtagctg gttttatatc aatggtgcct    840

tatatgatga aaactattta tcatgtaaat gtagcgacaa taggtaatag tgttattttt    900

cctggaacca tgagtgttat tgtttttggt tattttggtg gtttttttagt ggatagaaaa    960

ggatcattat ttgtttttat tttaggatca ttgtctatct ctataagttt tttaactatt   1020

gcatttttttg ttgagtttag tatgtggttg actactttta tgtttatatt tgttatgggc   1080

ggattatctt ttactaaaac agttatatca aaaatagtat caagtagtct ttctgaagaa   1140

gaagttgctt ctggaatgag tttgctaaat ttcacaagtt ttttatcaga gggaacaggt   1200

atagcaattg taggaggttt attgtcacta caattgatta atcgtaaact agttctggaa   1260

tttataaatt attcttctgg agtgtatagt aatattcttg tagccatggc tatccttatt   1320

attttatgtt gtcttttgac gattattgta tttaaacgtt ctgaaaagca gtttgaatag   1380
```

<210> SEQ ID NO 229
<211> LENGTH: 1365
<212> TYPE: DNA
<213> ORGANISM: Staphylococcus aureus

<400> SEQUENCE: 229
atgagaatag tgaatggacc aataataatg actagagaag aaagaatgaa gattgttcat 60
gaaattaagg aacgaatatt ggataaatat ggggatgatg ttaaggctat tggtgtttat 120
ggctctcttg gtcgtcagac tgatgggccc tattcggata ttgagatgat gtgtgtcatg 180
tcaacagaag aagcagagtt cagccatgaa tggacaaccg gtgagtggaa ggtggaagtg 240
aattttgata gcgaagagat tctactagat tatgcatctc aggtggaatc agattggcct 300
cttacacatg gtcaattttt ctctattttg ccgatttatg attcaggtgg atacttagag 360
aaagtgtatc aaactgctaa atcggtagaa gcccaaacgt tccacgatgc gatttgtgcc 420
cttatcgtag aagagctgtt tgaatatgca ggcaaatggc gtaatattcg tgtgcaagga 480
ccgacaacat ttctaccatc cttgactgta caggtagcaa tggcaggtgc catgttgatt 540
ggtctgcatc atcgcatctg ttatacgacg agcgcttcgg tcttaactga agcagttaag 600
caatcagatc ttccttcagg ttatgaccat ctgtgccagt tcgtaatgtc tggtcaactt 660
tccgactctg agaaacttct ggaatcgcta gagaatttct ggaatgggat tcaggagtgg 720
acagaacgac acggatatat agtggatgtg tcaaaacgca taccattttg aacgatgacc 780
tctaataatt gttaatcatg ttggttacgt atttattaac ttctcctagt attagtaatt 840
atcatggctg tcatggcgca ttaacggaat aaagggtgtg cttaaatcgg gccattttgc 900
gtaataagaa aaaggattaa ttatgagcga attgaattaa taataaggta atagatttac 960
attagaaaat gaaaggggat tttatgcgtg agaatgttac agtctatccc ggcattgcca 1020
gtcggggata ttaaaaagag tataggtttt tattgcgata aactaggttt cactttggtt 1080
caccatgaag atggattcgc agttctaatg tgtaatgagg ttcggattca tctatgggag 1140
gcaagtgatg aaggctggcg ctctcgtagt aatgattcac cggtttgtac aggtgcggag 1200
tcgtttattg ctggtactgc tagttgccgc attgaagtag agggaattga tgaattatat 1260
caacatatta agcctttggg cattttgcac cccaatacat cattaaaaga tcagtggtgg 1320
gatgaacgag actttgcagt aattgatccc gacaacaatt tgatt 1365

<210> SEQ ID NO 230
<211> LENGTH: 831
<212> TYPE: DNA
<213> ORGANISM: Staphylococcus aureus

<400> SEQUENCE: 230
atgggggttt cttttaatat tatgtgtcct aatagtagca tttattcaga tgaaaaatca 60
agggttttag tggacaagac aaagagtgga aaagtgagac catggagaga aaagaaaatc 120
gctaatgttg attactttga acttctgcat attcttgaat ttaaaaaggc tgaaagagta 180
aaagattgtg ctgaaatatt agagtataaa caaaatcgtg aaacaggcga aagaaagttg 240
tatcgagtgt ggttttgtaa atccaggctt tgtccaatgt gcaactggag gagagcaatg 300
aaacatggca ttcagtcaca aaaggttgtt gctgaagtta ttaaacaaaa gccaacagtt 360
cgttggttgt ttctcacatt aacagttaaa aatgtttatg atggcgaaga attaaataag 420
agtttgtcag atatggctca aggatttcgc cgaatgacgc aatataaaaa aattaataaa 480
aatcttgttg gttttatgcg tgcaacggaa gtgacaataa ataataaaga taattcttat 540
aatcagcaca tgcatgtatt ggtatgtgtg gaaccaactt attttaagaa tacagaaaac 600
tacgtgaatc aaaaacaatg gattcaattt tggaaaaagg caatgaaatt agactatgat 660

```
ccaaatgtaa aagttcaaat gattcgaccg aaaaataaat ataaatcgga tatacaatcg    720

gcaattgacg aaactgcaaa atatcctgta aaggatacgg attttatgac cgatgatgaa    780

gaaaagaatt tgtaacgttt gtctgatttg gaggaaggtt tacaccgtaa a             831
```

<210> SEQ ID NO 231
<211> LENGTH: 4193
<212> TYPE: DNA
<213> ORGANISM: Staphylococcus aureus

<400> SEQUENCE: 231

```
atgagccgct tgatacgcat gagtgtatta gcaagtggta gtacaggtaa cgccactttt     60

gtagaaaatg aaaaaggtag tctattagtt gatgttggtt tgactggcaa gaaaatggaa    120

gaattgttta gtcaaattga ccgtaatatt caagatttaa atggtatttt agtaacccat    180

gaacatattg atcatattaa aggattaggt gttttggcgc gtaaatatca attgccaatt    240

tatgcgaatg aaaagacttg gcaggcaatt gaaaagaaag atagtcgcat ccctatggat    300

cagaaattca tttttaatcc ttatgaaaca aaatctattg caggtttcga tgttgaatcg    360

tttaacgtgt cacatgatgc aatagatccg caattttata ttttccataa taactataag    420

aagtttacga ttttaacgga tacgggttac gtgtctgatc gtatgaaagg tatgatacgt    480

ggcagcgatg cgtttatttt tgagagtaat catgacgtcg atatgttgag aatgtgtcgt    540

tatccatgga agacgaaaca acgtatttta ggcgatatgg gtcatgtatc taatgaggat    600

gcgggtcatg cgatgacaga tgtgattaca ggtaacacga aacgtattta cctatcgcat    660

ttatcacaag acaataacat gaaagatttg gcgcgtatga gtgttggcca agtattgaac    720

gaacacgata ttgatacgga aaaagaagta ttgctatgtg atacggataa agctattcca    780

acgccaatat atacaatata aatgagagtc accctataaa gttcggcact gctgtgagac    840

gactttatcg ggtgcttttt tatgttattg gtgggaaatg gctgttgttg gaattaaggt    900

tctatttgaa atgtaaaaaa taattcgata ttaaatgtaa tttataaata atttacataa    960

aatcaatcat tttaatataa ggattatgat aatatattgg tgtatgacag ttaatggagg   1020

gaacgaaatg aaagctttat tacttaaaac aagtgtatgg ctcgttttgc tttttagtgt   1080

gatgggatta tggcaagtct cgaacgcggc tgagcagtat acaccaatca aagcacatgt   1140

agtaacaacg atagacaaag caacaacaga taagcaacaa gtaacgccaa caaaggaagc   1200

ggctcatcaa tttggtgaag aagcggcaac caacgtatca gcatcagcac agggaacagc   1260

tgatgaaata aacaataaag taacatccaa cgcattttct aacaaaccat ctacagcagt   1320

ttcaacaaaa gtaaacgaaa cgcacgatgt agatacacaa caagcctcaa cacaaaaacc   1380

aactcaatca gcaacattca cattatcaaa tgctaaaaca gcatcacttt caccacgaat   1440

gtttgctgcc aatgtaccac aaacaacaac acataaaata ttacatacaa atgatatcca   1500

tggccgacta gccgaagaaa aagggcgtgt catcggtatg gctaaattaa aaacaataaa   1560

agaacaagaa aagcctgatt taatgttaga cgcaggagac gccttccaag gtttaccact   1620

ttcaaaccag tctaaaggtg aagaaatggc taaagcaatg aatgcagtag gttatgatgc   1680

tatggcagtg ggtaaccatg aatttgactt tggatacgat cagttgaaaa agttagaggg   1740

tatgttagac ttcccgatgc taagtactaa cgtttacaaa gatgggaaac gcgcgtttaa   1800

gccttcaaca attgtaacga aaaatggtat tcgttatgga attattggcg taacgacacc   1860

agaaacaaag acgaaaacaa gacctgaggg cattaaaggt gttgaattta gagatccatt   1920

acaaagtgtg acagcagaaa tgatgcgtat ttataaagac gtagatacat ttgttgttat   1980
```

-continued

```
atcacattta gggattgatc cttcaacaca agaaacatgg cgtggtgatt acttagtgaa   2040
acaattaagt caaaatccac aattgaagaa acgtattaca gtcattgatg gtcattcaca   2100
taccgtactt caaaatggtc aaatttataa caatgatgca ttagcacaaa caggtacagc   2160
acttgcgaat atcggtaagg ttacatttaa ttaccgcaat ggagaggtat caaatattaa   2220
accgtcattg attaatgtta aagacgttga aaatgtaaca ccgaacaaag cattagctga   2280
acaaattaat caagctgatc aaacatttag agcacaaaca gcagaggtta ttattccaaa   2340
taataccatt gatttcaaag gagaaagaga tgacgttaga acgcgtgaaa caaatttagg   2400
aaacgcgatt gcagatgcta tggaagcgta tggcgttaag aatttctcta aaaagactga   2460
ctttgccgtg acaaatggtg gaggtattcg tgcctctatc gcaaaaggta aggtgacacg   2520
ctatgattta atctcagtat taccatttgg aaatacgatt gcgcaaattg atgtaaaagg   2580
ttcagacgtc tggacagctt tcgaacatag tttaggtgca ccaacaacac aaaaagacgg   2640
taagacagta ttaacagcga atggcggttt actacatatc tctgattcaa ttcgtgttta   2700
ctatgatatg aataaaccgt ctggcaaacg aattaacgct attcaaattt taaataaaga   2760
gacaggtaag tttgaaaata ttgatttaaa acgtgtatat catgtaacga tgaatgactt   2820
cacagcatca ggtggcgacg gatatagtat gttcggtggc cctagagaag aaggtatttc   2880
attagatcaa gtactagcaa gttatttaaa aacagctaac atagctaagt atgatacgac   2940
agaaccacaa cgtatgttat taggtaaacc agcagtaagt gaacaaccag ctaaaggaca   3000
acaaggtagc aaaggtagtg agtctggtaa agatgtacaa ccaattggtg acgacaaagc   3060
gatgaatcca gcgaaacaac cagcgacagg taaagttgta ttgttaccaa cgcatagagg   3120
aactgttagt agcggtacag aaggttctgg tcgcacatta gaaggagcta ctgtatcaag   3180
caagagtggg aaccaattgg ttagaatgtc agtgcctaaa ggtagcgcgc atgagaaaca   3240
gttaccaaaa actggaacta atcaaagctc aagcccagca gcgatgtttg tattagtagc   3300
aggtataggt ttaatcgcga ctgtacgacg tagaaaagct agttaaaata tattgaaaac   3360
aatactactg tatttcttaa ataagaggta cggtagtgtt tttttatgga aaaaagctat   3420
aaacgttgat aaacatggga tataaaaacg gggataagta ataagacatc aaggtgttta   3480
tccacagaaa tggggatagt tatccagaat tgtgtacaat ttaaagagaa atacccacaa   3540
tgcccacaga gttatccaca aatacacaag ttatacacta aaaattgggc ataaatgtca   3600
ggaaaatatc aaaaactgca aaaaatattg gtataataag agggaacagt gtgaacaagt   3660
taataacttg tggataactg gaaagttgat aacaatttgg aggaccaaac gacatgaaaa   3720
tcaccatttt agctgtaggg aaactaaaag agaaatattg gaagcaagcc atagcagaat   3780
atgaaaaacg tttaggccca tacaccaaga tagacatcat agaagttcca gacgaaaaag   3840
caccagaaaa tatgagcgac aaagaaattg agcaagtaaa agaaaaagaa ggccaacgaa   3900
tactagccaa aattaaacca caatccacag tcattacatt agaaatacaa ggaaagatgc   3960
tatcttccga aggattggcc caagaattga accaacgcat gacccaaggg caaagcgact   4020
ttgtattcgt cattggcgga tcaaacggcc tgcacaagga cgtcttacaa cgcagtaact   4080
acgcactatc attcagcaaa atgacattcc cacatcaaat gatgcgggtt gtgttaattg   4140
agcaagtgta tagagcattt aagattatgc gtggagaagc atatcataaa tga          4193
```

<210> SEQ ID NO 232
<211> LENGTH: 2996
<212> TYPE: DNA

<213> ORGANISM: Staphylococcus aureus

<400> SEQUENCE: 232

```
atgaaacgag ccattggtta tttgcgccaa agtacaacga aacaacaatc actcccagct     60
caaaagcaag caatagaatt attagctcca aagcacaata ttcaaaatat ccaatacatt    120
agtgataagc aatcaggcag aacagataat cgaacaggct atcaacaagt caccgaacgc    180
atccaacaaa gacaatgtga cgtattatgt tgttatcgct tgaatcgact tcatcgcaac    240
ttgaaaaatg cattaaaact catgaaactc tgtcaaaaat atcatgttca tattctaagt    300
gttcatgatg gctattttga tatggataaa gcgtttgatc gcctaaaact caatatattc    360
atgagtctgg ctgaacttga atccgataat attggagaac aagtcaaaaa tggacttaga    420
gaaaaggcaa aacaaggtaa actcataacg acccatgcgc ctttcggtta tcactatcaa    480
aatggtactt tcatcattaa taatgatgaa tcacctaccg tcaaagctgt attcaattat    540
tatcttcaag gatatggcta caagaagatt gcacaatatt tagaagacga taataaactt    600
attacccgca agccttatca ggtacgaaat ataattatga acccaaatta ttgtggtcgt    660
gtcatcaatc aatatggtca atataacaat atggtaccac ctattgtttc ggcaacgaaa    720
tatgaacatg ctcaagcaat ccgtaataag aagcaacttc actgtatacc ttcagagaat    780
cagctgaaac aaaagatcaa atgtccttgt tgtgactcaa cactgacaaa tatgacaata    840
agaaaaaaac atacattgcg atattatatt tgtcctaaaa atatgaatga atctcgcttt    900
gtctgttcat tcaaaggaat aaatgcacaa aaattagaag ttcaagtctt agctacatgt    960
cagaacttct ttcaaaacca acagctctat tcaaaaatta ataatgcaat tcatcaacgc   1020
ctcaaaaaac aaagagtgat agaagctaaa agtacgctaa ctcaagaaca actgatagat   1080
aaacttgcca aggtatgat tgatgctgaa tcattcagaa aacagactca tttgatgaat   1140
caaaagcaca aaaccatatc ctccataagt gataatcagt tacaaacatc actacaaaag   1200
gttatacaga aaagtttcac gttaaacatg ctgcatccct atattgatga aattcgcatt   1260
acaaaaaata aagcccttgt tgggatctat ttcaaaaatg aaccattgaa cattgtgaac   1320
caaacctcgc aatcatcgat tgcttaatca gaaaggatga aaaaatcatg caacaactca   1380
aacaaaaacg tgtcggtatc tatgttcgtg tatcaacgga aatccaaagt actgaaggct   1440
atagtatcga tggacaaatc aatcaaattc gagaatattg tgatttcaat aactttgttg   1500
ttgtagatgt atacgcggat agaggtatct ctggaaaatc tatgaaccga ccagaactac   1560
aacgtttgtt aaaagatgcg aacgaaggtc agattgattc tgttatggtc tacaaaacaa   1620
accgactagc acgtaacact tctgacttac tcaaaattgt tgaagacctt catcgtcaaa   1680
atgtcgaatt cttcagctta tctgagcgta tggaagtcaa tacaagcagt ggtaaattga   1740
tgctacaaat tctagcgagt ttttcagaat ttgaaagaaa taatattgtc gaaaatgtat   1800
tcatgggtca aacccgacgc gctcaagaag gctattatca aggcaatttg ccgctgggct   1860
atgacaaaat accggatagc aagcatgaac tcatgataaa ccaacatgaa gcgaatattg   1920
tcaaatatat atttgagtca tatgctaaag gccacggata tcgtaaaatt gcgaatgcac   1980
tcaatcacaa aggatacgtg actaaaaaag gaaagccttt cagtattggt tcagtgacct   2040
atatcttatc taatccattc tatgttggta aaattcaatt cgcaaagtac aaagattgga   2100
atgaaaagcg tcgtaaaggg ctgaatgata aaccaataat agctgaaggt aagcattccc   2160
ctattattat tcaagactta tgggataaag tccaattacg taaaaaacaa gtcagtcaaa   2220
aacctcaagt ccacggtaaa ggaactaatc tattaacagg tatcgttcat tgtccacaat   2280
```

```
gtggtgcacc aatggcagct agtaacacaa cgaacacatt gaaagatggt accaagaagc   2340

gaatacgtta ttattcttgc agtaacttcc gaaacaaagg ctcaaaagta tgttctgcga   2400

atagcgttag agctgatgtg attgagaaat acgtcatgga tcaaatactc gaaattgtca   2460

aaagtgataa agtcattaac caagtcttag aacgtgtcaa tcaagaaaat aaagtcgata   2520

ttggtgcatt gaaccacgat atcgcttata aacaacaaca atacgatgaa gtcagcggga   2580

aactccataa tttagttaaa accattgaag ataatccgga cctaacatct gcattgaaag   2640

caactattca tcaatatgaa acacaactca atgacattac aaatcaaatg aatcaactca   2700

aacagcaaca aaatcaagag aaactatctt atgatacgaa acaaatcgct gccctattac   2760

aacgaatatt tcaaaatata gaatcaatgg ataaagcaca actcaaagca ttatatctta   2820

cagtcattga ccgtattgat attcgtaaag acggtaatca taaaaaacag ttctacgtta   2880

cactaaaact caataatgaa attattaaac aacttttcaa taatacccct ctcgacgaag   2940

tgctcctcag cacttcgtct ttatttttgc ctcaaacgct ctttcttcaa atctaa       2996
```

<210> SEQ ID NO 233
<211> LENGTH: 1410
<212> TYPE: DNA
<213> ORGANISM: Staphylococcus aureus

<400> SEQUENCE: 233

```
gctgtaggga aactaaaaga gaaatattgg aagcaagcca tagcagaata tgaaaaacgt     60

ttaggcccat acaccaagat agacatcata gaagttccag acgaaaaagc accagaaaat    120

atgagcgaca aagaaattga gcaagtaaaa gaaaaagaag gccaacgaat actagccaaa    180

attaaaccac aatccacagt cattacatta gaaatacaag gaaagatgct atcttccgaa    240

ggattggccc aagaattgaa ccaacgcatg acccaagggc aaagcgactt tgtattcgtc    300

attggcggat caaacggcct gcacaaggac gtcttacaac gcagtaacta cgcactatca    360

ttcagcaaaa tgacattccc acatcaaatg atgcgggttg tgttaattga gcaagtgtat    420

agagcattta agattatgcg tggagaagca tatcataaat gatgcggttt tttcagccgc    480

ttcataaagg gattttgaat gtatcagaac atatgaggtt tatgtgaatt gctgttatgt    540

ttttaagaag catatcataa gtgatgcggt ttttattaat tagttgctaa aaaatgaagt    600

atgcaatatt aattattatt aaattttgat atatttaaag aaagattaag tttagggtga    660

atgaatggct tatcaaagtg aatatgcatt agaaaatgaa gtacttcaac aacttgagga    720

attgaactat gaaagagtaa atatacataa tattaaatta gaaattaatg aatatctcaa    780

agaactagga gtgttgaaaa atgaataagc agacaaatac tccagaacta agatttccag    840

agtttgatga ggaatggaaa aaaaggaaat taggtgaagt agtaaattat aaaaatggtg    900

gttcatttga aagtttagtg aaaaaccatg gtgtatataa actcataact cttaaatctg    960

ttaatacaga aggaaagttg tgtaattctg gaaaatatat cgatgataaa tgtgttgaaa   1020

cattgtgtaa tgatacttta gtaatgatac tgagcgagca agcaccagga ctagttggaa   1080

tgactgcaat tatacctaat aataatgagt atgtactaaa tcaacgagta gcagcactag   1140

tgcctaaaca atttatagat agtcaatttc tatctaagtt aattaataga aaccagaaat   1200

atttcagtgt gagatctgct ggaacaaaag tgaaaaatat ttctaaagga catgtagaaa   1260

actttaattt tttatctcct aattacactg aacaacaaaa aataggtaat ttcttcagca   1320

aactcgaccg ccagattgag ttagaagaag agaaacttga actcttatag caacaaaagc   1380
```

gtggatatat ttcagaagat ttttctcaag 1410

<210> SEQ ID NO 234
<211> LENGTH: 60
<212> TYPE: DNA
<213> ORGANISM: Staphylococcus aureus

<400> SEQUENCE: 234
tatgtcaaaa atcatgaacc tcattactta tgataccttg tgcaggccgt ttgatccgcc 60

<210> SEQ ID NO 235
<211> LENGTH: 60
<212> TYPE: DNA
<213> ORGANISM: Staphylococcus aureus

<400> SEQUENCE: 235
tatgtcaaaa atcatgaacc tcattactta tgataccttg tgcaggccgt ttgatccgcc 60

<210> SEQ ID NO 236
<211> LENGTH: 60
<212> TYPE: DNA
<213> ORGANISM: Staphylococcus aureus

<400> SEQUENCE: 236
tatgtcaaaa atcatgaacc tcattactta tgataccttg tgcaggccgt ttgatccgcc 60

<210> SEQ ID NO 237
<211> LENGTH: 60
<212> TYPE: DNA
<213> ORGANISM: Staphylococcus aureus

<400> SEQUENCE: 237
tatgtcaaaa atcatgaacc tcattactta tgataccttg tgcaggccgt ttgatccgcc 60

<210> SEQ ID NO 238
<211> LENGTH: 60
<212> TYPE: DNA
<213> ORGANISM: Staphylococcus aureus

<400> SEQUENCE: 238
tatgtcaaaa atcatgaacc tcattactta tgataccttg tgcaggccgt ttgatccgcc 60

<210> SEQ ID NO 239
<211> LENGTH: 60
<212> TYPE: DNA
<213> ORGANISM: Staphylococcus aureus

<400> SEQUENCE: 239
tatgtcaaaa atcatgaacc tcattactta tgataccttg tgcaggccgt ttgatccgcc 60

<210> SEQ ID NO 240
<211> LENGTH: 60
<212> TYPE: DNA
<213> ORGANISM: Staphylococcus aureus

<400> SEQUENCE: 240
tatgtcaaaa atcatgaacc tcattactta tgataccttg tgcaggccgt ttgatccgcc 60

<210> SEQ ID NO 241
<211> LENGTH: 60
<212> TYPE: DNA
<213> ORGANISM: Staphylococcus aureus

<400> SEQUENCE: 241
tatgtcaaaa atcatgaacc tcattactta tgataccttg tgcaggccgt ttgatccgcc 60

<210> SEQ ID NO 242
<211> LENGTH: 60
<212> TYPE: DNA
<213> ORGANISM: Staphylococcus aureus

<400> SEQUENCE: 242
tatgtcaaaa atcatgaacc tcattactta tgataccttg tgcaggccgt ttgatccgcc 60

<210> SEQ ID NO 243
<211> LENGTH: 60
<212> TYPE: DNA
<213> ORGANISM: Staphylococcus aureus

<400> SEQUENCE: 243
tatgtcaaaa atcatgaacc tcattactta tgataccttg tgcaggccgt ttgatccgcc 60

<210> SEQ ID NO 244
<211> LENGTH: 60
<212> TYPE: DNA
<213> ORGANISM: Staphylococcus aureus

<400> SEQUENCE: 244
tatgtcaaaa atcatgaacc tcattactta tgataccttg tgcaggccgt ttgatccgcc 60

<210> SEQ ID NO 245
<211> LENGTH: 60
<212> TYPE: DNA
<213> ORGANISM: Staphylococcus aureus

<400> SEQUENCE: 245
tatgtcaaaa atcatgaacc tcattactta tgataccttg tgcaggccgt ttgatccgcc 60

<210> SEQ ID NO 246
<211> LENGTH: 25
<212> TYPE: DNA
<213> ORGANISM: Staphylococcus aureus

<400> SEQUENCE: 246
cttggtgtaa accattggag ccacc 25

<210> SEQ ID NO 247
<211> LENGTH: 21
<212> TYPE: DNA
<213> ORGANISM: Staphylococcus aureus

<400> SEQUENCE: 247
cctcatgcaa tccatttgat c 21

<210> SEQ ID NO 248
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 248
gtcaaaaatc atgaacctca ttacttatg 29

<210> SEQ ID NO 249
<211> LENGTH: 19
<212> TYPE: DNA

<213> ORGANISM: Artificial Sequence
<220> FEATURE:
<223> OTHER INFORMATION: Synthetic nucleic acid sequence

<400> SEQUENCE: 249
tgtgcaggcc gtttgatcc 19

<210> SEQ ID NO 250
<211> LENGTH: 35
<212> TYPE: DNA
<213> ORGANISM: Staphylococcus aureus

<400> SEQUENCE: 250
acaaggacgt cttacaacgc agtaactatg cacta 35

<210> SEQ ID NO 251
<211> LENGTH: 35
<212> TYPE: DNA
<213> ORGANISM: Staphylococcus aureus

<400> SEQUENCE: 251
acaaggacgt cttacaacgc agtaactatg cacta 35

<210> SEQ ID NO 252
<211> LENGTH: 35
<212> TYPE: DNA
<213> ORGANISM: Staphylococcus aureus

<400> SEQUENCE: 252
acaaggacgt cttacaacgc agtaactatg cacta 35

<210> SEQ ID NO 253
<211> LENGTH: 35
<212> TYPE: DNA
<213> ORGANISM: Staphylococcus aureus

<400> SEQUENCE: 253
acaaggacgt cttacaacgc agtaactatg cacta 35

<210> SEQ ID NO 254
<211> LENGTH: 35
<212> TYPE: DNA
<213> ORGANISM: Staphylococcus aureus

<400> SEQUENCE: 254
acaaggacgt cttacaacgc agtaactatg cacta 35

<210> SEQ ID NO 255
<211> LENGTH: 35
<212> TYPE: DNA
<213> ORGANISM: Staphylococcus aureus

<400> SEQUENCE: 255
acaaggacgt cttacaacgc agtaactatg cacta 35

<210> SEQ ID NO 256
<211> LENGTH: 35
<212> TYPE: DNA
<213> ORGANISM: Staphylococcus aureus

<400> SEQUENCE: 256
acaaggacgt cttacaacgc agtaactatg cacta 35

<210> SEQ ID NO 257
<211> LENGTH: 35
<212> TYPE: DNA
<213> ORGANISM: Staphylococcus aureus

<400> SEQUENCE: 257
acaaggacgt cttacaacgt agtaactacg cacta 35

<210> SEQ ID NO 258
<211> LENGTH: 35
<212> TYPE: DNA
<213> ORGANISM: Staphylococcus aureus

<400> SEQUENCE: 258
acaaggacgt cttacaacgt agtaactacg cacta 35

<210> SEQ ID NO 259
<211> LENGTH: 35
<212> TYPE: DNA
<213> ORGANISM: Staphylococcus aureus

<400> SEQUENCE: 259
acaaggacgt cttacaacgt agtaactacg cacta 35

<210> SEQ ID NO 260
<211> LENGTH: 35
<212> TYPE: DNA
<213> ORGANISM: Staphylococcus aureus

<400> SEQUENCE: 260
acaaggacgt cttacaacgt agtaactacg cacta 35

<210> SEQ ID NO 261
<211> LENGTH: 35
<212> TYPE: DNA
<213> ORGANISM: Staphylococcus aureus

<400> SEQUENCE: 261
acaaggacgt cttacaacgt agtaactacg cacta 35

<210> SEQ ID NO 262
<211> LENGTH: 35
<212> TYPE: DNA
<213> ORGANISM: Staphylococcus aureus

<400> SEQUENCE: 262
acaaggacgt cttacaacgt agtaactacg cacta 35

<210> SEQ ID NO 263
<211> LENGTH: 35
<212> TYPE: DNA
<213> ORGANISM: Staphylococcus aureus

<400> SEQUENCE: 263
acaaggacgt cttacaacgc agtaactacg cacta 35

<210> SEQ ID NO 264
<211> LENGTH: 35
<212> TYPE: DNA
<213> ORGANISM: Staphylococcus aureus

<400> SEQUENCE: 264
acaaggacgt cttacaacgc agtaactacg cacta 35

-continued

<210> SEQ ID NO 265
<211> LENGTH: 35
<212> TYPE: DNA
<213> ORGANISM: Staphylococcus aureus

<400> SEQUENCE: 265
accaagacgt cttacaacgc agcaactatg cttta 35

<210> SEQ ID NO 266
<211> LENGTH: 35
<212> TYPE: DNA
<213> ORGANISM: Staphylococcus aureus

<400> SEQUENCE: 266
atgaggacgt cttacaacgc agcaactacg cactt 35

<210> SEQ ID NO 267
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 267
gacgtcttac aacgcagtaa ctatg 25

<210> SEQ ID NO 268
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 268
gacgtcttac aacgtagtaa ctacg 25

<210> SEQ ID NO 269
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 269
gacgtcttac aacgcagtaa ctacg 25

METHOD FOR THE DETECTION AND IDENTIFICATION OF METHICILLIN-RESISTANT *STAPHYLOCOCCUS AUREUS*

CROSS-REFERENCE TO RELATED APPLICATIONS

This application is a continuation of U.S. patent application Ser. No. 11/416,500, filed May 2, 2006, now U.S. Pat. No. 9,777,335, which is a continuation of U.S. patent application Ser. No. 10/479,674, now U.S. Pat. No. 7,449, 289, to Huletsky, et al., "SEQUENCES FOR DETECTION AND IDENTIFICATION OF METHICILLIN-RESISTANT *STAPHYLOCOCCUS AUREUS*," filed Sep. 7, 2004 which is a National Phase Application of International Patent Application PCT/CA02/00824, filed Jun. 4, 2002, now closed, which claims priority to Canadian Patent Application No. 2,348,042, filed Jun. 4, 2001, now abandoned.

REFERENCE TO SEQUENCE LISTING, TABLE, OR COMPUTER PROGRAM LISTING

The present application is being filed along with a sequence listing in electronic format. The sequence listing is provided as a file entitled GENOM_051C2_Substitute.TXT, created Apr. 6, 2018 which is 187 KB in size. The information in the electronic format of the sequence listing is incorporated herein by reference in its entirety.

BACKGROUND OF THE INVENTION

Clinical Significance of *Staphylococcus aureus*

The coagulase-positive species *Staphylococcus aureus* is well documented as a human opportunistic pathogen. Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abscesses. Food poisoning mediated by staphylococcal enterotoxins is another important syndrome associated with *S. aureus*. Toxic shock syndrome, a community-acquired disease, has also been attributed to infection or colonization with toxigenic *S. aureus* (Murray et al. Eds, 1999, Manual of Clinical Microbiology, $7^{th}$ Ed. ASM Press, Washington, D.C.).

Methicillin-resistant *S. aureus* (MRSA) emerged in the 1980s as a major clinical and epidemiologic problem in hospitals. MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defense. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the chromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

By nucleotide sequence determination of the DNA region surrounding the mecA gene from *S. aureus* strain N315 (isolated in Japan in 1982), Hiramatsu et al. have found that the mecA gene is carried by a novel genetic element, designated staphylococcal cassette chromosome mec (SCCmec), inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). The element is precisely excised from the chromosome of *S. aureus* strain N315 and integrates into a specific *S. aureus* chromosomal site in the same orientation through the function of a unique set of recombinase genes comprising ccrA and ccrB. Two novel genetic elements that shared similar structural features of SCCmec were found by cloning and sequencing the DNA region surrounding the mecA gene from MRSA strains NCTC 10442 (the first MRSA strain isolated in England in 1961) and 85/2082 (a strain from New Zealand isolated in 1985). The three SCCmec have been designated type I (NCTC 10442), type II (N315) and type III (85/2082) based on the year of isolation of the strains (Ito et al., 2001, Antimicrob. Agents Chemother. 45:1323-1336) (FIG. 1). Hiramatsu et al. have found that the SCCmec DNAs are integrated at a specific site in the methicillin-sensitive *S. aureus* (MSSA) chromosome. They characterized the nucleotide sequences of the regions around the left and right boundaries of SCCmec DNA (i.e. attL and attR, respectively) as well as those of the regions around the SCCmec DNA integration site (i.e. attBscc which is the bacterial chromosome attachment site for SCCmec DNA). The attBscc site was located at the 3' end of a novel open reading frame (ORF), orfX. The orfX potentially encodes a 159-amino acid polypeptide sharing identity with some previously identified polypeptides, but of unknown function (Ito et al., 1999, Antimicrob. Agents Chemother. 43:1449-1458). Recently, a new type of SCCmec (type IV) has been described by both Hiramatsu et al. (Ma et al, 2002, Antimicrob. Agents Chemother. 46:1147-1152) and Oliveira et al. (Oliveira et al, 2001, Microb. Drug Resist. 7:349-360). The sequences of the right extremity of the new type IV SCCmec from *S. aureus* strains CA05 and 8/6-3P published by Hiramatsu et al. (Ma et al., 2002, Antimicrob. Agents Chemother. 46:1147-1152) were nearly identical over 2000 nucleotides to that of type II SCCmec of *S. aureus* strain N315 (Ito et al., 2001, Antimicrob. Agents Chemother. 45:1323-1336). No sequence at the right extremity of the SCCmec type IV is available from the *S. aureus* strains HDE288 and PL72 described by Oliveira et al. (Oliveira et al., 2001, Microb. Drug Resist. 7:349-360).

Previous methods used to detect and identify MRSA (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244;

Hiramatsu et al., 1992, Microbiol. Immunol. 36:445-453), which are based on the detection of the mecA gene and *S. aureus*-specific chromosomal sequences, encountered difficulty in discriminating MRSA from methicillin-resistant coagulase-negative staphylococci (CNS) because the mecA gene is widely distributed in both *S. aureus* and CNS species (Suzuki et al., 1992, Antimicrob. Agents. Chemother. 36:429-434). Hiramatsu et al. (U.S. Pat. No. 6,156,507) have described a PCR assay specific for MRSA by using primers that can specifically hybridize to the right extremities of the 3 types of SCCmec DNAs in combination with a primer specific to the *S. aureus* chromosome, which corresponds to the nucleotide sequence on the right side of the SCCmec integration site. Since nucleotide sequences surrounding the SCCmec integration site in other staphylococcal species (such as *S. epidermidis* and *S. haemolyticus*) are different from those found in *S. aureus*, this PCR assay was specific for the detection of MRSA. This PCR assay also supplied information for MREP typing (standing for «mec right extremity polymorphism») of SCCmec DNA (Ito et al., 2001, Antimicrob. Agents Chemother. 45:1323-1336; Hiramatsu et al., 1996, J. Infect. Chemother. 2:117-129). This typing method takes advantage of the polymorphism at the right extremity of SCCmec DNAs adjacent to the integration site among the three types of SCCmec. Type III has a unique nucleotide sequence while type II has an insertion of 102 nucleotides to the right terminus of SCCmec type I. The MREP typing method described by Hiramatsu et al. (Ito et al., 2001, Antimicrob. Agents Chemother. 45:1323-1336; Hiramatsu et al., 1996, J. Infect. Chemother. 2:117-129) defines the SCCmec type I as MREP type i, SCCmec type II as MREP type ii and SCCmec type III as MREP type iii. It should be noted that the MREP typing method cannot differentiate the new SCCmec type IV described by Hiramatsu et al. (Ma et al., 2002, Antimicrob. Agents Chemother. 46:1147-1152) from SCCmec type II because these two SCCmec types exhibit the same nucleotide sequence to the right extremity.

The set of primers described by Hiramatsu et al. as being the optimal primer combination (SEQ ID NOs.: 22, 24, 28 in U.S. Pat. No. 6,156,507 corresponding to SEQ ID NOs.: 56, 58 and 60, respectively, in the present invention) have been used in the present invention to test by PCR a variety of MRSA and MSSA strains (FIG. 1 and Table 1). Twenty of the 39 MRSA strains tested were not amplified by the Hiramatsu et al. multiplex PCR assay (Tables 2 and 3). Hiramitsu's method indeed was successful in detecting less than 50% of the tested 39 MRSA strains.

This finding demonstrates that some MRSA strains have sequences at the right extremity of SCCmec-chromosome right extremity junction different from those identified by Hiramatsu et al. Consequently, the system developed by Hiramatsu et al. does not allow the detection of all MRSA. The present invention relates to the generation of SCCmec-chromosome right extremity junction sequence data required to detect more MRSA strains in order to improve the Hiramatsu et al. assay. There is a need for developing more ubiquitous primers and probes for the detection of most MRSA strains around the world.

SUMMARY OF THE INVENTION

It is an object of the present invention to provide a specific, ubiquitous and sensitive method using probes and/or amplification primers for determining the presence and/or amount of nucleic acids from all MRSA strains.

Ubiquity of at least 50% amongst the strains representing MRSA strains types IV to X is an objective of this invention.

Therefore, in accordance with the present invention is provided a method to detect the presence of a methicillin-resistant *Staphylococcus aureus* (MRSA) strain in a sample, the MRSA strain being resistant because of the presence of an SCCmec insert containing a mecA gene, said SCCmec being inserted in bacterial nucleic acids thereby generating a polymorphic right extremity junction (MREJ), the method comprising the step of annealing the nucleic acids of the sample with a plurality of probes and/or primers, characterized by:

the primers and/or probes are specific for MRSA strains and capable of annealing with polymorphic MREJ nucleic acids, the polymorphic MREJ comprising MREJ types i to x; and the primers and/or probes altogether can anneal with at least four MREJ types selected from MREJ types i to x.

In a specific embodiment, the primers and/or probes are all chosen to anneal under common annealing conditions, and even more specifically, they are placed altogether in the same physical enclosure.

A specific method has been developed using primers and/or probes having at least 10 nucleotides in length and capable of annealing with MREJ types i to iii, defined in any one of SEQ ID NOs: 1, 20, 21, 22, 23, 24, 25, 41, 199; 2, 17, 18, 19, 26, 40, 173, 174, 175, 176, 177, 178, 179, 180, 181, 182, 183, 185, 186, 197; 4, 5, 6, 7, 8, 9, 10, 11, 12, 13, 14, 15, 16, 104, 184, 198 and with one or more of MREJ types iv to ix, having SEQ ID NOs: 42, 43, 44, 45, 46, 51; 47, 48, 49, 50; 171; 165, 166; 167; 168. To be perfectly ubiquitous with the all the sequenced MREJs, the primers and/or probes altogether can anneal with said SEQ ID NOs of MREJ types i to ix.

The following specific primers and/or probes having the following sequences have been designed:

66, 100, 101, 105, 52, 53, 54, 55, 56, 57, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type i 66, 97, 99, 100, 101, 106, 117, 118, 124, 125, 52, 53, 54, 55, 56, 57 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89 for the detection of MREJ type ii 67, 98, 102, 107, 108, 64, 71, 72, 73, 74, 75, 76, 70, 103, 130, 132, 158, 159, 58, 59, 62, 126, 127, 128, 129, 131, 200, 201, 60, 61, 63, 32, 83, 84, 160, 161, 162, 163, 164, 85, 86, 87, 88, 89, for the detection of MREJ type iii 79, 77, 145, 147, 64, 71, 72, 73, 74, 75, 76, 70, 103, 130, 132, 158, 159, 59, 62, 126, 127, 128, 129, 131, 200, 201, 60, 61, 63, 68, 32, 83, 84, 160, 161, 162, 163, 164, 85, 86, 87, 88, 89, for the detection of MREJ type iv 65, 80, 146, 154, 155, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type v 202, 203, 204, 4, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vi 112, 113, 114, 119, 120, 121, 122, 123, 150, 151, 153, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vii 115, 116, 187, 188, 207, 208, 64, 71, 72, 73, 74, 75, 76, 70, 103, 130, 132, 158, 159

59, 62, 126, 127, 128, 129, 131, 200, 201, 60, 61, 63, 32, 83, 84, 160, 161, 162, 163, 164, 85, 86, 87, 88, 89, for the detection of MREJ type viii 109, 148, 149, 205, 206, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type ix.

Amongst these, the following primer pairs having the following sequences are used:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ As well, amongst these, the following probes having the following sequences are used:

SEQ ID NOs: 32, 83, 84, 160, 161, 162, 163, 164 for the detection of MREJ types i to ix.

In the most preferred embodied method, the following primers and/or probes having the following nucleotide sequences are used together. The preferred combinations make use of:

SEQ ID NOs: 64, 66, 84, 163, 164 for the detection of MREJ type i

SEQ ID NOs: 64, 66, 84, 163, 164 for the detection of MREJ type ii

SEQ ID NOs: 64, 67, 84, 163, 164 for the detection of MREJ type iii

SEQ ID NOs: 64, 79, 84, 163, 164 for the detection of MREJ type iv

SEQ ID NOs: 64, 80, 84, 163, 164 for the detection of MREJ type v

SEQ ID NOs: 64, 112, 84, 163, 164 for the detection of MREJ type vii.

All these probes and primers can even be used together in the same physical enclosure.

It is another object of this invention to provide a method for typing a MREJ of a MRSA strain, which comprises the steps of: reproducing the above method with primers and/or probes specific for a determined MREJ type, and detecting an annealed probe or primer as an indication of the presence of a determined MREJ type.

It is further another object of this invention to provide a nucleic acid selected from SEQ ID NOs:

SEQ ID NOs: 42, 43, 44, 45, 46, 51 for sequence of MREJ type iv;

SEQ ID NOs: 47, 48, 49, 50 for sequence of MREJ type v;

SEQ ID NOs: 171 for sequence of MREJ type vi;

SEQ ID NOs: 165, 166 for sequence of MREJ type vii;

SEQ ID NOs: 167 for sequence of MREJ type viii;

SEQ ID NOs: 168 for sequence of MREJ type ix.

Oligonucleotides of at least 10 nucleotides in length which hybridize with any of these nucleic acids and which hybridize with one or more MREJ of types selected from iv to ix are also objects of this invention. Amongst these, primer pairs (or probes) having the following SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, are also within the scope of this invention.

Further, internal probes having nucleotide sequences defined in any one of SEQ ID NOs: 32, 83, 84, 160, 161, 162, 163, 164, are also within the scope of this invention. Compositions of matter comprising the primers and/or probes annealing or hybridizing with one or more MREJ of types selected from iv to ix as well as with the above nucleic acids, comprising or not primers and/or probes, which hybridize with one or more MREJ of types selected from i to iii, are further objects of this invention. The preferred compositions would comprise the primers having the nucleotide sequences defined in SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, or probes, which SEQ ID NOs are: 32, 83, 84, 160, 161, 162, 163, 164, or both.

DETAILED DESCRIPTION OF THE INVENTION

Figure 1:
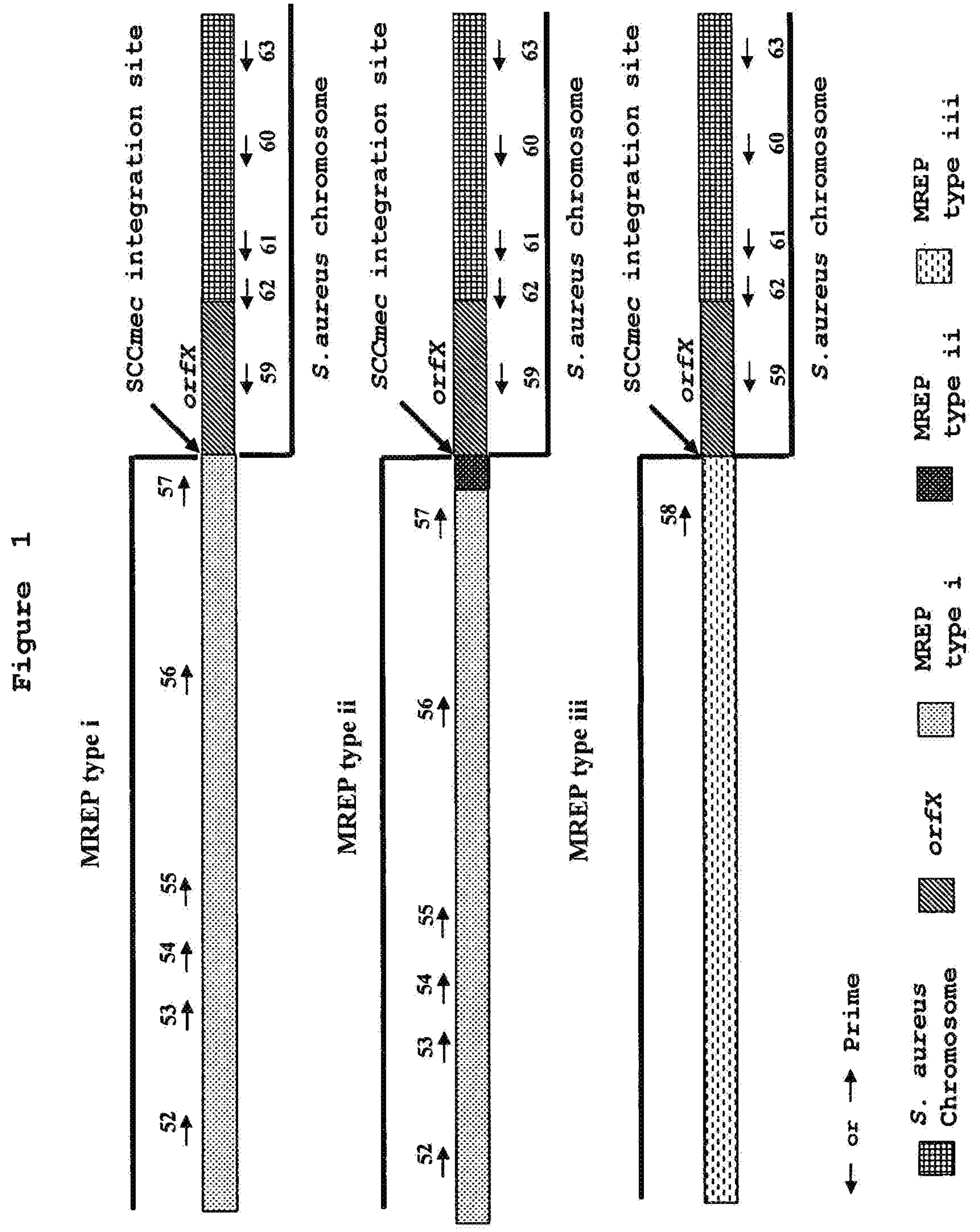
FIG. 1 is a diagram illustrating the position of the primers developed by Hiramatsu et al. (U.S. Pat. No. 6,156,507) in the SCCmec-chromosome right extremity junction for detection and identification of MRSA.

Here is particularly provided a method wherein each of MRSA nucleic acids or a variant or part thereof comprises a selected target region hybridizable with said primers or probes developed to be ubiquitous;

wherein each of said nucleic acids or a variant or part thereof comprises a selected target region hybridizable with said primers or probes;

said method comprising the steps of contacting said sample with said probes or primers and detecting the presence and/or amount of hybridized probes or amplified products as an indication of the presence and/or amount of MRSA.

In the method, sequences from DNA fragments of SCCmec-chromosome right extremity junction, thereafter named MREJ standing for «mec right extremity junction» including sequences from SCCmec right extremity and chromosomal DNA to the right of the SCCmec integration site are used as parental sequences from which are derived the primers and/or the probes. MREJ sequences include our proprietary sequences as well as sequences obtained from public databases and from U.S. Pat. No. 6,156,507 and were selected for their capacity to sensitively, specifically, ubiquitously and rapidly detect the targeted MRSA nucleic acids.

Our proprietary DNA fragments and oligonucleotides (primers and probes) are also another object of this invention.

Compositions of matter such as diagnostic kits comprising amplification primers or probes for the detection of MRSA are also objects of the present invention.

In the above methods and kits, probes and primers are not limited to nucleic acids and may include, but are not restricted to, analogs of nucleotides. The diagnostic reagents constituted by the probes and the primers may be present in any suitable form (bound to a solid support, liquid, lyophilized, etc.).

In the above methods and kits, amplification reactions may include but are not restricted to: a) polymerase chain reaction (PCR), b) ligase chain reaction (LCR), c) nucleic acid sequence-based amplification (NASBA), d) self-sustained sequence replication (3SR), e) strand displacement amplification (SDA), f) branched DNA signal amplification (bDNA), g) transcription-mediated amplification (TMA), h) cycling probe technology (CPT), i) nested PCR, j) multiplex PCR, k) solid phase amplification (SPA), l) nuclease dependent signal amplification (NDSA), m) rolling circle amplification technology (RCA), n) Anchored strand displacement amplification, o) Solid-phase (immobilized) rolling circle amplification.

In the above methods and kits, detection of the nucleic acids of target genes may include real-time or post-amplification technologies. These detection technologies can include, but are not limited to fluorescence resonance energy transfer (FRET)-based methods such as adjacent hybridization of probes (including probe-probe and probe-primer methods), TaqMan probe, molecular beacon probe, Scorpion probe, nanoparticle probe and Amplifluor probe. Other detection methods include target gene nucleic acids detection via immunological methods, solid phase hybridization methods on filters, chips or any other solid support. In these systems, the hybridization can be monitored by fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

In a preferred embodiment, a PCR protocol is used for nucleic acid amplification.

A method for detection of a plurality of potential MRSA strains having different MREJ types may be conducted in separate reactions and physical enclosures, one type at the time. Alternatively, it could be conducted simultaneously for different types in separate physical enclosures, or in the same physical enclosures. In the latter scenario a multiplex PCR reaction could be conducted which would require that the oligonucleotides are all capable of annealing with a target region under common conditions. Since many probes or primers are specific for a determined MREJ type, typing a MRSA strain is a possible embodiment. When a mixture of oligonucleotides annealing together with more than one type is used in a single physical enclosure or container, different labels would be used to distinguish one type from another.

We aim at developing a DNA-based test or kit to detect and identify MRSA. Although the sequences from orfX genes and some SCCmec DNA fragments are available from public databases and have been used to develop DNA-based tests for detection of MRSA, new sequence data allowing to improve MRSA detection and identification which are object of the present invention have either never been characterized previously or were known but not shown to be located at the right extremity of SCCmec adjacent to the integration site (Table 4). These novel sequences could not have been predicted nor detected by the MRSA-specific PCR assay developed by Hiramatsu et al. (U.S. Pat. No. 6,156,507). These sequences will allow to improve current DNA-based tests for the diagnosis of MRSA because they allow the design of ubiquitous primers and probes for the detection and identification of more MRSA strains including all the major epidemic clones from around the world.

The diagnostic kits, primers and probes mentioned above can be used to detect and/or identify MRSA, whether said diagnostic kits, primers and probes are used for in vitro or in situ applications. The said samples may include but are not limited to: any clinical sample, any environmental sample, any microbial culture, any microbial colony, any tissue, and any cell line.

It is also an object of the present invention that said diagnostic kits, primers and probes can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

In the methods and kits described herein below, the oligonucleotide probes and amplification primers have been derived from larger sequences (i.e. DNA fragments of at least 100 base pairs). All DNA sequences have been obtained either from our proprietary sequences or from public databases (Tables 5, 6, 7, 8 and 9).

It is clear to the individual skilled in the art that oligonucleotide sequences other than those described in the present invention and which are appropriate for detection and/or identification of MRSA may also be derived from the proprietary fragment sequences or selected public database sequences. For example, the oligonucleotide primers or probes may be shorter but of a length of at least 10 nucleotides or longer than the ones chosen; they may also be selected anywhere else in the proprietary DNA fragments or in the sequences selected from public databases; they may also be variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from said DNA fragment sequences for use in amplification methods other than PCR. Consequently, the core of this invention is the detection and/or identification of MRSA by targeting genomic DNA sequences which are used as a source of specific and ubiquitous oligonucleotide probes and/or amplification primers. Although the selection and evaluation of oligonucleotides suitable for diagnostic purposes require much effort, it is quite possible for the individual skilled in the art to derive, from the selected DNA fragments, oligonucleotides other than the ones listed in Tables 5, 6, 7, 8 and 9 which are suitable for diagnostic purposes. When a proprietary fragment or a public database sequence is selected for its specificity and ubiquity, it increases the probability that subsets thereof will also be specific and ubiquitous.

The proprietary DNA fragments have been obtained as a repertory of sequences created by amplifying MRSA nucleic acids with new primers. These primers and the repertory of nucleic acids as well as the repertory of nucleotide sequences are further objects of this invention (Tables 4, 5, 6, 7, 8 and 9).

Claims therefore are in accordance with the present invention.

Sequences for Detection and Identification of MRSA

In the description of this invention, the terms «nucleic acids» and «sequences» might be used interchangeably. However, «nucleic acids» are chemical entities while «sequences» are the pieces of information encoded by these «nucleic acids». Both nucleic acids and sequences are equivalently valuable sources of information for the matter pertaining to this invention.

Oligonucleotide Primers and Probes Design and Synthesis

As part of the design rules, all oligonucleotides (probes for hybridization and primers for DNA amplification by PCR) were evaluated for their suitability for hybridization or PCR amplification by computer analysis using standard programs (i.e. the GCG Wisconsin package programs, the primer analysis software Oligo™ 6 and MFOLD 3.0). The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems). Molecular beacon designs were evaluated using criteria established by Kramer et al. (http://www.molecular-beacons.org).

The oligonucleotide sequence of primers or probes may be derived from either strand of the duplex DNA. The primers or probes may consist of the bases A, G, C, or T or analogs and they may be degenerated at one or more chosen nucleotide position(s) (Nichols et al., 1994, Nature 369:492-493). Primers and probes may also consist of nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). The primers or probes may be of any suitable length and may be selected anywhere within the DNA sequences from proprietary fragments, or from selected database sequences which are suitable for the detection of MRSA.

Variants for a given target microbial gene are naturally occurring and are attributable to sequence variation within that gene during evolution (Watson et al., 1987, Molecular Biology of the Gene, $4^{th}$ ed., The Benjamin/Cummings Publishing Company, Menlo Park, Calif.; Lewin, 1989, Genes IV, John Wiley & Sons, New York, N.Y.). For example, different strains of the same microbial species may have a single or more nucleotide variation(s) at the oligonucleotide hybridization site. The person skilled in the art is well aware of the existence of variant nucleic acids and/or sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variations at the primer hybridization site, one has to amplify a larger DNA target with PCR primers outside that hybridization site. Sequencing of this larger fragment will allow the detection of sequence variation at this primer hybridization site. A similar strategy may be applied to show variations at the hybridization site of a probe. Insofar as the divergence of the target nucleic acids and/or sequences or a part thereof does not affect significantly the sensitivity and/or specificity and/or ubiquity of the amplification primers or probes, variant microbial DNA is under the scope of this invention. Variants of the selected primers or probes may also be used to amplify or hybridize to a variant target DNA.

DNA Amplification

For DNA amplification by the widely used PCR method, primer pairs were derived from our proprietary DNA fragments or from public database sequences.

During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols on a standard thermocycler (PTC-200 from MJ Research Inc., Watertown, Mass.) were as follows: Treated standardized bacterial suspensions or genomic DNA prepared from bacterial cultures or clinical specimens were amplified in a 20 µl PCR reaction mixture. Each PCR reaction contained 50 mM KCl, 10 mM Tris-HCl (pH 9.0), 2.5 mM $MgCl_2$, 0.4 µM of each primer, 200 µM of each of the four dNTPs (Pharmacia Biotech), 3.3 µg/µl bovine serum albumin (BSA) (Sigma-Aldrich Canada Ltd, Oakville, Ontario, Canada) and 0.5 unit of Taq DNA polymerase (Promega Corp., Madison, Wis.) combined with the TaqStart™ antibody (BD Biosciences, Palo Alto, Calif.). The TaqStart™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of bacterial cultures or of clinical specimens consists in a rapid protocol to lyse the microbial cells and eliminate or neutralize PCR inhibitors (described in co-pending application U.S. 60/306,163). For amplification from purified genomic DNA, the samples were added directly to the PCR amplification mixture. An internal control, derived from sequences not found in the target MREJ sequences or in the human genome, was used to verify the efficiency of the PCR reaction and the absence of significant PCR inhibition.

The number of cycles performed for the PCR assays varies according to the sensitivity level required. For example, the sensitivity level required for microbial detection directly from a clinical specimen is higher than for detection from a microbial culture. Consequently, more sensitive PCR assays having more thermal cycles are probably required for direct detection from clinical specimens.

The person skilled in the art of nucleic acid amplification knows the existence of other rapid amplification procedures such as ligase chain reaction (LCR), reverse transcriptase PCR (RT-PCR), transcription-mediated amplification (TMA), self-sustained sequence replication (3SR), nucleic acid sequence-based amplification (NASBA), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.; Westin et al., 2000, Nat. Biotechnol. 18:199-204). The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

Any oligonucleotide derived from the *S. aureus* MREJ DNA sequences and used with any nucleic acid amplification and/or hybridization technologies are also under the scope of this invention.

Evaluation of the MRSA Detection Method Developed by Hiramatsu et al.

According to Hiramatsu et al. (Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336, Ma et al., 2002, Antimicrob. Agents Chemother. 46:1147-1152), four types of SCCmec DNA are found among MRSA strains. They have found that SCCmec DNAs are integrated at a specific site of the MSSA chromosome (named orfX). They developed a MRSA-specific multiplex PCR assay including primers that can hybridize to the right extremity of SCCmec types I, II and III (SEQ ID NOs.: 18, 19, 20, 21, 22, 23, 24 in U.S. Pat. No. 6,156,507 corresponding to SEQ ID NOs.: 52, 53, 54, 55, 56, 57, 58, respectively, in the present invention) as well as primers specific to the *S. aureus* chromosome to the right of the SCCmec integration site (SEQ ID NO.: 25, 28, 27, 26, 29 in U.S. Pat. No. 6,156,507 corresponding to SEQ ID NOs.: 59, 60, 61, 62, 63, respectively, in the present invention) (Table 1 and FIG. 1). The set of primers described by Hiramatsu et al. as being the optimal primer combination (SEQ ID NOs.: 22, 24 and 28 in U.S. Pat. No. 6,156,507 corresponding to SEQ ID NOs.: 56, 58 and 60 in the present invention) was used in the present invention to test by PCR a variety of MRSA, MSSA, methicillin-resistant CNS (MRCNS) and methicillin-sensitive CNS (MSCNS) strains (Table 2). A PCR assay performed using a standard thermocycler (PTC-200 from MJ Research Inc.) was used to test the ubiquity, the specificity and the sensitivity of these primers using the following protocol: one μl of a treated standardized bacterial suspension or of a genomic DNA preparation purified from bacteria were amplified in a 20 μl PCR reaction mixture. Each PCR reaction contained 50 mM KCl, 10 mM Tris-HCl (pH 9.0), 0.1% Triton X-100, 2.5 mM $MgCl_2$, 0.4 μM of each of the SCCmec- and *S. aureus* chromosome-specific primers (SEQ ID NOs.: 22, 24 and 28 in U.S. Pat. No. 6,156,507 corresponding to SEQ ID NOs.: 56, 58 and 60 in the present invention), 200 μM of each of the four dNTPs (Pharmacia Biotech), 3.3 μg/μl BSA (Sigma), and 0.5 U Taq polymerase (Promega) coupled with TaqStart™ Antibody (BD Biosciences).

PCR reactions were then subjected to thermal cycling 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 μg/ml of ethidium bromide. Twenty of the 39 MRSA strains tested were not amplified with the PCR assay developed by Hiramatsu et al. (Example 1, Tables 2 and 3).

Figure 2:
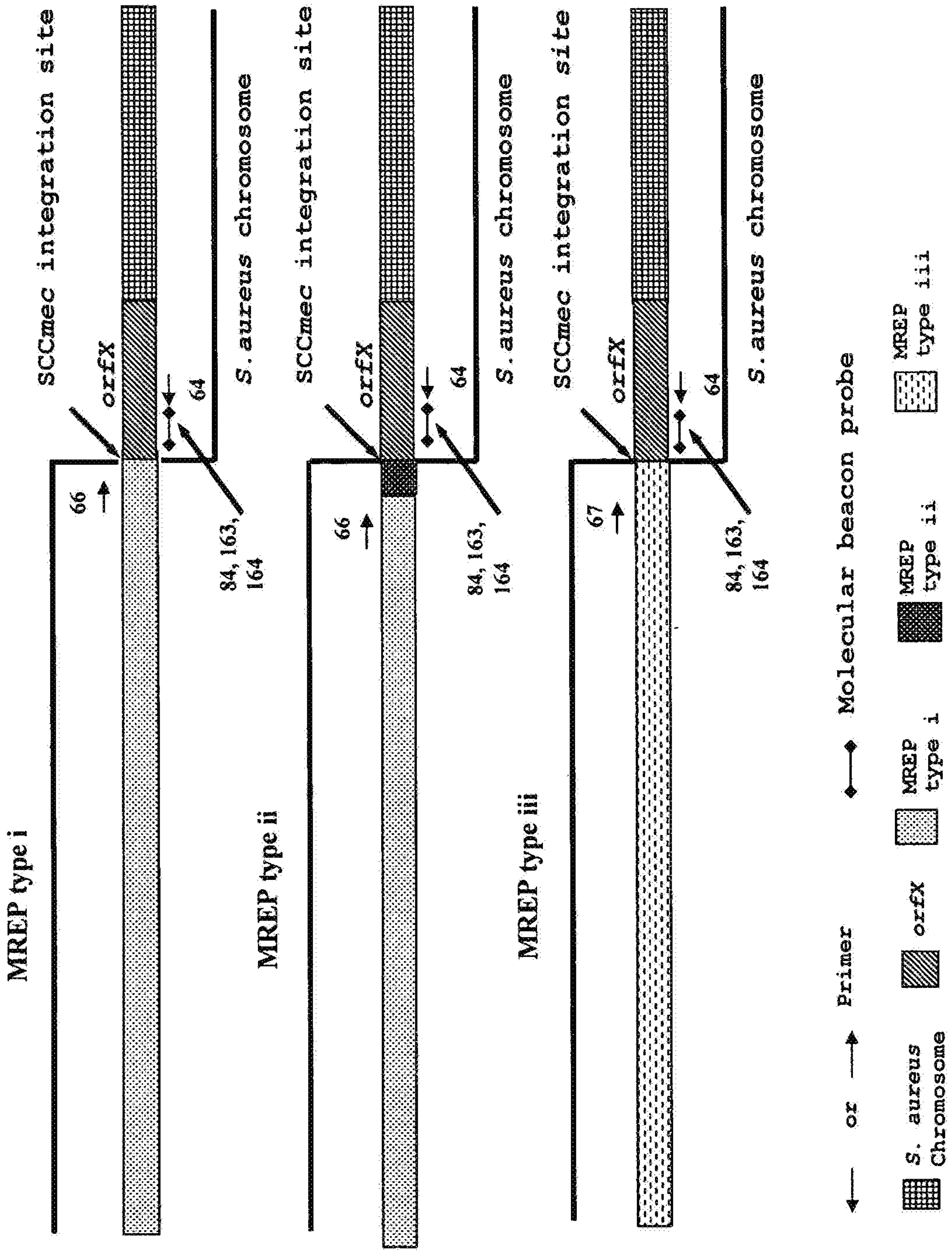
FIG. 2 is a diagram illustrating the position of the primers selected in the present invention in the SCCmec-orfX right extremity junction for detection and identification of MRSA.
Figure 2:
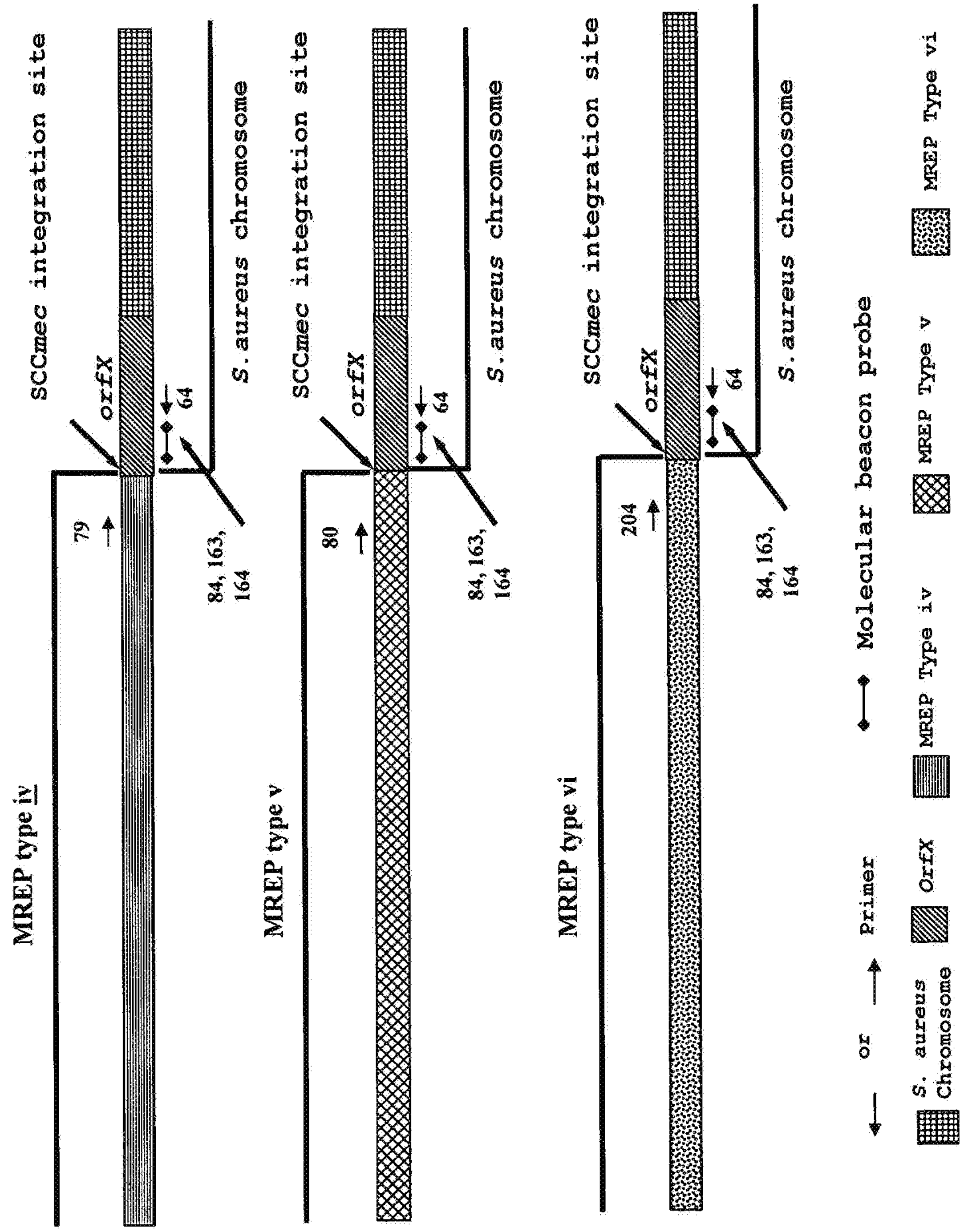
Figure 2:
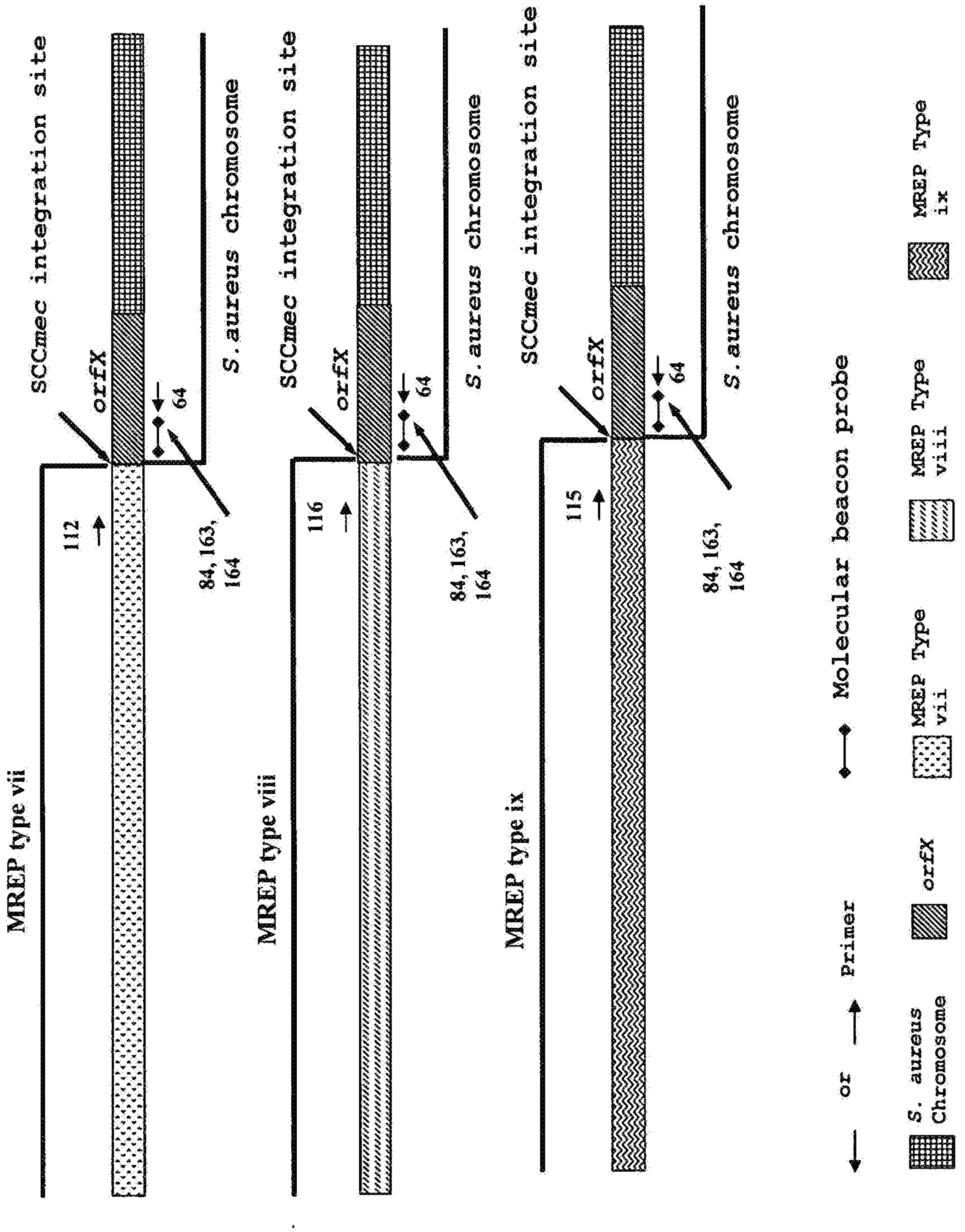

With a view of establishing a rapid diagnostic test for MRSAs, the present inventors developed new sets of primers specific to the right extremity of SCCmec types I and II (SEQ ID NOs.: 66, 100 and 101) (Annex 1), SCCmec type II (SEQ ID NOs.: 97 and 99), SCCmec type III (SEQ ID NOs.: 67, 98 and 102) and in the *S. aureus* chromosome to the right of the SCCmec integration site (SEQ ID NOs.: 64, 70, 71, 72, 73, 74, 75 and 76) (Table 5). These primers, amplifying short amplicons (171 to 278 bp), are compatible for use in rapid PCR assays (Table 7). The design of these primers was based on analysis of multiple sequence alignments of orfX and SCCmec sequences described by Hiramatsu et al. (U.S. Pat. No. 6,156,507) or available from GenBank (Table 10, Annex I). These different sets of primers were used to test by PCR a variety of MRSA, MSSA, MRCNS and MSCNS strains. Several amplification primers were developed to detect all three SCCmec types (SEQ ID NOs.: 97 and 99 for SCCmec type II, SEQ ID NOs.: 66, 100 and 101 for SCCmec types I and II and SEQ ID NOs.: 67, 98 and 102 for SCCmec type III). Primers were chosen according to their specificity for MRSA strains, their analytical sensitivity in PCR and the length of the PCR product. A set of two primers was chosen for the SCCmec right extremity region (SEQ ID NO.: 66 specific to SCCmec types I and II; SEQ ID NO.: 67 specific to SCCmec type III). Of the 8 different primers designed to anneal on the *S. aureus* chromosome to the right of the SCCmec integration site (targeting orfX gene) (SEQ ID NOs.: 64, 70, 71, 72, 73, 74, 75 and 76), only one (SEQ ID.: 64) was found to be specific for MRSA based on testing with a variety of MRSA, MSSA, MRCNS and MSCNS strains (Table 12). Consequently, a PCR assay using the optimal set of primers (SEQ ID NOs.: 64, 66 and 67) which could amplify specifically MRSA strains containing SCCmec types I, II and III was developed (FIG. 2, Annex I). While the PCR assay developed with this novel set of primers was highly sensitive (i.e. allowed the detection of 2 to 5 copies of genome for all three SCCmec types) (Table 11), it had the same shortcomings (i.e. lack of ubiquity) of the test developed by Hiramatsu et al. The 20 MRSA strains which were not amplified by the Hiramatsu et al. primers were also not detected by the set of primers comprising SEQ ID NOs.: 64, 66 and 67 (Tables 3 and 12). Clearly, diagnostic tools for achieving at least 50% ubiquity amongst the tested strains are needed.

With a view to establish a more ubiquitous (i.e. ability to detect all or most MRSA strains) detection and identification method for MRSA, we determined the sequence of the MREJ present in these 20 MRSA strains which were not amplified. This research has led to the discovery and identification of seven novel distinct MREJ target sequences which can be used for diagnostic purposes. These seven new MREJ sequences could not have been predicted nor detected with the system described in U.S. Pat. No. 6,156,507 by Hiramatsu et al. Namely, the present invention represents an improved method for the detection and identification of MRSA because it provides a more ubiquitous diagnostic method which allows for the detection of all major epidemic MRSA clones from around the world.

Sequencing of MREJ Nucleotide Sequences from MRSA Strains not Amplifiable with Primers Specific to SCCmec types I, II and III Since DNA from twenty MRSA strains were not amplified with the set of primers developed by Hiramatsu et al. (SEQ ID NOs.: 22, 24 and 28 in U.S. Pat. No. 6,156,507 corresponding to SEQ ID NOs.: 56, 58 and 60 in the present invention) (Tables 2 and 3) nor with the set of primers developed in the present invention based on the same three SCCmec types (I, II and III) sequences (SEQ ID NOs.: 64, 66 and 67) (Table 12), the nucleotide sequence of the MREJ was determined for sixteen of these twenty MRSA strains.

Figure 3:
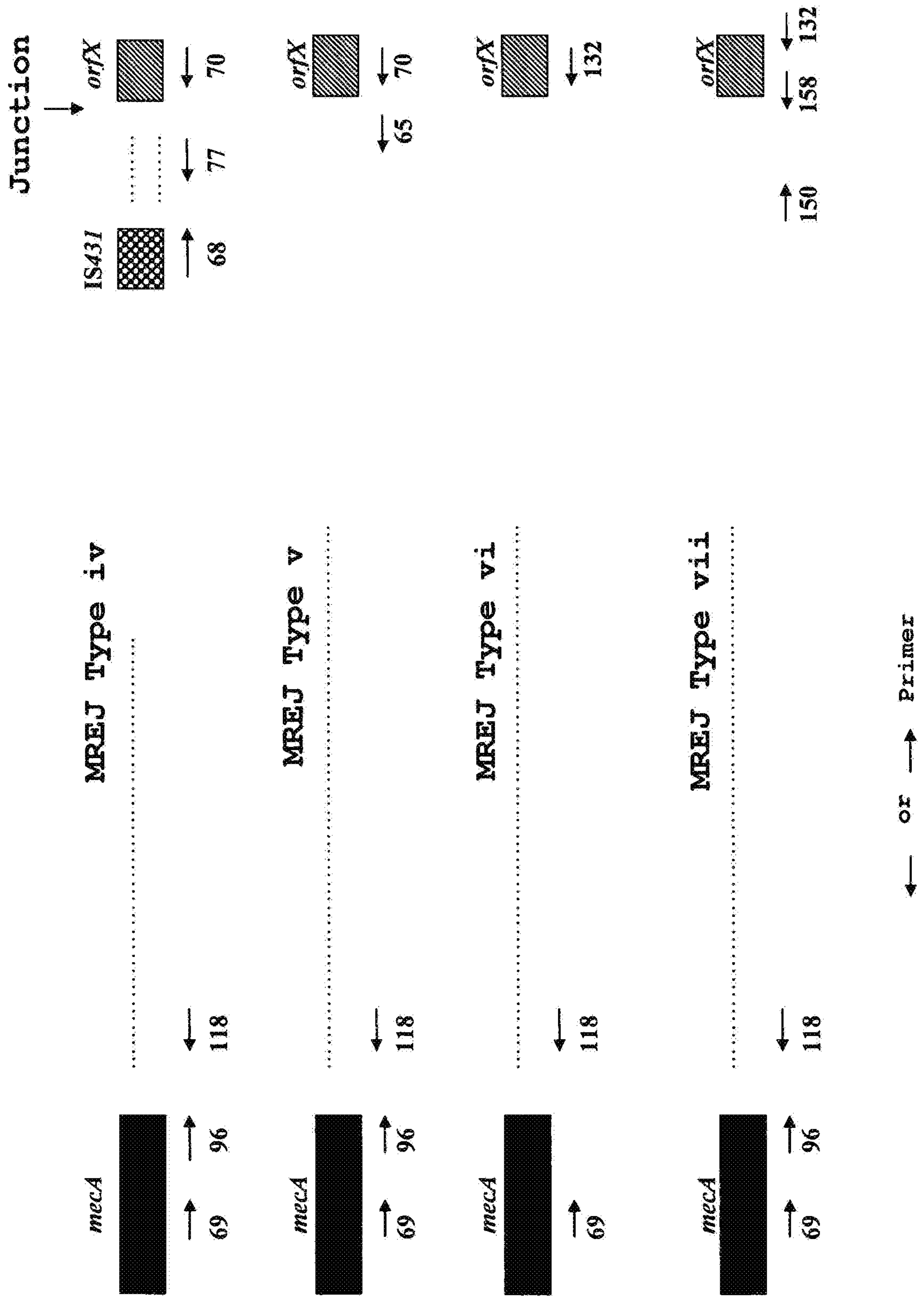
FIG. 3 is a diagram illustrating the position of the primers selected in the present invention to sequence new MREP types.
Figure 3:
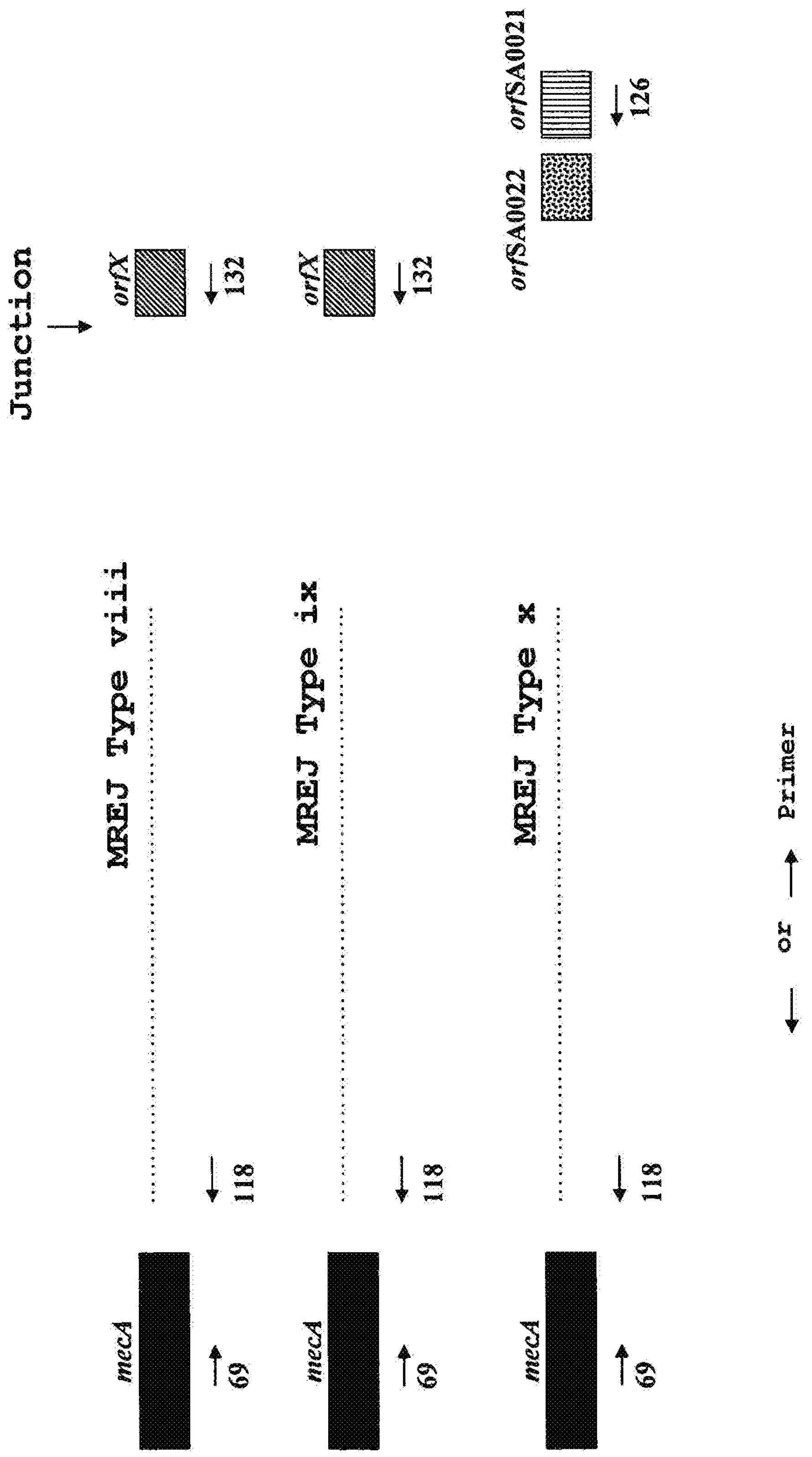

Transposase of IS431 is often associated with the insertion of resistance genes within the mec locus. The gene encoding this transposase has been described frequently in one or more copies within the right segment of SCCmec (Oliveira et al., 2000, Antimicrob. Agents Chemother. 44:1906-1910; Ito et al., 2001, Antimicrob. Agents Chemother. 45:1323-36). Therefore, in a first attempt to sequence the novel MREJ for 16 of the 20 MRSA strains described in Table 3, a primer was designed in the sequence of the gene coding for the transposase of IS431 (SEQ ID NO.: 68) and combined with an orfX-specific primer to the right of the SCCmec integration site (SEQ ID NO.: 70) (Tables 5 and 8). The strategy used to select these primers is illustrated in FIG. 3.

The MREJ fragments to be sequenced were amplified using the following amplification protocol: one μL of treated cell suspension (or of a purified genomic DNA preparation) was transferred directly into 4 tubes containing 394 of a PCR reaction mixture. Each PCR reaction contained 50 mM KCl, 10 mM Tris-HCl (pH 9.0), 0.1% Triton X-100, 2.5 mM $MgCl_2$, 1 μM of each of the 2 primers (SEQ ID NOs.: 68 and 70), 200 μM of each of the four dNTPs, 3.3 μg/μl of BSA (Sigma-Aldrich Canada Ltd) and 0.5 unit of Taq DNA polymerase (Promega) coupled with the TaqStart™ Antibody (BD Bisociences). PCR reactions were submitted to cycling using a standard thermocycler (PTC-200 from MJ Research Inc.) as follows: 3 min at 94° C. followed by 40 cycles of 5 sec at 95° C. for the denaturation step, 30 sec at 55° C. for the annealing step and 2 min at 72° C. for the extension step.

Subsequently, the four PCR-amplified mixtures were pooled and 10 μL of the mixture were resolved by electrophoresis in a 1.2% agarose gel containing 0.25 μg/mL of ethidium bromide. The amplicons were then visualized with an Alpha-Imager (Alpha Innotech Corporation, San Leandro, Calif.) by exposing to UV light at 254 nm. Amplicon size was estimated by comparison with a 1 kb molecular weight ladder (Life Technologies, Burlington, Ontario, Canada). The remaining PCR-amplified mixture (150 μL, total) was also resolved by electrophoresis in a 1.2% agarose gel. The amplicons were then visualized by staining with methylene blue (Flores et al., 1992, Biotechniques, 13:203-205). Amplicon size was once again estimated by comparison with a 1 kb molecular weight ladder. Of the sixteen strains selected from the twenty described in Table 3, six were amplified using SEQ ID NOs.: 68 and 70 as primers (CCRI-178, CCRI-8895, CCRI-8903, CCRI-1324, CCRI-1331 and CCRI-9504). For these six MRSA strains, an amplification product of 1.2 kb was obtained. The band corresponding to this specific amplification product was excised from the agarose gel and purified using the QIAquick™ gel extraction kit (QIAGEN Inc., Chatsworth, Calif.). The gel-purified DNA fragment was then used directly in the sequencing protocol. Both strands of the MREJ amplification products were sequenced by the dideoxynucleotide chain termination sequencing method by using an Applied Biosystems automated DNA sequencer (model 377) with their Big Dye™ Terminator Cycle Sequencing Ready Reaction Kit (Applied Biosystems, Foster City, Calif.). The sequencing reactions were performed by using the same primers (SEQ ID NOs.: 68 and 70) and 10 ng/100 bp per reaction of the gel-purified amplicons. Sequencing of MREJ from the six MRSA strains (CCRI-178, CCRI-8895, CCRI-8903, CCRI-1324, CCRI-1331 and CCRI-9504) described in Table 3 yielded SEQ ID NOs.: 42, 43, 44, 45, 46 and 51, respectively (Table 4).

In order to ensure that the determined sequence did not contain errors attributable to the sequencing of PCR artefacts, we have sequenced two preparations of the gel-purified MREJ amplification products originating from two independent PCR amplifications. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 4.

In order to sequence MREJ in strains for which no amplicon had been obtained using the strategy including primers specific to the transposase gene of IS431 and orfX, another strategy using primers targeting mecA and orfX sequences was used to amplify longer genomic fragments. A new PCR primer targeting mecA (SEQ ID NO.: 69) (Table 8) to be used in combination with the same primer in the orfX sequence (SEQ ID NO.: 70). The strategy used to select these primers is illustrated in FIG. 3.

The following amplification protocol was used: Purified genomic DNA (300 ng) was transferred to a final volume of 50 μl of a PCR reaction mixture. Each PCR reaction contained Herculase buffer (Stratagene, La Jolla, Calif.), 0.8 μM of each of the 2 primers (SEQ ID NOs.: 69 and 70), 0.56 mM of each of the four dNTPs and 5 units of Herculase (Stratagene). PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 30 min at 68° C. for the extension step.

Subsequently, 10 μL of the PCR-amplified mixture were resolved by electrophoresis in a 0.7% agarose gel containing 0.25 μg/mL of ethidium bromide. The amplicons were then visualized as described above. Amplicon size was estimated by comparison with a 1 kb molecular weight ladder (Life Technologies). A reamplification reaction was then performed in 2 to 5 tubes using the same protocol with 3 μl of the first PCR reaction used as test sample for the second amplification. The PCR-reamplified mixtures were pooled and also resolved by electrophoresis in a 0.7% agarose gel. The amplicons were then visualized by staining with methylene blue as described above. An amplification product of approximately 12 kb was obtained using this amplification strategy for all strains tested. The band corresponding to the specific amplification product was excised from the agarose gel and purified as described above. The gel-purified DNA fragment was then used directly in the sequencing protocol as described above. The sequencing reactions were performed by using the same amplification primers (SEQ ID NOs.: 69 and 70) and 425-495 ng of the gel-purified amplicons per reaction. Subsequently, internal sequencing primers (SEQ ID NOs.: 65, 77 and 96) (Table 8) were used to obtain sequence data on both strands for a larger portion of the amplicon. Five of the 20 MRSA strains (CCRI-1331, CCRI-1263, CCRI-1377, CCRI-1311 and CCRI-2025) described in Table 3 were sequenced using this strategy, yielding SEQ ID NOs.: 46, 47, 48, 49 and 50, respectively (Table 4). Sequence within mecA gene was also obtained from the generated amplicons yielding SEQ ID NOs: 27, 28, 29, 30 and 31 from strains CCRI-2025, CCRI-1263, CCRI-1311, CCRI-1331 and CCRI-1377, respectively (Table 4). Longer sequences within the mecA gene and from downstream regions were also obtained for strains CCRI-2025, CCRI-1331, and CCRI-1377 as described below.

In order to obtain longer sequences of the orfX gene, two other strategies using primers targeting mecA and orfX sequences (at the start codon) was used to amplify longer chromosome fragments. A new PCR primer was designed in orfX (SEQ ID NO.: 132) to be used in combination with the same primer in the mecA gene (SEQ ID NO.: 69). The strategy used to select these primers is illustrated in FIG. 3. Eight *S. aureus* strains were amplified using primers SEQ ID NOs.: 69 and 132 (CCRI-9860, CCRI-9208, CCRI-9504, CCRI-1331, CCRI-9583, CCRI-9681, CCRI-2025 and CCRI-1377). The strategy used to select these primers is illustrated in FIG. 3.

The following amplification protocol was used: Purified genomic DNA (350 to 500 ng) was transferred to a 50 μl PCR reaction mixture. Each PCR reaction contained 1× Herculase buffer (Stratagene), 0.8 μM of each of the set of 2 primers (SEQ ID NOs.: 69 and 132), 0.56 mM of each of the four dNTPs and 7.5 units of Herculase (Stratagene) with 1 mM $MgCl_2$. PCR reactions were subjected to thermocycling as described above.

Subsequently, 5 μL of the PCR-amplified mixture were resolved by electrophoresis in a 0.8% agarose gel containing 0.25 μg/mL of ethidium bromide. The amplicons were then visualized as described above. For one *S. aureus* strain (CCRI-9583), a reamplification was then performed by using primers SEQ ID NOs.: 96 and 158 (FIG. 3) in 4 tubes, using the same PCR protocol, with 2 μl of the first PCR reaction as test sample for the second amplification. The PCR-reamplified mixtures were pooled and also resolved by electrophoresis in a 0.8% agarose gel. The amplicons were then visualized by staining with methylene blue as described above. A band of approximately 12 to 20 kb was obtained using this amplification strategy depending on the strains tested. The band corresponding to the specific amplification product was excised from the agarose gel and purified using the QIAquick™ gel extraction kit or QIAEX II gel extraction kit (QIAGEN Inc.). Two strains, CCRI-9583 and CCRI-9589, were also amplified with primers SEQ ID NOs.: 132 and 150, generating an amplification product of 1.5 kb. Long amplicons (12-20 kb) were sequenced using 0.6 to 1 μg per reaction, while short amplicons (1.5 kb) were sequenced using 150 ng per reaction. Sequencing reactions were performed using different sets of primers for each *S. aureus* strain: 1) SEQ ID NOs.: 68, 70, 132, 145, 146, 147, 156, 157 and 158 for strain CCRI-9504; 2) SEQ ID NOs.: 70, 132, 154 and 155 for strain CCRI-2025; 3) SEQ ID NOs.: 70, 132, 148, 149, 158 and 159 for strain CCRI-9681; 4) SEQ ID NOs.: 70, 132, 187, and 188 for strain CCRI-9860; 5) SEQ ID NOs: 70, 132, 150 and 159 for strain CCRI-9589, 6) SEQ ID NOs.: 114, 123, 132, 150 and 158 for strain CCRI-9583; 7) SEQ ID NOs: 70, 132, 154 and 155 for strain CCRI-1377, 8) SEQ ID NOs.: 70, 132, 158 and 159 for strain CCRI-9208; 9) SEQ ID NOs: 68, 70, 132, 145, 146, 147 and 158 for strain CCRI-1331; and 10) SEQ ID NOs.: 126 and 127 for strain CCRI-9770.

In one strain (CCRI-9770), the orfX and oriSA0022 genes were shown to be totally or partially deleted based on amplification using primers specific to these genes (SEQ ID NOs: 132 and 159 and SEQ ID NOs.: 128 and 129, respectively) (Table 8). Subsequently, a new PCR primer was designed in oriSA0021 (SEQ ID NO.: 126) to be used in combination with the same primer in the mecA gene (SEQ ID NO.: 69). An amplification product of 4.5 kb was obtained with this primer set. Amplification, purification of amplicons and sequencing of amplicons were performed as described above.

To obtain the sequence of the SSCmec region containing mecA for ten of the 20 MRSA strains described in Table 3 (CCRI-9504, CCRI-2025, CCRI-9208, CCRI-1331, CCRI-9681, CCRI-9860, CCRI-9770, CCRI-9589, CCRI-9583 and CCRI-1377), the primer described above designed in mecA (SEQ ID NO.: 69) was used in combination with a primer designed in the downstream region of mecA (SEQ ID NO.: 118) (Table 8). An amplification product of 2 kb was obtained for all the strains tested. For one strain, CCRI-9583, a re-amplification with primers SEQ ID NOs.: 96 and 118 was performed with the amplicon generated with primers SEQ ID NOs.: 69 and 132 described above. The amplification, re-amplification, purification of amplicons and sequencing reactions were performed as described above. Sequencing reactions were performed with amplicons generated with SEQ ID NOs.: 69 and 132 described above or SEQ ID NOs.: 69 and 118. Different sets of sequencing primers were used for each *S. aureus* strain: 1) SEQ ID NOs.: 69, 96, 117, 118, 120, 151, 152 for strains CCRI-9504, CCRI-2025, CCRI-1331, CCRI-9770 and CCRI-1377; 2) SEQ ID NOs.: 69, 96, 118 and 120 for strains CCRI-9208, CCRI-9681 and CCRI-9589; 3) SEQ ID NOs.: 69, 96, 117, 118, 120 and 152 for strain CCRI-9860; and 4) SEQ ID NOs.: 96, 117, 118, 119, 120, 151 and 152 for strain CCRI-9583.

The sequences obtained for 16 of the 20 strains non-amplifiable by the Hiramatsu assay (Table 4) were then compared to the sequences available from public databases. In all cases, portions of the sequence had an identity close to 100% to publicly available sequences for orfX (SEQ ID NOs.: 42-51, 165-168 and 171) or mecA and downstream region (SEQ ID NOs.: 27-31, 189-193, 195, 197-199 and 225). However, while the orfX portion of the fragments (SEQ ID NOs.: 42-51, 165-168 and 171) shared nearly 100% identity with the orfX gene of MSSA strain NCTC 8325 described by Hiramatsu et al. (SEQ ID NO.: 3), the DNA sequence within the right extremity of SCCmec itself was shown to be very different from those of types I, II, III and IV described by Hiramatsu et al. (Table 13, FIG. 4). Six different novel sequence types were obtained.

It should be noted that Hiramatsu et al. demonstrated that SCCmec type I could be associated with MREP type i, SCCmec types II and IV are associated with MREP type ii, and SCCmec type III is associated with MREP type iii. Our MREJ sequencing data from various MRSA strains led to the discovery of 6 novel MREP types designated types iv, v vi, vii, viii, and ix. The MREJ comprising distinct MREP types were named according to the MREP numbering scheme. Hence, MREP type i is comprised within MREJ type i, MREP type ii is comprised within MREJ type ii and so on up to MREP type ix.

The sequences within the right extremity of SCCmec obtained from strains CCRI-178, CCRI-8895, CCRI-8903, CCRI-1324, CCRI-1331 and CCRI-9504 (SEQ ID NOs.: 42, 43, 44, 45, 46 and 51) were nearly identical to each other and exhibited nearly 100% identity with IS431 (GenBank accession numbers AF422691, ABO37671, AF411934). However, our sequence data revealed for the first time the location of this IS431 sequence at the right extremity of SCCmec adjacent to the integration site. Therefore, as the sequences at the right extremity of SCCmec from these 6 MRSA strains were different from those of SCCmec type I from strain NCTC 10442, SCCmec type II from strain N315, SCCmec type III from strain 85/2082 and SCCmec type IV from strains CA05 and 8/6-3P described by Hiramatsu et al. (Ito et al., 2001, Antimicrob. Agents Chemother. 45:1323-1336; Ma et al., 2002, Antimicrob. Agents Chemother. 46:1147-1152), these new sequences were designated as MREP type iv (SEQ ID NOs.: 42-46 and 51). A BLAST search with the SCCmec portion of MREP type iv sequences produced significant alignments with sequences coding for portions of a variety of known transposases. For example, when compared to Genbank accession no. AB037671, MREP type iv from SEQ ID NO. 51 shared 98% identity with the putative transposase of IS431 and its downstream region; two gaps of 7 nucleotides each were also present in the alignment.

Sequences obtained from strains CCRI-1263, CCRI-1377, CCRI-1311 and CCRI-2025 (SEQ ID NOs.: 47-50) were nearly identical to each other and different from all three SCCmec types and MREP type iv and, consequently, were designated as MREP type v. When compared with Genbank sequences using BLAST, MREP type v sequences did not share any significant homology with any published sequence, except for the first 28 nucleotides. That short stretch corresponded to the last 11 coding nucleotides of orfX, followed by the 17 nucleotides downstream, including the right inverted repeat (IR-R) of SCCmec.

Sequence obtained from strain CCRI-9208 was also different from all three SCCmec types and MREP types iv and v and, consequently, was designated as MREP type vi (SEQ ID NO.: 171). Upon a BLAST search, MREP type vi was shown to be unique, exhibiting no significant homology to any published sequence.

Sequences obtained from strains CCRI-9583 and CCRI-9589 were also different from all three SCCmec types and MREP types iv to vi and were therefore designated as MREP type vii (SEQ ID NOs.: 165 and 166). Upon a BLAST search, MREP type vii was also shown to be unique, exhibiting no significant homology to any published sequence.

Sequence obtained from strain CCRI-9860 was also different from all three SCCmec types and MREP types iv to vii and was therefore designated as MREP type viii (SEQ ID NO.: 167). Sequence obtained from strain CCRI-9681 was also different from all three SCCmec types and MREP types iv to viii and was therefore designated as MREP type ix (SEQ ID NO.: 168). BLAST searches with the SCCmec portion of MREP types viii and ix sequences yielded significant alignments, but only for the first ~150 nucleotides of each MREP type. For example, the beginning of the MREP type viii sequence had 88% identity with a portion of Genbank accession no. AB063173, but no significant homology with any published sequence was found for the rest of the sequence. In the same manner, the first ~150 nucleotides of MREP type ix had 97% identity with the same portion of AB063173, with the rest of the sequence being unique. The short homologous portion of MREP types viii and ix corresponds in AB063173 to the last 14 coding nucleotides of orfX, the IR-R of SCCmec, and a portion of orfCM009. Although sharing resemblances, MREP types viii and ix are very different from one another; as shown in Table 13, there is only 55.2% identity between both types for the first 500 nucleotides of the SCCmec portion.

Finally, we did not obtain any sequence within SSCmec from strain CCRI-9770. However, as described in the section "Sequencing of MREJ nucleotide sequences from MRSA strains not amplifiable with primers specific to SCCmec types I, II and III", this strain has apparently a partial or total deletion of the orfX and orfSA0022 genes in the chromosomal DNA to the right of the SCCmec integration site and this would represent a new right extremity junction. We therefore designated this novel sequence as MREP type x (SEQ ID NO.: 172). Future sequencing should reveal whether this so called MREJ type x contains a novel MREP type x or if the lack of amplification is indeed caused by variation in the chromosomal part of the MREJ.

The sequences of the first 500-nucleotide portion of the right extremity of all SCCmec obtained in the present invention were compared to those of SCCmec types I, II and III using GCG programs Pileup and Gap. Table 13 depicts the identities at the nucleotide level between SCCmec right extremities of the six novel sequences with those of SCCmec types I, II and III using the GCG program Gap. While SCCmec types I and II showed nearly 79.2% identity (differing only by a 102 bp insertion present in SCCmec type II) (FIGS. 1, 2 and 4), all other MREP types showed identities varying from 40.9 to 57.1%. This explains why the right extremities of the novel MREP types iv to ix disclosed in the present invention could not have been predicted nor detected with the system described by Hiramatsu et al.

Four strains (CCRI-1312, CCRI-1325, CCRI-9773 and CCRI-9774) described in Table 3 were not sequenced but rather characterized using PCR primers. Strains CCRI-1312 and CCRI-1325 were shown to contain MREP type v using specific amplification primers described in Examples 4, 5 and 6 while strains CCRI-9773 and CCRI-9774 were shown to contain MREP type vii using specific amplification primers described in Example 7.

To obtain the complete sequence of the SCCmec present in the MRSA strains described in the present invention, primers targeting the *S. aureus* chromosome to the left (upstream of the mecA gene) of the SCCmec integration site were developed. Based on available public database sequences, 5 different primers were designed (SEQ ID NOs.: 85-89) (Table 9). These primers can be used in combination with *S. aureus* chromosome-specific primers in order to sequence the entire SCCmec or, alternatively, used in combination with a mecA-specific primer (SEQ ID NO.: 81) in order to sequence the left extremity junction of SCCmec. We have also developed several primers specific to known SCCmec sequences spread along the locus in order to obtain the complete sequence of SCCmec (Table 9). These primers will allow to assign a SCCmec type to the MRSA strains described in the present invention.

Selection of Amplification Primers from SCCmec/orfX Sequences

The MREJ sequences determined by the inventors or selected from public databases were used to select PCR primers for detection and identification of MRSA. The strategy used to select these PCR primers was based on the analysis of multiple sequence alignments of various MREJ sequences.

Upon analysis of the six new MREP types iv to ix sequence data described above, primers specific to each new MREP type sequence (SEQ ID NOs.: 79, 80, 109, 112, 113, 115, 116 and 204) were designed (FIG. 2, Table 5, Examples 3, 4, 5, 6, 7 and 8). Primers specific to MREP types iv, v and vii (SEQ ID NOs.: 79, 80 and 112) were used in multiplex with the three primers to detect SCCmec types I, II and III (SEQ ID NOs: 64, 66 and 67) and the primer specific to the *S. aureus* orfX (SEQ ID NO. 64) (Examples 3, 4, 5, 6 and 7). Primers specific to MREP types vi, viii and ix (SEQ ID NOs.: 204, 115, 116 and 109) were also designed and tested against their specific target (Example 8).

Detection of Amplification Products

Classically, the detection of PCR amplification products is performed by standard ethidium bromide-stained agarose gel electrophoresis as described above. It is however clear that other methods for the detection of specific amplification products, which may be faster and more practical for routine diagnosis, may be used. Examples of such methods are described in co-pending patent application WO01/23604 A2.

Amplicon detection may also be performed by solid support or liquid hybridization using species-specific internal DNA probes hybridizing to an amplification product. Such probes may be generated from any sequence from our repertory and designed to specifically hybridize to DNA amplification products which are objects of the present invention. Alternatively, amplicons can be characterized by sequencing. See co-pending patent application WO01/23604 A2 for examples of detection and sequencing methods.

In order to improve nucleic acid amplification efficiency, the composition of the reaction mixture may be modified (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include the use of various polymerases or the addition of nucleic acid amplification facilitators such as betaine, BSA, sulfoxides, protein gp32, detergents, cations, tetramethylammonium chloride and others.

In a preferred embodiment, real-time detection of PCR amplification was monitored using molecular beacon probes in a SMART CYCLER® apparatus (Cepheid, Sunnyvale, Calif.). A multiplex PCR assay containing primers specific to MREP types i to v and orfX of *S. aureus* (SEQ ID NOs.: 64, 66, 67, 79 and 80), a molecular beacon probe specific to the orfX sequence (SEQ ID NO. 84, see Annex II and FIG. 2) and an internal control to monitor PCR inhibition was developed. The internal control contains sequences complementary to MREP type iv- and orfX-specific primers (SEQ ID NOs. 79 and 64). The assay also contains a molecular beacon probe labeled with tetrachloro-6-carboxyfluorescein (TET) specific to sequence within DNA fragment generated during amplification of the internal control. Each PCR reaction contained 50 mM KCl, 10 mM Tris-HCl (pH 9.0), 0.1% Triton X-100, 3.45 mM $MgCl_2$, 0.8 μM of each of the MREP-specific primers (SEQ ID NOs.: 66 and 67) and orfX-specific primer (SEQ ID NO.: 64), 0.4 μM of each of the MREP-specific primers (SEQ ID NOs.: 79 and 80), 80 copies of the internal control, 0.2 μM of the TET-labeled molecular beacon probe specific to the internal control, 0.2 μM of the molecular beacon probe (SEQ ID NO.: 84) labeled with 6-carboxyfluorescein (FAM), 330 μM of each of the four dNTPs (Pharmacia Biotech), 3.45 μg/μl of BSA (Sigma), and 0.875 U Taq polymerase (Promega) coupled with TaqStart Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies (Example 5). None of the 26 MRCNS or 10 MSCNS tested were positive with this multiplex assay. The eight MRSA strains (CCRI-9208, CCRI-9770, CCRI-9681, CCRI-9860, CCRI-9583, CCRI-9773, CCRI-9774, CCRI-9589) which harbor the new MREP types vi, viii, ix and x sequences described in the present invention remained undetectable (Example 5).

In a preferred embodiment, detection of MRSA using the real-time multiplex PCR assay on the SMART CYCLER® apparatus (Cepheid, Sunnyvale, Calif.) directly from clinical specimens was evaluated. A total of 142 nasal swabs were collected during a MRSA hospital surveillance program at the Montreal General Hospital (Montreal, Quebec, Canada). The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in co-pending patent application No. US 60/306,163. Classical identification of MRSA was performed by standard culture methods.

The PCR assay detected 33 of the 34 samples positive for MRSA based on the culture method. As compared to culture, the PCR assay detected 8 additional MRSA positive specimens for a sensitivity of 97.1% and a specificity of 92.6% (Example 6). This multiplex PCR assay represents a rapid and powerful method for the specific detection of MRSA carriers directly from nasal specimens and can be used with any types of clinical specimens such as wounds, blood or blood culture, CSF, etc.

In a preferred embodiment, a multiplex PCR assay containing primers specific to MREP types i, ii, iii, iv, v and vi and orfX of *S. aureus* (SEQ ID NOs.: 66, 67, 79, 80 and 112), and three molecular beacons probes specific to orfX sequence which allowed detection of the two sequence polymorphisms identified in this region of the orfX sequence was developed. Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable (Example 7). Primers specific to MREP types vi, viii and ix (SEQ ID NOs.: 204, 115, 116 and 109) were also designed and were shown to detect their specific target strains (Example 8). While the primers and probes derived from the teaching of Hiramatsu et al., permitted the detection of only 48.7% (19 strains out of 39) of the MRSA strains of Table 2, the primers and probes derived from the present invention enable the detection of 97.4% of the strains (38 strains out of 39) (see examples 7 and 8). Therefore it can be said that our assay has a ubiquity superior to 50% for the MRSA strains listed in Table 2.

Specificity, Ubiquity and Sensitivity Tests for Oligonucleotide Primers and Probes The specificity of oligonucleotide primers and probes was tested by amplification of DNA or by hybridization with staphylococcal species. All of the staphylococcal species tested were likely to be pathogens associated with infections or potential contaminants which can be isolated from clinical specimens. Each target DNA could be released from microbial cells using standard chemical and/or physical treatments to lyse the cells (Sambrook et al., 1989, Molecular Cloning: A Laboratory Manual, $2^{nd}$ ed., Cold Spring Harbor Laboratory Press, Cold Spring Harbor, N.Y.) or alternatively, genomic DNA purified with the GNOME™ DNA kit (Qbiogene, Carlsbad, Calif.) was used. Subsequently, the DNA was subjected to amplification with the set of primers. Specific primers or probes hybridized only to the target DNA.

Oligonucleotides primers found to amplify specifically DNA from the target MRSA were subsequently tested for their ubiquity by amplification (i.e. ubiquitous primers amplified efficiently most or all isolates of MRSA). Finally, the analytical sensitivity of the PCR assays was determined by using 10-fold or 2-fold dilutions of purified genomic DNA from the targeted microorganisms. For most assays, sensitivity levels in the range of 2-10 genome copies were obtained. The specificity, ubiquity and analytical sensitivity of the PCR assays were tested either directly with bacterial cultures or with purified bacterial genomic DNA.

Molecular beacon probes were tested using the SMART CYCLER® platform as described above. A molecular beacon probe was considered specific only when it hybridized solely to DNA amplified from the MREJ of *S. aureus*. Molecular beacon probes found to be specific were subsequently tested for their ubiquity (i.e. ubiquitous probes detected efficiently most or all isolates of the MRSA) by hybridization to bacterial DNAs from various MRSA strains.

Bacterial Strains

The reference strains used to build proprietary SCCmec-chromosome right extremity junction sequence data subrepertories, as well as to test the amplification and hybridization assays, were obtained from (i) the American Type Culture Collection (ATCC), (ii) the Laboratoire de santé publique du Québec (LSPQ) (Ste-Anne de Bellevue, Québec, Canada), (iii) the Centers for Disease Control and Prevention (CDC) (Atlanta, Ga.), (iv) the Institut Pasteur (Paris, France), and V) the Harmony Collection (London, United Kingdom) (Table 14). Clinical isolates of MRSA, MSSA, MRCNS and MSCNS from various geographical areas were also used in this invention (Table 15). The identity of our MRSA strains was confirmed by phenotypic testing and reconfirmed by PCR analysis using *S. aureus*-specific primers and mecA-specific primers (SEQ ID NOs.: 69 and 81) (Martineau et al., 2000, Antimicrob. Agents Chemother. 44:231-238).

For sake of clarity, below is a list of the Examples, Tables, Figures and Annexes of this invention.

DESCRIPTION OF THE EXAMPLES

Example 1

Primers developed by Hiramatsu et al. can only detect MRSA strains belonging to MREP types i, ii, and iii while missing prevalent novel MREP types.

Example 2

Detection and identification of MRSA using primers specific to MREP types i, ii and iii sequences developed in the present invention.

Example 3

Development of a multiplex PCR assay on a standard thermocycler for detection and identification of MRSA based on MREP types i, ii, iii, iv and v sequences.

Example 4

Development of a real-time multiplex PCR assay on the SMART CYCLER® for detection and identification of MRSA based on MREP types i, ii, iii, iv and v sequences.

Example 5

Development of a real-time multiplex PCR assay on the SMART CYCLER® for detection and identification of MRSA based on MREP types i, ii, iii, iv and v sequences and including an internal control.

Example 6

Detection of MRSA using the real-time multiplex assay on the SMART CYCLER® based on MREP types i, ii, iii, iv and v sequences for the detection of MRSA directly from clinical specimens.

Example 7

Development of a real-time multiplex PCR assay on the SMART CYCLER® for detection and identification of MRSA based on MREP types i, ii, iii, iv, v, vi and vii sequences.

Example 8

Development of real-time PCR assays on the SMART CYCLER® for detection and identification of MRSA based on MREP types vi, viii and ix.

DESCRIPTION OF THE TABLES

Table 1 provides information about all PCR primers developed by Hiramatsu et al. in U.S. Pat. No. 6,156,507.

Table 2 is a compilation of results (ubiquity and specificity) for the detection of SCCmec-orfX right extremity junction using primers described by Hiramatsu et al. in U.S. Pat. No. 6,156,507 on a standard thermocycler.

Table 3 is a list of MRSA strains not amplifiable using primers targeting types I, II and III of SCCmec-orfX right extremity junction sequences.

Table 4 is a list of novel sequences revealed in the present invention.

Table 5 provides information about all primers developed in the present invention.

Table 6 is a list of molecular beacon probes developed in the present invention.

Table 7 shows amplicon sizes of the different primer pairs described by Hiramatsu et al. in U.S. Pat. No. 6,156,507 or developed in the present invention.

Table 8 provides information about primers developed in the present invention to sequence the SCCmec-chromosome right extremity junction.

Table 9 provides information about primers developed in the present invention to obtain sequence of the complete SCCmec.

Table 10 is a list of the sequences available from public databases (GenBank, genome projects or U.S. Pat. No. 6,156,507) used in the present invention to design primers and probes.

Table 11 gives analytical sensitivity of the PCR assay developed in the present invention using primers targeting types I, II and III of SCCmec-orfX right extremity junction sequences and performed using a standard thermocycler.

Table 12 is a compilation of results (ubiquity and specificity) for the detection of MRSA using primers developed in the present invention which target types I, II and III of SCCmec-orfX right extremity junction sequences and performed using a standard thermocycler.

Table 13 shows a comparison of sequence identities between the first 500 nucleotides of SCCmec right extremities between 9 types of MREP.

Table 14 provides information about the reference strains of MRSA, MSSA, MRCNS and MSCNS used to validate the PCR assays developed in the present invention.

Table 15 provides information about the origin of clinical strains of MRSA, MSSA, MRCNS and MSCNS used to validate the PCR assays described in the present invention.

Table 16 depicts the analytical sensitivity of the PCR assay developed in the present invention using primers targeting 5 types of MREP sequences and performed on a standard thermocycler.

Table 17 is a compilation of results (ubiquity and specificity) for the PCR assay developed in the present invention using primers targeting 5 types of MREP sequences and performed on a standard thermocycler.

Table 18 depicts the analytical sensitivity of the PCR assay developed in the present invention using the SMART CYCLER® platform for the detection of 5 types of MREP.

Table 19 is a compilation of results (ubiquity and specificity) for the PCR assay developed in the present invention using primers and a molecular beacon probe targeting 5 types of MREP sequences and performed on the SMART CYCLER® platform.

Table 20 depicts the analytical sensitivity of the PCR assay developed in the present invention using the SMART CYCLER® platform for the detection of 6 MREP types.

Table 21 is a compilation of results (ubiquity and specificity) for the PCR assay developed in the present invention using primers and a molecular beacon probe targeting 6 types of MREP sequences and performed on the SMART CYCLER® platform.

Figure Legends

FIG. 1. Schematic organization of types I, II and III SCCmec-orfX right extremity junctions and localization of the primers (SEQ ID NOs: 52-63) described by Hiramatsu et al. for the detection and identification of MRSA. Amplicon sizes are depicted in Table 7.

FIG. 2. Schematic organization of MREP types i, ii, iii, iv, v, vi, vii, viii and ix and localization of the primers and molecular beacon targeting all MREP types (SEQ ID NOs. 20, 64, 66, 67, 79, 80, 84, 112, 115, 116, 84, 163 and 164) which were developed in the present invention. Amplicon sizes are depicted in Table 7.

FIG. 3. Schematic organization of the SCCmec-chromosome right extremity junctions and localization of the primers (SEQ ID NOs. 65, 68, 69, 70, 77, 96, 118, 126, 132, 150 and 158) developed in the present invention for the sequencing of MREP types iv, v, vi, vii, viii, ix and x.

Figure 4:
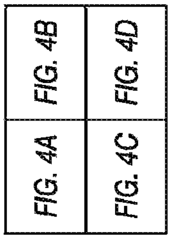
FIGS. 4A-4D illustrate a sequence alignment of nine MREP types (represented by portions of SEQ ID NOs.: 1, 2, 104, 51, 50, 171, 165, 167 and 168 for types i, ii, iii, iv, v, vi, vii, viii and ix, respectively).
Figure 4A:
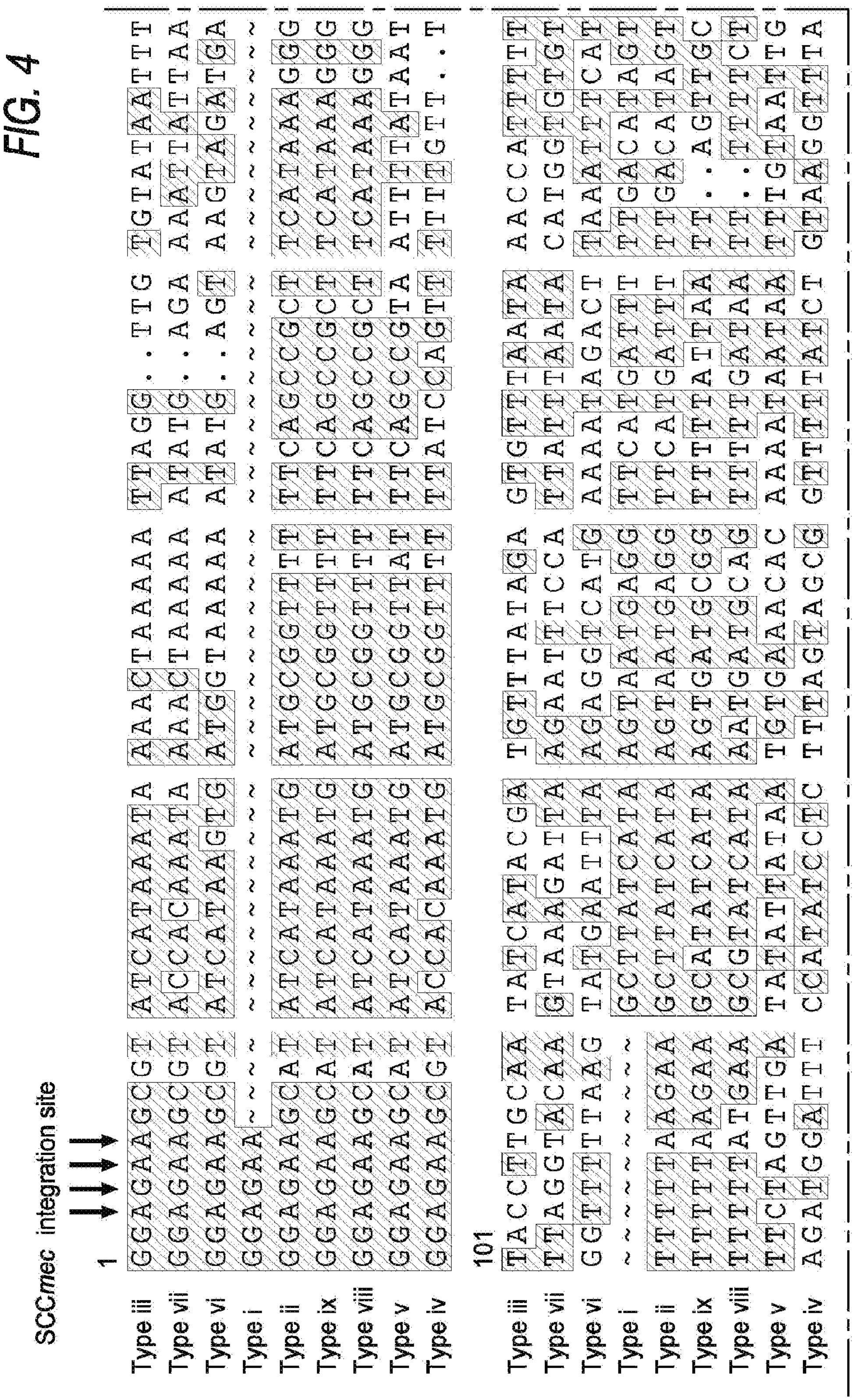
Figure 4B:
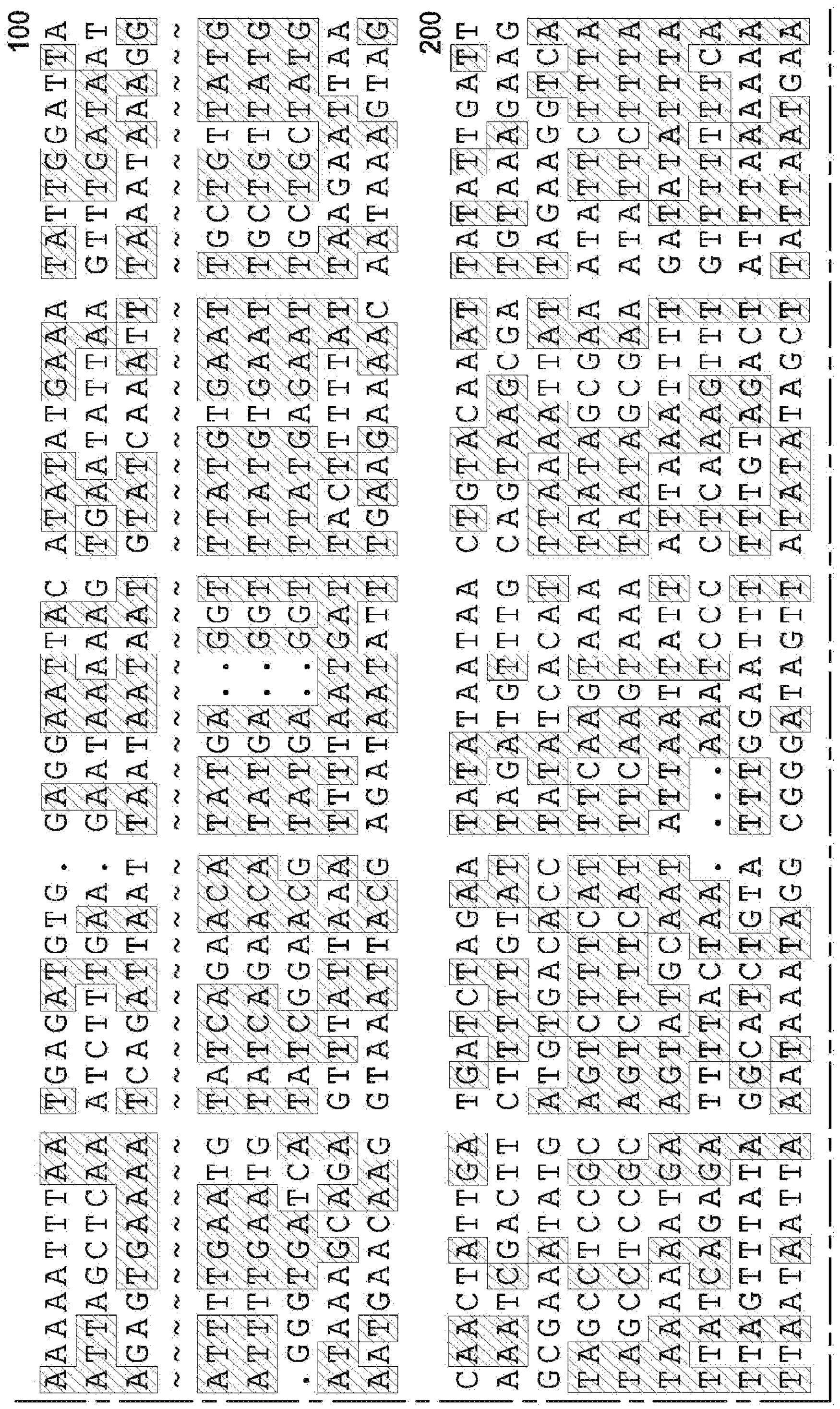
Figure 4C:
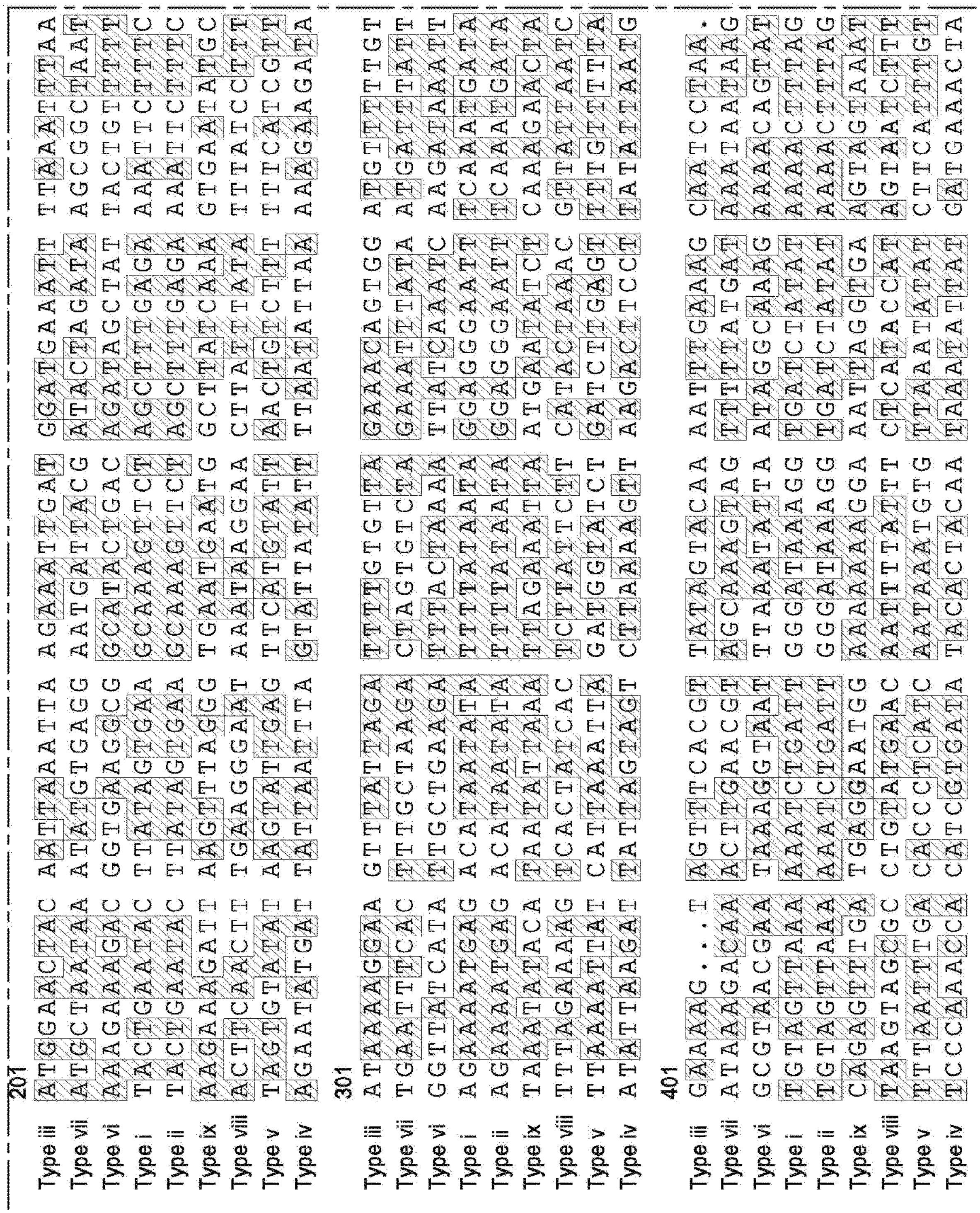
Figure 4D:
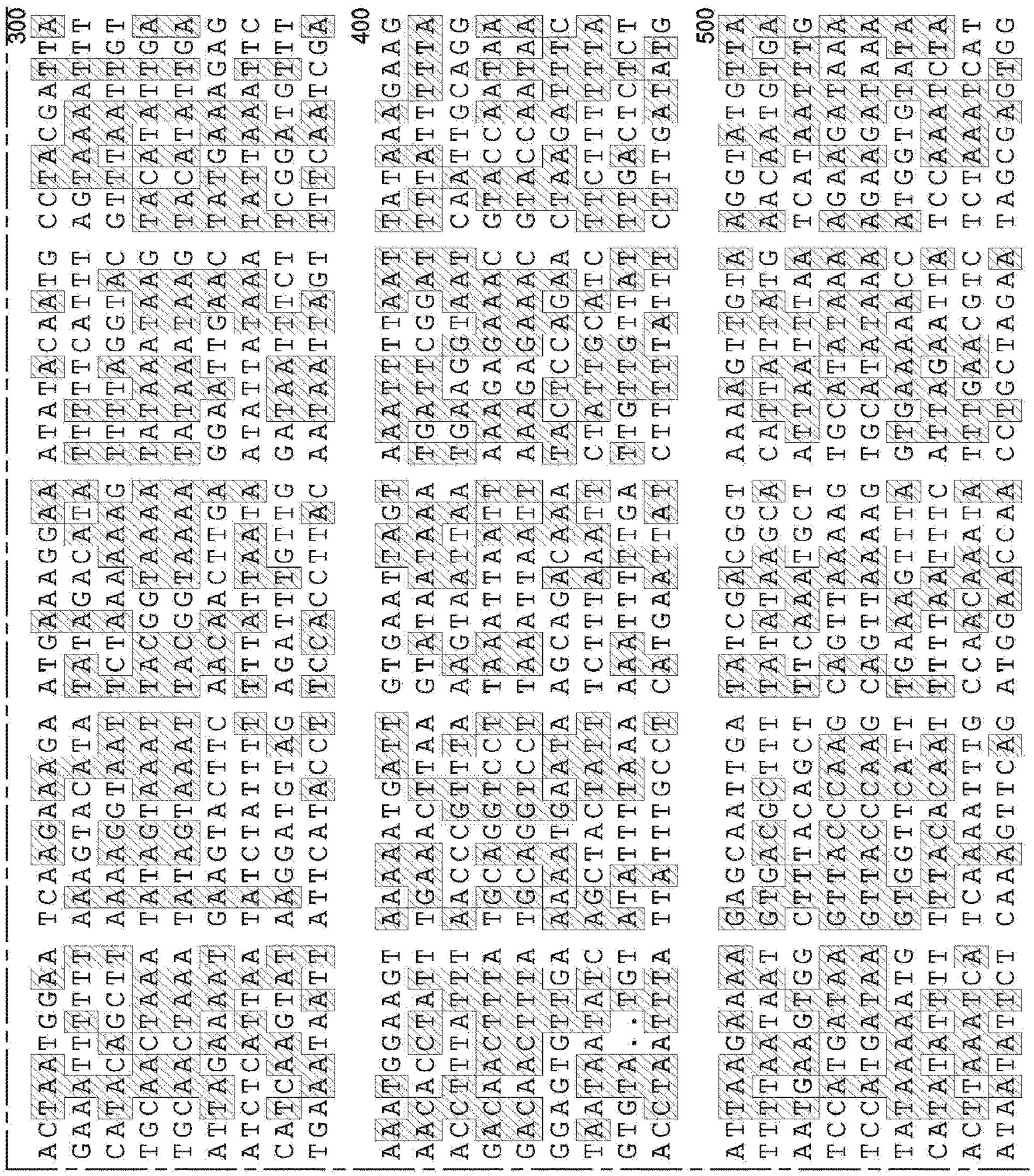

FIG. 4. Multiple sequence alignment of representatives of nine MREP types (represented by portions of SEQ ID NOs.: 1, 2, 104, 51, 50, 171, 165, 167 and 168 for types i, iii, iv, v, vi, vii, viii and ix, respectively).

DESCRIPTION OF THE ANNEXES

The Annexes show the strategies used for the selection of primers and internal probes:

Annex I illustrates the strategy for the selection of primers from SCCmec and orfX sequences specific for SCCmec types I and II.

Annex II illustrates the strategy for the selection of specific molecular beacon probes for the real-time detection of SCCmec-orfX right extremity junctions.

As shown in these Annexes, the selected amplification primers may contain inosines and/or base ambiguities. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degeneracies in the amplification primers allows mismatch tolerance thereby permitting the amplification of a wider array of target nucleotide sequences (Dieffenbach and Dveksler, 1995, PCR Primer: A Laboratory Manual, Cold Spring Harbor Laboratory Press, Plainview, N.Y.).

EXAMPLES

Example 1

Primers Developed by Hiramatsu et al. can only Detect MRSA Strains Belonging to MREP types i, ii, and iii while Missing Prevalent Novel MREP types.

As shown in FIG. 1, Hiramatsu et al. have developed various primers that can specifically hybridize to the right extremities of types I, II and III SCCmec DNAs. They combined these primers with primers specific to the *S. aureus* chromosome region located to the right of the SCCmec integration site for the detection of MRSA. The primer set (SEQ ID NOs.: 22, 24 and 28 in U.S. Pat. No. 6,156,507 corresponding to SEQ ID NOs.: 56, 58 and 60 in the present invention) was shown by Hiramatsu et al. to be the most specific and ubiquitous for detection of MRSA.

This set of primers gives amplification products of 1.5 kb for SCCmec type I, 1.6 kb for SCCmec type II and 1.0 kb for SCCmec type III (Table 7). The ubiquity and specificity of this multiplex PCR assay was tested on 39 MRSA strains, 41 MSSA strains, 9 MRCNS strains and 11 MSCNS strains (Table 2). One µL of a treated standardized bacterial suspension or of a bacterial genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of the SCCmec- and orfX-specific primers (SEQ ID NOs.: 56, 58 and 60), 200 µM of each of the four dNTPs (Pharmacia Biotech), 3.3 µg/µl of BSA (Sigma), and 0.5 U Taq polymerase (Promega) coupled with TaqStart™ Antibody (BD Biosciences).

PCR reactions were then subjected to thermal cycling: 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 µg/ml of ethidium bromide.

None of the MRCNS or MSCNS strains tested were detected with the set of primers detecting SCCmec types I, II and III. Twenty of the 39 MRSA strains tested were not detected with this multiplex PCR assay (Tables 2 and 3). One of these undetected MRSA strains corresponds to the highly epidemic MRSA Portuguese clone (strain CCRI-9504; De Lencastre et al., 1994. Eur. J. Clin. Microbiol. Infect. Dis. 13:64-73) and another corresponds to the highly epidemic MRSA Canadian clone CMRSA1 (strain CCRI-9589; Simor et al. CCDR 1999, 25-12, June 15). These data demonstrate that the primer set developed by Hiramatsu et al. (SEQ ID NOs.: 22, 24 and 28 in U.S. Pat. No. 6,156,507 corresponding to SEQ ID NOs.: 56, 58 and 60 in the present invention) is not ubiquitous for the detection of MRSA and suggest that some MRSA strains have sequences at the SCCmec right extremity junction which are different from those identified by Hiramatsu et al. other types of SCCmec sequences or other sequences at the right extremity of SCCmec (MREP type) are found in MRSA. A limitation of this assay is the non-specific detection of 13 MSSA strains (Table 2).

Example 2

Detection and Identification of MRSA using Primers Specific to MREP Types i, ii and iii Sequences Developed in the Present Invention.

Based on analysis of multiple sequence alignments of orfX and SCCmec sequences described by Hiramatsu et al. or available from GenBank, a set of primers (SEQ ID NOs: 64, 66, 67) capable of amplifying short segments of types I, II and III of SCCmec-orfX right extremity junctions from MRSA strains and discriminating from MRCNS (Annex I and FIG. 2) were designed. The chosen set of primers gives amplification products of 176 bp for SCCmec type I, 278 pb for SCCmec type II and 223 bp for SCCmec type III and allows rapid PCR amplification. These primers were used in multiplex PCR to test their ubiquity and specificity using 208 MRSA strains, 252 MSSA strains, 41 MRCNS strains and 21 MRCNS strains (Table 12). The PCR amplification and detection was performed as described in Example 1. PCR reactions were then subjected to thermal cycling (3 minutes at 94° C. followed by 30 or 40 cycles of 1 second at 95° C. for the denaturation step and 30 seconds at 60° C. for the annealing-extension step, and then followed by a terminal extension of 2 minutes at 72° C.) using a standard thermocycler (PTC-200 from MJ Research Inc.). Detection of the PCR products was made as described in Example 1.

None of the MRCNS or MSCNS strains tested were detected with this set of primers (Table 12). However, the twenty MRSA strains which were not detected with the primer set developed by Hiramatsu et al. (SEQ ID NOs: 56, 58 and 60) were also not detected with the primers developed in the present invention (Tables 3 and 12). These data also demonstrate that some MRSA strains have sequences at the SCCmec-chromosome right extremity junction which are different from those identified by Hiramatsu et al. Again, as observed with the Hiramatsu primers, 13 MSSA strains were also detected non-specifically (Table 12). The clinical significance of this finding remains to be established since these apparent MSSA strains could be the result of a recent deletion in the mec locus (Deplano et al., 2000, J. Antimicrob. Chemotherapy, 46:617-619; Inglis et al., 1990, J. Gen. Microbiol., 136:2231-2239; Inglis et al., 1993, J. Infect. Dis., 167:323-328; Lawrence et al. 1996, J. Hosp. Infect., 33:49-53; Wada et al., 1991, Biochem. Biophys. Res. Comm., 176:1319-1326).

Example 3

Development of a Multiplex PCR Assay on a Standard Thermocycler for Detection and Identification of MRSA Based on MREP Types i, ii, iii, iv and v Sequences.

Upon analysis of two of the new MREP types iv and v sequence data described in the present invention, two new primers (SEQ ID NOs.: 79 and 80) were designed and used in multiplex with the three primers SEQ ID NOs.: 64, 66 and 67 described in Example 2. PCR amplification and detection of the PCR products was performed as described in Example 2. Sensitivity tests performed by using ten-fold or two-fold dilutions of purified genomic DNA from various MRSA strains of each MREP type showed a detection limit of 5 to 10 genome copies (Table 16). Specificity tests were performed using 0.1 ng of purified genomic DNA or 1 µl of a standardized bacterial suspension. All MRCNS or MSCNS strains tested were negative with this multiplex assay (Table 17). Twelve of the 20 MRSA strains which were not detected with the multiplex PCR described in Examples 1 and 2 were now detected with this multiplex assay. Again, as observed with the Hiramatsu primers, 13 MS SA strains were also detected non-specifically (Table 12). The eight MRSA strains (CCRI-9208, CCRI-9583, CCRI-9773, CCRI-9774, CCRI-9589, CCRI-9860, CCRI-9681, CCRI-9770) and which harbor the new MREP types vi, vii, viii, ix and x sequences described in the present invention remained undetectable.

Example 4

Development of a Real-Time Multiplex PCR Assay on the SMART CYCLER® for Detection and Identification of MRSA Based on MREP Types i, ii, iii, iv and v Sequences.

The multiplex PCR assay described in Example 3 containing primers (SEQ ID NOs.: 64, 66, 67, 79 and 80) was adapted to the SMART CYCLER® platform (Cepheid). A molecular beacon probe specific to the orfX sequence was developed (SEQ ID NO. 84, see Annex II). Each PCR reaction contained 50 mM KCl, 10 mM Tris-HCl (pH 9.0), 0.1% Triton X-100, 3.5 mM $MgCl_2$, 0.4 µM of each of the SCCmec- and orfX-specific primers (SEQ ID NOs.: 64, 66, 67, 79 and 80), 0.2 μM of the FAM-labeled molecular beacon probe (SEQ ID NO.: 84), 200 μM of each of the four dNTPs, 3.3 μg/μl of BSA, and 0.5 U Taq polymerase coupled with TaqStart Antibody. The PCR amplification on the SMART CYCLER® was performed as follows: 3 min. at 94° C. for initial denaturation, then forty-five cycles of three steps consisting of 5 seconds at 95° C. for the denaturation step, 15 seconds at 59° C. for the annealing step and 10 seconds at 72° C. for the extension step. Fluorescence detection was performed at the end of each annealing step. Sensitivity tests performed by using purified genomic DNA from several MRSA strains of each MREP type showed a detection limit of 2 to 10 genome copies (Table 18). None of the MRCNS or MSCNS were positive with this multiplex assay (Table 19). Again, as observed with the Hiramatsu primers, 13 MSSA strains were also detected non-specifically. Twelve of the twenty MRSA strains which were not detected with the multiplex PCR described in Examples 1 and 2 were detected by this multiplex assay. As described in Example 3, the eight MRSA strains which harbor the new MREP types vi, vii, viii, ix and x sequences described in the present invention remained undetectable.

Example 5

Development of a Real-Time Multiplex PCR Assay on the SMART CYLCER® for Detection and Identification of MRSA Based on MREP Types i, ii, iii, iv and v Sequences including an Internal Control.

The multiplex PCR assay described in Example 4 containing primers specific to MREP types i to v and orfX of *S. aureus* (SEQ ID NOs.: 64, 66, 67, 79 and 80) and a molecular beacon probe specific to the orfX sequence (SEQ ID NO. 84, see Annex II) was optimized to include an internal control to monitor PCR inhibition. This internal control contains sequences complementary to MREP type iv- and orfX-specific primers (SEQ ID NOs. 79 and 64). The assay also contains a TET-labeled molecular beacon probe specific to sequence within the amplicon generated by amplification of the internal control. Each PCR reaction contained 50 mM KCl, 10 mM Tris-HCl (pH 9.0), 0.1% Triton X-100, 3.45 mM $MgCl_2$, 0.8 μM of each of the MREP-specific primers (SEQ ID NOs.: 66 and 67) and orfX-specific primer (SEQ ID NO.: 64), 0.4 μM of each of the MREP-specific primers (SEQ ID NOs.: 79 and 80), 80 copies of the internal control, 0.2 μM of the TET-labeled molecular beacon probe specific to the internal control, 0.2 μM of the FAM-labeled molecular beacon probe (SEQ ID NO.: 84), 330 μM of each of the four dNTPs (Pharmacia Biotech), 3.45 μg/μl of BSA (Sigma), and 0.875 U Taq polymerase (Promega) coupled with TaqStart Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies. None of the 26 MRCNS or 10 MSCNS were positive with this multiplex assay. Again, as observed with the Hiramatsu primers, 13 MSSA strains were also detected non-specifically. As described in Examples 3 and 4, the eight MRSA strains which harbor the new MREP types vi to x sequences described in the present invention remained undetectable.

Example 6

Detection of MRSA using the Real-Time Multiplex Assay on the SMART CYLCER® Based on MREP Types i, ii, iii, iv and v Sequences Directly from Clinical Specimens.

The assay described in Example 5 was adapted for detection directly from clinical specimens. A total of 142 nasal swabs collected during a MRSA hospital surveillance program at the Montreal General Hospital (Montreal, Quebec, Canada) were tested. The swab samples were tested at the Centre de Recherche en Infectiologie de l'Universite Laval within 24 hours of collection. Upon receipt, the swabs were plated onto mannitol agar and then the nasal material from the same swab was prepared with a simple and rapid specimen preparation protocol described in co-pending patent application No. US 60/306,163. Classical identification of MRSA was performed by standard culture methods.

The PCR assay described in Example 5 detected 33 of the 34 samples positive for MRSA based on the culture method. As compared to culture, the PCR assay detected 8 additional MRSA positive specimens for a sensitivity of 97.1% and a specificity of 92.6%. This multiplex PCR assay represents a rapid and powerful method for the specific detection of MRSA carriers directly from nasal specimens and can be used with any type of clinical specimens such as wounds, blood or blood culture, CSF, etc.

Example 7

Development of a Real-Time Multiplex PCR Assay on the SMART CYCLER® for Detection and Identification of MRSA Based on MREP Types i, ii, iii, iv, v and vii Sequences.

Upon analysis of the new MREP type vii sequence data described in the present invention (SEQ ID NOs.:165 and 166), two new primers (SEQ ID NOs.: 112 and 113) were designed and tested in multiplex with the three primers SEQ ID NOs.: 64, 66 and 67 described in Example 2. Primer SEQ ID NO.: 112 was selected for use in the multiplex based on its sensitivity. Three molecular beacon probes specific to the orfX sequence which allowed detection of two sequence polymorphisms identified in this region of the orfX sequence, based on analysis of SEQ ID NOs.: 173-186, were also used in the multiplex (SEQ ID NOs.: 84, 163 and 164). Each PCR reaction contained 50 mM KCl, 10 mM Tris-HCl (pH 9.0), 0.1% Triton X-100, 3.45 mM $MgCl_2$, 0.8 μM of each of the SCCmec-specific primers (SEQ ID NOs.: 66 and 67) and orfX-specific primer (SEQ ID NO.: 64), 0.4 μM of each of the SCCmec-specific primers (SEQ ID NOs.: 79 and 80), 0.2 μM of the FAM-labeled molecular beacon probe (SEQ ID NO.: 84), 330 μM of each of the four dNTPs (Pharmacia Biotech), 3.45 μg/μl of BSA (Sigma), and 0.875 U of Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. The detection of fluorescence was done at the end of each annealing step. Sensitivity tests performed by using purified genomic DNA from several MRSA strains of each MREP type showed a detection limit of 2 genome copies (Table 20). None of the 26 MRCNS or 8 MSCNS were positive with this multiplex assay. Again, as observed with the Hiramatsu primers, 13 MSSA strains were also detected non-specifically (Table 21). Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable.

Example 8

Development of Real-Time PCR Assays on the SMART CYCLER® for Detection and Identification of MRSA Based on MREP Types vi, viii, ix.

Upon analysis of the new MREP types vi, viii and ix sequence data described in the present invention, one new primers specific to MREP type vi (SEQ ID NO.: 201), one primer specific to MREP type viii (SEQ ID NO.: 115), a primer specific to MREP type ix (SEQ ID NO.: 109) and a primer specific to both MREP types viii and ix (SEQ ID NO.: 116) were designed. Each PCR primer was used in combination with the orfX-specific primer (SEQ ID NO.: 64) and tested against its specific target strain. Each PCR reaction contained 50 mM KCl, 10 mM Tris-HCl (pH 9.0), 0.1% Triton X-100, 3.45 mM $MgCl_2$, 0.4 μM of each of the SCCmec- and orfX-specific primers, 200 μM of each of the four dNTPs, 3.4 μg/μl of BSA, and 0.875 U Taq polymerase coupled with TaqStart™ Antibody. The PCR amplification was performed as described en Example 7. Sensitivity tests performed by using genomic DNA purified from their respective MRSA target strains showed that the best primer pair combination was SEQ ID NOs.: 64 and 115 for the detection of MREP types viii and ix simultaneously. These new SCCmec-specific primers may be used in multiplex with primers specific to MREP types i, ii, ii, iv, v and vii (SEQ ID NOs.: 64, 66, 67, 79 and 80) described in previous examples to provide a more ubiquitous MRSA assay.

In conclusion, we have improved the ubiquity of detection of MRSA strains. New MREJ types iv to x have been identified. Amongst strains representative of these new types, Hiramitsu's primers and/or probes succeeded in detecting less than 50% thereof. We have therefore amply passed the bar of at least 50% ubiquity, since our primers and probes were designed to detect 100% of the strains tested as representatives of MREJ types iv to ix. Therefore, although ubiquity depends on the pool of strains and representatives that are under analysis, we know now that close to 100% ubiquity is an attainable goal, when using the sequences of the right junctions (MREJ) to derive probes and primers dealing with polymorphism in this region. Depending on how many unknown types of MREJ exist, we have a margin of maneuver going from 50% (higher than Hiramatsu's primers for the tested strains) to 100% if we sequence all the existing MREJs to derive properly the present diagnostic tools and methods, following the above teachings.

This invention has been described herein above, and it is readily apparent that modifications can be made thereto without departing from the spirit of this invention. These modifications are under the scope of this invention, as defined in the appended claims.

TABLE 1

PCR amplification primers reported by Hiramatsu et al. in U.S. Pat. No. 6,156,507 found in the sequence listing

| SEQ ID NO.: (present invention) | Target | Position[a, b] | SEQ ID NO.: (U.S. Pat. No. 6,156,507) |
|---|---|---|---|
| 52 | MREP types i and ii | 480 | 18 |
| 53 | MREP types i and ii | 758 | 19 |
| 54 | MREP types i and ii | 927 | 20 |
| 55 | MREP types i and ii | 1154 | 21 |
| 56 | MREP types i and ii | 1755 | 22 |
| 57 | MREP types i and ii | 2302 | 23 |
| 58 | MREP type iii | 295[c] | 24 |
| 59 | orfX | 1664 | 25 |
| 60 | orfSA0022[d] | 3267 | 28 |
| 61 | orfSA0022[d] | 3585 | 27 |
| 62 | orfX | 1389 | 26 |
| 63 | orfSA0022[d] | 2957 | 29 |

[a]Position refers to nucleotide position of the 5' end of primer.
[b]Numbering for SEQ ID NOs.: 52-57 refers to SEQ ID NO.: 2; numbering for SEQ ID NO.: 58 refers to SEQ ID NO.: 4; numbering for SEQ ID NOs.: 59-63 refers to SEQ ID NO.: 3.
[c]Primer is reverse-complement of target sequence.
[d]orfSA0022 refers to the open reading frame designation from GenBank accession number AP003129 (SEQ ID NO.: 231).

TABLE 2

Specificity and ubiquity tests performed on a standard thermocycler using the optimal set of primers described by Hiramatsu et al. (SEQ ID NOs.: 22, 24 and 28 in U.S. Pat. No. 6,156,507 corresponding to SEQ ID NOs.: 56, 58 and 60, respectively, in the present invention) for the detection of MRSA

| | PCR results for SCCmec - orfX right extremity junction | |
|---|---|---|
| Strains | Positive (%) | Negative (%) |
| MRSA - 39 strains | 19 (48.7) | 20 (51.2) |
| MSSA - 41 strains | 13 (31.7) | 28 (68.3) |
| MRCNS - 9 strains* | 0 (0%) | 9 (100%) |
| MSCNS - 11 strains* | 0 (0%) | 11 (100%) |

*Details regarding CNS strains:

MRCNS: *S. caprae* (1)
*S. cohni cohnii* (1)
*S. epidermidis* (1)
*S. haemolyticus* (2)
*S. hominis* (1)
*S. sciuri* (1)
*S. simulans* (1)
*S. warneri* (1)

MSCNS: *S. cohni cohnii* (1)
*S. epidermidis* (1)
*S. equorum* (1)
*S. gallinarum* (1)
*S. haemolyticus* (1)
*S. lentus* (1)
*S. lugdunensis* (1)
*S. saccharolyticus* (1)
*S. saprophyticus* (2)
*S. xylosus* (1)

TABLE 3

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| *Staphylococcus aureus* strain designation: | | |
|---|---|---|
| Original | CCRI[a] | Origin |
| ATCC BAA-40[b] | CCRI-9504 | Portugal |
| ATCC 33592 | CCRI-178 | USA |
| R991282 | CCRI-2025 | Québec, Canada |

TABLE 3-continued

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| *Staphylococcus aureus* strain designation: | | |
|---|---|---|
| Original | CCRI[a] | Origin |
| 4508 | CCRI-9208 | Québec, Canada |
| 19121 | CCRI-8895 | Denmark |
| Z109 | CCRI-8903 | Denmark |
| 45302 | CCRI-1263 | Ontario, Canada |
| R655 | CCRI-1324 | Québec, Canada |
| MA 50428 | CCRI-1311 | Québec, Canada |
| MA 50609 | CCRI-1312 | Québec, Canada |
| MA 51363 | CCRI-1331 | Québec, Canada |
| MA 51561 | CCRI-1325 | Québec, Canada |
| 14A0116 | CCR1-9681 | Poland |
| 23 (CCUG 41787) | CCRI-9860 | Sweden |
| SE26-1 | CCRI-9770 | Ontario, Canada |
| SE1-1 | CCRI-9583 | Ontario, Canada |
| ID-61880[c] | CCRI-9589 | Ontario, Canada |
| SE47-1 | CCRI-9773 | Ontario, Canada |
| SE49-1 | CCRI-9774 | Ontario, Canada |
| 39795-2 | CCRI-1377 | Québec, Canada |

[a]CCRI stands for "Collection of the Centre de Recherche en Infectiologie".
[b]Portuguese clone.
[c]Canadian clone EMRSA1.

TABLE 4

*Staphylococcus aureus* MREJ nucleotide sequences revealed in the present invention

| SEQ | *Staphylococcus aureus* strain designation: | | |
|---|---|---|---|
| ID NO. | Original | CCRI[a] | Genetic Target |
| 27 | R991282 | CCRI-2025 | mecA |
| 28 | 45302 | CCRI-1263 | mecA |
| 29 | MA 50428 | CCRI-1311 | mecA |
| 30 | MA 51363 | CCRI-1331 | mecA |
| 31 | 39795-2 | CCRI-1377 | mecA and 1.5 kb of downstream region |
| 42 | ATCC 33592 | CCRI-178 | MREP type iv |
| 43 | 19121 | CCRI-8895 | MREP type iv |
| 44 | Z109 | CCRI-8903 | MREP type iv |
| 45 | R655 | CCRI-1324 | MREP type iv |
| 46 | MA 51363 | CCRI-1331 | MREP type iv |
| 47 | 45302 | CCRI-1263 | MREP type v |
| 48 | 39795-2 | CCRI-1377 | MREP type v |
| 49 | MA 50428 | CCRI-1311 | MREP type v |
| 50 | R991282 | CCRI-2025 | MREP type v |
| 51 | ATCC BAA-40 | CCRI-9504 | MREP type iv |
| 165 | SE1-1 | CCRI-9583 | MREP type vii |
| 166 | ID-61880 | CCRI-9589 | MREP type vii |
| 167 | 23 (CCUG 41787) | CCRI-9860 | MREP type viii |
| 168 | 14A016 | CCRI-9681 | MREP type ix |
| 171 | 4508 | CCRI-9208 | MREP type vi |
| 172 | SE26-1 | CCRI-9770 | orfSA0021[b] and 75 bp of orfSA0022[b] |
| 173 | 26 (98/10618) | CCRI-9864 | MREP type ii |
| 174 | 27 (98/26821) | CCRI-9865 | MREP type ii |
| 175 | 28 (24344) | CCRI-9866 | MREP type ii |
| 176 | 12 (62305) | CCRI-9867 | MREP type ii |
| 177 | 22 (90/14719) | CCRI-9868 | MREP type ii |
| 178 | 23 (98/14719) | CCRI-9869 | MREP type ii |
| 179 | 32 (97S99) | CCRI-9871 | MREP type ii |
| 180 | 33 (97S100) | CCRI-9872 | MREP type ii |
| 181 | 38 (825/96) | CCRI-9873 | MREP type ii |
| 182 | 39 (842/96) | CCRI-9874 | MREP type ii |
| 183 | 43 (N8-892/99) | CCRI-9875 | MREP type ii |

TABLE 4-continued

*Staphylococcus aureus* MREJ nucleotide sequences revealed in the present invention

| | | | |
|---|---|---|---|
| 184 | 46 (9805-0137) | CCRI-9876 | MREP type iii |
| 185 | 1 | CCRI-9882 | MREP type ii |
| 186 | 29 | CCRI-9885 | MREP type ii |
| 189 | SE1-1 | CCRI-9583 | mecA and 2.2 kb of downstream region, including IS431mec |
| 190 | ATCC BAA-40 | CCRI-9504 | mecA and 1.5 kb of downstream region |
| 191 | 4508 | CCRI-9208 | mecA and 0.9 kb of downstream region |
| 192 | ID-61880 | CCRI-9589 | mecA and 0.9 kb of downstream region |
| 193 | 14A016 | CCRI-9681 | mecA and 0.9 kb of downstream region |
| 195 | SE26-1 | CCRI-9770 | mecA and 1.5 kb of downstream region, including IS431mec |
| 197 | ATCC 43300 | CCRI-175 | MREP type ii |
| 198 | R522 | CCRI-1262 | MREP type iii |
| 199 | 13370 | CCRI-8894 | MREP type i |
| 219 | ATCC BAA-40 | CCRI-9504 | tetK |

| SEQ | *Staphylococcus aureus* strain designation: | | |
|---|---|---|---|
| ID NO. | Original | CCRI[b] | Genetic Target[a] |
| 220 | MA 51363 | CCRI-1331 | mecA and 1.5 kb of downstream region |
| 221 | 39795-2 | CCRI-1377 | IS431mec and 0.6 kb of upstream region |
| 222 | R991282 | CCRI-2025 | mecA and 1.5 kb of downstream region |
| 223 | R991282 | CCRI-2025 | IS431mec and 0.6 kb of upstream region |
| 224 | 23 (CCUG 41787) | CCRI-9860 | mecA and 1.5 kb of downstream region |
| 225 | 23 (CCUG 41787) | CCRI-9860 | IS431mec and 0.6 kb of upstream region |
| 233 | 14A016 | CCRI-9681 | MREP type ix |

[a]CCRI stands for "Collection of the Centre de Recherche en Infectiologie".
[b]orfSA0021 and orfSA0022 refer to the open reading frame designation from GenBank accession number AP003129 (SEQ ID NO.: 231).

TABLE 5

PCR primers developed in the present invention

| SEQ | | Originating DNA | |
|---|---|---|---|
| ID NO. | Target | Position[a] | SEQ ID NO. |
| 64 | orfX | 1720 | 3 |
| 70 | orfX | 1796 | 3 |
| 71 | orfX | 1712 | 3 |
| 72 | orfX | 1749 | 3 |
| 73 | orfX | 1758 | 3 |
| 74 | orfX | 1794 | 3 |
| 75 | orfX | 1797 | 3 |
| 76 | orfX | 1798 | 3 |
| 66 | MREP types i and ii | 2327 | 2 |
| 100 | MREP types i and ii | 2323 | 2 |
| 101 | MREP types i and ii | 2314 | 2 |
| 97 | MREP type ii | 2434 | 2 |
| 99 | MREP type ii | 2434 | 2 |
| 67 | MREP type iii | 207[b] | 4 |
| 98 | MREP type iii | 147[b] | 4 |
| 102 | MREP type iii | 251[b] | 4 |
| 79 | MREP type iv | 74[b] | 43 |
| 80 | MREP type v | 50[b] | 47 |
| 109 | MREP type ix | 652[b] | 168 |
| 204 | MREP type vi | 642[b] | 171 |
| 112 | MREP type vii | 503[b] | 165 |
| 113 | MREP type vii | 551[b] | 165 |

TABLE 5-continued

PCR primers developed in the present invention

| SEQ ID NO. | Target | Originating DNA Position[a] | SEQ ID NO. |
|---|---|---|---|
| 115 | MREP type viii | 514[b] | 167 |
| 116 | MREP type viii | 601[b] | 167 |

[a]Position refers to nucleotide position of 5' end of primer.
[b]Primer is reverse-complement of target sequence.

TABLE 6

Molecular beacon probes developed in the present invention

| SEQ ID NO. | Target | Position |
|---|---|---|
| 32 | orfX | 86[a] |
| 83 | orfX | 86[a] |
| 84 | orfX | 34[a, b] |
| 160 | orfX | 55[a, b] |
| 161 | orfX | 34[a, b] |
| 162 | orfX | 114[a] |
| 163 | orfX | 34[a, b] |
| 164 | orfX | 34[a, b] |

[a]Position refers to nucleotide position of the 5' end of the molecular beacon's loop on SEQ ID NO.: 3.
[b]Sequence of molecular beacon's loop is reverse-complement of SEQ ID NO.: 3.

TABLE 7

Length of amplicons obtained with the different primer pairs which are objects of the present invention

| SEQ ID NO. | Target[d] | Amplicon length[a] |
|---|---|---|
| 59/52[b] | orfX/MREP type i and ii | 2079 (type i); 2181 (type ii) |
| 59/53[b] | orfX/MREP type i and ii | 1801 (type i); 1903 (type ii) |
| 59/54[b] | orfX/MREP type i and ii | 1632 (type i); 1734 (type ii) |
| 59/55[b] | orfX/MREP type i and ii | 1405 (type i); 1507 (type ii) |
| 59/56[b] | orfX/MREP type i and ii | 804 (type i); 906 (type ii) |
| 59/57[b] | orfX/MREP type i and ii | 257 (type i); 359 (type ii) |
| 60/52[b] | orfSA0022/MREP type i and ii | 2794 (type i); 2896 (type ii) |
| 60/53[b] | orfSA0022/MREP type i and ii | 2516 (type i); 2618 (type ii) |
| 60/54[b] | orfSA0022/MREP type i and ii | 2347 (type i); 2449 (type ii) |
| 60/55[b] | orfSA0022/MREP type i and ii | 2120 (type i); 2222 (type ii) |
| 60/56[b] | orfSA0022/MREP type i and ii | 1519 (type i); 1621 (type ii) |
| 60/57[b] | orfSA0022/MREP type i and ii | 972 (type i); 1074 (type ii) |
| 61/52[b] | orfSA0022/MREP type i and ii | 2476 (type i); 2578 (type ii) |
| 61/53[b] | orfSA0022/MREP type i and ii | 2198 (type i); 2300 (type ii) |
| 61/54[b] | orfSA0022/MREP type i and ii | 2029 (type i); 2131 (type ii) |
| 61/55[b] | orfSA0022/MREP type i and ii | 1802 (type i); 1904 (type ii) |
| 61/56[b] | orfSA0022/MREP type i and ii | 1201 (type i); 1303 (type ii) |
| 61/57[b] | orfSA0022/MREP type i and ii | 654 (type i); 756 (type ii) |
| 62/52[b] | orfX/MREP type i and ii | 2354 (type i); 2456 (type ii) |
| 62/53[b] | orfX/MREP type i and ii | 2076 (type i); 2178 (type ii) |
| 62/54[b] | orfX/MREP type i and ii | 1907 (type i); 2009 (type ii) |
| 62/55[b] | orfX/MREP type i and ii | 1680 (type i); 1782 (type ii) |
| 62/56[b] | orfX/MREP type i and ii | 1079 (type i); 1181 (type ii) |
| 62/57[b] | orfX/MREP type i and ii | 532 (type i); 634 (type ii) |
| 63/52[b] | orfSA0022/MREP type i and ii | 3104 (type i); 3206 (type ii) |
| 63/53[b] | orfSA0022/MREP type i and ii | 2826 (type i); 2928 (type ii) |
| 63/54[b] | orfSA0022/MREP type i and ii | 2657 (type i); 2759 (type ii) |
| 63/55[b] | orfSA0022/MREP type i and ii | 2430 (type i); 2532 (type ii) |
| 63/56[b] | orfSA0022/MREP type i and ii | 1829 (type i); 1931 (type ii) |
| 63/57[b] | orfSA0022/MREP type i and ii | 1282 (type i); 1384 (type ii) |
| 59/58[b] | orfX/MREP type iii | 361 |
| 60/58[b] | orfSA0022/MREP type iii | 1076 |
| 61/58[b] | orfSA0022/MREP type iii | 758 |
| 62/58[b] | orfX/MREP type iii | 656 |
| 63/58[b] | orfSA0022/MREP type iii | 1386 |
| 70/66 | orfX/MREP type i and ii | 100 (type i); 202 (type ii) |
| 70/67 | orfX/MREP type iii | 147 (type iii) |
| 64/66[c] | orfX/MREP type i and ii | 176 (type i); 278 (type ii) |

TABLE 7-continued

Length of amplicons obtained with the different primer pairs which are objects of the present invention

| SEQ ID NO. | Target[d] | Amplicon length[a] |
|---|---|---|
| 64/67[c] | orfX/MREP type iii | 223 |
| 64/79[c] | orfX/MREP type iv | 215 |
| 64/80[c] | orfX/MREP type v | 196 |
| 64/97[c] | orfX/MREP type ii | 171 |
| 64/98[c] | orfX/MREP type iii | 163 |
| 64/99[c] | orfX/MREP type ii | 171 |
| 64/100[c] | orfX/MREP types i and ii | 180 (type i); 282 (type ii) |
| 64/101[c] | orfX/MREP types i and ii | 189 (type i); 291 (type ii) |
| 64/102[c] | orfX/MREP type iii | 263 |
| 64/109[c] | orfX/MREP type ix | 369 |
| 64/204[c] | orfX/MREP type vi | 348 |
| 64/112[c] | orfX/MREP type vii | 214 |
| 64/113[c] | orfX/MREP type vii | 263 |
| 64/115[c] | orfX/MREP type viii | 227 |
| 64/116[c] | orfX/MREP type viii | 318 |

[a]Amplicon length is given in base pairs for MREP types amplified by the set of primers.
[b]Set of primers described by Hiramatsu et al. in U.S. Pat. No. 6,156,507.
[c]Set of primers developed in the present invention.
[d]orfSA0022 refers to the open reading frame designation from GenBank accession number AP003129 (SEQ ID NO.: 231).

TABLE 8

Other primers developed in the present invention

| SEQ ID NO. | Target | Originating DNA Position[a] | SEQ ID NO. |
|---|---|---|---|
| 77 | MREP type iv | 993 | 43 |
| 65 | MREP type v | 636 | 47 |
| 70 | orfX | 1796 | 3 |
| 68 | IS431 | 626 | 92 |
| 69 | mecA | 1059 | 78 |
| 96 | mecA | 1949 | 78 |
| 81 | mecA | 1206 | 78 |
| 114 | MREP type vii | 629[b] | 165 |
| 117 | MREP type ii | 856 | 194 |
| 118 | MREP type ii | 974[b] | 194 |
| 119 | MREP type vii | 404 | 189 |
| 120 | MREP type vii | 477[b] | 189 |
| 123 | MREP type vii | 551 | 165 |
| 124 | MREP type ii | 584 | 170 |
| 125 | MREP type ii | 689[b] | 170 |
| 126 | orfSA0021 | 336 | 231 |
| 127 | orfSA0021 | 563 | 231 |
| 128 | orfSA0022[d] | 2993 | 231 |
| 129 | orfSA0022[d] | 3467[b] | 231 |
| 132 | orfX | 3700 | 231 |
| 145 | MREP type iv | 988 | 51 |
| 146 | MREP type v | 1386 | 51 |
| 147 | MREP type iv | 891[b] | 51 |
| 148 | MREP type ix | 664 | 168 |
| 149 | MREP type ix | 849[b] | 168 |
| 150 | MREP type vii | 1117[b] | 165 |
| 151 | MREP type vii | 1473 | 189 |
| 152 | IS431mec | 1592[b] | 189 |
| 154 | MREP type v | 996[b] | 50 |
| 155 | MREP type v | 935 | 50 |
| 156 | tetK from plasmid pT181 | 1169[b] | 228 |
| 157 | tetK from plasmid pT181 | 136 | 228 |
| 158 | orfX | 2714[b] | 2 |
| 159 | orfX | 2539 | 2 |
| 187 | MREP type viii | 967[b] | 167 |
| 188 | MREP type viii | 851 | 167 |

[a]Position refers to nucleotide position of the 5' end of primer.
[b]Primer is reverse-complement of target sequence.

TABLE 9

Amplification and/or sequencing primers developed in the present invention

| SEQ ID NO. | Target | Originating DNA Position[a] | Originating DNA SEQ ID NO. |
|---|---|---|---|
| 85 | *S. aureus* chromosome | 197[b] | 35 |
| 86 | *S. aureus* chromosome | 198[b] | 37 |
| 87 | *S. aureus* chromosome | 197[b] | 38 |
| 88 | *S. aureus* chromosome | 1265[b] | 39 |
| 89 | *S. aureus* chromosome | 1892 | 3 |
| 103 | orfX | 1386 | 3 |
| 105 | MREP type i | 2335 | 2 |
| 106 | MREP type ii | 2437 | 2 |
| 107 | MREP type iii | 153[b] | 4 |
| 108 | MREP type iii | 153[b] | 4 |
| 121 | MREP type vii | 1150 | 165 |
| 122 | MREP type vii | 1241[b] | 165 |
| 130 | orfX | 4029[b] | 231 |
| 131 | region between orfSA0022 and orfSA0023[d] | 3588 | 231 |
| 133 | merB from plasmid pI258 | 262 | 226 |
| 134 | merB from plasmid pI258 | 539[b] | 226 |
| 135 | merR from plasmid pI258 | 564 | 226 |
| 136 | merR from plasmid pI258 | 444 | 227 |
| 137 | merR from plasmid pI258 | 529 | 227 |
| 138 | merR from plasmid pI258 | 530[b] | 227 |
| 139 | rep from plasmid pUB110 | 796 | 230 |
| 140 | rep from plasmid pUB110 | 761[b] | 230 |
| 141 | rep from plasmid pUB110 | 600 | 230 |
| 142 | aadD from plasmid pUB110 | 1320[b] | 229 |
| 143 | aadD from plasmid pUB110 | 759 | 229 |
| 144 | aadD from plasmid pUB110 | 646 | 229 |
| 153 | MREP type vii | 1030 | 165 |
| 200 | orfSA0022[d] | 871[c] | 231 |
| 201 | orfSA0022[d] | 1006 | 231 |
| 202 | MREP type vi | 648 | 171 |
| 203 | MREP type vi | 883[b] | 171 |
| 205 | MREP type ix | 1180 | 168 |
| 206 | MREP type ix | 1311[b] | 233 |
| 207 | MREP type viii | 1337 | 167 |
| 208 | MREP type viii | 1441[b] | 167 |
| 209 | ccrA | 184 | 232 |
| 210 | ccrA | 385 | 232 |
| 211 | ccrA | 643[b] | 232 |
| 212 | ccrA | 1282[b] | 232 |
| 213 | ccrB | 1388 | 232 |
| 214 | ccrB | 1601 | 232 |
| 215 | ccrB | 2139[b] | 232 |
| 216 | ccrB | 2199[b] | 232 |
| 217 | ccrB | 2847[b] | 232 |
| 218 | ccrB | 2946[b] | 232 |

[a]Position refers to nucleotide position of the 5' end of primer.

[b]Primer is reverse-complement of target sequence.

[c]Primer contains two mismatches.

[d]orfSA0022 and orfSA0023 refer to the open reading frame designation from GenBank accession number AP003129 (SEQ ID NO.: 231).

TABLE 10

Origin of the nucleic acids and/or sequences available from public databases found in the sequence listing

| SEQ ID NO. | Staphylococcal strain | Source | Accession number | Genetic Target[a, b] |
|---|---|---|---|---|
| 1 | NCTC 10442 | Database | AB033763 | SCCmec type I MREJ |
| 2 | N315 | Database | D86934 | SCCmec type II MREJ |
| 3 | NCTC 8325 | Database | AB014440 | MSSA chromosome |
| 4 | 86/560 | Database | AB013471 | SCCmec type III MREJ |
| 5 | 86/961 | Database | AB013472 | SCCmec type III MREJ |
| 6 | 85/3907 | Database | AB013473 | SCCmec type III MREJ |
| 7 | 86/2652 | Database | AB013474 | SCCmec type III MREJ |
| 8 | 86/1340 | Database | AB013475 | SCCmec type III MREJ |
| 9 | 86/1762 | Database | AB013476 | SCCmec type III MREJ |
| 10 | 86/2082 | Database | AB013477 | SCCmec type III MREJ |
| 11 | 85/2111 | Database | AB013478 | SCCmec type III MREJ |
| 12 | 85/5495 | Database | AB013479 | SCCmec type III MREJ |
| 13 | 85/1836 | Database | AB013480 | SCCmec type III MREJ |
| 14 | 85/2147 | Database | AB013481 | SCCmec type III MREJ |
| 15 | 85/3619 | Database | AB013482 | SCCmec type III MREJ |
| 16 | 85/3566 | Database | AB013483 | SCCmec type III MREJ |
| 17 | 85/2232 | Database | AB014402 | SCCmec type II MREJ |
| 18 | 85/2235 | Database | AB014403 | SCCmec type II MREJ |
| 19 | MR108 | Database | AB014404 | SCCmec type II MREJ |
| 20 | 85/9302 | Database | AB014430 | SCCmec type I MREJ |
| 21 | 85/9580 | Database | AB014431 | SCCmec type I MREJ |
| 22 | 85/1940 | Database | AB014432 | SCCmec type I MREJ |
| 23 | 85/6219 | Database | AB014433 | SCCmec type I MREJ |
| 24 | 64/4176 | Database | AB014434 | SCCmec type I MREJ |
| 25 | 64/3846 | Database | AB014435 | SCCmec type I MREJ |
| 26 | HUC19 | Database | AF181950 | SCCmec type II MREJ |
| 33 | G3 | U.S. Pat. No. 6,156,507 | SEQ ID NO.: 15 | *S. epidermidis* SCCmec type II MREJ |
| 34 | SH 518 | U.S. Pat. No. 6,156,507 | SEQ ID NO.: 16 | *S. haemolyticus* SCCmec type II MREJ |
| 35 | ATCC 25923 | U.S. Pat. No. 6,156,507 | SEQ ID NO.: 9 | *S. aureus* chromosome |
| 36 | STP23 | U.S. Pat. No. 6,156,507 | SEQ ID NO.: 10 | *S. aureus* chromosome |
| 37 | STP43 | U.S. Pat. No. 6,156,507 | SEQ ID NO.: 12 | *S. aureus* chromosome |
| 38 | STP53 | U.S. Pat. No. 6,156,507 | SEQ ID NO.: 13 | *S. aureus* chromosome |
| 39 | 476 | Genome project[c] | | *S. aureus* chromosome |
| 40 | 252 | Genome project[c] | | SCCmec type II MREJ |

TABLE 10-continued

Origin of the nucleic acids and/or sequences available from public databases found in the sequence listing

| SEQ ID NO. | Staphylococcal strain | Source | Accession number | Genetic Target[a, b] |
|---|---|---|---|---|
| 41 | COL | Genome project[d] | | SCCmec type I MREJ |
| 78 | NCTC 8325 | Database | X52593 | mecA |
| 82 | NCTC 10442 | Database | AB033763 | mecA |
| 90 | N315 | Database | D86934 | mecA |
| 91 | 85/2082 | Database | AB037671 | mecA |
| 92 | NCTC 10442 | Database | AB033763 | IS431 |
| 93 | N315 | Database | D86934 | IS431 |
| 94 | HUC19 | Database | AF181950 | IS431 |
| 95 | NCTC 8325 | Database | X53818 | IS431 |
| 104 | 85/2082 | Database | AB037671 | SCCmec type III MREJ |
| 226 | unknown | Database | L29436 | merB on plasmid pI258 |
| 227 | unknown | Database | L29436 | merR on plasmid pI258 |
| 228 | unknown | Database | S67449 | tetK on plasmid pT181 |
| 229 | HUC19 | Database | AF181950 | aadD on plasmid pUB110 |
| 230 | HUC19 | Database | AF181950 | rep on plasmid pUB110 |
| 231 | N315 | Database | AP003129 | orfSA0021, orfSA0022, orfSA0023 |
| 232 | 85/2082 | Database | AB037671 | ccrA/ccrB |

[a]MREJ refers to mec right extremity junction and includes sequences from SCCmec-right extremity and chromosomal DNA to the right of SCCmec integration site.
[b]Unless otherwise specified, all sequences were obtained from *S. aureus* strains.
[c]Sanger Institute genome project (http://www.sanger.ac.uk).
[d]TIGR genome project (http://www.tigr.org).

TABLE 11

Analytical sensitivity of the MRSA-specific PCR assay targeting MREP types i, ii and iii on a standard thermocycler using the set of primers developed in the present invention (SEQ ID NOs.: 64, 66 and 67)

| Strain designation: Original | CCRI[a] (MREP type) | Detection limit (number of genome copies) |
|---|---|---|
| 13370 | CCRI-8894 (I) | 5 |
| ATCC 43300 | CCRI-175 (II) | 2 |
| 35290 | CCRI-1262 (III) | 2 |

[a]CCRI stands for "Collection of the Centre de Recherche en Infectiologie".

TABLE 12

Specificity and ubiquity tests performed on a standard thermocycler using the set of primers targeting MREP types i, ii and iii developed in the present invention (SEQ ID NOs.: 64, 66 and 67) for the detection of MRSA

| Strains | PCR results for MREJ Positive (%) | Negative (%) |
|---|---|---|
| MRSA - 208 strains | 188 (90.4) | 20 (9.6) |
| MSSA - 252 strains | 13 (5.2) | 239 (94.8) |
| MRCNS - 41 strains* | 0 | 42 (100) |
| MSCNS - 21 strains* | 0 | 21 (100) |

*Details regarding CNS strains:

MRCNS: *S. caprae* (2)
*S. cohni cohnii* (3)
*S. cohni urealyticum* (4)
*S. epidermidis* (8)
*S. haemolyticus* (9)
*S. hominis* (4)
*S. sciuri* (4)
*S. sciuri sciuri* (1)
*S. simulans* (3)
*S. warneri* (3)

MSCNS: *S. cohni cohnii* (1)
*S. epidermidis* (3)
*S. equorum* (2)

TABLE 12-continued

Specificity and ubiquity tests performed on a standard thermocycler using the set of primers targeting MREP types i, ii and iii developed in the present invention (SEQ ID NOs.: 64, 66 and 67) for the detection of MRSA

*S. felis* (1)
*S. gallinarum* (1)
*S. haemolyticus* (1)
*S. hominis* (1)
*S. lentus* (1)
*S. lugdunensis* (1)
*S. saccharolyticus* (1)
*S. saprophyticus* (5)
*S. simulans* (1)
*S. warneri* (1)
*S. xylosus* (1)

TABLE 13

Percentage of sequence identity for the first 500 nucleotides of SCCmec right extremities between all 9 types of MREP[a,b]

| MREP type | i | ii | iii | iv | v | vi | vii | viii | ix |
|---|---|---|---|---|---|---|---|---|---|
| i | — | 79.2 | 42.8 | 42.8 | 41.2 | 44.4 | 44.6 | 42.3 | 42.1 |
| ii | | | 43.9 | 47.5 | 44.7 | 41.7 | 45.0 | 52.0 | 57.1 |
| iii | | | | 46.8 | 44.5 | 42.9 | 45.0 | 42.8 | 45.2 |
| iv | | | | | 45.8 | 41.4 | 44.3 | 48.0 | 41.3 |
| v | | | | | | 45.4 | 43.7 | 47.5 | 44.3 |
| vi | | | | | | | 45.1 | 41.1 | 47.2 |
| vii | | | | | | | | 42.8 | 40.9 |
| viii | | | | | | | | | 55.2 |
| ix | | | | | | | | | — |

[a]"First 500 nucleotides" refers to the 500 nucleotides within the SCCmec right extremity, starting from the integration site of SCCmec in the *Staphylococcus aureus* chromosome as shown on FIG. 4.
[b]Sequences were extracted from SEQ ID NOs.: 1, 2, 104, 51, 50, 171, 165, 167, and 168 for types i to ix, respectively.

TABLE 14

Reference strains used to test sensitivity and/or specificity and/or ubiquity of the MRSA-specific PCR assays targeting MREJ sequences

| Staphylococcal species | Strains | Source[a] |
|---|---|---|
| MRSA (n = 45) | 33591 | ATCC |
| | 33592 | ATCC |
| | 33593 | ATCC |
| | BAA-38 | ATCC |
| | BAA-39 | ATCC |
| | BAA-40 | ATCC |
| | BAA-41 | ATCC |
| | BAA-42 | ATCC |
| | BAA-43 | ATCC |
| | BAA-44 | ATCC |
| | F182 | CDC |
| | 23 (CCUG 41787) | HARMONY Collection |
| | ID-61880 (EMRSA1) | LSPQ |
| | MA 8628 | LSPQ |
| | MA 50558 | LSPQ |
| | MA 50428 | LSPQ |
| | MA 50609 | LSPQ |
| | MA 50884 | LSPQ |
| | MA 50892 | LSPQ |
| | MA 50934 | LSPQ |
| | MA 51015 | LSPQ |
| | MA 51056 | LSPQ |
| | MA 51085 | LSPQ |
| | MA 51172 | LSPQ |
| | MA 51222 | LSPQ |
| | MA 51363 | LSPQ |
| | MA 51561 | LSPQ |
| | MA 52034 | LSPQ |
| | MA 52306 | LSPQ |
| | MA 51520 | LSPQ |
| | MA 51363 | LSPQ |
| | 98/10618 | HARMONY Collection |
| | 98/26821 | HARMONY Collection |
| | 24344 | HARMONY Collection |
| | 62305 | HARMONY Collection |
| | 90/10685 | HARMONY Collection |
| | 98/14719 | HARMONY Collection |
| | 97S99 | HARMONY Collection |
| | 97S100 | HARMONY Collection |
| | 825/96 | HARMONY Collection |
| | 842/96 | HARMONY Collection |
| | N8-890/99 | HARMONY Collection |
| | 9805-01937 | HARMONY Collection |
| | 1 | Kreiswirth-1 |
| | 29 | Kreiswirth-1 |
| MRCNS (n = 4) | 29060 | ATCC |
| | 35983 | ATCC |
| | 35984 | ATCC |
| | 2514 | LSPQ |
| MSSA (n = 28) | MA 52263 | LSPQ |
| | 6538 | ATCC |
| | 13301 | ATCC |
| | 25923 | ATCC |
| | 27660 | ATCC |
| | 29213 | ATCC |
| | 29247 | ATCC |
| | 29737 | ATCC |
| | RN 11 | CDC |
| | RN 3944 | CDC |
| | RN 2442 | CDC |
| | 7605060113 | CDC |
| | BM 4611 | Institut Pasteur |
| | BM 3093 | Institut Pasteur |
| | 3511 | LSPQ |
| | MA 5091 | LSPQ |
| | MA 8849 | LSPQ |
| | MA 8871 | LSPQ |
| | MA 50607 | LSPQ |
| | MA 50612 | LSPQ |
| | MA 50848 | LSPQ |
| | MA 51237 | LSPQ |
| | MA 51351 | LSPQ |
| | MA 52303 | LSPQ |
| | MA 51828 | LSPQ |
| | MA 51891 | LSPQ |
| | MA 51504 | LSPQ |
| | MA 52535 | LSPQ |
| | MA 52783 | LSPQ |
| MSCNS (n = 17) | 12228 | ATCC |
| | 14953 | ATCC |
| | 14990 | ATCC |
| | 15305 | ATCC |
| | 27836 | ATCC |
| | 27848 | ATCC |
| | 29070 | ATCC |
| | 29970 | ATCC |
| | 29974 | ATCC |
| | 35539 | ATCC |
| | 35552 | ATCC |
| | 35844 | ATCC |
| | 35982 | ATCC |
| | 43809 | ATCC |
| | 43867 | ATCC |
| | 43958 | ATCC |
| | 49168 | ATCC |

[a]ATCC stands for "American Type Culture Collection". LSPQ stands for "Laboratoire de Santé Publique du Québec". CDC stands for "Center for Disease Control and Prevention".

TABLE 15

Clinical isolates used to test the sensitivity and/or specificity and/or ubiquity of the MRSA-specific PCR assays targeting MREJ sequences

| Staphylococcal species | Number of strains | Source |
|---|---|---|
| MRSA (n = 177) | 150 | Canada |
| | 10 | China |
| | 10 | Denmark |
| | 9 | Argentina |
| | 1 | Egypt |
| | 1 | Sweden |
| | 1 | Poland |
| | 3 | Japan |
| | 1 | France |
| MSSA (n = 224) | 208 | Canada |
| | 10 | China |
| | 4 | Japan |
| | 1 | USA |
| | 1 | Argentina |
| MRCNS (n = 38) | 32 | Canada |
| | 3 | China |
| | 1 | France |
| | 1 | Argentina |
| | 1 | USA |
| MSCNS (n = 17) | 14 | UK |
| | 3 | Canada |

TABLE 16

Analytical sensitivity of tests performed on a standard thermocycler using the set of primers targeting MREP types i, ii, iii, iv and v (SEQ ID NOs.: 64, 66, 67, 79 and 80) developed in the present invention for the detection and identification of MRSA

| *Staphylococcus aureus* strain designation: | | Detection limit |
|---|---|---|
| Original | CCRI[a] (MREP type) | (number of genome copies) |
| 13370 | CCRI-8894 (i) | 10 |
| ATCC 43300 | CCRI-175 (ii) | 5 |
| 9191 | CCRI-2086 (ii) | 10 |

TABLE 16-continued

Analytical sensitivity of tests performed on a standard thermocycler using the set of primers targeting MREP types i, ii, iii, iv and v (SEQ ID NOs.: 64, 66, 67, 79 and 80) developed in the present invention for the detection and identification of MRSA

| *Staphylococcus aureus* strain designation: | | Detection limit |
|---|---|---|
| Original | CCRI[a] (MREP type) | (number of genome copies) |
| 35290 | CCRI-1262 (iii) | 5 |
| 352 | CCRI-1266 (iii) | 10 |
| 19121 | CCRI-8895 (iv) | 5 |
| ATCC 33592 | CCRI-178 (iv) | 5 |
| MA 50428 | CCRI-1311 (v) | 5 |
| R991282 | CCRI-2025 (v) | 5 |

[a]CCRI stands for "Collection of the Centre de Recherche en Infectiologie".

TABLE 17

Specificity and ubiquity tests performed on a standard thermocycler using the set of primers targeting MREP types i, ii, iii, iv and v (SEQ ID NO.: 64, 66, 67, 79 and 80) developed in the present invention for the detection and identification of MRSA

| | PCR results for SCCmec - orfX right extremity junction | |
|---|---|---|
| Strains | Positive (%) | Negative (%) |
| MRSA - 35 strains[a] | 27 (77.1) | 8 (22.9) |
| MSSA - 44 strains | 13 (29.5) | 31 (70.5) |
| MRCNS - 9 strains* | 0 | 9 (100) |
| MSCNS - 10 strains* | 0 | 10 (100) |

[a]MRSA strains include the 20 strains listed in Table 3.
*Details regarding CNS strains:
MRCNS: *S. caprae* (1)
*S. cohni cohnii* (1)
*S. epidermidis* (1)
*S. haemolyticus* (2)
*S. hominis* (1)
*S. sciuri* (1)
*S. simulans* (1)
*S. warneri* (1)
MSCNS: *S. cohni* (1)
*S. epidermidis* (1)
*S. equorum* (1)
*S. haemolyticus* (1)
*S. lentus* (1)
*S. lugdunensis* (1)
*S. saccharolyticus* (1)
*S. saprophyticus* (2)
*S. xylosus* (1)

TABLE 18

Analytical sensitivity of tests performed on the SMART CYCLER ® thermocycler using the set of primers targeting MREP types i, ii, iii, iv and v (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a] (MREP type) | (number of genome copies) |
| 13370 | CCRI-8894 (i) | 2 |
| ATCC 43300 | CCRI-175 (ii) | 2 |
| 9191 | CCRI-2086 (ii) | 10 |
| 35290 | CCRI-1262 (iii) | 2 |
| 352 | CCRI-1266 (iii) | 10 |
| ATCC 33592 | CCRI-178 (iv) | 2 |
| MA 51363 | CCRI-1331 (iv) | 5 |

TABLE 18-continued

Analytical sensitivity of tests performed on the SMART CYCLER ® thermocycler using the set of primers targeting MREP types i, ii, iii, iv and v (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a] (MREP type) | (number of genome copies) |
| 19121 | CCRI-8895 (iv) | 10 |
| Z109 | CCRI-8903 (iv) | 5 |
| 45302 | CCRI-1263 (v) | 10 |
| MA 50428 | CCRI-1311 (v) | 5 |
| MA 50609 | CCRI-1312 (v) | 5 |
| MA 51651 | CCRI-1325 (v) | 10 |
| 39795-2 | CCRI-1377 (v) | 10 |
| R991282 | CCRI-2025 (v) | 2 |

[a]CCRI stands for "Collection of the Centre de Recherche en Infectiologie".

TABLE 19

Specificity and ubiquity tests performed on the SMART CYCLER ® thermocycler using the set of primers targeting MREP types i, ii, iii, iv and v (SEQ ID NO.: 64, 66, 67, 79 and 80) and molecular beacon probe (SEQ ID NO.: 84) developed in the present invention for the detection of MRSA

| | PCR results for MREJ | |
|---|---|---|
| Strains | Positive (%) | Negative (%) |
| MRSA - 29 strains[a] | 21 (72.4) | 8 (27.6) |
| MSSA - 35 strains | 13 (37.1) | 22 (62.9) |
| MRCNS - 14 strains | 0 | 14 (100) |
| MSCNS - 10 strains | 0 | 10 (100) |

[a]MRSA strains include the 20 strains listed in Table 3.
Details regarding CNS strains:
MRCNS: *S. epidermidis* (1)
*S. haemolyticus* (5)
*S. simulans* (5)
*S. warneri* (3)
MSCNS: *S. cohni cohnii* (1)
*S. epidermidis* (1)
*S. gallinarum* (1)
*S. haemolyticus* (1)
*S. lentus* (1)
*S. lugdunensis* (1)
*S. saccharolyticus* (1)
*S. saprophyticus* (2)
*S. xylosus* (1)

TABLE 20

Analytical sensitivity of tests performed on the SMART CYCLER ® thermocycler using the set of primers targeting MREP types i, ii, iii, iv, v and vii (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a] (MREP type) | (number of genome copies) |
| 13370 | CCRI-8894 (i) | 2 |
| ATCC 43300 | CCRI-175 (ii) | 2 |
| 35290 | CCRI-1262 (iii) | 2 |
| ATCC 33592 | CCRI-178 (iv) | 2 |
| R991282 | CCRI-2025 (v) | 2 |
| SE-41-1 | CCRI-9771 (vii) | 2 |

[a]CCRI stands for "Collection of the Centre de Recherche en Infectiologie".

TABLE 21

Specificity and ubiquity tests performed on the SMART CYCLER ® thermocycler using the set of primers targeting MREP types i, ii, iii, iv, vi and vii (SEQ ID NOs.: 64, 66, 67, 79 and 80) and molecular beacon probe (SEQ ID NO.: 84) developed in the present invention for the detection and identification of MRSA

| Strains | PCR results for MREJ Positive (%) | Negative (%) |
|---|---|---|
| MRSA - 23 strains[a] | 19 (82.6) | 4 (17.4) |
| MSSA - 25 strains | 13 (52) | 12 (48) |
| MRCNS - 26 strains | 0 | 26 (100) |
| MSCNS - 8 strains | 0 | 8 (100) |

[a]MRSA strains include the 20 strains listed in Table 3.

Details regarding CNS strains:

MRCNS: *S. capitis* (2), *S. caprae* (1), *S. cohnii* (1), *S. epidermidis* (9), *S. haemolyticus* (5), *S. hominis* (2), *S. saprophyticus* (1), *S. sciuri* (2), *S. simulans* (1), *S. warneri* (2)

MSCNS: *S. cohni cohnii* (1), *S. epidermidis* (1), *S. haemolyticus* (1), *S. lugdunensis* (1), *S. saccharolyticus* (1), *S. saprophyticus* (2), *S. xylosus* (1)

Annex I:
Strategy for the selection of specific amplification primers for types i and ii MREP

| A. SEQ ID NO.: | Types i and ii MREP 2324 ... 2358 | orfX 2583 ... 2607 |
|---|---|---|
| 2 | TAT **GTCAAAAATC ATGAACCTCA TTACTTATG**A TA... | CCT **TGTGCAGGCC GTTTGATCC**G CC |
| 1 | TAT **GTCAAAAATC ATGAACCTCA TTACTTATG**A TA... | CCT **TGTGCAGGCC GTTTGATCC**G CC |
| 17[a] | TAT **GTCAAAAATC ATGAACCTCA TTACTTATG**A TA... | CCT **TGTGCAGGCC GTTTGATCC**G CC |
| 18[a] | TAT **GTCAAAAATC ATGAACCTCA TTACTTATG**A TA... | CCT **TGTGCAGGCC GTTTGATCC**G CC |
| 19[a] | TAT **GTCAAAAATC ATGAACCTCA TTACTTATG**A TA... | CCT **TGTGCAGGCC GTTTGATCC**G CC |
| 20[a] | TAT **GTCAAAAATC ATGAACCTCA TTACTTATG**A TA... | CCT **TGTGCAGGCC GTTTGATCC**G CC |
| 21[a] | TAT **GTCAAAAATC ATGAACCTCA TTACTTATG**A TA... | CCT **TGTGCAGGCC GTTTGATCC**G CC |
| 22[a] | TAT **GTCAAAAATC ATGAACCTCA TTACTTATG**A TA... | CCT **TGTGCAGGCC GTTTGATCC**G CC |
| 23[a] | TAT **GTCAAAAATC ATGAACCTCA TTACTTATG**A TA... | CCT **TGTGCAGGCC GTTTGATCC**G CC |
| 24[a] | TAT **GTCAAAAATC ATGAACCTCA TTACTTATG**A TA... | CCT **TGTGCAGGCC GTTTGATCC**G CC |
| 25[a] | TAT **GTCAAAAATC ATGAACCTCA TTACTTATG**A TA... | CCT **TGTGCAGGCC GTTTGATCC**G CC |
| 26 | TAT **GTCAAAAATC ATGAACCTCA TTACTTATG**A TA... | CCT **TGTGCAGGCC GTTTGATCC**G CC |
| 33[c] | | CtT **gGTGtAaaCC aTTgGAgCC**a CC |
| 34[c] | | CCT **caTGCAatCC aTTTGATC** |
| Selected sequence for type i MREP and ii primer (SEQ ID No.: 66) | **GTCAAAAATC ATGAACCTCA TTACTTATG** | |
| Selected sequence for orfX primer[b] (SEQ ID NO.: 64) | | **TGTGCAGGCC GTTTGATCC** |

The sequence positions refer to SEQ ID NO.: 2.

Nucleotides in capitals are identical to the selected sequences or match those sequences.
Mismatches are indicated by lower-case letters. Dots indicate gaps in the displayed sequences.
[a]These sequences are the reverse-complements of SEQ ID NOs.: 17-25.
[b]This sequence is the reverse-complement of the selected primer.
[c]SEQ ID NOs.: 33 and 34 were obtained from CNS species.

Annex II:
Strategy for the selection of a specific molecular beacon probe for the real-time detection of MREJ

| | orfX |
|---|---|
| SEQ ID NO.: | 327 371 |
| 165 | ACAAG **GACGT CTTACAACGC AGTAACTAtG** CACTA |
| 180 | ACAAG **GACGT CTTACAACGC AGTAACTAtG** CACTA |
| 181 | ACAAG **GACGT CTTACAACGC AGTAACTAtG** CACTA |
| 182 | ACAAG **GACGT CTTACAACGC AGTAACTAtG** CACTA |
| 183 | ACAAG **GACGT CTTACAACGC AGTAACTAtG** CACTA |
| 184 | ACAAG **GACGT CTTACAACGC AGTAACTAtG** CACTA |
| 186 | ACAAG **GACGT CTTACAACGC AGTAACTAtG** CACTA |
| 174 | ACAAG **GACGT CTTACAACGt AGTAACTACG** CACTA |
| 175 | ACAAG **GACGT CTTACAACGt AGTAACTACG** CACTA |
| 178 | ACAAG **GACGT CTTACAACGt AGTAACTACG** CACTA |
| 176 | ACAAG **GACGT CTTACAACGt AGTAACTACG** CACTA |
| 173 | ACAAG **GACGT CTTACAACGt AGTAACTACG** CACTA |
| 177 | ACAAG **GACGT CTTACAACGt AGTAACTACG** CACTA |
| 169 | ACAAG **GACGT CTTACAACGC AGTAACTACG** CACTA |
| 199 | ACAAG **GACGT CTTACAACGC AGTAACTACG** CACTA |
| 33[a,b] | ACcAa **GACGT CTTACAACGC AGcAACTAtG** CttTA |
| 34[a,b] | AtgAG **GACGT CTTACAACGC AGcAACTACG** CACTt |
| Selected sequence for orfX molecular beacon probes (SEQ ID NO.: 163)[c] | **GACGT CTTACAACGC AGTAACTAtG** |
| (SEQ ID NO.: 164)[c] | **GACGT CTTACAACGt AGTAACTACG** |
| (SEQ ID NO.: 84)[c] | **GACGT CTTACAACGC AGTAACTACG** |

Nucleotide discrepancies between the orfX sequences and SEQ ID NO.: 84 are shown in lower-case. Other entries in the sequence listing also present similar variations. The stem of the molecular beacon probes are not shown for sake of clarity. The sequence positions refer to SEQ ID NO.: 165.

[a]These sequences are the reverse-complements of SEQ ID NOs.: 33 and 34.

[b]SEQ ID NOs.: 33 and 34 were obtained from CNS species.

[c]The sequences presented are the reverse-complement of the selected molecular beacon probes.

What is claimed is:

1. A method to detect the presence of an MREJ type v methicillin-resistant *Staphylococcus aureus* (MRSA) strain nucleic acid in a sample, comprising:

a) performing an amplification reaction comprising contacting a sample to be analyzed for the presence of said MREJ type v MRSA strain nucleic acid with a first amplification primer and a second amplification primer to generate a first amplicon if said MREJ type v MRSA strain nucleic acid is present in said sample, said MREJ type v MRSA strain nucleic acid including a staphylococcal cassette chromosome mec (SCCmec) element containing a mecA gene inserted into chromosomal DNA, said chromosomal DNA being orfX, thereby generating a polymorphic right extremity junction (MREJ) type v nucleic acid sequence that comprises nucleic acid sequences from both the SCCmec element right extremity and orfX adjoining said right extremity;

wherein said first primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with an SCCmec element right extremity of an MREJ type v nucleic acid sequence selected from the group consisting of: SEQ ID NOs: 47-50, and the complements thereof, wherein said second primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with orfX, wherein said first amplicon generated if said MREJ type v MRSA strain nucleic acid is present in said sample comprises polymorphic right extremity junction (MREJ) type v sequence and orfX sequence, including the junction of the two, and is indicative of the presence of MREJ type v MRSA strain nucleic acid in said sample; and b) generating and detecting said first amplicon.

2. The method of claim 1, wherein said first amplification primer that specifically hybridizes with said SCCmec element right extremity of an MREJ type v nucleic acid sequence comprises at least 10 consecutive residues of SEQ ID NO:80, or the complement thereof.

3. The method of claim 2, wherein said second amplification primer comprises at least ten consecutive residues of SEQ ID NO: 64 or the complement thereof.

4. The method of claim 1, wherein said amplification reaction comprises PCR.

5. The method of claim 1, wherein said method comprises the use of at least one first or second amplification primer and/or a probe comprising a nucleic acid sequence or complement thereof selected from the group consisting of SEQ ID NOs: 65, 80, 154, 155, 64, 71, 72, 73, 74, 75, 76, 70, 103, 130, 132, 158, 159, 59, 62, 32, 83, 84, 160, 161, 162, 163, and 164 for the detection of MREJ type v nucleic acid.

6. The method of claim 1, wherein said second and first amplification primers are a primer pair consisting of SEQ ID NOs: 64 and 80, or the complements thereof.

7. The method of claim 6, further comprising the use of at least one probe having a nucleic acid sequence selected from the group consisting of SEQ ID NOs: 32, 83, 84, 160, 161, 162, 163, 164, and the complements thereof.

8. The method of claim 1, wherein said method comprises the use of at least one first or second amplification primer and/or a probe comprising a nucleic acid sequence or complement thereof selected from the group consisting of: SEQ ID NOs: 64, 80, 84, 163, and 164, for the detection of MREJ type v nucleic acid.

9. The method of claim 1, further comprising detecting the presence of at least one further methicillin-resistant *Staphylococcus aureus* (MRSA) strain nucleic acid in said sample, said at least one further MRSA strain including an SCCmec element containing a mecA gene inserted into chromosomal DNA, thereby generating a polymorphic right extremity junction (MREJ) type i, ii, iii, iv, vi, viii or ix nucleic acid sequence that comprises nucleic acid sequences from both the SCCmec element right extremity and chromosomal DNA adjoining said right extremity, wherein said method further comprises contacting said sample with at least one additional primer to generate a second amplicon if said at least one further MREJ type i, ii, iii, iv, vi, viii or ix MRSA strain nucleic acid is present in said sample, wherein said at least one additional primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with said polymorphic nucleic acid sequences from the SCCmec element right extremity of said at least one of MREJ type i, ii, iii, iv, vi, viii and ix nucleic acid sequences, or complements thereof, selected from the group consisting of:

a) SEQ ID NOs: 1, 20-25, and 41 for MREJ type i;
b) SEQ ID NOs: 2, 17-19, 26, 40, 173-183, 185, 186 and 197 for MREJ type ii;
c) SEQ ID NOs: 4-16, 104, 184 and 198 for MREJ type iii;
d) SEQ ID NOs: 42-46 and 51 for MREJ type iv;
e) SEQ ID NO: 171 for MREJ type vi;
f) SEQ ID NO: 167 for MREJ type viii; and
g) SEQ ID NO: 168 for MREJ type ix, wherein said second amplicon generated if said at least one further MREJ type i, ii, iii, iv, vi, viii or ix MRSA strain nucleic acid is present in said sample comprises polymorphic right extremity junction (MREJ) type i, ii, iii, iv, vi, viii or ix sequence and orfX sequence, including the junction of the two, and is indicative of the presence of said at least one further MREJ type i, ii, iii, iv, vi, viii or ix MRSA strain nucleic acid in said sample; and detecting said second amplicon if present.

10. The method of claim 9, wherein said at least one additional primer comprises at least one primer selected from the following SEQ ID NOs or complements thereof: 66, 100, 101, 105, 52, 53, 54, 55, 56, 57, 97, 99, 106, 117, 118, 124, 125, 58, 67, 98, 102, 107, 108, 79, 77, 145, 146, 147, 202, 203, 204, 114, 119, 120, 121, 122, 123, 150, 151, 153, 115, 116, 187, 188, 207, 208, 109, 148, 149, 205, and 206.

11. The method of claim 10, further comprising use of at least one second amplification primer and/or a probe selected from the following SEQ ID NOs or complements thereof: 64, 71, 72, 73, 74, 75, 76, 70, 103, 130, 132, 158, 159, 59, 62, 32, 83, 84, 160, 161, 162, 163, and 164.

12. The method of claim 9, further comprising the use of at least one primer pair selected from the following SEQ ID NOs, or the complements thereof:

a) 64/66, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56 and 63/57, for the detection of type i MREJ nucleic acid;
b) 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56 and 63/57, for the detection of type ii MREJ nucleic acid;
c) 64/67, 64/98, 64/102, 59/58, 60/58, 61/58, 62/58 and 63/58, for the detection of type iii MREJ nucleic acid;
d) 64/79, for the detection of type iv MREJ nucleic acid;
e) 64/204, for the detection of type vi MREJ nucleic acid;
f) 64/115 and 64/116, for the detection of type viii MREJ nucleic acid; and
g) 64/109, for the detection of type ix MREJ nucleic acid.

13. The method of claim 12, comprising the use of at least one probe having a nucleic acid sequence, or the complement thereof, selected from the group consisting of: SEQ ID NOs: 32, 83, 84, 160, 161, 162, 163 and 164.

14. The method of claim 9, comprising the use of primers and probes having the following nucleic acid sequences, or the complements thereof:

a) SEQ ID NOs: 64, 66, and at least one of 84, 163, 164 for the detection of MREJ type i or ii nucleic acid;
b) SEQ ID NOs: 64, 67, and at least one of 84, 163, 164 for the detection of MREJ type iii nucleic acid; and
c) SEQ ID NOs: 64, 79, and at least one of 84, 163, 164 for the detection of MREJ type iv nucleic acid.

15. The method of claim 9, wherein multiple primers and/or probes are used together in the same physical enclosure.

16. The method of claim 9, further comprising distinctively detecting said first amplicon as an indication of the presence of said MREJ type v nucleic acid and said second amplicon if present as an indication of said at least one further MREJ type nucleic acid selected from MREJ types i, ii, iii, iv, vi, viii and ix, wherein the presence or absence of said second amplicon produced by a primer is indicative of the presence or absence, respectively, of the corresponding MREJ type i, ii, iii, iv, vi, viii or ix MRSA nucleic acid.

17. The method of claim 9, wherein a plurality of primers and/or probes all chosen to hybridize under the same hybridization conditions are used.

18. The method of claim 1, comprising detecting the presence or absence of at least three further MRSA strain nucleic acids in said sample, said at least three further MRSA strain nucleic acids including an SCCmec element containing a mecA gene inserted into chromosomal DNA, thereby generating a polymorphic right extremity junction (MREJ) type i, ii, iii, iv, vi, viii or ix nucleic acid sequence that comprises nucleic acid sequences from both the SCCmec element right extremity and chromosomal DNA adjoining said right extremity, wherein said method further comprises contacting said sample with at least three additional primers to generate a second, third or fourth amplicon if said at least three further MREJ type i, ii, iii, iv, vi, viii or ix MRSA strain nucleic acids are present in said sample, wherein said at least three additional primers are at least 10 nucleotides in length and each specifically hybridizes under conditions of 50 mM KCl, 10 mM Tris-HCl (pH 9.0), 0.1% Triton X-100, 2.5 mM $MgCl_2$ at 55° C. with said polymorphic nucleic acid sequences from the SCCmec element right extremity of one of said at least three further MRSA strains of MREJ type i-iv, vi, and viii-ix nucleic acid sequences, or complements thereof, selected from the group consisting of:

a) SEQ ID NOs: 1, 20-25, and 41 for MREJ type i;
b) SEQ ID NOs: 2, 17-19, 26, 40, 173-183, 185, 186 and 197 for MREJ type ii;
c) SEQ ID NOs: 4-16, 104, 184 and 198 for MREJ type iii;
d) SEQ ID NOs: 42-46 and 51 for MREJ type iv;
e) SEQ ID NO: 171 for MREJ type vi;
f) SEQ ID NO: 167 for MREJ type viii; and
g) SEQ ID NO: 168 for MREJ type ix wherein said second, third and fourth amplicon generated if said at least three further MREJ type i, ii, iii, iv, vi, viii or ix MRSA strain nucleic acids are present in said sample comprises polymorphic right extremity junction (MREJ) type i, ii, iii, iv, vi, viii or ix nucleic acid sequence and orfX sequence, including the junction of the two, and said second, third and fourth amplicons are indicative of the presence of said at least three further MREJ type i, ii, iii, iv, vi, viii or ix MRSA strain nucleic acids in said sample; and detecting the presence or absence of each second, third and/or fourth amplicon distinctively, wherein the presence or absence of each second, third and/or fourth amplicon produced by a primer is indicative of the presence or absence, respectively, of the corresponding one of said three further MREJ type MRSA nucleic acids, thereby determining the presence or absence in a sample of at least three further MREJ types of MRSA nucleic acids.

19. The method of claim 18, for further determining the presence or absence of MREJ type i, type ii, and type iii nucleic acids.

20. The method of claim 18, for further determining the presence or absence of MREJ type i, type ii, type iii and type iv nucleic acids.

21. The method of claim 18, for further determining the presence or absence of MREJ type i, type ii, type iii, type iv, type vi, type type viii and type ix nucleic acids.

22. The method of claim 18, for further determining the presence or absence of MREJ type i, type ii, type iii, type iv and type vi nucleic acids.

23. The method of claim 1, wherein said method comprises the use of at least one second amplification primer and/or a probe specific for the *S. aureus* chromosome comprising a nucleic acid sequence, or the complement thereof, selected from the group consisting of SEQ ID NOs: 32, 59, 62, 70-76, 83, 84, 103, 130, 132, and 160-164.

24. The method of claim 9, wherein multiplex PCR is used.

25. The method of claim 1, comprising the use of at least one probe having a nucleic acid sequence, or the complement thereof, selected from the group consisting of SEQ ID NOs: 84, 163 and 164.

26. The method of claim 1, wherein said method comprises the use of at least one first amplification primer comprising a nucleic acid sequence or complement thereof selected from the group consisting of SEQ ID NOs: 65, 80, 154, 155, for the detection of MREJ type v nucleic acid.

27. The method of claim 26, wherein said method further comprises the use of at least one second amplification primer and/or probe comprising a nucleic acid sequence or complement thereof selected from the group consisting of SEQ ID NOs: 64, 71, 72, 73, 74, 75, 76, 70, 103, 130, 132, 158, 159, 59, 62, 32, 83, 84, 160, 161, 162, 163, and 164.

* * * * *